(12) United States Patent
DiMarchi et al.

(10) Patent No.: US 9,587,005 B2
(45) Date of Patent: Mar. 7, 2017

(54) GLUCAGON ANALOGS EXHIBITING GIP RECEPTOR ACTIVITY

(71) Applicant: Indiana University Research and Technology Corporation, Indianapolis, IN (US)

(72) Inventors: Richard D. DiMarchi, Carmel, IN (US); Brian P. Ward, Lebanon, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 0 days.

(21) Appl. No.: 14/981,187

(22) Filed: Dec. 28, 2015

(65) Prior Publication Data

US 2016/0115215 A1    Apr. 28, 2016

Related U.S. Application Data

(60) Continuation of application No. 13/728,110, filed on Dec. 27, 2012, now Pat. No. 9,249,206, which is a division of application No. 13/331,816, filed on Dec. 20, 2011, now Pat. No. 8,507,428.

(60) Provisional application No. 61/514,609, filed on Aug. 3, 2011, provisional application No. 61/426,285, filed on Dec. 22, 2010.

(51) Int. Cl.
*A61K 38/00* (2006.01)
*A61K 38/26* (2006.01)
*C07K 14/605* (2006.01)

(52) U.S. Cl.
CPC ............ *C07K 14/605* (2013.01); *A61K 38/00* (2013.01)

(58) Field of Classification Search
CPC ...................................................... A61K 38/26
See application file for complete search history.

(56) References Cited

PUBLICATIONS

Azizeh et al., J. Med. Chem 1997, 40: 2555-2562.*
DiMarchi et al., Novel Glucagon-Like Chimera Peptides—Virtues of combinatorial Pharmacology, AAPS; 2005.*

* cited by examiner

*Primary Examiner* — Gyan Chandra
(74) *Attorney, Agent, or Firm* — Barnes & Thornburg LLP

(57) ABSTRACT

Provided herein are glucagon analogs which exhibit potent activity at the GIP receptor, and, as such are contemplated for use in treating diabetes and obesity. In exemplary embodiments, the glucagon analog of the present disclosures exhibit an EC50 at the GIP receptor which is within the nanomolar or picomolar range.

18 Claims, 20 Drawing Sheets

GLUCAGON ANALOGS EXHIBITING GIP RECEPTOR ACTIVITY

CROSS-REFERENCE TO RELATED APPLICATIONS

This application claims priority to U.S. Provisional Patent Application No. 61/426,285, filed on Dec. 22, 2010, and U.S. Provisional Patent Application No. 61/514,609, filed on Aug. 3, 2011, both applications of which are incorporated by reference in their entirety into the present application.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: 193 kilobytes ACII (Text) file named "DOCS_223734_SeqListing.txt," created on Dec. 27, 2012.

BACKGROUND

According to the most recent data from the National Diabetes Fact Sheet of the American Diabetes Association, 23.6 million children and adults in the United States are afflicted with diabetes. Each year, 1.6 million new cases of diabetes are diagnosed in people aged 20 years or older. According to a study recently published in the *Journal of the American Medical Association*, over two-thirds of adults in the United States are either overweight or obese (Flegal et al., *JAMA* 303(3): 235-241 (2010)) and over one third of this population is obese.

The incretin hormones, glucagon-like peptide-1 (GLP-1) and glucose dependent insulinotropic peptide (GIP), are naturally-occurring peptide hormones. Both GLP-1 and GIP stimulate insulin synthesis and secretion in a glucose-dependent manner and do not produce hypoglycemia (see, e.g., Nauck et al., J. Clin. Endocrinol. Metab. 76:912-917 (1993) and Irwin et al., Regul. Pept. 153:70-76 (2009)).

GLP-1 has been shown to be effective as adjunctive therapy for diabetes and is associated with weight loss. What remains unclear about (HP-targeted therapy, however, is whether successful treatment of diabetes and obesity will be achieved through antagonizing the effects of this hormone (e.g., via GIP receptor antagonism) or through mimicking or enhancing the effects of GIP.

SUMMARY

Provided herein are peptides that are GIP agonist peptides contemplated for use in treating subjects in need thereof, e.g. with diabetes and obesity.

Native glucagon does not activate the GIP receptor, and normally has about 1% of the activity of native GLP-1 at the GLP-1 receptor. In some embodiments, the peptides are glucagon analogs comprising a structure based on the amino acid sequence of native human glucagon (SEQ ID NO: 1) but differing at one or more positions as compared to SEQ ID NO: 1, wherein the differences, or modifications, enhance the agonist activity of the analog at the GIP receptor. Such glucagon analogs will have agonist activity at the GIP receptor greater than that of native glucagon and, in some aspects, greater than that of native GIP. In some or any embodiments, the GIP agonist has a GIP percentage potency of at least 0.1%. In some or any aspects of the present disclosures, the glucagon analog additionally exhibits agonist activity at one or both of the glucagon receptor and the GLP-1 receptor. Accordingly, GIP agonists, GIP-GLP-1 co-agonists, GIP-glucagon co-agonists, and GIP-GLP-1-glucagon triagonists are provided herein.

In exemplary embodiments, the selectivity of the GIP agonist peptide of the present disclosures for the human GLP-1 receptor versus the GIP receptor is less than 100-fold. In some or any embodiments, the GIP agonist peptide has GIP percentage potency within 20-fold or 10-fold different (higher or lower) of the glucagon percentage potency and/or GLP-1 percentage potency.

In some embodiments of the present disclosures, the glucagon analogs comprise (i) an amino acid comprising an imidazole side chain at position 1, (ii) a DPP-IV protective amino acid at position 2, (iii) an amino acid comprising a non-native acyl or alkyl group, optionally at any of positions 9, 10, 12, 16, 20, or 37-43, and optionally wherein the non-native acyl or alkyl group is linked to such amino acid via a spacer; (iv) an alpha helix stabilizing amino acid at one or more of positions 16, 17, 18, 19, 20 or 21, and (v) up to ten (e.g., up to 1, 2, 3, 4, 5, 6, 7, 8 or 9) additional amino acid modifications relative to SEQ ID NO: 1. In exemplary embodiments, the glucagon analog comprising (i) an amino acid comprising an imidazole side chain at position 1, (ii) a DPP-IV protective amino acid at position 2, optionally, aminoisobutyric acid, (iii) an amino acid comprising a non-native acyl or alkyl group, optionally at any of positions 9, 10, 12, 16, 20, or 37-43, optionally wherein the non-native acyl or alkyl group is linked to such amino acid via a spacer; (iv) an alpha, alpha disubstituted amino acid at position 20, and (v) up to ten (e.g., up to 1, 2, 3, 4, 5, 6, 7, 8 or 9) additional amino acid modifications relative to SEQ ID NO: 1. In alternative exemplary embodiments, the glucagon analog comprising (i) an amino acid comprising an imidazole side chain at position 1, (ii) a DPP-IV protective amino acid at position 2, optionally, aminoisobutyric acid, (iii) an amino acid comprising a non-native acyl or alkyl group, optionally at any of positions 9, 10, 12, 16, 20, or 37-43, optionally wherein the non-native acyl or alkyl group is linked to such amino acid via a spacer; (iv) an alpha helix stability amino acid at one or more of positions 16-21, optionally, position 16, wherein the analog does not comprise an alpha helix stabilizing amino acid at position 20, and (v) up to ten (e.g., up to 1, 2, 3, 4, 5, 6, 7, 8 or 9) additional amino acid modifications relative to SEQ ID NO: 1. In exemplary embodiments, when the glucagon analog lacks a hydrophilic moiety, the glucagon analog exhibits a GIP percentage potency of at least 0.1% (e.g., at least 1%, at least 10%, at least 20%). In exemplary embodiments, the glucagon analog has less than 100-fold (e.g., less than 50-fold, less than 25-fold, less than 10-fold) selectivity for the human GLP-1 receptor versus the GIP receptor. In exemplary embodiments, the glucagon analog exhibits an EC50 at the GLP-1 receptor which is within 100-fold (e.g., within 50-fold, within 25-fold, within 10-fold) of its EC50 at the GIP receptor.

Throughout the application, all references to a particular amino acid position by number (e.g., position 28) refer to the amino acid at that position in native glucagon (SEQ ID NO: 1) or the corresponding amino acid position in any analog thereof. For example, a reference herein to "position 28" would mean the corresponding position 27 for a glucagon analog in which the first amino acid of SEQ ID NO: 1 has been deleted. Similarly, a reference herein to "position 28" would mean the corresponding position 29 for a glucagon analog in which one amino acid has been added before the N-terminus of SEQ ID NO: 1.

In some embodiments, the GIP agonist peptides comprise an amino acid sequence of any of SEQ ID NOs: 27-33, 35-41, 43-46, 76-80, 83-87, 89, and 90, or any of SEQ ID NOs: 48, 52, 53, and 74, or any of SEQ ID NOs: 50, 51, 54, 56, 58-60, 62-66, 68-70, 72, 73, 75, 81, 82, 88, and 92. In some embodiments, the GIP agonist peptides comprise a structure based on a parent sequence comprising any of SEQ ID NOs: 27-33, 35-41, 43-46, 76-80, 83-87, 89, and 90, or any of SEQ ID NOs: 48, 52, 53, and 74, or any of SEQ ID NOs: 50, 51, 54, 56, 58-60, 62-66, 68-70, 72, 73, 75, 81, 82, 88, and 92, but differs from the parent sequence at one or more positions, as further described herein.

The invention accordingly provides a peptide comprising, consisting essentially of, or consisting of the sequence of SEQ ID NO: 28. Also provided is a peptide comprising, consisting essentially of, or consisting of the sequence of SEQ ID NO: 37. The invention further provides a peptide comprising, consisting essentially of, or consisting of the sequence of SEQ ID NO: 89. The invention furthermore provides a peptide comprising, consisting essentially of, or consisting of the sequence of SEQ ID NO: 180. The invention moreover provides a peptide comprising, consisting essentially of, or consisting of the sequence of SEQ ID NO: 31.

The invention provides a peptide comprising the sequence of SEQ ID NO: 184, (SEQ ID NO: 184)
HX$_2$X$_3$GTFTSDX$_{10}$SKYLDX$_{16}$RX$_{18}$AX$_{20}$X$_{21}$FVQWLX$_{27}$X$_{28}$X$_{29}$GPSS GX$_{35}$PPPS wherein:
X$_2$ is AIB;
X$_3$ is Gln or Gln analog;
X$_{10}$ is Tyr or an amino acid covalently attached to a C12 to C18 acyl or alkyl group;
X$_{16}$ is any amino acid, optionally, any amino acid other than Gly, Pro, and Ser;
X$_{18}$ is Arg or Ala;
X$_{20}$ is negative charged amino acid or a charge-neutral amino acid, optionally, AIB or Gln;
X$_{21}$ is an acidic amino acid, optionally, Asp or Glu;
X$_{27}$ is Leu, Ala, Nle, or Met;
X$_{28}$ is Ala or an acidic amino acid (optionally, Asp or Glu);
X$_{29}$ is Ala or Gly;
X$_{35}$ is Ala or a basic amino acid (optionally, Arg or Lys);
wherein, when X$_{28}$ is an acidic amino acid, X$_{35}$ is a basic amino acid;
wherein, when X$_{10}$ is Tyr, the peptide comprises at position 40 an amino acid covalently attached to a C12 to C18 acyl or alkyl group, and, wherein, optionally, the peptide comprises Gly at position 41, and
wherein the C-terminal amino acid of the peptide is amidated.

The invention also provides a peptide comprising the sequence of SEQ ID NO: 184 with up to 3 amino acid modifications relative to SEQ ID NO: 184, wherein the analog exhibits agonist activity at each of the human GIP receptor, the human GLP-1 receptor and the human glucagon receptor.

The invention additionally provides a peptide comprising the sequence of SEQ ID NO: 185, (SEQ ID NO: 185)
HX$_2$QGTFTSDX$_{10}$SKYLDX$_{16}$RX$_{18}$AX$_{20}$X$_{21}$FVQWLX$_{27}$X$_{28}$X$_{29}$GPSS GAPPPS wherein:
X$_2$ is AIB;
X$_{10}$ is Tyr or an amino acid covalently attached to a C12 to C18 acyl or alkyl group;
X$_{16}$ is Glu, an alpha, alpha disubstituted amino acid, Lys or
X$_{18}$ is Arg or Ala;
X$_{20}$ is AIB or Gln;
X$_{21}$ is Asp or Glu;
X$_{27}$ is Leu, Nle, or Met;
X$_{28}$ is Ala, Asp or Glu;
X$_{29}$ is Gly of Thr;
and
wherein, when X$_{10}$ is Tyr, the peptide comprises at position 40 an amino acid covalently attached to a C12 to C18 acyl or alkyl group, and, wherein, optionally, the peptide comprises Gly at position 41, and
wherein the C-terminal amino acid of the peptide is amidated.

The invention further provides a peptide comprising the sequence of SEQ ID NO: 185 with up to 3 amino acid modifications relative to SEQ ID NO: 185, wherein the analog exhibits agonist activity at each of the human GIP receptor, the human GLP-1 receptor and the human glucagon receptor.

Furthermore provided is a peptide comprising the sequence of SEQ ID NO: 186:

(SEQ ID NO: 186)
HX$_2$X$_3$GTFTSDX$_{10}$SKYLDX$_{16}$RX$_{18}$AX$_{20}$X$_{21}$FVQWLX$_{27}$X$_{28}$X$_{29}$ wherein:
X$_2$ is AIB;
X$_3$ is Gln or Gln analog;
X$_{10}$ is Tyr or an amino acid covalently attached to a C10 to C26 acyl or alkyl group;
X$_{16}$ is any amino acid, optionally, any amino acid other than Gly, Pro, and Ser;
X$_{18}$ is Arg or Ala;
X$_{20}$ is a negative charged amino acid or a charge-neutral amino acid, optionally, AIB or Gln;
X$_{21}$ is X$_{21}$ is an acidic amino acid, optionally, Asp or Glu;
X$_{27}$ is Leu, Ala, Nle, or Met;
X$_{28}$ is Ala or an acidic amino acid (optionally, Asp or Glu);
X$_{29}$ is Ala, Gly or Thr; and
wherein the peptide comprises an amino acid covalently attached to a C10 to C26 acyl or alkyl group, optionally, at position 10, and the C-terminal amino acid of the peptide is amidated.

Moreover provided is a peptide comprising the sequence of SEQ ID NO: 186 with up to 3 amino acid modifications relative to SEQ ID NO: 186, wherein the analog exhibits agonist activity at each of the human GIP receptor, the human GLP-1 receptor and the human glucagon receptor.

The invention provides a peptide comprising the sequence of SEQ ID NO: 187:

(SEQ ID NO: 187)
HX$_2$QGTFTSDX$_{10}$SKYLDX$_{16}$RX$_{18}$AX$_{20}$X$_{21}$FVQWLX$_{27}$X$_{28}$X$_{29}$ wherein:
X$_2$ is AIB;
X$_{10}$ is Tyr or an amino acid covalently attached to a C10 to C26 acyl or alkyl group;
X$_{16}$ is Glu, alpha, alpha-disubstituted amino acid, or Lys;
X$_{18}$ is Arg or Ala;
X$_{20}$ is a negative charged amino acid or a charge-neutral amino acid, optionally, AIB or Gln;
X$_{21}$ is Asp or Glu;

$X_{27}$ is Leu, Ala, Nle, or Met;
$X_{28}$ is Ala, Asp or Glu;
$X_{29}$ is Gly or Thr; and
wherein the peptide comprises an amino acid covalently attached to a C12 to C18 acyl or alkyl group, optionally, at position 10, and the C-terminal amino acid of the peptide is amidated.

The invention also provides SEQ ID NO: 187 with up to 3 amino acid modifications relative to SEQ ID NO: 187, wherein the analog exhibits agonist activity at each of the human GIP receptor, the human GLP-1 receptor and the human glucagon receptor.

The invention further provides an analog of any one of SEQ ID NOs: 184, 185, 186, and 187, as described herein, but $X_3$ or the amino acid at position 3 is Gln or Gln analog or an amino acid which reduces glucagon activity, including, those described herein. In exemplary embodiments, the amino acid which reduces glucagon activity is an acidic, basic, or hydrophobic amino acid (e.g., Glu, Orn, or Nle). Optionally, the amino acid at position 3 is Glu.

Furthermore provided herein is an analog of glucagon (SEQ ID NO: 1) having GIP agonist activity, comprising:
(a) an amino acid comprising an imidazole side chain at position 1,
(b) at position 16, an amino acid of Formula IV:

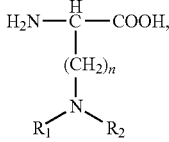

[Formula IV]

wherein n is 1 to 7, wherein each of R1 and R2 is independently selected from the group consisting of H, C1-C18 alkyl, (C1-C18 alkyl)OH, (C1-C18 alkyl)NH2, (C1-C18 alkyl)SH, (C0-C4 alkyl)(C3-C6)cycloalkyl, (C0-C4 alkyl)(C2-C5 heterocyclic), (C0-C4 alkyl)(C6-C10 aryl)R7, and (C1-C4 alkyl)(C3-C9 heteroaryl), wherein R7 is H or OH, wherein optionally the side chain of the amino acid of Formula IV comprises a free amino group,
(c) an α,α-disubstituted amino acid at position 20,
(d) up to ten additional amino acid modifications relative to SEQ ID NO: 1,
wherein, when the analog lacks a hydrophilic moiety, the glucagon analog exhibits at least 0.1% activity of native GIP at the GIP receptor, wherein the glucagon analog has less than 100-fold selectivity for the human GLP-1 receptor versus the GIP receptor.

Also provided herein are dimers and multimers comprising two or more GIP agonist peptides of the present disclosures. Conjugates comprising a GIP agonist peptide of the present disclosures and a conjugate moiety are additionally provided herein. In some aspects, the conjugate is a fusion polypeptide comprising the GIP agonist peptide of the present disclosures fused to a heterologous peptide. The present disclosures also provides kits comprising the GIP agonist peptides, dimers, multimers, or conjugates of the present disclosures (or a combination thereof).

Pharmaceutical compositions comprising any of the GIP agonist peptides, dimers, multimers, or conjugates of the present disclosures (or a combination thereof) and a pharmaceutically acceptable carrier, diluent, or excipient are further provided by the present disclosures. The pharmaceutical compositions are preferably sterile and suitable for parenteral administration. The pharmaceutical compositions are contemplated for use in methods of treating or preventing diabetes or obesity, or medical conditions associated with diabetes or obesity. Accordingly, in exemplary embodiments the present disclosure provides a method of reducing weight gain or inducing weight loss, a method of treating or preventing diabetes or obesity, and a method of inducing temporary paralysis of the intestinal tract. Further applications of the peptide analogs and pharmaceutical compositions comprising the same are provided in the following description.

BRIEF DESCRIPTION OF THE DRAWINGS

FIG. 3A depicts the chemical structures of different acylated amino acid residues. From left to right, (i) a Lys residue directly acylated with a C16 fatty acid, (ii) a Lys residue acylated with a C16 fatty acid via a gamma-glutamic acid spacer, (iii) a Lys residue acylated with a C16 fatty acid via a (gamma-glutamic acid-gamma-glutamic acid) dipeptide spacer, (iv) a Lys residue acylated with a C16 succinoyl. FIG. 3B represents structures of three exemplary succinic anhydrides. FIG. 3C represents a synthesis scheme of SEQ ID NO: 156.

FIG. 5A depicts three types of double acylated compounds: (1) one site comprising two acyl groups in a branched formation, (2) one site comprising two acyl groups in a linear formation, and (3) two sites each connected to a fatty acyl group via a gammaGlu spacer. FIG. 5B represents a synthesis scheme of a peptide comprising two acyl groups of different sizes in a branched formation. FIG. 5C represents a synthesis scheme of a peptide comprising two acyl groups of same size in a branched formation. FIG. 5D represents a synthesis scheme of a peptide comprising two acyl groups in a linear formation. FIG. 5E represents a graph of the change in body weight (%) as measured on Day 7 of the study of mice that received a peptide injection or a vehicle control injection. FIG. 5F represents a graph of the change in blood glucose levels (mg/dL) as measured on Day 7 of the study of mice that received a peptide injection or a vehicle control injection.

FIG. 9A depicts a structure of a homodimer, wherein each peptide comprises a Lys residue at the $40^{th}$ position. Each Lys residue is covalently attached via the epsilon NH2 group to a Cys residue. Each Cys residue is peptide bonded to a gammaGlu residue, which, in turn, is attached to a C16 fatty acyl group. The sulfur atoms of each Cys residue forms a disulfide bridge. FIG. 9B depicts a structure of a homodimer that is linked via a thioether bond. Each peptide comprises a Lys residue at the $40^{th}$ position. The Lys of the top peptide is attached to a Cys residue, which is peptide bonded to a gammaGlu residue, which, in turn, is attached to a C16 fatty acyl group. The sulfur of the Cys residue is linked via a thioether bond to a chemical moiety which, in turn, is attached to the Lys residue of the bottom peptide.

FIG. 12A represents the acylated peptide of SEQ ID NO: 157, FIG. 12B represents the acylated peptide of SEQ ID NO: 158, and FIG. 12C represents the acylated peptide of SEQ ID NO: 159.

DETAILED DESCRIPTION

Figure 1:
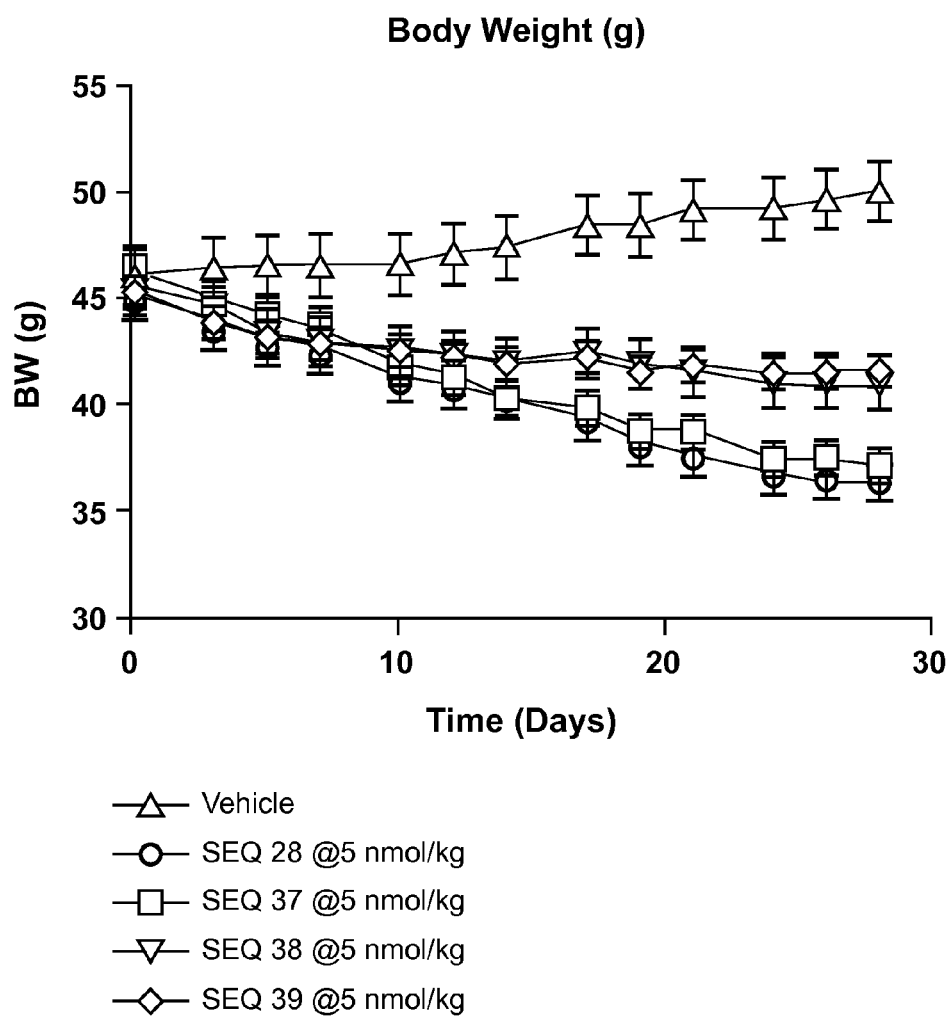
FIG. 1 represents a graph of the body weight (grams) of mice injected with 5 nmol/kg of: a peptide of SEQ ID NO: 28 (○), a peptide of SEQ ID NO: 37 (□), a peptide of SEQ ID NO: 38 ▽ or a peptide of SEQ ID NO: 39 (◇), or injected with a vehicle control (Δ), as a function of time after first injection.

The present disclosures provide GIP agonist peptides (e.g., analogs of native human glucagon (SEQ ID NO: 1) (also referred to as "glucagon analogs"), analogs of any of SEQ ID NOs: 27-33, 35-41, 43-46, 76-80, 83-87, 89, and 90, or any of SEQ ID NOs: 48, 52, 53, and 74, or any of SEQ ID NOs: 50, 51, 54, 56, 58-60, 62-66, 68-70, 72, 73, 75, 81, 82, 88, and 92, analogs of any of SEQ ID NOs: 184-199) which exhibit agonist activity at the GIP receptor. As used herein, the term "peptide" encompasses a sequence of 2 or more amino acids and typically less than 100, or less than 50 amino acids. The amino acids can be naturally occurring or coded or non-naturally occurring or non-coded. Non-naturally occurring amino acids refer to amino acids that do not naturally occur in vivo but which, nevertheless, can be incorporated into the peptide structures described herein. "Non-coded" as used herein refer to an amino acid that is not an L-isomer of any of the following 20 amino acids: Ala, Cys, Asp, Glu, Phe, Gly, His, Ile, Lys, Leu, Met, Asn, Pro, Gln, Arg, Ser, Thr, Val, Trp, Tyr. The term "GIP agonist peptide" refers to a compound that binds to and activates downstream signaling of the GIP receptor. The GIP agonist peptide may have any of the levels of activity at the GIP receptor (e.g., absolute activity level or relative activity level), selectivity for the GIP receptor, or GIP percentage potency, described herein. See, for example, the section entitled GIP Receptor Activity. However, this term should not be construed as limiting the compound to having activity at only the GIP receptor. Rather, the GIP agonist peptides of the present disclosures may exhibit additional activities at other receptors, as further discussed herein. GIP agonist peptides, for example, may exhibit agonist activity at the GLP-1 receptor and/or glucagon receptor.

Activity of the Presently Disclosed Peptides

GIP Receptor Activity

In some or any embodiments, the peptides of the present disclosures exhibit an EC50 for GIP receptor activation which is in the nanomolar range. In exemplary embodiments, the EC50 of the peptide at the GIP receptor is less than 1000 nM, less than 900 nM, less than 800 nM, less than 700 nM, less than 600 nM, less than 500 nM, less than 400 nM, less than 300 nM, less than 200 nM. In some embodiments, the EC50 of the peptide at the GIP receptor is about 100 nM or less, e.g., about 75 nM or less, about 50 nM or less, about 25 nM or less, about 10 nM or less, about 5 nM or less, or about 1 nM or less. In some or any embodiments, the peptide of the present disclosures exhibits an EC50 for GIP receptor activation which is in the picomolar range. In exemplary embodiments, the EC50 of the GIP agonist peptide at the GIP receptor is less than 1000 pM, less than 900 pM, less than 800 pM, less than 700 pM, less than 600 pM, less than 500 pM, less than 400 pM, less than 300 pM, less than 200 pM. In some embodiments, the EC50 of the peptide at the GIP receptor is about 100 pM or less, e.g., about 75 pM or less, about 50 pM or less, about 25 pM or less, about 10 pM or less, about 5 pM or less, or about 1 pM or less. The term "about" as used herein means greater or lesser than the value or range of values stated by 10 percent, but is not intended to designate any value or range of values to only this broader definition. Each value or range of values preceded by the term "about" is also intended to encompass the embodiment of the stated absolute value or range of values.

Suitable methods of determining the EC50 of a peptide for activation of a receptor, e.g., the GIP receptor, are known in the art. One exemplary in vitro assay, in which cAMP induction as represented by luciferase activity is measured in HEK293 cells over-expressing the GIP receptor, is described herein at Example 2.

In some or any embodiments, the peptides (e.g., glucagon analogs, analogs of any of SEQ ID NOs: 27-33, 35-41, 43-46, 76-80, 83-87, 89, and 90, or any of SEQ ID NOs: 48, 52, 53, and 74, or any of SEQ ID NOs: 50, 51, 54, 56, 58-60, 62-66, 68-70, 72, 73, 75, 81, 82, 88, and 92) of the present disclosures exhibit enhanced activity at the GIP receptor, as compared to native human glucagon. Native glucagon (SEQ ID NO: 1) does not activate the GIP receptor; native glucagon exhibits essentially 0% (e.g., less than 0.001%, less than 0.0001%) activity of native GIP at the GIP receptor. A peptide's relative activity at the GIP receptor relative to native glucagon is calculated as the inverse ratio of (EC50 of the peptide of the present disclosures/EC50 of native glucagon)×100%.

A peptide's relative activity at the GIP receptor compared to native GIP is calculated as the inverse ratio of (EC50 of the peptide of the present disclosures/EC50 of native GIP)× 100% (a value also referred to herein as "GIP percentage potency").

In some or any embodiments of the present disclosures, the peptides of the present disclosures exhibit GIP percentage potency that is at least or about 0.1%. In exemplary embodiments, the peptides exhibit at least or about 0.5%, at least or about 1%, at least or about 5%, at least or about 10%, at least or about 20%, at least or about 30%, at least or about 40%, at least or about 50%, at least or about 60%, at least or about 70%, at least or about 80%, at least or about 90%, or at least or about 100% of the activity of native GIP at the GIP receptor.

In some embodiments of the present disclosures, the peptides of the present disclosures exhibit activity at the GIP receptor which is greater than that of native GIP. In exemplary embodiments, the GIP agonist peptide exhibits a GIP percentage potency of at least or about 125%, at least or about 150%, at least or about 175% at least or about 200%, at least or about 300%, at least or about 400%, at least or about 500%, at least or about 600%, at least or about 700%, at least or about 800%, at least or about 900%, or at least or about 1000%. In some embodiments, the GIP agonist peptides described herein exhibit a GIP percentage potency of no more than 1000% or no more than 10,000%.

In some aspects, the peptides of the present disclosures exhibit a GIP percentage potency within the range of about 0.001 to about 10,000 percent, or about 0.01 to about 10,000 percent, or about 0.1 to about 10,000 percent, or about 1 to about 10,000 percent, or about 0.001 to about 5000 percent, or about 0.01 to about 5000 percent, or about 0.1 to about 5000 percent, or about 0.1 to about 1000 percent.

Co-Agonists

In some or any embodiments, the peptide of the present disclosures is a co-agonist peptide insofar as it activates the GIP receptor and a second receptor different from the GIP receptor.

GIP/GLP-1 Co-Agonists

By way of example, the peptide of the present disclosures in some aspects exhibits activity at both the GIP receptor and the GLP-1 receptor ("GLP-1/GIP receptor co-agonists"). In some aspects, the peptides exhibit activity at the GLP-1 and GIP receptors, but the glucagon activity has been significantly reduced or destroyed, e.g., by an amino acid modification at position 3. For example, substitution at this position with an acidic, basic, or a hydrophobic amino acid (glutamic acid, ornithine, norleucine) reduces glucagon activity. In some or any embodiments, the GIP agonist peptide is a peptide which exhibits about 10% or less (e.g., about 5% or less, or about 1% or less, or about 0.1% or less) of the activity of native glucagon at the glucagon receptor.

In some or any embodiments, the EC50 of the peptide of the present disclosures at the GIP receptor is within about 50-fold or less, about 40-fold or less, about 30-fold or less, about 20-fold or less, or about 10-fold or less, or about 5-fold or less different (higher or lower) from its EC50 at the GLP-1 receptor. For example, the EC50 at the GIP receptor can be 10-fold higher or 10-fold lower than the EC50 at the GLP-1 receptor. In some or any embodiments, the GIP percentage potency of the peptide of the present disclosures is less than or about 50-, 40-, 30-, 20-, 10-, or 5-fold different (higher or lower) from its GLP-1 percentage potency.

Accordingly, the peptide of the present disclosures has less than 100-fold selectivity for the human GLP-1 receptor versus the GIP receptor. As used herein, the term "selectivity" of a molecule for a first receptor relative to a second receptor refers to the following ratio: EC50 of the molecule at the second receptor divided by the EC50 of the molecule at the first receptor. For example, a molecule that has an EC50 of 1 nM at a first receptor and an EC50 of 100 nM at a second receptor has 100-fold selectivity for the first receptor relative to the second receptor. In exemplary embodiments, the selectivity of the peptide of the present disclosures for the human GLP-1 receptor versus the GIP receptor is less than 100-fold (e.g., less than or about 90-fold, less than or about 80-fold, less than or about 70-fold, less than or about 60-fold, less than or about 50-fold, less than or about 40-fold, less than or about 30-fold, less than or about 20-fold, less than or about 10-fold, less than or about 5-fold).

In some or any embodiments, the peptides of the present disclosures exhibit enhanced activity at the GLP-1 receptor, as compared to native human glucagon. Native glucagon has about 1% of the activity of native GLP-1 at the GLP-1 receptor. A peptide's relative activity at the GLP-1 receptor relative to native glucagon is calculated as the inverse ratio of (EC50 of the peptide of the present disclosures/EC50 of native glucagon)×100%.

A peptide's relative activity at the GLP-1 receptor compared to native GLP-1 is calculated as the inverse ratio of (EC50 of the peptide of the present disclosures/EC50 of native GLP-1)×100% (a value referred to herein as "GLP-1 percentage potency").

In some or any embodiments of the present disclosures, the peptides of the present disclosures exhibit a GLP-1 percentage potency of at least or about 0.1%. In exemplary embodiments, the peptides exhibit a GLP-1 percentage potency of at least or about 0.5%, at least or about 1%, at least or about 5%, at least or about 10%, at least or about 20%, at least or about 30%, at least or about 40%, at least or about 50%, at least or about 60%, at least or about 70%, at least or about 80%, at least or about 90%, or at least or about 100%.

In some embodiments of the present disclosures, the peptides of the present disclosures exhibit activity at the GLP-1 receptor which is greater than that of native GLP-1. In exemplary embodiments, the peptide of the present disclosures exhibits a GLP-1 percentage potency of at least or about 125%, at least or about 150%, at least or about 175% at least or about 200%, at least or about 300%, at least or about 400%, at least or about 500%, at least or about 600%, at least or about 700%, at least or about 800%, at least or about 900%, or at least or about 1000%. In some embodiments, the peptides of the present disclosures exhibit a GLP-1 percentage potency of no more than 1000% or no more than 10,000%.

GIP/Glucagon Co-Agonists

By way of another example, the peptide of the present disclosures in some aspects exhibits activity at both the GIP receptor and the glucagon receptor ("glucagon/GIP receptor co-agonists"). In some embodiments, GLP-1 activity has been significantly reduced or destroyed, e.g., by an amino acid modification at position 7, e.g., substitution with Ile, a deletion of the amino acid(s) C-terminal to the amino acid at position 27 or 28, yielding a 27- or 28-amino acid peptide, or a combination thereof. In some embodiments, the peptide of the present disclosures is a peptide which exhibits about 10% or less (e.g., about 5% or less, or about 1% or less, or about 0.1% or less) of the activity of native GLP-1 at the GLP-1 receptor.

In some or any embodiments, the EC50 of the peptide of the present disclosures at the GIP receptor is within about 50-fold or less, about 40-fold or less, about 30-fold or less, about 20-fold or less, or about 10-fold or less, or about 5-fold or less different (higher or lower) from its EC50 at the glucagon receptor. In some or any embodiments, the GIP percentage potency of the peptide of the present disclosures is less than or about 50-, 40-, 30-, 20-, 10-, or 5-fold different (higher or lower) from its glucagon percentage potency.

In some embodiments, the peptides of the present disclosures exhibit enhanced activity at the glucagon receptor, as compared to native human glucagon. A peptide's relative activity at the glucagon receptor compared to native glucagon is calculated as the inverse ratio of (EC50 of the peptide of the present disclosures/EC50 of native glucagon)×100% (a value referred to herein as "glucagon percentage potency").

In some embodiments of the present disclosures, the peptides of the present disclosures exhibit a glucagon percentage potency of at least or about 0.1%. In exemplary embodiments, the peptides exhibit a glucagon percentage potency of at least or about 0.5%, at least or about 1%, at least or about 5%, at least or about 10%, at least or about 20%, at least or about 30%, at least or about 40%, at least or about 50%, at least or about 60%, at least or about 70%, at least or about 80%, at least or about 90%, or at least or about 100%.

In some embodiments of the present disclosures, the peptides of the present disclosures exhibit activity at the glucagon receptor which is greater than that of native glucagon. In exemplary embodiments, the peptide of the present disclosures exhibits a glucagon percentage potency of at least or about 125%, at least or about 150%, at least or about 175% at least or about 200%, at least or about 300%, at least or about 400%, at least or about 500%, at least or about 600%, at least or about 700%, at least or about 800%, at least or about 900%, or at least or about 1000%. In some embodiments, the peptides of the present disclosures exhibit a glucagon percentage potency of no more than 1000% or no more than 10,000%.

Triagonists

In some embodiments, the peptides of the present disclosures exhibit activity at two or more receptors, other than the GIP receptor. Accordingly, the present disclosures provide in some aspects GIP triagonist peptides. In some aspects, the peptides of the present disclosures exhibit activity at each of the glucagon, GIP and GLP-1 receptors ("glucagon/GIP/GLP-1 triagonists").

In some embodiments, the EC50 of the peptide of the present disclosures at the GIP receptor is within 50-fold or less, 20-fold or less, or 10-fold or less different (higher or lower) than the EC50 of the peptide of the present disclosures at (a) the GLP-1 receptor, (b) the glucagon receptor, or both. In some embodiments, the EC50 of the peptide of the present disclosures at the GIP receptor is within about 40-fold, about 30-fold, about 20-fold different (higher or lower) from its EC50 at the GLP-1 receptor, and optionally within about 50-fold different from its EC50 at the glucagon receptor. In some embodiments, the GIP percentage potency of the peptide of the present disclosures is less than or about 50-fold, 20-fold or 10-fold different (higher or lower) from (a) its GLP-1 percentage potency, (b) its glucagon percentage potency, or both. In some embodiments, the GIP percentage potency of the peptide of the present disclosures is within about 40-fold, about 30-fold, about 20-fold different (higher or lower) from its GLP-1 percentage potency, and optionally within about 50-fold different from its its glucagon percentage potency. In some embodiments, the peptide of the present disclosures does not have at least 100-fold selectivity for the human GLP-1 receptor versus the GIP receptor. In exemplary embodiments, the selectivity of the peptide of the present disclosures for the human GLP-1 receptor versus the GIP receptor is less than 100-fold (e.g., less than or about 90-fold, less than or about 80-fold, less than or about 70-fold, less than or about 60-fold, less than or about 50-fold, less than or about 40-fold, less than or about 30-fold, less than or about 20-fold, less than or about 10-fold, less than or about 5-fold).

GIP Agonism in the Absence of GLP-1 Agonism and Glucagon Agonism

In some embodiments, the peptide of the present disclosures exhibits activity at only the GIP receptor, and not at any other receptor, e.g., GLP-1 receptor, glucagon receptor. In exemplary embodiments, the peptide of the present disclosures exhibits activity at the GIP receptor, and the glucagon and GLP-1 activity have been significantly reduced or destroyed, e.g., by amino acid modifications at positions 3 and 7. In some embodiments, the peptide of the present disclosures is a peptide which exhibits a GLP-1 percentage potency of about 10% or less (e.g., about 5% or less, or about 1% or less, or about 0.1% or less). In some embodiments, the peptide of the present disclosures is a peptide which exhibits a glucagon percentage potency of about 10% or less (e.g., about 5% or less, or about 1% or less, or about 0.1% or less).

Activity of Conjugates

In some or any embodiments, when the peptide of the present disclosures is conjugated to a heterologous moiety (e.g., a hydrophilic moiety), as further described herein, the peptide of the present disclosures exhibits a decreased activity (e.g., a lower percentage potency or higher EC50) than when the peptide of the present disclosures is in a free or unconjugated form. Thus, it is contemplated that when any of the foregoing absolute activity levels (e.g. GIP percentage potency, GLP-1 percentage potency or glucagon percentage potency, but not relative ratios) is applied to a peptide in conjugated form, e.g. pegylated, such absolute activity levels are reduced by about 10-fold, 20-fold, 30-fold, 40-fold, 50-fold, or 100-fold, and that such fold reduced activity levels are contemplated within the scope of the disclosure. Conversely, when unconjugated, the peptide of the present disclosures exhibits a GIP percentage potency that is about 10-fold, about 20-fold, about 30-fold, about 40-fold, about 50-fold, about 100-fold or more higher than the potency of the peptide of the present disclosures when conjugated to a heterologous moiety.

Structure of the Presently Disclosed Peptides

Glucagon Analogs

In some embodiments, the peptides of the present disclosures are structurally similar to native human glucagon (SEQ ID NO: 1), e.g., is an analog of native human glucagon (also referred to herein as "glucagon analog" or "peptide analog of glucagon"). As used herein, the terms "glucagon analog" and "peptide analog of glucagon," and the like, refer to peptides that are structurally similar to native human glucagon and these terms do not necessarily imply that the peptides activate the glucagon receptor.

In some or any embodiments, the peptide of the present disclosures is an analog of native human glucagon (SEQ ID NO: 1) comprising an amino acid sequence based on the amino acid sequence of SEQ ID NO: 1 but differs from SEQ ID NO: 1 inasmuch as the amino acid sequence of the glucagon analog comprises one or more (e.g., 1, 2, 3, 4, 5, 6, 7, 8, 9, 10, 11, 12, 13, 14, 15, and in some instances, 16 or more (e.g., 17, 18, 19, 20, 21, 22, 23, 24, 25, etc.), specified or optional amino acid modifications. In some or any embodiments, the peptide of the present disclosures comprises a total of 1, up to 2, up to 3, up to 4, up to 5, up to 6, up to 7, up to 8, up to 9, or up to 10 additional amino acid modifications (e.g., in addition to the specified amino acid modifications), relative to the native human glucagon sequence (SEQ ID NO: 1). For example, with regard to an analog of glucagon (SEQ ID NO: 1) comprising (a) an amino acid comprising an imidazole side chain at position 1, (b) an DPP-IV protective amino acid at position 2, (c) an acylated amino acid or alkylated amino acid at any of positions 9, 10, 12, 16, 20, or 37-43, (d) an alpha helix stabilizing amino acid at one or more of positions 16, 17, 18, 19, 20, and 21, and (e) up to ten additional amino acid modifications relative to SEQ ID NO: 1, the present disclosures provides an analog of glucagon comprising (a)-(d) with up to 10 additional amino acid modifications in addition to the amino acid modifications specified in (a)-(d). In some or any embodiments, the modifications are any of those described herein, e.g., acylation, alkylation, pegylation, truncation at C-terminus, substitution of the amino acid at one or more of positions 1, 2, 3, 7, 10, 12, 15, 16, 17, 18, 19, 20, 21, 23, 24, 27, 28, and 29.

As used herein an "amino acid modification" refers to (i) a substitution of an amino acid of SEQ ID NO: 1 with a different amino acid (naturally-occurring or coded or non-coded or non-naturally-occurring amino acid), (ii) an addition of an amino acid (naturally-occurring or coded or non-coded or non-naturally-occurring amino acid), to SEQ ID NO: 1 or (iii) a deletion of one or more amino acids of SEQ ID NO: 1.

In some or any embodiments, the amino acid substitution is a conservative amino acid substitution, e.g., a conservative substitution of the amino acid at one or more of positions 2, 5, 7, 10, 11, 12, 13, 14, 16, 17, 18, 19, 20, 21, 24, 27, 28 or 29. As used herein, the term "conservative amino acid substitution" is defined herein as the substitution of one amino acid with another amino acid having similar properties, e.g., size, charge, hydrophobicity, hydrophilicity, and/or aromaticity, and includes exchanges within one of the following five groups:

I. Small aliphatic, nonpolar or slightly polar residues:
Ala, Ser, Thr, Pro, Gly;
II. Polar, negatively charged residues and their amides and esters:
Asp, Asn, Glu, Gln, cysteic acid and homocysteic acid;
III. Polar, positively charged residues:
His, Arg, Lys; Ornithine (Orn)
IV. Large, aliphatic, nonpolar residues:
Met, Leu, Ile, Val, Cys, Norleucine (Nle), homocysteine
V. Large, aromatic residues:
Phe, Tyr, Trp, acetyl phenylalanine In alternative embodiments, the amino acid substitution is not a conservative amino acid substitution, e.g., is a non-conservative amino acid substitution.

As used herein the term "charged amino acid" refers to an amino acid that comprises a side chain that is negative-charged (i.e., de-protonated) or positive-charged (i.e., protonated) in aqueous solution at physiological pH. For example negative-charged amino acids include aspartic acid, glutamic acid, cysteic acid, homocysteic acid, and homoglutamic acid, whereas positive-charged amino acids include arginine, lysine and histidine. Charged amino acids include the charged amino acids among the 20 coded amino acids, as well as atypical or non-naturally occurring or non-coded amino acids. As used herein the term "acidic amino acid" refers to an amino acid that comprises a second acidic moiety (other than the alpha carboxylic acid of the amino acid), including for example, a side chain carboxylic acid or sulfonic acid group.

In some embodiments, the peptide of the present disclosures comprises an amino acid sequence which has at least 25% sequence identity to the amino acid sequence of native human glucagon (SEQ ID NO: 1). In some embodiments, the peptide of the present disclosures comprises an amino acid sequence which is at least 30%, at least 40%, at least 50%, at least 60%, at least 70%, at least 80%, at least 85%, at least 90% or has greater than 90% sequence identity to SEQ ID NO: 1. In some embodiments, the amino acid sequence of the presently disclosed peptide which has the above-referenced % sequence identity is the full-length amino acid sequence of the presently disclosed peptide. In some embodiments, the amino acid sequence of the peptide of the present disclosures which has the above-referenced % sequence identity is only a portion of the amino acid sequence of the presently disclosed peptide. In some embodiments, the presently disclosed peptide comprises an amino acid sequence which has about A % or greater sequence identity to a reference amino acid sequence of at least 5 contiguous amino acids (e.g., at least 6, at least 7, at least 8, at least 9, at least 10 amino acids) of SEQ ID NO: 1, wherein the reference amino acid sequence begins with the amino acid at position C of SEQ ID NO: 1 and ends with the amino acid at position D of SEQ ID NO: 1, wherein A is 25, 30, 35, 40, 45, 50, 55, 60, 65, 70, 75, 80, 85, 90, 91, 92, 93, 94, 95, 96, 97, 98, 99; C is 1, 2, 3, 4, 5, 6, 7, 8, 9, 10, 11, 12, 13, 14, 15, 16, 17, 18, 19, 20, 21, 22, 23, 24, 25, 26, 27, or 28 and D is 5, 6, 7, 8, 9, 10, 11, 12, 13, 14, 15, 16, 17, 18, 19, 20, 21, 22, 23, 24, 25, 26, 27, 28 or 29. Any and all possible combinations of the foregoing parameters are envisioned, including but not limited to, e.g., wherein A is 90% and C and D are 1 and 27, or 6 and 27, or 8 and 27, or 10 and 27, or 12 and 27, or 16 and 27.

The analogs of native human glucagon (SEQ ID NO: 1) described herein may comprise a peptide backbone of any number of amino acids, i.e., can be of any peptide length. In some embodiments, the peptides described herein are the same length as SEQ ID NO: 1, i.e., are 29 amino acids in length. In some embodiments, the presently disclosed peptide is longer than 29 amino acids in length, e.g., the presently disclosed peptide comprises a C-terminal extension of 1-21 amino acids, as further described herein. Accordingly, the peptide of the present disclosures in some embodiments, is 30, 31, 32, 33, 34, 35, 36, 37, 38, 39, 40, 41, 42, 43, 44, 45, 46, 47, 48, 49, or 50 amino acids in length. In some embodiments, the presently disclosed peptide is up to 50 amino acids in length. In some embodiments, the presently disclosed peptide is longer than 29 amino acids in length (e.g., greater than 50 amino acids, (e.g., at least or about 60, at least or about 70, at least or about 80, at least or about 90, at least or about 100, at least or about 150, at least or about 200, at least or about 250, at least or about 300, at least or about 350, at least or about 400, at least or about 450, at least or about 500 amino acids in length) due to fusion with another peptide. In other embodiments, the presently disclosed peptide is less than 29 amino acids in length, e.g., 28, 27, 26, 25, 24, 23, amino acids.

In accordance with the foregoing, in some aspects, the peptide of the present disclosures is an analog of native human glucagon (SEQ ID NO: 1) comprising an amino acid sequence based on SEQ ID NO: 1, which sequence comprises one or more amino acid modifications which affect GIP activity, glucagon activity, and/or GLP-1 activity, enhance stability, e.g., by reducing degradation of the peptide (e.g., by improving resistance to DPP-IV proteases), enhance solubility, increase half-life, delay the onset of action, extend the duration of action at the GIP, glucagon, or GLP-1 receptor, or a combination of any of the foregoing. Such amino acid modifications, in addition to other modifications, are further described below, and any of these modifications can be applied individually or in combination.

Amino Acids Comprising a Non-Native Acyl Group

In accordance with some or any embodiments, the GIP agonist peptides which are analogs of glucagon (SEQ ID NO: 1) comprise an amino acid comprising a non-native acyl group (referred to herein as an "acylated amino acid", regardless of how it is prepared, e.g., by incorporation of a previously-acylated amino acid into the peptide, or acylation of the peptide after synthesis). In some or any aspects, the acylated amino acid is located at any of positions 9, 10, 12, 13, 14, 16, 17, 20, 37, 38, 39, 40, 41, 42, or 43 of the glucagon analog. In exemplary aspects, the acylated amino acid is located at any of positions 9, 10, 12, 16, 20, or 40 of the glucagon analog or at any of positions 10, 13, 14, 16, 17, or 40 of the glucagon analog. In exemplary aspects, the acylated amino acid is located at any one or more of positions 10, 14, and 40. In exemplary aspects, the acylated amino acid is located at any of positions 10, 12, or 16 of the peptide analog.

The acylated amino acid in some embodiments causes the GIP agonist peptide to have one or more of (i) a prolonged half-life in circulation, (ii) a delayed onset of action, (iii) an extended duration of action, (iv) an improved resistance to proteases, such as DPP-IV, and (v) increased potency at any one or more of the GIP receptor, GLP-1 receptor, and glucagon receptor.

Direct Acylation

In some embodiments, the acyl group is directly linked to an amino acid of the GIP agonist peptide. In accordance with one embodiment, the GIP agonist peptide comprises an acyl group which is attached to the peptide via an ester, thioester, or amide linkage.

In specific aspects, the GIP agonist peptide comprises an acyl group upon direct acylation of an amine, hydroxyl, or thiol of a side chain of an amino acid of the GIP agonist peptide. In some embodiments, acylation is at position 9, 10, 12, 13, 14, 16, 17, 20, or 40 (e.g., at any one of positions 10, 14, and 40) of the GIP agonist peptide. In this regard, the GIP agonist peptide comprises the amino acid sequence of SEQ ID NO: 1, or a modified amino acid sequence thereof comprising one or more of the amino acid modifications described herein, wherein at least one of the amino acids at positions 9, 10, 12, 13, 14, 16, 17, 20, and 40 (e.g., at any one of positions 10, 14, and 40) of the GIP agonist peptide is an amino acid comprising a side chain amine, hydroxyl, or thiol.

In some embodiments, the amino acid comprising a side chain amine is an amino acid of Formula I:

wherein n = 1 to 4

In some embodiments, the amino acid of Formula I, is the amino acid wherein n is 4 (Lys) or n is 3 (Orn). In some embodiments, the amino acid comprising a side chain amine is an aromatic amino acid comprising a side chain amine. In exemplary aspects, the aromatic amino acid comprising a side chain amine is 4-amino-phenylalanine (4-aminoPhe), p-amino phenylglycine, p-amino homophenylalanine, or 3-amino tyrosine. In exemplary aspects, the aromatic amino acid comprising a side chain amine is 4-amino-Phe.

In other embodiments, the amino acid comprising a side chain hydroxyl is an amino acid of Formula II:

wherein n = 1 to 4

In some exemplary embodiments, the amino acid of Formula II is the amino acid wherein n is 1 (Ser). In exemplary aspects, the amino acid of Formula II is the amino acid wherein n is 2 (homoserine). In similar exemplary embodiments, the amino acid comprising a side chain hydroxyl is a Thr or homothreonine. In similar exemplary embodiments, the amino acid comprising a side chain hydroxyl is an aromatic amino acid comprising a side chain hydroxyl. In exemplary aspects, the aromatic amino acid comprising a side chain hydroxyl is tyrosine, homotyrosine, methyl-tyrosine, or 3-amino tyrosine.

In yet other embodiments, the amino acid comprising a side chain thiol is an amino acid of Formula III:

wherein n = 1 to 4

In some exemplary embodiments, the amino acid of Formula III is the amino acid wherein n is 1 (Cys).

In yet other embodiments, the amino acid comprising a side chain amine, hydroxyl, or thiol is a disubstituted amino acid comprising the same structure of Formula I, Formula II, or Formula III, except that the hydrogen bonded to the alpha carbon of the amino acid of Formula I, Formula II, or Formula III is replaced with a second side chain.

Acylation Spacers

In alternative embodiments, the acyl group is linked via a spacer to an amino acid of the GIP agonist peptide, wherein the spacer is positioned between the amino acid of the GIP agonist peptide and the acyl group. In some embodiments, the GIP agonist peptide comprises a spacer between the peptide and the acyl group. In some embodiments, the GIP agonist peptide is covalently bound to the spacer, which is covalently bound to the acyl group.

In some embodiments, the spacer is an amino acid comprising a side chain amine, hydroxyl, or thiol, or a dipeptide or tripeptide comprising an amino acid comprising a side chain amine, hydroxyl, or thiol. The amino acid to which the spacer is attached can be any amino acid (e.g., a singly or doubly α-substituted amino acid) comprising a moiety which permits linkage to the spacer. For example, an amino acid comprising a side chain $NH_2$, —OH, or —COOH (e.g., Lys, Orn, Ser, Asp, or Glu) is suitable. In this respect, the GIP agonist peptide in some aspects comprises the amino acid sequence of SEQ ID NO: 1, or a modified amino acid sequence thereof comprising one or more of the amino acid modifications described herein, wherein at least one of the amino acids at positions 9, 10, 12, 13, 14, 16, 17, 20, and 37-43 (e.g., position 10, 14, or 40) is an amino acid comprising a side chain amine, hydroxyl, or carboxylate.

In some embodiments, the spacer is an amino acid comprising a side chain amine, hydroxyl, or thiol, or a dipeptide or tripeptide comprising an amino acid comprising a side chain amine, hydroxyl, or thiol.

When the acyl group is attached through an amine group of a spacer, the acyl group in some aspects is attached through the alpha amine or through a side chain amine of the spacer amino acid. In the instance in which the acyl group is attached via an alpha amine, the amino acid of the spacer can be any amino acid. For example, the amino acid of the spacer can be a hydrophobic amino acid, e.g., Gly, Ala, Val, Leu, Ile, Trp, Met, Phe, Tyr, 6-amino hexanoic acid, 5-aminovaleric acid, 7-aminoheptanoic acid, and 8-aminooctanoic acid. Alternatively, in some aspects, the amino acid of the spacer is an acidic residue, e.g., Asp, Glu, homoglutamic acid, homocysteic acid, cysteic acid, gamma-glutamic acid.

In the instance in which the acyl group is attached through a side chain amine of the amino acid spacer, the spacer is an amino acid comprising a side chain amine, e.g., an amino acid of Formula I (e.g., Lys or Orn). In this instance, it is possible for both the alpha amine and the side chain amine of the amino acid of the spacer to be attached to an acyl group, such that the GIP agonist peptide is diacylated. Embodiments of the invention include such diacylated molecules. In some embodiments, the acyl group is attached to a 4-amino-Phe, p-amino phenylglycine, p-amino homophenylalanine, or 3-amino tyrosine.

When the acyl group is attached through a hydroxyl group of a spacer, the amino acid or one of the amino acids of the dipeptide or tripeptide can be an amino acid of Formula II. In a specific exemplary embodiment, the amino acid is Ser. In similar exemplary embodiments, the acyl group is attached to a Thr or homothreonine. In similar exemplary embodiments, the acyl group is attached via the hydroxyl of an aromatic amino acid comprising a side chain hydroxyl, e.g., tyrosine, homotyrosine, methyl-tyrosine, or 3-amino tyrosine.

When the acyl group is attached through a thiol group of a spacer, the amino acid or one of the amino acids of the dipeptide or tripeptide can be an amino acid of Formula III. In a specific exemplary embodiment, the amino acid is Cys.

In some embodiments, the spacer is a hydrophilic bifunctional spacer. In exemplary embodiments, the hydrophilic bifunctional spacer comprises two or more reactive groups, e.g., an amine, a hydroxyl, a thiol, and a carboxyl group or any combinations thereof. In exemplary embodiments, the hydrophilic bifunctional spacer comprises a hydroxyl group and a carboxylate. In other embodiments, the hydrophilic bifunctional spacer comprises an amine group and a carboxylate. In other embodiments, the hydrophilic bifunctional spacer comprises a thiol group and a carboxylate. In a specific embodiment, the spacer comprises an amino poly(alkyloxy)carboxylate. In this regard, the spacer can comprise, for example, $NH_2(CH_2CH_2O)_n(CH_2)_mCOOH$, wherein m is any integer from 1 to 6 and n is any integer from 2 to 12, such as, e.g., 8-amino-3,6-dioxaoctanoic acid, which is commercially available from Peptides International, Inc. (Louisville, Ky.).

In exemplary embodiments, the spacer comprises a small polyethylene glycol moiety (PEG) comprising a structure $[—O—CH_2—CH_2—]_n$, wherein n is an integer between 2 and 16, (e.g., 2, 3, 4, 5, 6, 7, 8, 9, 10, 11, 12, 13, 14, 15, 16). Such small PEGS are referred to herein as a "miniPEG." In exemplary aspects, the miniPEG is a functionalized miniPEG comprising one or more functional groups. Suitable functional groups include, but are not limited to, an amine, a hydroxyl, a thiol, and a carboxyl group or any combinations thereof. In exemplary aspects, the miniPEG is a miniPEG acid comprising a structure $\{[—O—CH_2—CH_2-]_n COO—\}$, wherein n is defined as above. In exemplary aspects, the miniPEG is an amido miniPEG comprising a structure $\{—N—CH_2—CH_2—[—O—CH_2—CH_2—]_n\}$, wherein n is defined as above. In exemplary aspects, the miniPEG is an amido miniPEG acid comprising a structure $\{—N—CH_2—CH_2—[—O—CH_2—CH_2—]_n COO—\}$, wherein n is defined as above. Suitable reagents for use in acylating an amino acid with a miniPEG are commercially available from vendors, such as Peptides International (Louisville, Ky.). Also, suitable techniques for acylating an amino acid with a miniPEG are described herein (see Example 1).

In some embodiments, the spacer is a hydrophobic bifunctional spacer. Hydrophobic bifunctional spacers are known in the art. See, e.g., *Bioconjugate Techniques*, G. T. Hermanson (Academic Press, San Diego, Calif., 1996), which is incorporated by reference in its entirety. In exemplary embodiments, the hydrophobic bifunctional spacer comprises two or more reactive groups, e.g., an amine, a hydroxyl, a thiol, and a carboxyl group or any combinations thereof. In exemplary embodiments, the hydrophobic bifunctional spacer comprises a hydroxyl group and a carboxylate. In other embodiments, the hydrophobic bifunctional spacer comprises an amine group and a carboxylate. In other embodiments, the hydrophobic bifunctional spacer comprises a thiol group and a carboxylate. Suitable hydrophobic bifunctional spacers comprising a carboxylate and a hydroxyl group or a thiol group are known in the art and include, for example, 8-hydroxyoctanoic acid and 8-mercaptooctanoic acid.

In some embodiments, the bifunctional spacer is not a dicarboxylic acid comprising an unbranched, methylene of 1-7 carbon atoms between the carboxylate groups. In some embodiments, the bifunctional spacer is a dicarboxylic acid comprising an unbranched, methylene of 1-7 carbon atoms between the carboxylate groups.

The spacer (e.g., amino acid, dipeptide, tripeptide, hydrophilic bifunctional spacer, or hydrophobic bifunctional spacer) in specific embodiments is 3 to 10 atoms (e.g., 6 to 10 atoms, (e.g., 6, 7, 8, 9, or 10 atoms) in length. In more specific embodiments, the spacer is about 3 to 10 atoms (e.g., 6 to 10 atoms) in length and the acyl group is a C12 to C18 fatty acyl group, e.g., C14 fatty acyl group, C16 fatty acyl group, such that the total length of the spacer and acyl group is 14 to 28 atoms, e.g., about 14, 15, 16, 17, 18, 19, 20, 21, 22, 23, 24, 25, 26, 27, or 28 atoms. In some embodiments, the length of the spacer and acyl group is 17 to 28 (e.g., 19 to 26, 19 to 21) atoms.

In accordance with some or any of the foregoing embodiments, the bifunctional spacer can be a synthetic or naturally occurring amino acid (including, but not limited to, any of those described herein) comprising an amino acid backbone that is 3 to 10 atoms in length (e.g., 6-amino hexanoic acid, 5-aminovaleric acid, 7-aminoheptanoic acid, and 8-aminooctanoic acid). Alternatively, the spacer can be a dipeptide or tripeptide spacer having a peptide backbone that is 3 to 10 atoms (e.g., 6 to 10 atoms) in length. Each amino acid of the dipeptide or tripeptide spacer can be the same as or different from the other amino acid(s) of the dipeptide or tripeptide and can be independently selected from the group consisting of: naturally-occurring or coded and/or non-coded or non-naturally occurring amino acids, including, for example, any of the D or L isomers of the naturally-occurring amino acids (Ala, Cys, Asp, Glu, Phe, Gly, His, Ile, Lys, Leu, Met, Asn, Pro, Arg, Ser, Thr, Val, Trp, Tyr), or any D or L isomers of the non-naturally occurring or non-coded amino acids selected from the group consisting of: β-alanine (β-Ala), N-α-methyl-alanine (Me-Ala), aminobutyric acid (Abu), γ-aminobutyric acid (γ-Abu), aminohexanoic acid (ε-Ahx), aminoisobutyric acid (Aib), aminomethylpyrrole carboxylic acid, aminopiperidinccarboxylic acid, aminoscrinc (Ams), aminotctrahydropyran-4-carboxylic acid, arginine N-methoxy-N-methyl amide, β-aspartic acid (β-Asp), azetidine carboxylic acid, 3-(2-benzothiazolyl)alanine, α-tert-butylglycine, 2-amino-5-ureido-n-valeric acid (citrulline, Cit), β-Cyclohexylalanine (Cha), acetamidomethyl-cysteine, diaminobutanoic acid (Dab), diaminopropionic acid (Dpr), dihydroxyphenylalanine (DOPA), dimethylthiazolidine (DMTA), γ-Glutamic acid (γ-Glu), homoserine (Hse), hydroxyproline (Hyp), isoleucine N-methoxy-N-methyl amide, methyl-isoleucine (MeIle), isonipecotic acid (Isn), methyl-leucine (MeLeu), methyl-lysine, dimethyl-lysine, trimethyl-lysine, methanoproline, methionine-sulfoxide (Met(O)), methionine-sulfone (Met(O₂)), norleucine (Nle), methyl-norleucine (Me-Nle), norvaline (Nva), ornithine (Orn), para-aminobenzoic acid (PABA), penicillamine (Pen), methylphenylalanine (MePhe), 4-Chlorophenylalanine (Phe(4-Cl)), 4-fluorophenylalanine (Phe(4-F)), 4-nitrophenylalanine (Phe(4-NO₂)), 4-cyanophenylalanine ((Phe(4-CN)), phenylglycine (Phg), piperidinylalanine, piperidinylglycine, 3,4-dehydroproline, pyrrolidinylalanine, sarcosine (Sar), selenocysteine (Sec), O-Benzyl-phosphoserine, 4-amino-3-hydroxy-6-methylheptanoic acid (Sta), 4-amino-5-cyclohexyl-3-hydroxypentanoic acid (ACHPA), 4-amino-3-hydroxy-5-phenylpentanoic acid (AHPPA), 1,2,3,4,-tetrahydro-isoquinoline-3-carboxylic acid (Tie), tetrahydropyranglycine, thienylalanine (Thi), O-benzyl-phosphotyrosine, O-Phosphotyrosine, methoxytyrosine, ethoxytyrosine, O-(bis-dimethylamino-phosphono)-tyrosine, tyrosine sulfate tetrabutylamine, methyl-valine (Me-Val), and alkylated 3-mercaptopropionic acid. In exemplary aspects, the spacer is a Cys residue or a Lys residue.

In some embodiments, the spacer comprises an overall negative charge, e.g., comprises one or two negative-charged amino acids. In some embodiments, the dipeptide is not any of the dipeptides of general structure A-B, wherein A is selected from the group consisting of Gly, Gln, Ala, Arg, Asp, Asn, Ile, Leu, Val, Phe, and Pro, wherein B is selected from the group consisting of Lys, His, Trp. In some embodiments, the amino acids of the dipeptide spacer are selected from the group consisting of: Ala, β-Ala, Leu, Pro, γ-aminobutyric acid, Glu and γ-Glu.

In some exemplary embodiments, the GIP agonist peptide comprises an acyl group upon acylation of an amine, hydroxyl, or thiol of a spacer, which spacer is attached to a side chain of an amino acid at position 9, 10, 12, 13, 14, 16, 17, 20, or 37-43 (e.g., at any one or more of positions 10, 14, and 40), or at the C-terminal amino acid of the GIP agonist peptide.

In yet more specific embodiments, the acyl group is attached to the amino acid at any of positions 9, 10, 12, 13, 14, 16, 17, 20, or 37-43 (e.g., at any one or more of positions 10, 14, and 40) of the peptide analog and the length of the spacer and acyl group is 14 to 28 atoms. The amino acid at any of positions 9, 10, 12, 13, 14, 16, 17, 20, or 37-43 (e.g., at any one or more of positions 10, 14, and 40), in some aspects, is an amino acid of Formula I, e.g., Lys, or a disubstituted amino acid related to Formula I. In more specific embodiments, the peptide analog lacks an intramolecular bridge, e.g., a covalent intramolecular bridge. The glucagon analog, for example, can be a glucagon analog comprising one or more alpha, alpha-disubstituted amino acids, e.g., AIB, for stabilizing the alpha helix of the analog.

Acyl Groups

The acyl group of the acylated amino acid can be of any size, e.g., any length carbon chain, and can be linear or branched. In some specific embodiments, the acyl group is a C4 to C30 fatty acid. For example, the acyl group can be any of a C4 fatty acid, C6 fatty acid, C8 fatty acid, C10 fatty acid, C12 fatty acid, C14 fatty acid, C16 fatty acid, C18 fatty acid, C20 fatty acid, C22 fatty acid, C24 fatty acid, C26 fatty acid, C28 fatty acid, or a C30 fatty acid. In some embodiments, the acyl group is a C8 to C20 fatty acid, e.g., a C14 fatty acid or a C16 fatty acid.

In an alternative embodiment, the acyl group is a bile acid. The bile acid can be any suitable bile acid, including, but not limited to, cholic acid, chenodeoxycholic acid, deoxycholic acid, lithocholic acid, taurocholic acid, glycocholic acid, and cholesterol acid.

In exemplary embodiments, the acyl group is a succinic acid or a succinic acid derivative. By "succinic acid derivative" as used herein is meant a compound comprising a substituted succinic acid or a substituted cyclic succinic acid (i.e., succinic anhydride) or a substituted expanded ring succinic anhydride, (i.e. a 6-8 membered ring comprising the —C(O)—O—C(O)— moiety and 3 to 5 additional carbons), wherein the substituted succinic acid, substituted cyclic succinic acid (i.e., succinic anhydride), or substituted expanded ring succinic anhydride is substituted with one or more alkyl chains or one or more functionalized carbon chains.

In exemplary aspects, the succinic acid derivative comprises a structure of Formula V:

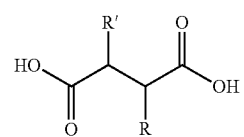

[Formula V]

wherein each of R and R' is independently H, a linear or branched C4-C30 carbon chain, or a linear or branched C4-C30 functionalized carbon chain. In exemplary embodiments, R and/or R' is a carbon chain comprising a C4 to C30 alkyl chain. For example, the alkyl group can be any of a C4 alkyl, C6 alkyl, C8 alkyl, C10 alkyl, C12 alkyl, C14 alkyl, C16 alkyl, C18 alkyl, C20 alkyl, C22 alkyl, C24 alkyl, C26 alkyl, C28 alkyl, or a C30 alkyl. In some embodiments, the alkyl group is a C8 to C20 alkyl, e.g., a C14 alkyl or a C16 alkyl. In exemplary aspects, the functionalized carbon chain comprises a functional group, including, but not limited, carboxyl, sulfhydryl, amine, ketyl, sulfoxyl or amido.

In exemplary aspects, the succinic acid derivative comprises a succinic anhydride comprising a structure of Formula VI:

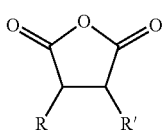

[Formula VI]

wherein each of R and R' is independently H, a linear or branched C4-C30 carbon chain, or a linear or branched C4-C30 functionalized carbon chain. In exemplary embodiments, R and/or R' is a carbon chain comprising a C4 to C30 alkyl chain. For example, the alkyl group can be any of a C4 alkyl, C6 alkyl, C8 alkyl, C10 alkyl, C12 alkyl, C14 alkyl, C16 alkyl, C18 alkyl, C20 alkyl, C22 alkyl, C24 alkyl, C26 alkyl, C28 alkyl, or a C30 alkyl. In some embodiments, the alkyl group is a C8 to C20 alkyl, e.g., a C14 alkyl or a C16 alkyl. In exemplary aspects, the functionalized carbon chain comprises a functional group, including, but not limited, carboxyl, sulfhydryl, amine, ketyl, sulfoxyl or amido.

In exemplary aspects, the succinic acid derivative is a succinic anhydride derivative, including those of Formula VII:

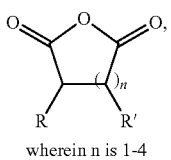

[Formula VII]

wherein n is 1-4 and
wherein each of R and R' is independently H, a linear or branched C4-C30 carbon chain, or a linear or branched C4-C30 functionalized carbon chain. In exemplary embodiments, R and/or R' is a carbon chain comprising a C4 to C30 alkyl chain. For example, the alkyl group can be any of a C4 alkyl, C6 alkyl, C8 alkyl, C10 alkyl, C12 alkyl, C14 alkyl, C16 alkyl, C18 alkyl, C20 alkyl, C22 alkyl, C24 alkyl, C26 alkyl, C28 alkyl, or a C30 alkyl. In some embodiments, the alkyl group is a C8 to C20 alkyl, e.g., a C14 alkyl or a C16 alkyl. In exemplary aspects, the functionalized carbon chain comprises a functional group, including, but not limited, carboxyl, sulfhydryl, amine, ketyl, sulfoxyl or amido.

Figure 3A:
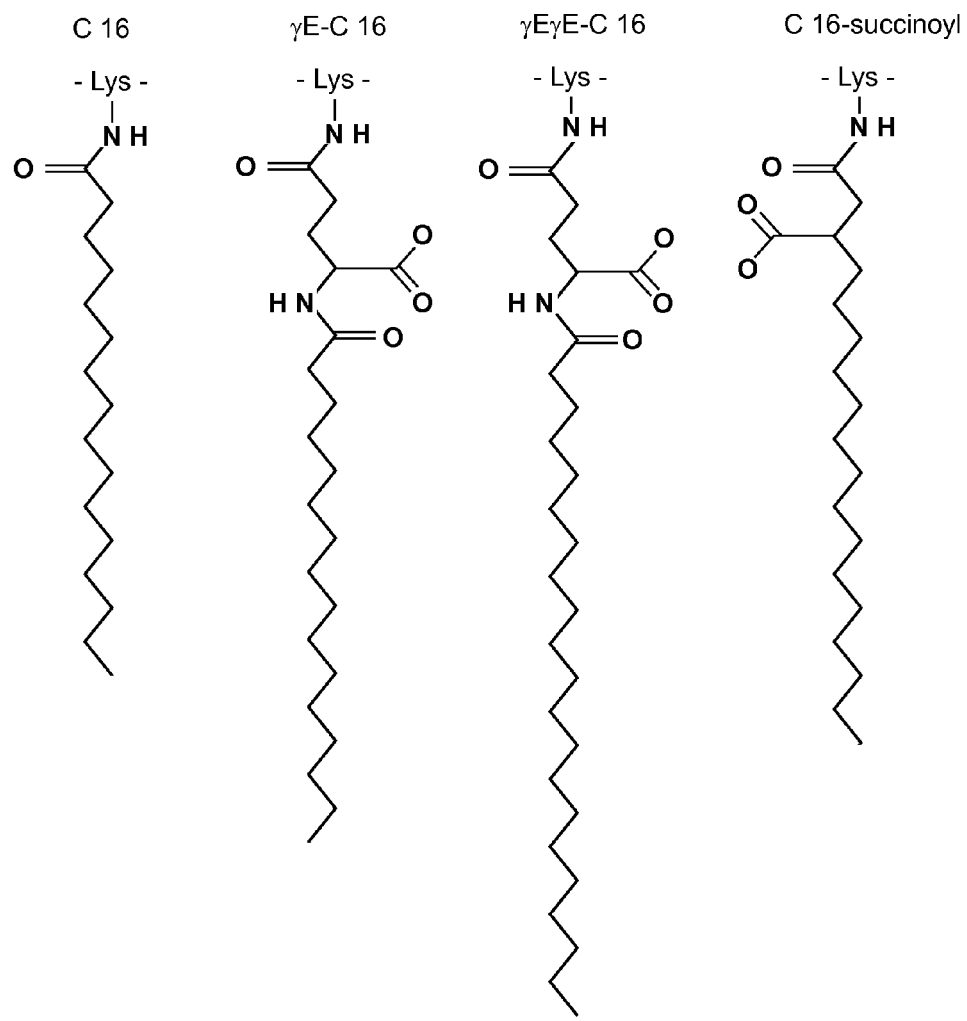
FIGS. 3A-3C relate to acylated peptides comprising a succinoyl group.

When only one of R and R' of Formulae V-VI is H, the acylated amino acid is referred to as "Cx Succinoyl." As used herein, the term "Cx Succinoyl," wherein x is an integer, refers to a structure wherein R is an alkyl chain of y carbons and y=x−1, and y does not include the carbons of succinoyl moiety. For example a structure of Formula VI wherein R is a C15 alkyl group and R' is a H is referred to as C16 Succinoyl. For example, FIG. 3A depicts a C16 Succinoyl Lys, wherein a Lys has been succinoylated at the amine. When neither R nor R' of Formulae V-VI is H, then the acylated amino acid is referred to as "Cx,Cx' Succinoyl." As used herein, the term "Cx,Cx' Succinoyl," wherein x and x' are integers, refers to a structure wherein R is an alkyl chain of y carbons and R' is an alkyl chain of y' carbons, and y'=x'−1. For example, a structure of Formula VI wherein R is a C15 alkyl group and R' is a C13 alkyl group is referred to as C16,C14 succinoyl. When the succinic acid derivative is a substituted expanded ring succinic anhydride and neither R nor R' of Formula VII is H, then the acylated amino acid is referred to as "Cx,Cx'-n-Succinoyl." As used herein, the term "Cx,Cx'-n-Succinoyl," wherein x, x', and n are integers, refers to a structure wherein R is an alkyl chain of y carbons, R' is an alkyl chain of y' carbons, and the succinic anhydride ring is extend by n carbons. For example, a structure of Formula VII wherein R and R' are C15 alkyl groups and n=2 is referred to as C16,C16-2-Succinoyl.

In exemplary embodiments, the acyl group is a maleic acid or a maleic acid derivative. By "maleic acid derivative" as used herein is meant a compound comprising a substituted maleic acid or a substituted cyclic maleic acid (i.e., maleic anhydride) or a substituted expanded ring maleic anhydride, (i.e. a 6-8 membered ring comprising the —C(O)—O—C(O)— moiety and 3 to 5 additional carbons), wherein the substituted maleic acid, substituted cyclic malcic acid (i.e., maleic anhydride), or substituted expanded ring maleic anhydride is substituted with one or more alkyl chains or one or more functionalized carbon chains.

In exemplary aspects, the maleic acid derivative comprises a structure of Formula VIII:

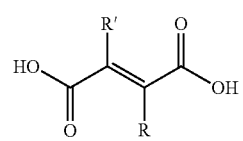

[Formula VIII]

wherein each of R and R' is independently H, a linear or branched C4-C30 carbon chain, or a linear or branched C4-C30 functionalized carbon chain. In exemplary embodiments, R and/or R' is a carbon chain comprising a C4 to C30 alkyl chain. For example, the alkyl group can be any of a C4 alkyl, C6 alkyl, C8 alkyl, C10 alkyl, C12 alkyl, C14 alkyl, C16 alkyl, C18 alkyl, C20 alkyl, C22 alkyl, C24 alkyl, C26 alkyl, C28 alkyl, or a C30 alkyl. In some embodiments, the alkyl group is a C8 to C20 alkyl, e.g., a C14 alkyl or a C16 alkyl. In exemplary aspects, the functionalized carbon chain comprises a functional group, including, but not limited, carboxyl, sulfhydryl, amine, ketyl, sulfoxyl or amido.

In exemplary aspects, the maleic acid derivative comprises a maleic anhydride comprising a structure of Formula IX:

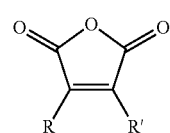

[Formula IX]

wherein each of R and R' is independently H, a linear or branched C4-C30 carbon chain, or a linear or branched C4-C30 functionalized carbon chain. In exemplary embodiments, R and/or R' is a carbon chain comprising a C4 to C30 alkyl chain. For example, the alkyl group can be any of a C4 alkyl, C6 alkyl, C8 alkyl, C10 alkyl, C12 alkyl, C14 alkyl, C16 alkyl, C18 alkyl, C20 alkyl, C22 alkyl, C24 alkyl, C26 alkyl, C28 alkyl, or a C30 alkyl. In some embodiments, the alkyl group is a C8 to C20 alkyl, e.g., a C14 alkyl or a C16 alkyl. In exemplary aspects, the functionalized carbon chain comprises a functional group, including, but not limited, carboxyl, sulfhydryl, amine, ketyl, sulfoxyl or amido.

In exemplary aspects, the maleic acid derivative is a maleic anhydride derivative, including those of Formula X:

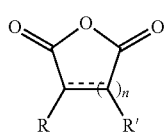

[Formula X]

wherein n is 1-4, there is at least one C=C double bond between two non-carbonyl carbons, and wherein each of R and R' is independently H, a linear or branched C4-C30 carbon chain, or a linear or branched C4-C30 functionalized carbon chain. In exemplary embodiments, R and/or R' is a carbon chain comprising a C4 to C30 alkyl chain. For example, the alkyl group can be any of a C4 alkyl, C6 alkyl, C8 alkyl, C10 alkyl, C12 alkyl, C14 alkyl, C16 alkyl, C18 alkyl, C20 alkyl, C22 alkyl, C24 alkyl, C26 alkyl, C28 alkyl, or a C30 alkyl. In some embodiments, the alkyl group is a C8 to C20 alkyl, e.g., a C14 alkyl or a C16 alkyl. In exemplary aspects, the functionalized carbon chain comprises a functional group, including, but not limited, carboxyl, sulfhydryl, amine, ketyl, sulfoxyl or amino.

When only one of R and R' of Formulae VIII-IX is H, the acylated amino acid is referred to as "Cx Maleoyl." As used herein, the term "Cx Maleoyl," wherein x is an integer, refers to a structure wherein R is an alkyl chain of y carbons and y=x−1, and y does not include the carbons of maleoyl moiety. For example a structure of Formula IX wherein R is a C15 alkyl group and R' is a H is referred to as C16 Maleoyl. When neither R nor R' of Formulae VIII-IX is H, then the acylated amino acid is referred to as "Cx,Cx' Maleoyl." As used herein, the term "Cx,Cx' Maleoyl," wherein x and x' are integers, refers to a structure wherein R is an alkyl chain of y carbons and R' is an alkyl chain of y' carbons and y'=x'−1. For example, a structure of Formula IX wherein R is a C15 alkyl group and R' is a C13 alkyl group is referred to as C16,C14 maleoyl. When the maleic acid derivative is a substituted expanded ring maleic anhydride and neither R nor R' of Formula X is H, then the acylated amino acid is referred to as "Cx,Cx'-n-Maleoyl." As used herein, the term "Cx,Cx'-n-Maleoyl," wherein x, x', and n are integers, refers to a structure wherein R is an alkyl chain of y carbons, R' is an alkyl chain of y' carbons, and the maleic anhydride ring is extend by n carbons. For example, a structure of Formula X wherein R and R' are C15 alkyl groups and n=2 is referred to as C16,C16-2-Maleoyl.

Methods of Attaching an Acyl Group

Suitable methods of attaching acyl groups to peptides via amines, hydroxyls, and thiols of the peptides are known in the art. See, for example, Example 1 (for methods of acylating through an amine), Miller, *Biochem Biophys Res Commun* 218: 377-382 (1996); Shimohigashi and Stammer, *Int J Pept Protein Res* 19: 54-62 (1982); and Previero et al., *Biochim Biophys Acta* 263: 7-13 (1972) (for methods of acylating through a hydroxyl); and San and Silvius, J Pept Res 66: 169-180 (2005) (for methods of acylating through a thiol); Bioconjugate Chem. "Chemical Modifications of Proteins: History and Applications" pages 1, 2-12 (1990); Hashimoto et al., Pharmacuetical Res. "Synthesis of Palmitoyl Derivatives of Insulin and their Biological Activity" Vol. 6, No: 2 pp. 171-176 (1989).

In some embodiments, the GIP agonist peptide comprises an acylated amino acid by acylation of a long chain alkane by the GIP agonist peptide. In specific aspects, the long chain alkane comprises an amine, hydroxyl, or thiol group (e.g., octadecylamine, tetradecanol, and hexadecanethiol) which reacts with a carboxyl group, or activated form thereof, of the GIP agonist peptide. The carboxyl group, or activated form thereof, of the GIP agonist peptide can be part of a side chain of an amino acid (e.g., glutamic acid, aspartic acid) of the GIP agonist peptide or can be part of the peptide backbone.

In exemplary embodiments, the GIP agonist peptide comprises an acyl group by acylation of the long chain alkane by a spacer which is attached to the GIP agonist peptide. In specific aspects, the long chain alkane comprises an amine, hydroxyl, or thiol group which reacts with a carboxyl group, or activated form thereof, of the spacer. Suitable spacers comprising a carboxyl group, or activated form thereof, are described herein and include, for example, bifunctional spacers, e.g., amino acids, dipeptides, tripeptides, hydrophilic bifunctional spacers and hydrophobic bifunctional spacers.

As used herein, the term "activated form of a carboxyl group" refers to a carboxyl group with the general formula R(C=O)X, wherein X is a leaving group and R is the glucagon analog or the spacer. For example, activated forms of a carboxyl groups may include, but are not limited to, acyl chlorides, anhydrides, and esters. In some embodiments, the activated carboxyl group is an ester with a N-hydroxysuccinimidc ester (NHS) leaving group.

With regard to these aspects, in which a long chain alkane is acylated by the glucagon analog or the spacer, the long chain alkane may be of any size and can comprise any length of carbon chain. The long chain alkane can be linear or branched. In exemplary aspects, the long chain alkane is a C4 to C30 alkane. For example, the long chain alkane can be any of a C4 alkane, C6 alkane, C8 alkane, C10 alkane, C12 alkane, C14 alkane, C16 alkane, C18 alkane, C20 alkane, C22 alkane, C24 alkane, C26 alkane, C28 alkane, or a C30 alkane. In some embodiments, the long chain alkane comprises a C8 to C20 alkane, e.g., a C14 alkane, C16 alkane, or a C18 alkane.

Also, in some embodiments, an amine, hydroxyl, or thiol group of the GIP agonist peptide is acylated with a cholesterol acid. In a specific embodiment, the GIP agonist peptide is linked to the cholesterol acid through an alkylated desamino Cys spacer, i.e., an alkylated 3-mercaptopropionic acid spacer.

When the acyl group is a succinic acid, succinic acid derivative, maleic acid, or maleic acid derivative the peptide is succinoylated/maleoylated by the reaction of an amine, hydroxyl, or thiol group of the GIP agonist peptide, or spacer, with a succinic acid, succinic acid derivative, maleic acid, or maleic acid derivative of Formula V, Formula VI, Formula VII, Formula VIII, Formula IX or formula X. Methods of succinoylation are described herein.

Additional Acyl Groups

The peptide in some or any embodiments comprises an acylated amino acid at a position other than positions 9, 10, 12, 13, 14, 16, 17, 20, or 37-43 (e.g., at any one or more of positions 10, 14, and 40). The location of the acylated amino acid may be any position within the GIP agonist peptide, including any of positions 1-29, a position C-terminal to the 29$^{th}$ amino acid (e.g., the amino acid at position 30, 31, 32, 33, 34, 35, 36, 44, 45, 46, 47, etc., at a position within a C-terminal extension or at the C-terminus), optionally together with a second acylated amino acid at any of positions 9, 10, 12, 13, 14, 16, 17, 20, or 37-43 (e.g., at any one or more of positions 10, 14, and 40), provided that the GIP agonist activity of the peptide analog is retained, if not enhanced. Nonlimiting examples include positions 5, 7, 11, 13, 14, 17, 18, 19, 21, 24, 27, 28, or 29.

Consistent with the foregoing, the glucagon analog, in exemplary aspects, comprises two (or more) acylated amino acids, and may be considered a dual acylated peptide or a diacylated peptide, when there are two acyl groups. In exemplary aspects, all of the acylated amino acids are located at two positions of positions 9, 10, 12, 13, 14, 16, 17, 20, or 37-43 (e.g., at any one or more of positions 10, 14, and 40). In exemplary aspects, the acylations occur at two of positions 10, 14, and 40. In exemplary aspects, the peptide comprising a first acylated amino acid at position 10 and a second acylated amino acid at position 40.

In yet additional exemplary embodiments, the glucagon analog comprises two (or more) acyl groups attached to a single amino acid of the peptide backbone. The peptide may be considered as a dual acylated peptide or a diacylated peptide, when there are two acyl groups. The two (or more) acyl groups may be the same acyl group or different acyl groups, arranged in a branched or linear formation. For example, to achieve a branched formation, the glucagon analog may comprise one acylated amino acid (which is part of the peptide backbone) attached to a spacer comprising at least three functional groups—at least two of which are each covalently attached to an acyl group and one of which is attached to the acylated amino acid of the peptide backbone. In exemplary aspects, a branched formation may be achieved through, e.g., a Lys residue comprising two amine groups (a side chain amine and an alpha amine) for direct attachment to a fatty acyl group or indirect attachment to a fatty acyl group via a spacer. In exemplary aspects, an additional spacer may be placed between the amino acid of the peptide backbone and the spacer comprising at least three functional groups. For example, the amino acid of the peptide backbone may be attached (e.g., via its side chain) to a first spacer, which, in turn, is attached to a second spacer, wherein the second spacer comprises at least three functional groups—at least two of which are each covalently attached to an alkyl group and one of which is attached to the first spacer.

In exemplary aspects, wherein the alkyl groups are arranged in a linear formation, the glucagon analog comprises one acylated amino acid (which is part of the peptide backbone) directly attached to a first acyl group, which, in turn, is attached to a spacer, which, in turn, is attached to a second acyl group.

Figure 5A:
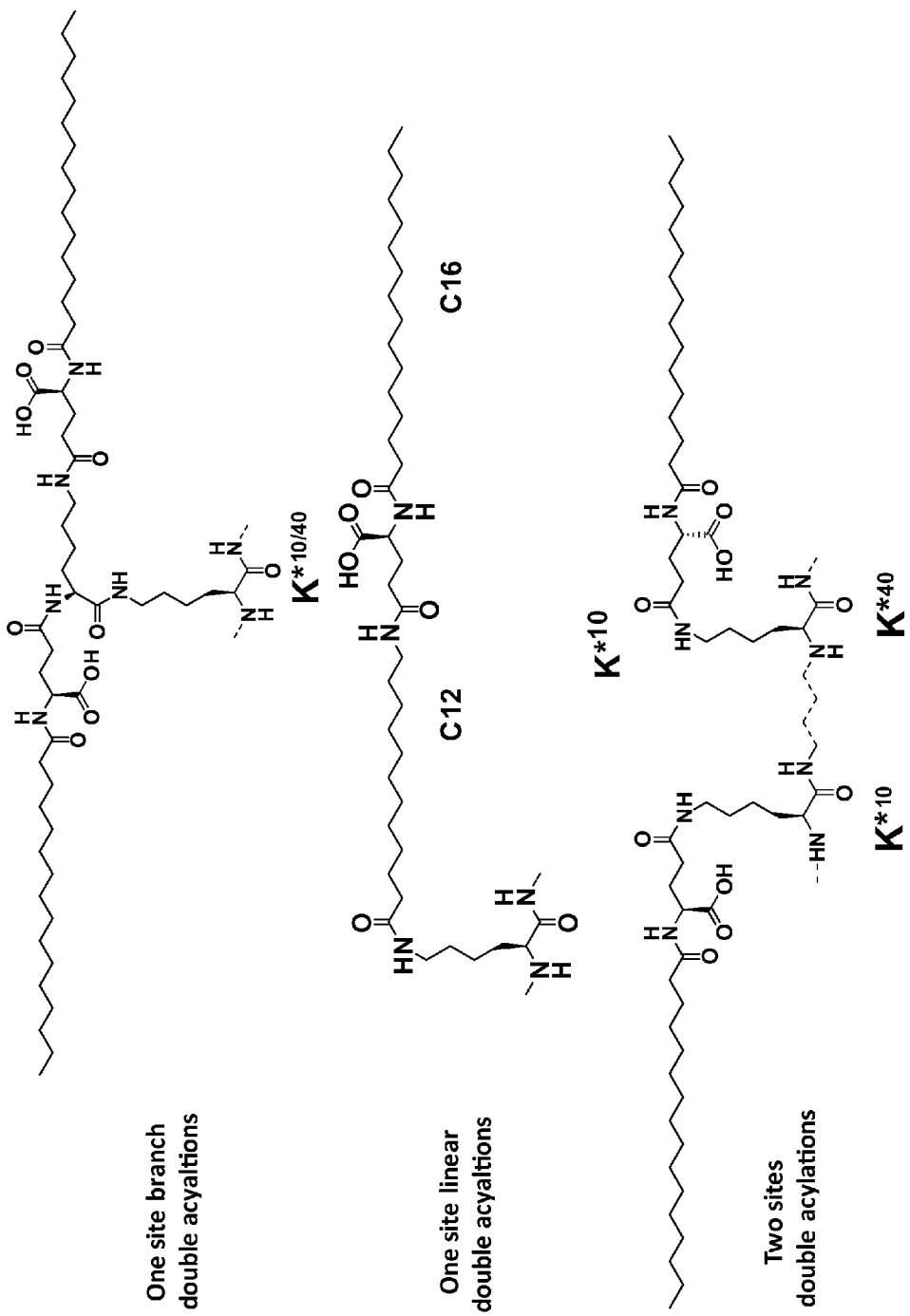
FIGS. 5A-5F relate to dual acylated peptides.

Exemplary structures of dual acylated compounds are depicted in FIG. 5A.

Hydrophilic Moieties and Acyl Groups

The GIP agonist peptides comprising an acylated amino acid optionally further comprises a hydrophilic moiety. In some or any embodiments the hydrophilic moiety comprises a polyethylene glycol (PEG) chain. The incorporation of a hydrophilic moiety is accomplished through any suitable means, such as any of the methods described herein. In this regard, the GIP agonist peptide can comprise SEQ ID NO: 1, including any of the modifications described herein, in which at least one of the amino acids at any of positions 9, 10, 12, 13, 14, 16, 17 20, and 37-43 (e.g., at one or more of positions 10, 14, and 40) is an acylated amino acid and at least one of the amino acids at position 16, 17, 21, 24, or 29, a position within a C-terminal extension, or the C-terminal amino acid is a Cys, Lys, Orn, homo-Cys, or Ac-Phe, of which the side chain is covalently bonded to a hydrophilic moiety (e.g., PEG). In some embodiments, the amino acid at any of positions 9, 10, 12, 13, 14, 16, 17, 20, and 37-43 (e.g., at one or more of positions 10, 14, and 40) of the GIP agonist peptide is attached (optionally via a spacer) to the acyl group and that amino acid is further attached to a hydrophilic moiety or is further attached to a Cys, Lys, Orn, homo-Cys, or Ac-Phe, which is attached to the hydrophilic moiety.

Alternatively, the acylated glucagon analog can comprise a spacer, wherein the spacer is both acylated and modified to comprise the hydrophilic moiety. Nonlimiting examples of suitable spacers include a spacer comprising one or more amino acids selected from the group consisting of Cys, Lys, Orn, homo-Cys, and Ac-Phe.

In some aspects, the GIP agonist peptide in some embodiments are acylated at the same amino acid position where a hydrophilic moiety is linked, or at a different amino acid position. Nonlimiting examples include acylation at position 9, 10, 12, 13, 14, 16, 17, 20, or 40 (e.g., at one or more of positions 10, 14, and 40) and pegylation at one or more positions in the C-terminal portion of the glucagon analog, e.g., position 24, 28 or 29, within a C-terminal extension (e.g., 37-43), or at the C-terminus (e.g., through adding a C-terminal Cys).

In some specific embodiments, the GIP agonist peptide comprising an acylated amino acid lacks an intramolecular bridge, e.g., a covalent intramolecular bridge (e.g., a lactam bridge).

Amino Acids Comprising a Non-Native Alkyl Group

In accordance with some or any embodiments, the GIP agonist peptides which are analogs of glucagon (SEQ ID NO: 1) comprise an amino acid comprising a non-native alkyl group (referred to herein as an "alkylated amino acid," regardless of how it is prepared, e.g., by incorporation of a previously-alkylated amino acid into the peptide, or alkylation of the peptide after synthesis). In some or any aspects, the alkylated amino acid is located at any of positions 9, 10, 12, 13, 14, 16, 17, 20, 37, 38, 39, 40, 41, 42, or 43 (e.g., at one or more of positions 10, 14, and 40). In exemplary aspects, the alkylated amino acid is located at any of positions 9, 10, 12, 16, 20, or 40 or at any of positions 10, 13, 14, 16, 17, or 40. In exemplary aspects, the alkylated amino acid is located at any of positions 10, 12, 16, or 40 or at any of positions 10, 12, or 16. In exemplary aspects, the alkylated amino acid is located at any one or more of positions 10, 14, and 40.

The alkylated amino acid in some embodiments causes the GIP agonist peptide to have one or more of (i) a prolonged half-life in circulation, (ii) a delayed onset of action, (iii) an extended duration of action, (iv) an improved resistance to proteases, such as DPP-IV, and (v) increased potency at any one or more of the GIP receptor, GLP-1 receptor, and glucagon receptor.

Direct Alkylation

In some embodiments, the alkyl group is directly linked to an amino acid of the GIP agonist peptide. In accordance with one embodiment, the GIP agonist peptide comprises an alkyl group which is attached to the peptide via an ether, thioether, or amine linkage.

In specific aspects, the GIP agonist peptide comprises an alkyl group upon direct alkylation of an amine, hydroxyl, or thiol of a side chain of an amino acid of the GIP agonist peptide. In some or any embodiments, the alkyl group is linked to the amino acid of the GIP agonist peptide by reacting the amine, hydroxyl, or thiol with an activated alkyl group. Alkyl groups in some aspects are activated with a leaving group, for example, a halogen, sulfonate ester, pyridylthiol, ammonium salt, or phenoxyl.

In some or any embodiments, the alkylated amino acid is located at one of positions 9, 10, 12, 13, 14, 16, 17, 20, or 40 (e.g., at any one of positions 10, 14, and 40) or at one of positions 10, 12, or 16. In this regard, the GIP agonist peptide comprises the amino acid sequence of SEQ ID NO: 1, or a modified amino acid sequence thereof, comprising one or more of the amino acid modifications described herein, wherein at least one of the amino acids at positions 9, 10, 12, 13, 14, 16, 17, 20, and 40 (e.g., at any one of positions 10, 14, and 40) is an amino acid comprising a side chain amine, hydroxyl, or thiol.

In some embodiments, the amino acid comprising a side chain amine is an amino acid of Formula I. In some embodiments, the amino acid of Formula I, is the amino acid wherein n is 4 (Lys) or n is 3 (Orn). In some embodiments, the amino acid comprising a side chain amine is an aromatic amino acid comprising a side chain amine. In exemplary aspects, the aromatic amino acid comprising a side chain amine is 4-amino-phenylalanine (4-aminoPhe), p-amino phenylglycine, p-amino homophenylalaninc, or 3-amino tyrosine. In exemplary aspects, the aromatic amino acid comprising a side chain amine is 4-amino-Phe.

In other embodiments, the amino acid comprising a side chain hydroxyl is an amino acid of Formula II. In some exemplary embodiments, the amino acid of Formula II is the amino acid wherein n is 1 (Ser). In exemplary aspects, the amino acid of Formula II is the amino acid wherein n is 2 (homoserine). In similar exemplary embodiments, the amino acid comprising a side chain hydroxyl is a Thr or homo-threonine. In similar exemplary embodiments, the amino acid comprising a side chain hydroxyl is an aromatic amino acid comprising a side chain hydroxyl. In exemplary aspects, the aromatic amino acid comprising a side chain hydroxyl is tyrosine, homotyrosine, methyl-tyrosine, or 3-amino tyrosine.

Figure 6:
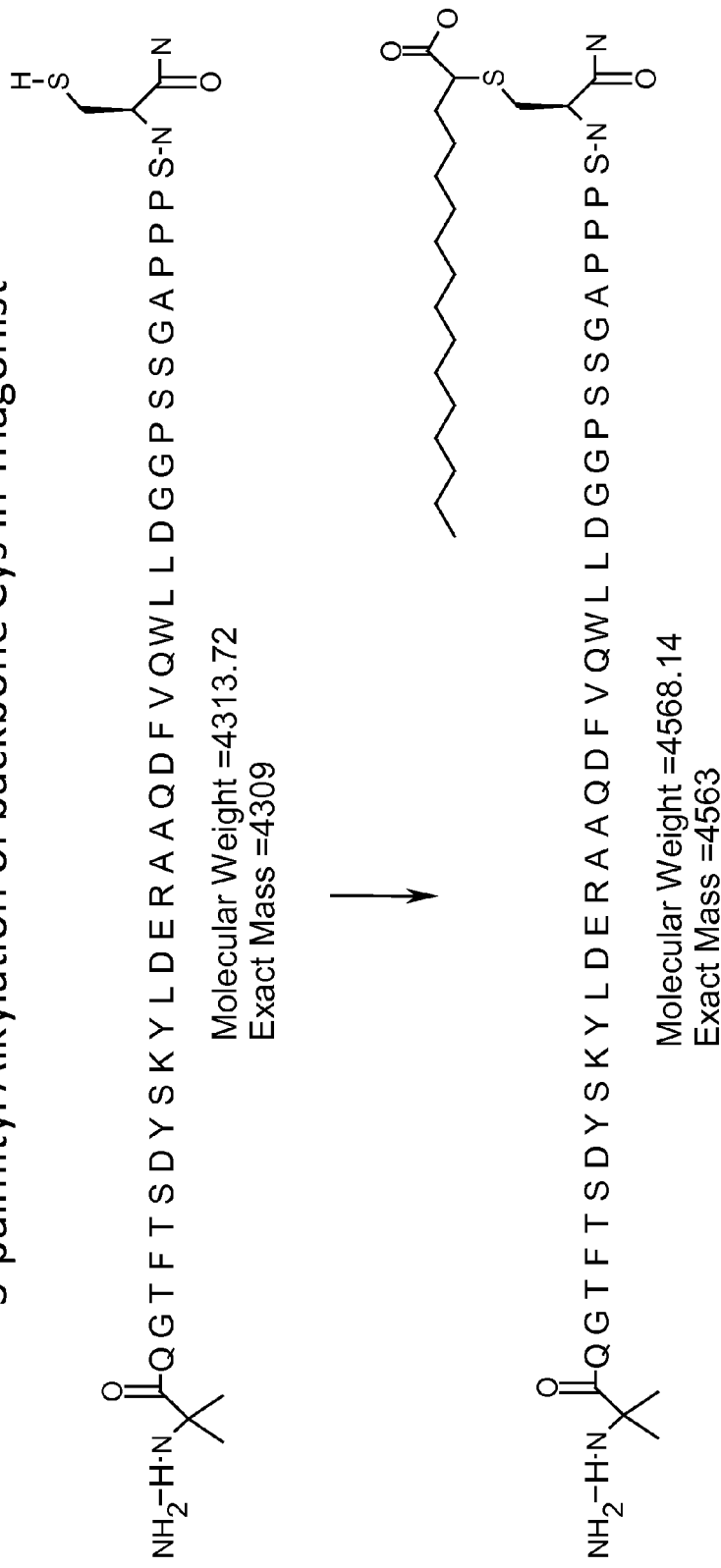
FIG. 6 depicts S-palmityl alkylation of a Cys residue which is part of a peptide backbone.
Figure 7:
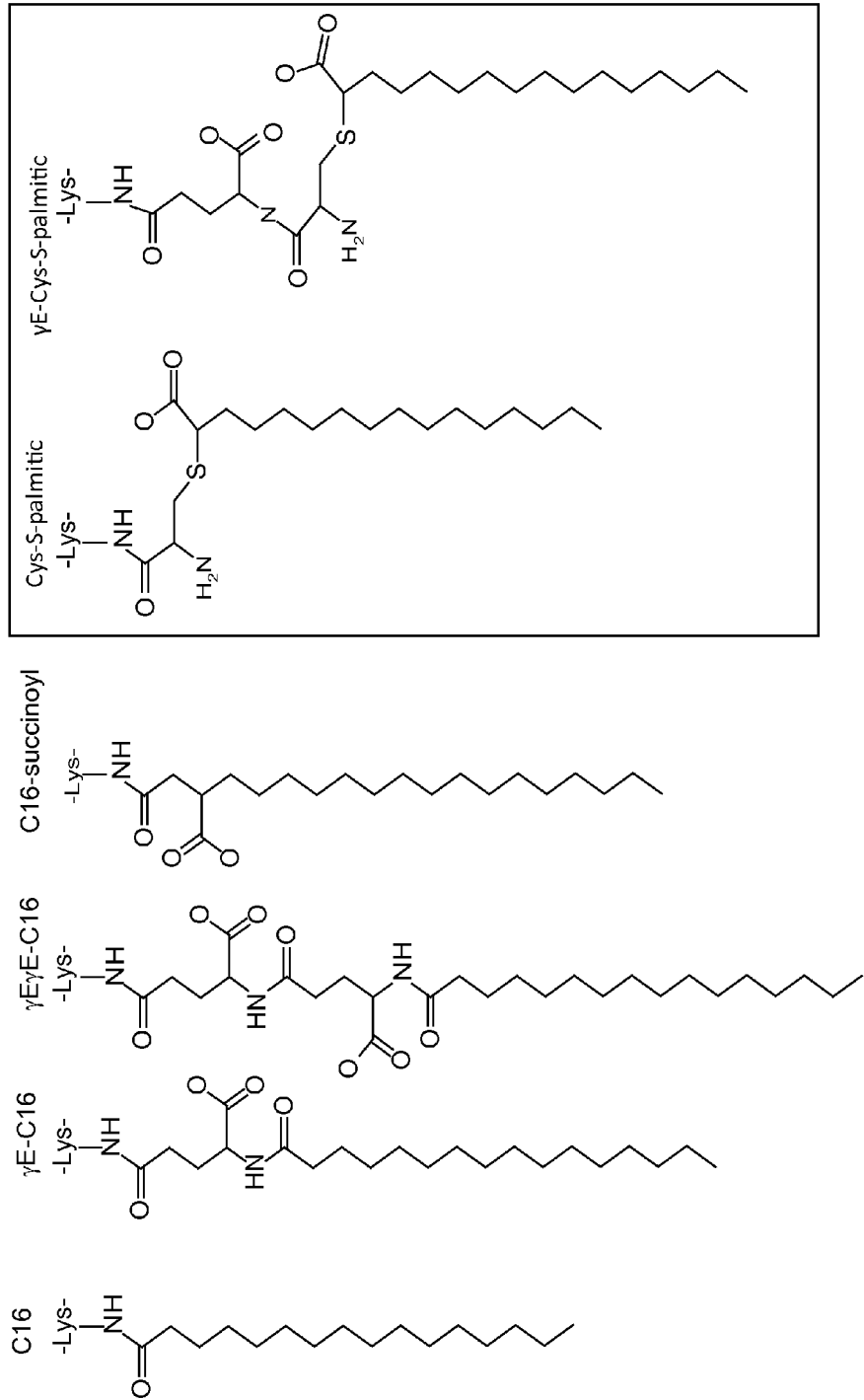
FIG. 7 depicts two types of S-palmityl alkylation of a Cys residue, wherein the Cys residue is part of an acylation spacer. In one type (left structure inside box), a Cys is attached to a peptide backbone Lys residue and the Cys is S-palmityl alkylated. In another type (right structure inside box), a Cys is part of a dipeptide spacer (gammaGlu-Cys) of which the gamma Glu is attached to a peptide backbone Lys and the Cys is S-palmityl alkylated.

In yet other embodiments, the amino acid comprising a side chain thiol is an amino acid of Formula III. In some exemplary embodiments, the amino acid of Formula III is the amino acid wherein n is 1 (Cys). In some or any exemplary embodiments, the amino acid of Formula III is covalently attached to an alkyl group, e.g., a non-functionalized or functionalized carbon chain. In exemplary aspects, the amino acid is S-palmityl-alkylated (i.e. S-palmitate-alkylated) in which the sulfur atom of a Cys residue is covelantly bound to the β carbon of palmitate. In other embodiments, the amino acid of Formula III is covalently bound to the β carbon of a Cn acetate through the sulfur atom of a Cys residue, wherein n is an integer from 4 to 30. Examples of different ways to S-palmityl alkylate are shown in FIGS. 6 and 7.

In yet other embodiments, the amino acid comprising a side chain amine, hydroxyl, or thiol is a disubstituted amino acid comprising the same structure of Formula I, Formula II, or Formula III, except that the hydrogen bonded to the alpha carbon of the amino acid of Formula I, Formula II, or Formula III is replaced with a second side chain.

Alkylation Spacers

In alternative embodiments, the non-native alkyl group is linked via a spacer to an amino acid of the GIP agonist peptide, wherein the spacer is positioned between the amino acid of the GIP agonist peptide and the non-native alkyl group. In some embodiments, the GIP agonist peptide is covalently bound to the spacer, which is covalently bound to the non-native alkyl group.

In exemplary embodiments, the glucagon analog is modified to comprise a non-native alkyl group by alkylation of an amine, hydroxyl, or thiol of a spacer, which spacer is attached to a side chain of an amino acid at one of positions 9, 10, 12, 13, 14, 16, 17, 20, or 37-43 (e.g., at any one of positions 10, 14, and 40). In exemplary embodiments, the alkyl group is attached to the spacer by reacting the amine, hydroxyl, or thiol of the spacer with an alkyl group that has a leaving group (e.g., halogen, sulfonate ester, pyridylthiol, ammonium salt, phenoxyl).

The amino acid to which the spacer is attached can be any amino acid comprising a moiety which permits linkage to the spacer. For example, an amino acid comprising a side chain $NH_2$, —OH, or —COOH (e.g., Lys, Orn, Ser, Asp, or Glu) is suitable. In this respect, the alkylated glucagon analog can comprise a modified amino acid sequence of SEQ ID NO: 1, comprising one or more of the amino acid modifications described herein, with at least one of the amino acids at positions 9, 10, 12, 13, 14, 16, 17, 20, or 37-43 (e.g., at any one or more of positions 10, 14, and 40). modified to any amino acid comprising a side chain amine, hydroxyl, or carboxylate.

In some embodiments, the spacer is an amino acid comprising a side chain amine, hydroxyl, or thiol, or a dipeptide or tripeptide comprising an amino acid comprising a side chain amine, hydroxyl, or thiol. The amino acid to which the spacer is attached can be any amino acid (e.g., a singly or doubly α-substituted amino acid) comprising a moiety which permits linkage to the spacer. For example, an amino acid comprising a side chain $NH_2$, —OH, or —COOH (e.g., Lys, Orn, Ser, Asp, or Glu) is suitable. In this respect, the GIP agonist peptide in some aspects comprises the amino acid sequence of SEQ ID NO: 1, or a modified amino acid sequence thereof comprising one or more of the amino acid modifications described herein, wherein at least one of the amino acids at positions 9, 10, 12, 13, 14, 16, 17, 20, and 37-43 (e.g., at any one of positions 10, 14, and 40) is an amino acid comprising a side chain amine, hydroxyl, or carboxylate.

In some embodiments, the spacer is an amino acid comprising a side chain amine, hydroxyl, or thiol, or a dipeptide or tripeptide comprising an amino acid comprising a side chain amine, hydroxyl, or thiol.

When the alkyl group is attached through an amine group of a spacer, the alkyl group in some aspects is attached through the alpha amine or through a side chain amine of the spacer amino acid. In the instance in which the alkyl group is attached via an alpha amine, the amino acid of the spacer can be any amino acid. For example, the amino acid of the spacer can be a hydrophobic amino acid, e.g., Gly, Ala, Val, Leu, Ile, Trp, Met, Phe, Tyr, 6-amino hexanoic acid, 5-aminovaleric acid, 7-aminoheptanoic acid, and 8-aminooctanoic acid. Alternatively, in some aspects, the amino acid of the spacer is an acidic residue, e.g., Asp, Glu, homoglutamic acid, homocystcic acid, cysteic acid, gamma-glutamic acid.

In the instance in which the alkyl group is attached through a side chain amine of the amino acid spacer, the spacer is an amino acid comprising a side chain amine, e.g., an amino acid of Formula I (e.g., Lys or Orn). In this instance, it is possible for both the alpha amine and the side chain amine of the amino acid of the spacer to be attached to an alkyl group, such that the GIP agonist peptide is dialkylated. Embodiments of the invention include such dialkylated molecules. In some embodiments, the alkyl group is attached to a 4-amino-Phe, p-amino phenylglycine, p-amino homophenylalanine, or 3-amino tyrosine.

When the alkyl group is attached through a hydroxyl group of a spacer, the amino acid or one of the amino acids of the dipeptide or tripeptide can be an amino acid of Formula II. In a specific exemplary embodiment, the amino acid is Ser. In similar exemplary embodiments, the alkyl group is attached to a Thr or homothreonine. In similar exemplary embodiments, the alkyl group is attached via the hydroxyl of an aromatic amino acid comprising a side chain hydroxyl, e.g., tyrosine, homotyrosine, methyl-tyrosine, or 3-amino tyrosine.

When the alkyl group is attached through a thiol group of a spacer, the amino acid or one of the amino acids of the dipeptide or tripeptide can be an amino acid of Formula III. In a specific exemplary embodiment, the amino acid is Cys. When the alkyl group is attached through a thiol group of a spacer, the amino acid or one of the amino acids of the dipeptide or tripeptide can be an amino acid of Formula III. In a specific exemplary embodiment, the amino acid is Cys. In exemplary embodiments, the spacer is a Cys residue, which is covalently attached to an alkyl group, e.g., a non-functionalized or functionalized carbon chain. In exemplary aspects, the Cys residue is S-palmityl alkylated (i.e., S-palmitate alkylated), optionally, wherein the Cys residue is attached to a Lys residue which is part of the peptide backbone. In alternative embodiments, the spacer is a dipeptide comprising a Cys residue, which is covalently attached to an alkyl group. In exemplary aspects, the Cys is S-palmityl alkylated, and the Cys is attached to another amino acid of the spacer, which, in turn, is attached to, e.g., a Lys residue which is part of the peptide backbone. Further exemplification of S-palmityl alkylation is provided herein in Example 20.

In other exemplary embodiments, the spacer is a bifunctional spacer comprising (i) a first end comprising a leaving group that reacts with an alkyl group that comprises an amine, hydroxyl, or thiol and (ii) a second end comprising a functional group that reacts with the side chain of the amino acid of the glucagon analog. In exemplary aspects, the amino acid of the glucagon analog is an amino acid of Formula I (e.g., Lys) or Formula II (e.g., Ser) and the amino acid is functionalized with a carboxylic acid or carboxylic acid derivative. In alternative exemplary aspects, the amino acid of the glucagon analog is an amino acid of Formula III and the amino acid is functionalized with a haloacetabmide, maleimido, or disulfide. In some embodiments, the amino acid of the glucagon analog is an amino acid comprising a side chain carboxylate, e.g., Glu, Asp, functionalized with an amine, hydroxyl, or thiol.

In some or any embodiments, the spacer is a hydrophilic bifunctional spacer. In exemplary embodiments, the hydrophilic bifunctional spacer comprises two or more reactive groups, e.g., an amine, a hydroxyl, a thiol, and a carboxyl group or any combinations thereof. In exemplary embodiments, the hydrophilic bifunctional spacer comprises a hydroxyl group and a carboxylate. In other embodiments, the hydrophilic bifunctional spacer comprises an amine group and a carboxylate. In other embodiments, the hydrophilic bifunctional spacer comprises a thiol group and a carboxylate. In a specific embodiment, the spacer comprises an amino poly(alkyloxy)carboxylate. In this regard, the spacer can comprise, for example, $NH_2(CH_2CH_2O)_n(CH_2)_m COOH$, wherein m is any integer from 1 to 6 and n is any integer from 2 to 12, such as, e.g., 8-amino-3,6-dioxaoctanoic acid, which is commercially available from Peptides International, Inc. (Louisville, Ky.).

In exemplary embodiments, the spacer comprises a small polyethylene glycol moiety (PEG) comprising a structure $[-O-CH_2-CH_2-]_n$, wherein n is an integer between 2 and 16, (e.g., 2, 3, 4, 5, 6, 7, 8, 9, 10, 11, 12, 13, 14, 15, 16). Such small PEGS are referred to herein as a "miniPEG." In exemplary aspects, the miniPEG is a functionalized miniPEG comprising one or more functional groups. Suitable functional groups include, but are not limited to, an amine, a hydroxyl, a thiol, and a carboxyl group or any combinations thereof. In exemplary aspects, the miniPEG is a miniPEG acid comprising a structure $\{[-O-CH_2-CH_2-]_n-COO-\}$, wherein n is defined as above. In exemplary aspects, the miniPEG is an amido miniPEG comprising a structure $\{-N-CH_2-CH_2-[-O-CH_2-CH_2-]_n\}$, wherein n is defined as above. In exemplary aspects, the miniPEG is an amido miniPEG acid comprising a structure $\{-N-CH_2-CH_2-[-O-CH_2-CH_2-]_n-COO-\}$, wherein n is defined as above. Suitable reagents for use in alkylating an amino acid with a miniPEG are commercially available from vendors, such as Peptides International (Louisville, Ky.).

In some embodiments, the spacer is a hydrophobic bifunctional spacer. Hydrophobic bifunctional spacers are known in the art. See, e.g., *Bioconjugate Techniques*, G. T. Hermanson (Academic Press, San Diego, Calif., 1996), which is incorporated by reference in its entirety. In exemplary embodiments, the hydrophobic bifunctional spacer comprises two or more reactive groups, e.g., an amine, a hydroxyl, a thiol, and a carboxyl group or any combinations thereof. In exemplary embodiments, the hydrophobic bifunctional spacer comprises a hydroxyl group and a carboxylate. In other embodiments, the hydrophobic bifunctional spacer comprises an amine group and a carboxylate. In other embodiments, the hydrophobic bifunctional spacer comprises a thiol group and a carboxylate. Suitable hydrophobic bifunctional spacers comprising a carboxylate and a hydroxyl group or a thiol group are known in the art and include, for example, 8-hydroxyoctanoic acid and 8-mercaptooctanoic acid.

In some embodiments, the bifunctional spacer is not a dicarboxylic acid comprising an unbranched, methylene of 1-7 carbon atoms between the carboxylate groups. In some embodiments, the bifunctional spacer is a dicarboxylic acid comprising an unbranched, methylene of 1-7 carbon atoms between the carboxylate groups.

The spacer (e.g., amino acid, dipeptide, tripeptide, hydrophilic bifunctional spacer, or hydrophobic bifunctional spacer) in specific embodiments is 3 to 10 atoms (e.g., 6 to 10 atoms, (e.g., 6, 7, 8, 9, or 10 atoms) in length. In more specific embodiments, the spacer is about 3 to 10 atoms (e.g., 6 to 10 atoms) in length and the non-native alkyl group is a C12 to C18 alkyl, e.g., C14 alkyl, C16 alkyl, such that the total length of the spacer and alkyl group is 14 to 28 atoms, e.g., about 14, 15, 16, 17, 18, 19, 20, 21, 22, 23, 24, 25, 26, 27, or 28 atoms. In some embodiments, the length of the spacer and alkyl group is 17 to 28 (e.g., 19 to 26, 19 to 21) atoms.

In accordance with some or any of the foregoing embodiments, the bifunctional spacer can be a synthetic or naturally occurring amino acid (including, but not limited to, any of those described herein) comprising an amino acid backbone that is 3 to 10 atoms in length (e.g., 6-amino hexanoic acid, 5-aminovaleric acid, 7-aminoheptanoic acid, and 8-aminooctanoic acid). Alternatively, the spacer can be a dipeptide or tripeptide spacer having a peptide backbone that is 3 to 10 atoms (e.g., 6 to 10 atoms) in length. Each amino acid of the dipeptide or tripeptide spacer can be the same as or different from the other amino acid(s) of the dipeptide or tripeptide and can be independently selected from the group consisting of: naturally-occurring or coded and/or non-coded or non-naturally occurring amino acids, including, for example, any of the D or L isomers of the naturally-occurring amino acids (Ala, Cys, Asp, Glu, Phe, Gly, His, Ile, Lys, Leu, Met, Asn, Pro, Arg, Ser, Thr, Val, Trp, Tyr), or any D or L isomers of the non-naturally occurring or non-coded amino acids selected from the group consisting of: β-alanine (β-Ala), N-α-methyl-alanine (Me-Ala), aminobutyric acid (Abu), γ-aminobutyric acid (γ-Abu), aminohexanoic acid (ε-Ahx), aminoisobutyric acid (Aib), aminomethylpyrrole carboxylic acid, aminopiperidinecarboxylic acid, aminoserine (Ams), aminotetrahydropyran-4-carboxylic acid, arginine N-methoxy-N-methyl amide, β-aspartic acid (β-Asp), azetidine carboxylic acid, 3-(2-benzothiazolyl)alanine, α-tert-butylglycine, 2-amino-5-ureido-n-valeric acid (citrulline, Cit), β-Cyclohexylalanine (Cha), acetamidomethyl-cysteine, diaminobutanoic acid (Dab), diaminopropionic acid (Dpr), dihydroxyphenylalanine (DOPA), dimethylthiazolidine (DMTA), γ-Glutamic acid (γ-Glu), homoserine (Hse), hydroxyproline (Hyp), isoleucine N-methoxy-N-methyl amide, methyl-isoleucine (MeIle), isonipecotic acid (Isn), methyl-leucine (MeLeu), methyl-lysine, dimethyl-lysine, trimethyl-lysine, methanoproline, methionine-sulfoxide (Met(O)), methionine-sulfone (Met($O_2$)), norleucine (Nle), methyl-norleucine (Me-Nle), norvaline (Nva), ornithine (Orn), para-aminobenzoic acid (PABA), penicillamine (Pen), methylphenylalanine (MePhe), 4-Chlorophenylalanine (Phe(4-Cl)), 4-fluorophenylalanine (Phe(4-F)), 4-nitrophenylalanine (Phe(4-$NO_2$)), 4-cyanophenylalanine ((Phe (4-CN)), phenylglycine (Phg), piperidinylalanine, piperidinylglycine, 3,4-dehydroproline, pyrrolidinylalanine, sarcosine (Sar), selenocysteine (Sec), O-Benzyl-phosphoserine, 4-amino-3-hydroxy-6-methylheptanoic acid (Sta), 4-amino-5-cyclohexyl-3-hydroxypentanoic acid (ACHPA), 4-amino-3-hydroxy-5-phenylpentanoic acid (AHPPA), 1,2, 3,4,-tetrahydro-isoquinoline-3-carboxylic acid (Tie), tetrahydropyranglycine, thienylalanine (Thi), O-benzyl-phosphotyrosine, O-Phosphotyrosine, methoxytyrosine, ethoxytyrosine, O-(bis-dimethylamino-phosphono)-tyrosine, tyrosine sulfate tetrabutylamine, methyl-valine (Me-Val), and alkylated 3-mercaptopropionic acid. In exemplary aspects, the spacer is a Cys residue.

In some embodiments, the spacer comprises an overall negative charge, e.g., comprises one or two negative-charged amino acids. In some embodiments, the dipeptide is not any of the dipeptides of general structure A-B, wherein A is selected from the group consisting of Gly, Gln, Ala, Arg, Asp, Asn, Ile, Leu, Val, Phe, and Pro, wherein B is selected from the group consisting of Lys, His, Trp. In some embodiments, the amino acids of the dipeptide spacer are selected from the group consisting of: Ala, β-Ala, Leu, Pro, γ-aminobutyric acid, Glu, and γ-Glu.

In some exemplary embodiments, the GIP agonist peptide comprises an alkyl group upon alkylation of an amine, hydroxyl, or thiol of a spacer, which spacer is attached to a side chain of an amino acid at position 9, 10, 12, 13, 14, 16, 17, 20, or 37-43, (e.g., at any one or more of positions 10, 14, and 40), or at the C-terminal amino acid of the GIP agonist peptide.

In yet more specific embodiments, the alkyl group is attached to the amino acid at any of positions 9, 10, 12, 13, 14, 16, 17, 20, or 37-43 (e.g., at any one or more of positions 10, 14, and 40), of the peptide analog and the length of the spacer and alkyl group is 14 to 28 atoms. The amino acid at any of positions 9, 10, 12, 13, 14, 16, 17, 20, or 37-43, (e.g., at any one or more of positions 10, 14, and 40), in some aspects, is an amino acid of Formula I, e.g., Lys, or a disubstituted amino acid related to Formula I. In more specific embodiments, the peptide analog lacks an intramolecular bridge, e.g., a covalent intramolecular bridge. The glucagon analog, for example, can be a glucagon analog comprising one or more alpha, alpha-disubstituted amino acids, e.g., AIB, for stabilizing the alpha helix of the analog.

Alkyl Groups

The non-native alkyl group of the alkylated amino acid can be of any size, e.g., any length carbon chain, and can be linear or branched. In some specific embodiments, the alkyl group is a C4 to C30 alkyl. For example, the alkyl group can be any of a C4 alkyl, C6 alkyl, C8 alkyl, C10 alkyl, C12 alkyl, C14 alkyl, C16 alkyl, C18 alkyl, C20 alkyl, C22 alkyl, C24 alkyl, C26 alkyl, C28 alkyl, or a C30 alkyl. In some embodiments, the alkyl group is a C8 to C20 alkyl, e.g., a C14 alkyl or a C16 alkyl.

In exemplary embodiments, the non-native alkyl group of the alkylated amino acid is a functionalized linear or branched carbon chain of any length. In some specific embodiments, the carbon chain is a C4 to C30 alkyl. For example, the alkyl group can be any of a C4 alkyl, C6 alkyl, C8 alkyl, C10 alkyl, C12 alkyl, C14 alkyl, C16 alkyl, C18 alkyl, C20 alkyl, C22 alkyl, C24 alkyl, C26 alkyl, C28 alkyl, or a C30 alkyl. In some embodiments, the alkyl group is a C8 to C20 alkyl, e.g., a C14 alkyl or a C16 alkyl. In exemplary aspects, the functionalized carbon chain comprises a functional group, including, but not limited, carboxy, sulfhydryl, amine, ketyl, sulfoxyl or amido.

In exemplary embodiments, the non-native alkyl group is a carboxy-functionalized carbon chain of structure —Cx-COOH, wherein x is an integer, optionally an integer between 4-30 (e.g., 4, 5, 6, 7, 8, 9, 10, 11, 12, 13, 14, 15, 16, 17, 18, 19, 20, 21, 22, 23, 24, 25, 26, 27, 28, 29, 30), wherein the carboxy carbon is the alpha carbon and each of the carbons of Cx are designated beta, gamma, delta, epsilon, etc., wherein the beta carbon is attached to the alpha carbon. For example, wherein, when x is 4, the non-native alkyl group would be designated as follows: $C_\epsilon$—$C_\delta$—$C$—$C_\beta$—$C_\alpha$OOH. In exemplary embodiments, the carboxy-functionalized carbon chain is attached via a carbon other than the carboxy carbon, i.e., one of the carbons of Cx. In exemplary aspects, the carboxy-functionalized carbon chain is attached via the beta, gamma, delta, or epsilon carbon of the carboxy-functionalized carbon chain to the side chain of the alkylated amino acid. In alternative embodiments, the carboxy-functionalized carbon chain is attached via the beta, gamma, delta, or epsilon carbon of the carboxy-functionalized carbon chain to the side chain of a spacer which spacer is attached to the alkylated amino acid. In exemplary aspects, the carboxy-functionalized carbon chain is attached via the beta carbon of the carboxy-functionalized carbon chain to the side chain of the alkylated amino acid. In alternative embodiments, the carboxy-functionalized carbon chain is attached via the beta carbon of the carboxy-functionalized carbon chain to the side chain of a spacer which spacer is attached to the alkylated amino acid.

Methods of Attaching an Alkyl Group

Methods of attaching an alkyl group to an amino acid are known in the art. For example, an alkyl groups activated with a leaving group may be reacted with an amino acid comprising a nucleophilic side chain, e.g., a side chain comprising an amine, hydroxyl, or thiol. The leaving group in exemplary aspects is a halogen, sulfonate ester, pyridyl-thiol, ammonium salt, or phenoxyl.

In exemplary embodiments, the amino acid to be attached to an alkyl group is a Cys residue and the sulfur atom is alkylated, e.g., "S-alkylated." In exemplary embodiments, the sulfur of the Cys is reacted with the leaving group of an alkyl group comprising a carboxy-functionalized carbon chain of structure —Cx-COOH, wherein x is an integer, optionally an integer between 4-30 (e.g., 4, 5, 6, 7, 8, 9, 10, 11, 12, 13, 14, 15, 16, 17, 18, 19, 20, 21, 22, 23, 24, 25, 26, 27, 28, 29, 30), wherein the carboxy carbon is the alpha carbon and each of the carbons of Cx are designated beta, gamma, delta, epsilon, etc., wherein the beta carbon is attached to the alpha carbon. For example, wherein, when x is 4, the non-native alkyl group would be designated as follows: $C_\epsilon$—$C_\delta$—C—$C_\beta$—$C_\alpha$OOH. In exemplary embodiments, the carboxy-functionalized carbon chain is attached via a carbon other than the carboxy carbon, i.e., one of the carbons of Cx. In exemplary aspects, the carboxy-functionalized carbon chain is attached via the beta, gamma, delta, or epsilon carbon of the carboxy-functionalized carbon chain to the side chain of the alkylated amino acid. In alternative embodiments, the carboxy-functionalized carbon chain is attached via the beta, gamma, delta, or epsilon carbon of the carboxy-functionalized carbon chain to the side chain of a spacer which spacer is attached to the alkylated amino acid. In exemplary aspects, the carboxy-functionalized carbon chain is attached via the beta carbon of the carboxy-functionalized carbon chain to the side chain of the alkylated amino acid. In alternative embodiments, the carboxy-functionalized carbon chain is attached via the beta carbon of the carboxy-functionalized carbon chain to the side chain of a spacer which spacer is attached to the alkylated amino acid.

In exemplary aspects, the leaving group is a halogen, such as iodine, bromine, chlorine, or fluorine, sulfonate esters such as tosylate, triflates, or fluorosulfonates, pyridylthiol, ammonium salt, diazonium salts, nitrates, phosphates or phenoxyl.

In specific aspects, the alkyl group comprises an iodine leaving group and a carboxy-functionalized carbon chain comprising a total of 16 carbons (including the carbon of the carboxylate). Alkylation with such an iodo-carboxylic acid may be referred to as "S-palmityl alkylation" which is synonymous with "S-palmitate alkylation." Further exemplification of S-palmityl alkylation is provided herein in Examples 1 and 20.

Additional Alkyl Groups

The peptide in some aspects comprises an alkylated amino acid at a position other than positions 9, 10, 12, 13, 14, 16, 17, 20, or 37-43 (e.g., at any one or more of positions 10, 14, and 40). The location of the alkylated amino acid may be any position within the GIP agonist peptide, including any of positions 1-29, a position C-terminal to the $29^{th}$ amino acid (e.g., the amino acid at position 30, 31, 32, 33, 34, 35, 36, 44, 45, 46, 47, etc., at a position within a C-terminal extension or at the C-terminus), optionally together with a second alkylated amino acid at any of positions 9, 10, 12, 13, 14, 16, 17, 20, or 37-43 (e.g., at any one or more of positions 10, 14, and 40), provided that the GIP agonist activity of the peptide analog is retained, if not enhanced. Nonlimiting examples include positions 5, 7, 11, 13, 14, 17, 18, 19, 21, 24, 27, 28, or 29.

Consistent with the foregoing, the glucagon analog, in exemplary aspects, comprises two (or more) alkylated amino acids. In exemplary aspects, all of the alkylated amino acids are located at two positions of positions 9, 10, 12, 13, 14, 16, 17, 20, or 37-43 (e.g., at any one or more of positions 10, 14, and 40). In exemplary aspects, the peptide comprising a first alkylated amino acid at position 10 and a second alkylated amino acid at position 40.

In yet additional exemplary embodiments, the glucagon analog comprises additional alkyl groups attached to one amino acid of the peptide backbone. The two (or more) alkyl groups may be the same alkyl group or different alkyl groups, arranged in a branched or linear formation. For example, to achieve a branched formation, the glucagon analog may comprise one alkylated amino acid (which is part of the peptide backbone) attached to a spacer comprising at least three functional groups—at least two of which are each covalently attached to an alkyl group and one of which is attached to the alkylated amino acid of the peptide backbone. In exemplary aspects, a branched formation may be achieved through, e.g., a Lys residue comprising two amine groups (a side chain amine and an alpha amine) for direct attachment to a fatty alkyl group or indirect attachment to a fatty alkyl group via a spacer. In exemplary aspects, an additional spacer may be placed between the amino acid of the peptide backbone and the spacer comprising at least three functional groups. For example, the amino acid of the peptide backbone may be attached (e.g., via its side chain) to a first spacer, which, in turn, is attached to a second spacer, wherein the second spacer comprises at least three functional groups—at least two of which are each covalently attached to an alkyl group and one of which is attached to the first spacer.

In exemplary aspects, wherein the alkyl groups are arranged in a linear formation, the glucagon analog comprises one alkylated amino acid (which is part of the peptide backbone) directly attached to a first alkyl group, which, in turn, is attached to a spacer, which, in turn, is attached to a second alkyl group.

Exemplary structures of dual alkylated compounds are derivable from the dual acylated compounds depicted in FIG. 5A.

Hydrophilic Moieties and Alkyl Groups

The GIP agonist peptides comprising an alkylated amino acid optionally further comprises a hydrophilic moiety. In some specific embodiments the hydrophilic moiety comprises a polyethylene glycol (PEG) chain. The incorporation of a hydrophilic moiety in some aspects is accomplished through any suitable means, such as any of the methods described herein. In this regard, the GIP agonist peptide can comprise SEQ ID NO: 1, including any of the modifications described herein, in which at least one of the amino acids at any of positions 9, 10, 12, 13, 14, 16, 17, 20, and 37-43 (e.g., at any one or more of positions 10, 14, and 40) of the GIP agonist peptide comprises an alkyl group and at least one of the amino acids at position 16, 17, 21, 24, or 29, a position within a C-terminal extension, or the C-terminal amino acid is a Cys, Lys, Orn, homo-Cys, or Ac-Phe, of which the side chain is covalently bonded to a hydrophilic moiety (e.g., PEG). In some embodiments, the amino acid at any of positions 9, 10, 12, 13, 14, 16, 17, 20, and 37-43 (e.g., at any one or more of positions 10, 14, and 40) of the GIP agonist peptide is attached (optionally via a spacer) to the alkyl group and that amino acid is further attached to a hydrophilic moiety or is further attached to a Cys, Lys, Orn, homo-Cys, or Ac-Phe, which is attached to the hydrophilic moiety.

Alternatively, the alkylated glucagon analog can comprise a spacer, wherein the spacer is both alkylated and modified to comprise the hydrophilic moiety. Nonlimiting examples of suitable spacers include a spacer comprising one or more amino acids selected from the group consisting of Cys, Lys, Orn, homo-Cys, and Ac-Phe.

In some aspects, the GIP agonist peptide in some embodiments are alkylated at the same amino acid position where a hydrophilic moiety is linked, or at a different amino acid position. Nonlimiting examples include alkylation at position 9, 10, 12, 13, 14, 16, 17, 20, or 40 (e.g., at any one or more of positions 10, 14, and 40) and pegylation at one or more positions in the C-terminal portion of the glucagon analog, e.g., position 24, 28 or 29, within a C-terminal extension (e.g., 37-43), or at the C-terminus (e.g., through adding a C-terminal Cys).

Additional Alkyl Group Embodiment

In specific embodiments, the GIP agonist peptide comprising an alkylated amino acid lacks an intramolecular bridge, e.g., a covalent intramolecular bridge (e.g., a lactam bridge).

Stabilization of the Alpha Helix and Alpha Helix Stabilizing Amino Acids

Without being bound to any particular theory, the GIP agonist peptides which are glucagon analogs comprise a helical structure, e.g., an alpha helix. In some or any embodiments, the GIP agonist peptide comprises amino acids which stabilize the alpha helical structure. Accordingly, in some aspects, the GIP agonist peptide comprises one or more alpha helix stabilizing amino acids. As used herein, the term "alpha helix promoting amino acid" is used interchangeably with the term "alpha helix stabilizing amino acid" and refers to an amino acid which provides increased stability to an alpha helix of the GIP agonist peptides of which it is a part. Alpha helix promoting amino acids are known in the art. See, for example, Lyu et al., *Proc Natl Acad Sci U.S.A.* 88: 5317-5320 (1991); Branden & Tooze, *Introduction to Protein Structure*, Garland Publishing, New York, N.Y., 1991; Fasman, *Prediction of Protein Structure and the Principles of Protein Conformation*, ed. Fasman, Plenum, NY, 1989). Suitable alpha helix promoting amino acids for purposes herein include, but are not limited to: alanine, norvaline, norleucine, alpha aminobutyric acid, alpha-aminoisobutyric acid (AIB), leucine, isoleucine, valine, and the like. In some embodiments, the alpha helix promoting amino acid is any amino acid which is part of an alpha helix found in a naturally-occurring protein, e.g., Leu, Phe, Ala, Met, Gly, Ile, Ser, Asn, Glu, Asp, Lys, Arg.

In exemplary embodiments, the alpha helix promoting amino acid provides more stability to the alpha helix as compared to glycine or alanine. In exemplary embodiments, the alpha helix promoting amino acid is an alpha, alpha di-substituted amino acid, e.g., AIB.

Alpha Helix: Position of Alpha Helix Promoting Amino Acids

In some or any embodiments of the present disclosures, the GIP agonist peptide comprises an amino acid sequence which is similar to native glucagon (SEQ ID NO: 1) and the GIP agonist peptide comprises at least one alpha helix promoting amino acid at one or more of positions 16-21 of the peptide analog (e.g., one or more of positions 16, 17, 18, 19, 20, 21). In some or any embodiments, the peptide analog comprises an alpha helix promoting amino acid at one, two, three, or all of positions 16, 17, 20, and 21.

Alpha Helix: Alpha, Alpha Di-Substituted Amino Acids

In some or any embodiments, the alpha helix promoting amino acid is an alpha,alpha di-substituted amino acid. In specific embodiments, the alpha, alpha di-substituted amino acid comprises $R^1$ and $R^2$, each of which is bonded to the alpha carbon, wherein each of $R^1$ and $R^2$ is independently selected from the group consisting of C1-C4 alkyl, optionally substituted with a hydroxyl, amide, thiol, halo, or $R^1$ and $R^2$ together with the alpha carbon to which they are attached form a ring (e.g., a C3-C8 ring). In exemplary embodiments, each of $R^1$ and $R^2$ is selected from the group consisting of: methyl, ethyl, propyl, and n-butyl, or $R^1$ and $R^2$ together form a cyclooctane or cycloheptane (e.g., 1-aminocyclooctane-1-carboxylic acid). In exemplary embodiments, $R^1$ and $R^2$ are the same. In other embodiments, $R^1$ is different from $R^2$. In exemplary aspects, each of $R^1$ and $R^2$ is a C1-C4 alkyl. In some aspects, each of $R^1$ and $R^2$ is a C1 or C2 alkyl. In exemplary embodiments, each of $R^1$ and $R^2$ is methyl, such that the alpha, alpha disubstituted amino acid is alpha-aminoisobutyric acid (AIB). In other exemplary embodiments, the alpha, alpha disubstituted amino acid is ACPC.

In some aspects, the GIP agonist peptide described herein comprises one or more alpha, alpha di-substituted amino acids and the GIP agonist peptide specifically lacks a covalent intramolecular bridge (e.g., a lactam), since the alpha, alpha disubstituted amino acid is capable of stabilizing the alpha helix in the absence of a covalent bridge. In some aspects, the GIP agonist peptide comprises one or more alpha, alpha di-substituted amino acids at the C-terminus (around positions 12-29). In some or any embodiments, one, two, three, four or more of positions 16, 17, 18, 19, 20, 21, 24 or 29 or, one, two, three, four, five, or all of positions 16, 17, 18, 19, 20, or 21 of the GIP agonist peptide is substituted with an α,α-disubstituted amino acid, e.g., amino iso-butyric acid (AIB), an amino acid disubstituted with the same or a different group selected from methyl, ethyl, propyl, and n-butyl, or with a cyclooctane or cycloheptane (e.g., 1-aminocyclooctane-1-carboxylic acid). For example, substitution of position 20 with AIB enhances GIP activity, in the absence of an intramolecular bridge, e.g., a non-covalent intramolecular bridge (e.g., a salt bridge) or a covalent intramolecular bridge (e.g., a lactam). In some or any embodiments, one, two, three or more of positions 16, 20, 21 or 24 are substituted with AIB. In exemplary embodiments, one, two or all of the amino acids corresponding to positions 2, 16, and 20 of native human glucagon (SEQ ID NO: 1) are substituted with an alpha, alpha disubstituted amino acid such as AIB. In exemplary aspects, the glucagon analog comprises an AIB at positions 2 and 16 or at positions 2 and 20. In other exemplary aspects, the glucagon analog comprises a D-Ser at position 2 and an AIB at position 16 or position 20.

Alpha Helix: Intramolecular Bridges

In some exemplary embodiments, the alpha helix promoting amino acid is an amino acid which is linked to another amino acid of the GIP agonist peptide via an intramolecular bridge. In such embodiments, each of these two amino acids linked via an intramolecular bridge is considered an alpha helix promoting amino acid. In exemplary embodiments, the GIP agonist peptide comprises one or two intramolecular bridges. In exemplary embodiments, the GIP agonist peptide comprises one intramolecular bridge in combination with at least one other alpha helix promoting amino acid, e.g., an alpha, alpha-disubstituted amino acid.

In some embodiments, the intramolecular bridge is a bridge which connects two parts of the GIP agonist peptide via noncovalent bonds, including, for example, van der Waals interactions, hydrogen bonds, ionic bonds, hydrophobic interactions, dipole-dipole interactions, and the like. In this regard, the glucagon analog comprises a non-covalent intramolecular bridge. In some embodiments, the non-covalent intramolecular bridge is a salt bridge.

In some embodiments, the intramolecular bridge is a bridge which connects two parts of the GIP agonist peptide via covalent bonds. In this regard, the GIP agonist peptide comprises a covalent intramolecular bridge.

In some embodiments, the intramolecular bridge (e.g., non-covalent intramolecular bridge, covalent intramolecular bridge) is formed between two amino acids that are 3 amino acids apart, e.g., amino acids at positions i and i+4, wherein i is any integer between 12 and 25 (e.g., 12, 13, 14, 15, 16, 17, 18, 19, 20, 21, 22, 23, 24, and 25). More particularly, the side chains of the amino acid pairs 12 and 16, 16 and 20, 20 and 24 or 24 and 28 (amino acid pairs in which i=12, 16, 20, or 24) are linked to one another and thus stabilize the alpha helix. Alternatively, i can be 17. In some specific embodiments, the GIP agonist peptide comprises an intramolecular bridge between amino acids 17 and 21. In some specific embodiments, the GIP agonist peptide comprises an intramolecular bridge between the amino acids at positions 16 and 20 or 12 and 16 and a second intramolecular bridge between the amino acids at positions 17 and 21. GIP agonist peptides comprising one or more intramolecular bridges are contemplated herein. In specific embodiments, wherein the amino acids at positions i and i+4 are joined by an intramolecular bridge, the size of the linker is about 8 atoms, or about 7-9 atoms.

In other embodiments, the intramolecular bridge is formed between two amino acids that are two amino acids apart, e.g., amino acids at positions j and j+3, wherein j is any integer between 12 and 26 (e.g., 12, 13, 14, 15, 16, 17, 18, 19, 20, 21, 22, 23, 24, 25, and 26). In some specific embodiments, j is 17. In specific embodiments, wherein amino acids at positions j and j+3 are joined by an intramolecular bridge, the size of the linker is about 6 atoms, or about 5 to 7 atoms.

In yet other embodiments, the intramolecular bridge is formed between two amino acids that are 6 amino acids apart, e.g., amino acids at positions k and k+7, wherein k is any integer between 12 and 22 (e.g., 12, 13, 14, 15, 16, 17, 18, 19, 20, 21, and 22). In some specific embodiments, k is 12, 13, or 17. In an exemplary embodiment, k is 17.

Alpha Helix: Amino Acids Involved in Intramolecular Bridges

Examples of amino acid pairings that are capable of bonding (covalently or non-covalently) to form a six-atom linking bridge include Orn and Asp, Glu and an amino acid of Formula I, wherein n is 2, and homoglutamic acid and an amino acid of Formula I, wherein n is 1, wherein Formula I is:

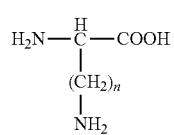
[Formula I]

wherein n = 1 to 4

Examples of amino acid pairings that are capable of bonding to form a seven-atom linking bridge include Orn-Glu (lactam ring); Lys-Asp (lactam); or Homoser-Homoglu (lactone). Examples of amino acid pairings that may form an eight-atom linker include Lys-Glu (lactam); Homolys-Asp (lactam); Orn-Homoglu (lactam); 4-aminoPhe-Asp (lactam); or Tyr-Asp (lactone). Examples of amino acid pairings that may form a nine-atom linker include Homolys-Glu (lactam); Lys-Homoglu (lactam); 4-aminoPhe-Glu (lactam); or Tyr-Glu (lactone). Any of the side chains on these amino acids may additionally be substituted with additional chemical groups, so long as the three-dimensional structure of the alpha-helix is not disrupted. One of ordinary skill in the art can envision alternative pairings or alternative amino acid analogs, including chemically modified derivatives, that would create a stabilizing structure of similar size and desired effect. For example, a homocysteine-homocysteine disulfide bridge is 6 atoms in length and may be further modified to provide the desired effect.

Even without covalent linkage, the amino acid pairings described above (or similar pairings that one of ordinary skill in the art can envision) may also provide added stability to the alpha-helix through non-covalent bonds, for example, through formation of salt bridges or hydrogen-bonding interactions. Accordingly, salt bridges may be formed between: Orn and Glu; Lys and Asp; Homo-serine and Homo-glutamate; Lys and Glu; Asp and Arg; Homo-Lys and Asp; Orn and Homo-Glutamate; 4-aminoPhe and Asp; Tyr and Asp; Homo-Lys and Glu; Lys and Homo-Glu; 4-aminoPhe and Glu; or Tyr and Glu. In some embodiments, the analog comprises a salt bridge between any of the following pairs of amino acids: Orn and Glu; Lys and Asp; Lys and Glu; Asp and Arg; Homo-Lys and Asp; Orn and Homo-Glutamate; Homo-Lys and Glu; and Lys and Homo-Glu. Salt bridges may be formed between other pairs of oppositely charged side chains. See, e.g., Kallenbach et al., *Role of the Peptide Bond in Protein Structure and Folding*, in The Amide Linkage: Structural Significance in Chemistry, Biochemistry, and Materials Science, John Wiley & Sons, Inc. (2000).

In some embodiments, the non-covalent intramolecular bridge is a hydrophobic bridge. In accordance with one embodiment, the alpha helix of the analog is stabilized through the incorporation of hydrophobic amino acids at positions j and j+3 or i and i+4. For instance, i can be Tyr and i+4 can be either Val or Leu; i can be Phe and i+4 can be Met; or i can be Phe and i+4 can be Ile. It should be understood that, for purposes herein, the above amino acid pairings can be reversed, such that the indicated amino acid at position i could alternatively be located at i+4, while the i+4 amino acid can be located at the i position. It should also be understood that suitable amino acid pairings can be formed for j and j+3.

Alpha Helix: Covalent Intramolecular Bridge

In some embodiments, the covalent intramolecular bridge is a lactam ring or lactam bridge. The size of the lactam ring can vary depending on the length of the amino acid side chains, and in one embodiment the lactam is formed by linking the side chains of an ornithine to a aspartic acid side chain. Lactam bridges and methods of making the same are known in the art. See, for example, Houston, Jr., et al., *J Peptide Sci* 1: 274-282 (2004), and Example 1 herein. In some embodiments, the analog comprises a modified sequence of SEQ ID NO: 1 and a lactam bridge between i and i+4, wherein i is as defined herein above. In some embodiments, the GIP agonist peptide comprises two lactam bridges: one between the amino acids at positions 16 and 20 and another between the amino acids at positions 17 and 21. In some embodiments, the GIP agonist peptide comprises one lactam bridge and one salt bridge. Further exemplary embodiments, are described herein in the section entitled "EXAMPLES." Further exemplary embodiments include the following pairings, optionally with a lactam bridge: Glu at position 12 with Lys at position 16; native Lys at position 12 with Glu at position 16; Glu at position 16 with Lys at position 20; Lys at position 16 with Glu at position 20; Glu at position 20 with Lys at position 24; Lys at position 20 with Glu at position 24; Glu at position 24 with Lys at position 28; Lys at position 24 with Glu at position 28.

In some embodiments, the covalent intramolecular bridge is a lactone. Suitable methods of making a lactone bridge are known in the art. See, for example, Sheehan et al., *J Am Chem Soc* 95: 875-879 (1973).

In some aspects, olefin metathesis is used to cross-link one or two turns of the alpha helix of the analog using an all-hydrocarbon cross-linking system. The GIP agonist peptide in this instance comprises α-methylated amino acids bearing olefinic side chains of varying length and configured with either R or S stereochemistry at the j and j+3 or i and i+4 positions. In some embodiments, the olefinic side comprises $(CH_2)n$, wherein n is any integer between 1 to 6. In some embodiments, n is 3 for a cross-link length of 8 atoms. In some embodiments, n is 2 for a cross-link length of 6 atoms. An exemplary GIP agonist peptide comprising an olefinic cross-link is described herein as SEQ ID NO: 17. Suitable methods of forming such intramolecular bridges are described in the art. See, for example, Schafmeister et al., *J. Am. Chem. Soc.* 122: 5891-5892 (2000) and Walensky et al., *Science* 305: 1466-1470 (2004). In alternative embodiments, the analog comprises O-allyl Ser residues located on adjacent helical turns, which are bridged together via ruthenium-catalyzed ring closing metathesis. Such procedures of cross-linking are described in, for example, Blackwell et al., *Angew, Chem., Int. Ed.* 37: 3281-3284 (1998).

In specific aspects, use of the unnatural thio-dialanine amino acid, lanthionine, which has been widely adopted as a peptidomimetic of cystine, is used to cross-link one turn of the alpha helix. Suitable methods of lanthionine-based cyclization are known in the art. See, for instance, Matteucci et al., *Tetrahedron Letters* 45: 1399-1401 (2004); Mayer et al., *J. Peptide Res.* 51: 432-436 (1998); Polinsky et al., *J. Med. Chem.* 35: 4185-4194 (1992); Osapay et al., *J. Med. Chem.* 40: 2241-2251 (1997); Fukase et al., *Bull. Chem. Soc. Jpn.* 65: 2227-2240 (1992); Harpp et al., *J. Org. Chem.* 36: 73-80 (1971); Goodman and Shao, *Pure Appl. Chem.* 68: 1303-1308 (1996); and Osapay and Goodman, *J. Chem. Soc. Chem. Commun.* 1599-1600 (1993).

In some embodiments, α, ω-diaminoalkane tethers, e.g., 1,4-diaminopropane and 1,5-diaminopentane) between two Glu residues at positions i and i+7 are used to stabilize the alpha helix of the analog. Such tethers lead to the formation of a bridge 9-atoms or more in length, depending on the length of the diaminoalkane tether. Suitable methods of producing peptides cross-linked with such tethers are described in the art. See, for example, Phelan et al., J. Am. Chem. Soc. 119: 455-460 (1997).

In yet other embodiments, a disulfide bridge is used to cross-link one or two turns of the alpha helix of the analog. Alternatively, a modified disulfide bridge in which one or both sulfur atoms are replaced by a methylene group resulting in an isosteric macrocyclization is used to stabilize the alpha helix of the analog. Suitable methods of modifying peptides with disulfide bridges or sulfur-based cyclization are described in, for example, Jackson et al., *J. Am. Chem. Soc.* 113: 9391-9392 (1991) and Rudinger and Jost, *Experientia* 20: 570-571 (1964).

In yet other embodiments, the alpha helix of the analog is stabilized via the binding of metal atom by two His residues or a His and Cys pair positioned at j and j+3, or i and i+4. The metal atom can be, for example, Ru(III), Cu(II), Zn(II), or Cd(II). Such methods of metal binding-based alpha helix stabilization are known in the art. See, for example, Andrews and Tabor, *Tetrahedron* 55: 11711-11743 (1999); Ghadiri et al., *J. Am. Chem. Soc.* 112: 1630-1632 (1990); and Ghadiri et al., *J. Am. Chem. Soc.* 119: 9063-9064 (1997).

The alpha helix of the GIP agonist peptide can alternatively be stabilized through other means of peptide cyclizing, which means are reviewed in Davies, J. Peptide. Sci. 9: 471-501 (2003). The alpha helix can be stabilized via the formation of an amide bridge, thioether bridge, thioester bridge, urea bridge, carbamate bridge, sulfonamide bridge, and the like. For example, a thioester bridge can be formed between the C-terminus and the side chain of a Cys residue. Alternatively, a thioester can be formed via side chains of amino acids having a thiol (Cys) and a carboxylic acid (e.g., Asp, Glu). In another method, a cross-linking agent, such as a dicarboxylic acid, e.g., suberic acid (octanedioic acid), etc. can introduce a link between two functional groups of an amino acid side chain, such as a free amino, hydroxyl, thiol group, and combinations thereof.

Additional Descriptions

Provided below are additional descriptions of the glucagon analogs of the present disclosures. As discussed herein, the position of the amino acid in the descriptions below is referenced with regard to the amino acid numbering of SEQ ID NO: 1. Also, while the descriptions below are discussed in reference to native human glucagon (SEQ ID NO: 1), e.g., modifications of SEQ ID NO: 1, these descriptions do not necessarily imply (i) that such modifications are present in all of the presently disclosed peptides and (ii) that the only method of making the presently disclosed peptides is to start with native human glucagon and modify that sequence. Rather, the descriptions are provided to describe some embodiments of the glucagon analogs of the present disclosures, and the peptides of the present disclosures may be made de novo without utilizing native human glucagon as a starting material, as further described in the section entitled "METHODS OF MAKING PEPTIDES."

Position 1

In some embodiments, the glucagon analog comprises an amino acid modification at position 1, relative to SEQ ID NO: 1, e.g., the glucagon analog comprises an amino acid which is not His at position 1. In exemplary aspects, the glucagon analog comprises a large, aromatic amino acid at position 1. In exemplary embodiments, the large, aromatic amino acid is Tyr, Phe, Trp, amino-Phe (e.g., 4-amino-Phe), chloro-Phe, sulfo-Phe, 4-pyridyl-Ala, methyl-Tyr, or 3-amino Tyr.

In other exemplary embodiments, the glucagon analog comprises an amino acid comprising an imidazole side chain at position 1. In exemplary aspects, the amino acid at position 1 comprises a structure of Formula A

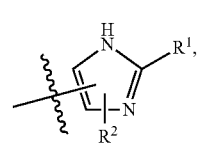

[Formula A]

wherein each of R1 and R2 independently is selected from the group consisting of H, (C1-6)alkyl, O(C1-6)alkyl, (C1-6)alkyl-OH, F, and (C1-C6)alkyl of which at least one H is replaced by F.

In exemplary aspects, the amino acid at position 1 is the native residue of glucagon (SEQ ID NO: 1) L-histidine (His), or is a derivative of His (His derivative), e.g., a derivative of His in which the alpha atoms are modified. The His derivative in exemplary aspects is D-histidine, desaminohistidine, hydroxyl-histidine, acetyl-histidine, homo-histidine, N-methyl histidine, alpha-methyl histidine, imidazole acetic acid, or alpha, alpha-dimethyl imidiazole acetic acid (DMIA).

In yet other aspects, the amino acid at position 1 is a DPP-IV protective amino acid, as described herein. In some aspects, the DPP-IV protective amino acid is a derivative of His.

Position 2

In some embodiments, the presently disclosed peptides comprise a DPP-IV protective amino acid at position 2. As used herein, the term "DPP-IV protective amino acid" refers to an amino acid which achieves substantial resistance of the presently disclosed peptide against dipeptidyl peptidase IV (DPP IV) cleavage. In some aspects, the DPP-IV protective amino acid is one of D-serine, D-alanine, valine, glycine, N-methyl serine, N-methyl alanine, or alpha, aminoisobutyric acid (AIB). In some aspects, the DPP-IV protective amino acid is an α,α-disubstituted amino acid. In some aspects, the α,α-disubstituted amino acid comprises R1 and R2, each of which is bonded to the alpha carbon, wherein each of R1 and R2 is independently selected from the group consisting of C1-C4 alkyl, optionally substituted with a hydroxyl, amide, thiol, halo, or R1 and R2 together with the alpha carbon to which they are attached form a ring. In some aspects, the α,α-disubstituted amino acid is AIB or 1-aminocyclopropane-1-carboxylate (ACPC).

The term "$C_1$-$C_n$ alkyl" wherein n can be from 1 through 6, as used herein, represents a branched or linear alkyl group having from one to the specified number of carbon atoms. Typical $C_1$-$C_6$ alkyl groups include, but are not limited to, methyl, ethyl, n-propyl, iso-propyl, butyl, iso-butyl, sec-butyl, tert-butyl, pentyl, hexyl and the like.

In exemplary embodiments, the DPP-IV protective amino acid is the D-isomer of Ser (D-Ser), or a conservative amino acid substitution thereof. For example, the DPP-IV protective amino acid can comprise a side chain structure of —(C1-C4 alkyl)OH. Optionally, when the side chain structure comprises —(C3 alkyl)OH or —(C4 alkyl)OH, the carbon chain may be straight chained or branched.

In exemplary aspects, when the DPP-IV protective amino acid is D-Ser and the amino acid at position 1 is His, the GIP agonist peptide is not conjugated to a heterologous moiety, e.g., a hydrophilic moiety (e.g., PEG). In other aspects of the present disclosures, the DPP-IV protective amino acid is not D-serine.

Position 3

In some embodiments, the glucagon analog comprises at position 3 an acidic, basic, or hydrophobic amino acid residue. Without being bound to any particular theory, such glucagon analogs exhibit a reduced glucagon receptor activity. In some embodiments, the acidic, basic, or hydrophobic amino acid is glutamic acid, ornithine, norleucine. The glucagon analogs that are substituted with, for example, glutamic acid, ornithine, or norleucine in some aspects have about 10% or less of the activity of native glucagon at the glucagon receptor, e.g., about 1-10%, or about 0.1-10%, or greater than about 0.1% but less than about 10%. In some embodiments, the glucagon analogs exhibit about 0.5%, about 1% or about 7% of the activity of native glucagon.

In some embodiments, the glucagon analog comprises the native amino acid of SEQ ID NO: 1 at position 3, e.g., glutamine, or comprises a glutamine analog. Without being bound to a particular theory, such glucagon analogs comprising a glutamine analog do not exhibit a substantial loss of activity at the glucagon receptor, and in some cases, the glucagon analog comprising the glutamine analog enhances glucagon receptor activity. In some embodiments, the glutamine analog comprises at position 3 an amino acid comprising a side chain of Structure I, II or III:

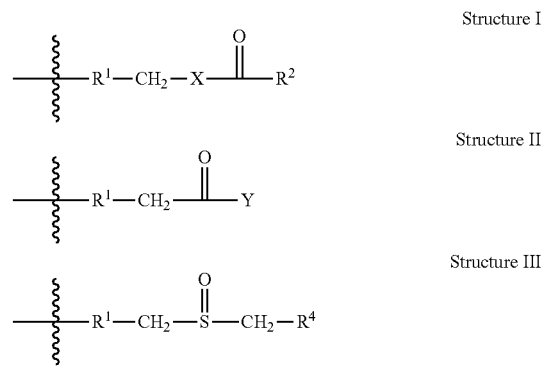

wherein $R^1$ is $C_{0-3}$ alkyl or $C_{0-3}$ heteroalkyl; $R^2$ is $NHR^4$ or $C_{1-3}$ alkyl; $R^3$ is $C_{1-3}$ alkyl; $R^4$ is H or $C_{1-3}$ alkyl; X is NH, O, or S; and Y is $NHR^4$, $SR^3$, or $OR^3$. In some embodiments, X is NH or Y is $NHR^4$. In some embodiments, $R^1$ is $C_{0-2}$ alkyl or $C_1$ heteroalkyl. In some embodiments, $R^2$ is $NHR^4$ or $C_1$ alkyl. In some embodiments, $R^4$ is H or $C^1$ alkyl. In exemplary embodiments, an amino acid comprising a side chain of Structure I is provided where, $R^1$ is $CH_2$—S, X is NH, and $R^2$ is $CH_3$ (acetamidomethyl-cysteine, C(Acm)); $R^1$ is $CH_2$, X is NH, and $R^2$ is $CH_3$ (acetyldiaminobutanoic acid, Dab(Ac)); $R^1$ is $C_0$ alkyl, X is NH, $R^2$ is $NHR^4$, and $R^4$ is H (carbamoyldiaminopropanoic acid, Dap(urea)); or $R^1$ is $CH_2$—$CH_2$, X is NH, and $R^2$ is $CH_3$ (acetylornithine, Orn (Ac)). In exemplary embodiments, an amino acid comprising a side chain of Structure II is provide where, $R^1$ is $CH_2$, Y is $NHR^4$, and $R^4$ is $CH_3$ (methylglutamine, Q(Me)); In exemplary embodiments, an amino acid comprising a side chain of Structure III is provided where, $R^1$ is $CH_2$ and $R^4$ is H (methionine-sulfoxide, M(O)); In specific embodiments, the amino acid at position 3 is substituted with Dab(Ac)

Position 7

In some embodiments, the glucagon analog comprises an amino acid modification at position 7, relative to SEQ ID NO: 1, e.g., the glucagon analog comprises an amino acid other than Thr at position 7. In some aspects, the amino acid at position 7 is a large, aliphatic amino acid, e.g., Ile, Leu, Ala, and the like. Without being bound to a particular theory, glucagon analogs comprising such an amino acid at position 7 are believed to exhibit drastically reduced activity at the GLP-1 receptor.

Position 9

In some embodiments, the glucagon analog comprises an amino acid modification at position 9, relative to SEQ ID NO: 1, e.g., the glucagon analog comprises an amino acid other than Asp at position 9. In some embodiments, the glucagon analog comprises a negative charged amino acid other than Asp, e.g., Glu, homoglutamic acid, cysteic acid, homocysteic acid. In some aspects, the amino acid at position 9 is an acylated amino acid or an alkylated amino acid, as discussed herein.

Position 10

In some embodiments, the glucagon analog comprises an amino acid modification at position 10, relative to SEQ ID NO: 1, e.g., the glucagon analog comprises an amino acid other than Tyr at position 10. In some aspects, the amino acid at position 10 is Trp. Without being bound to a particular theory, glucagon analogs comprising such an amino acid at position 10 are believed to exhibit activity at the GIP receptor, GLP-1 receptor, and/or the glucagon receptor which is not reduced, as compared to the corresponding peptide with a Tyr at position 10.

In some embodiments, the glucagon analog comprises an an acylated amino acid or an alkylated amino acid, as discussed herein.

Position 12

In some embodiments, the glucagon analog comprises an amino acid modification at position 12, relative to SEQ ID NO: 1. e.g., the glucagon analog comprises an amino acid other than Lys at position 10. In some aspects, the amino acid at position 12 is a large, aliphatic, nonpolar amino acid, optionally, isoleucine. In some aspects, the amino acid at position 12 is Arg. Without being bound to a particular theory, glucagon analogs comprising a large, aliphatic, nonpolar amino acid, e.g., Ile, exhibit enhanced activity at the GIP receptor. In some embodiments, the glucagon analog comprises an an acylated amino acid or an alkylated amino acid, as discussed herein.

Position 15

In some embodiments, the glucagon analogs comprise an amino acid modification at position 15, relative to SEQ ID NO: 1, e.g., the glucagon analog comprises an amino acid other than Asp at position 15. In some aspects, the amino acid at position 15 is deleted or is glutamic acid, homoglutamic acid, cysteic acid or homocysteic acid. Without being bound to a particular theory, such glucagon analogs exhibit improved stability, e.g., by way of reducing degradation or cleavage of the analog over time, especially in acidic or alkaline buffers, e.g., buffers at a pH within the range of 5.5 to 8. In some embodiments, the glucagon analogs comprising this modification retains at least 75%, 80%, 90%, 95%, 96%, 97%, 98% or 99% of the original analog after 24 hours at 25° C.

Position 16

In some embodiments, the glucagon analogs comprise an amino acid modification at position 16, relative to SEQ ID NO: 1, e.g., the glucagon analog comprises an amino acid other than Ser at position 16. In some aspects, the amino acid at position 16 is glutamic acid or with another negative-charged amino acid having a side chain with a length of 4 atoms, or alternatively with any one of glutamine, homoglutamic acid, or homocysteic acid, or a charged amino acid having a side chain containing at least one heteroatom, (e.g., N, O, S, P) and with a side chain length of about 4 (or 3-5) atoms. In some embodiments, the glucagon analog comprises at position 16 an amino acid selected from the group consisting of glutamic acid, glutamine, homoglutamic acid, homocysteic acid, threonine or glycine or is an amino acid selected from the group consisting of glutamic acid, glutamine, homoglutamic acid and homocysteic acid.

Without being bound to a particular theory, such glucagon analogs exhibit enhanced stability, e.g., by way of reducing degradation of the peptide over time, especially in acidic or alkaline buffers, e.g., buffers at a pH within the range of 5.5 to 8. Such glucagon analogs are less susceptible to cleavage of the Asp15-Ser16 peptide bond.

In some embodiments, the amino acid at position 16 is a negatively charged amino acid, optionally in combination with an alpha helix promoting amino acid (e.g., an alpha, alpha disubstituted amino acid, or AIB) at position 20. Such glucagon analogs exhibit GIP activity.

In alternative embodiments, the glucagon analog comprises at position 16 a Thr or an alpha helix promoting amino acid, as described above. In some embodiments, the alpha helix promoting amino acid is AIB or Glu.

In some aspects, the amino acid at position 16 is a positive charged amino acid, e.g., Formula IV:

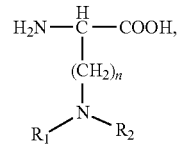

[Formula IV]

wherein n is 1 to 16, or 1 to 10, or 1 to 7, or 1 to 6, or 2 to 6, or 2 or 3 or 4 or 5, each of $R_1$ and $R_2$ is independently selected from the group consisting of H, $C_1$-$C_{18}$ alkyl, ($C_1$-$C_{18}$ alkyl)OH, ($C_1$-$C_{18}$ alkyl)NH$_2$, ($C_1$-$C_{18}$ alkyl)SH, ($C_0$-$C_4$ alkyl)($C_3$-$C_6$)cycloalkyl, ($C_0$-$C_4$ alkyl)($C_2$-$C_5$ heterocyclic), ($C_0$-$C_4$ alkyl)($C_6$-$C_{10}$ aryl)$R_7$, and ($C_1$-$C_4$ alkyl)($C_3$-$C_9$ heteroaryl), wherein $R_7$ is H or OH, Lys.

In some embodiments, the glucagon analog comprises an an acylated amino acid or an alkylated amino acid, as discussed herein.

In yet additional embodiments, the amino acid at position 16 is an amino acid comprising a side chain which is conjugated to a heterologous moiety, as described herein under the section entitled "CONJUGATES."

Positions 17 and 18

In some embodiments, the glucagon analog comprises an amino acid modification at either or both of positions 17 and 18, relative to SEQ ID NO: 1, such that the dibasic Arg-Arg site at positions 17 and 18 is eliminated. In some embodiments, the glucagon analog comprises an amino acid other than Arg at one or both of positions 17 and 18. Without being bound to any particular theory, it is believed that elimination of the dibasic site improves the in vivo efficacy of the glucagon analog. In some aspects, the amino acid at position 17 is not a basic amino acid. In some aspects, the amino acid at position 17 is an aliphatic amino acid. In some embodiments, the amino acid at position 17 is substituted with another amino acid as described herein, e.g., an amino acid comprising a hydrophilic moiety, an alpha helix promoting amino acid. In some embodiments, the alpha helix promoting amino acid forms a non-covalent intramolecular bridge with an amino acid at j+3 or i+4. In some aspects, the amino acid at position 17 is Gln.

In some aspects, the amino acid at position 18 is not a basic amino acid. In some aspects, the amino acid at position 18 is an aliphatic amino acid. In some embodiments, the amino acid at position 18 is a small aliphatic amino acid, e.g., Ala.

In some specific aspects, the amino acid at position 18 is a small aliphatic amino acid, e.g., Ala, and the amino acid at position 17 is Arg. In other aspects, the amino acid at position 18 is a small aliphatic amino acid, e.g., Ala, and amino acid at position 17 is Gln.

In some aspects, the amino acid at position 17 is an amino acid comprising a side chain which is conjugated to a heterologous moiety, as described herein under the section entitled "CONJUGATES."

Position 20

In some embodiments, the glucagon analog comprises an amino acid modification at position 20, relative to SEQ ID NO: 1, e.g., the amino acid at position 20 is an amino acid other than Gln. In some aspects, the amino acid at position 20 is an alpha helix promoting amino acid, e.g. as described above. In some aspects, the amino acid at position 20 is an alpha, alpha disubstituted amino acid, e.g., AIB, ACPC. In some embodiments, the alpha helix promoting amino acid forms a non-covalent intramolecular bridge with an amino acid at j−3 or i−4.

In some specific embodiments the amino acid is a hydrophilic amino acid having a side chain that is either charged or has an ability to hydrogen-bond, and is at least about 5 (or about 4-6) atoms in length, for example, lysine, citrulline, arginine, or ornithine. In other aspects, the amino acid at position 20 is Ser, Thr, Ala or AIB.

In some aspects, the amino acid at position 20 is a an acylated amino acid or alkylated amino acid, as discussed herein.

In some aspects, the amino acid at position 20 is an amino acid comprising a side chain which is conjugated to a heterologous moiety, as described herein under the section entitled "CONJUGATES.

Without being bound to a particular theory, such glucagon analogs exhibit enhanced activity at the GLP-1 receptor and/or GIP receptor or exhibit reduced degradation that occurs through deamidation of Gln and/or exhibit increased stability.

Position 21

In some embodiments, the glucagon analog comprises an amino acid modification at position 21, relative to SEQ ID NO: 1, e.g., the amino acid at position 21 is an amino acid other than Asp. In exemplary aspects, the amino acid at position 21 is Ser, Thr, Ala or AIB. In other aspects, the amino acid at position 21 is Lys, Arg, Orn, or Citrulline. In some aspects, the amino acid at position 21 is Glu, homoglutamic acid or homocysteic acid. In some aspects, the amino acid at position 21 is an amino acid comprising a side chain which is conjugated to a heterologous moiety, as described herein under the section entitled "CONJUGATES.

In some embodiments, the amino acid at position 21 is an alpha helix promoting amino acid. In some embodiments, the alpha helix promoting amino acid forms a non-covalent intramolecular bridge with an amino acid at j−3 or i−4.

Without being bound to a particular theory, such glucagon analogs exhibit reduced degradation that occurs through degradation through dehydration of Asp to form a cyclic succinimide intermediate followed by isomerization to iso-aspartate and/or exhibit increased stability.

Position 23

In some aspects, the glucagon analog comprises an amino acid modification at position 23, relative to SEQ ID NO: 1. In some aspects, the amino acid at position 23 is an amino acid other than Val, including but not limited to Ile.

Position 24

In some aspects, the glucagon analog comprises an amino acid modification at position 24, relative to SEQ ID NO: 1. In some aspects, the amino acid at position 24 is an amino acid other than Gln, e.g., Ala, Asn, Cys. In some aspects, the amino acid at position 24 is an amino acid comprising a side chain which is conjugated to a heterologous moiety, as described herein under the section entitled "CONJUGATES.

Position 27

In some aspects, the glucagon analog comprises an amino acid modification at position 27, relative to SEQ ID NO: 1. In some aspects, the amino acid at position 27 is an amino acid other than Met. In some embodiments, the glucagon analog comprises at position 27 an amino acid which prevents oxidative degradation of the peptide. In some aspects, the amino acid at position 27 is methionine sulfoxide, leucine, isoleucine or norleucine. In some specific embodiments, the amino acid at position 27 is leucine or norleucine.

In other aspects, the amino acid at position 27 is an aliphatic amino acid (e.g., Gly, Ala, Val, Leu, Ile) or an amino acid of Formula IV, as described herein, e.g., Lys. In exemplary embodiments, the amino acid at position 27 is Val or Lys. Without being bound to any particular theory, such an amino acid modification reduces glucagon activity.

Position 28

In some aspects, the glucagon analog comprises an amino acid modification at position 28, relative to SEQ ID NO: 1. In some aspects, the amino acid at position 28 is an amino acid other than Asn. In some aspects, the amino acid at position 28 is Ala, Ser, Thr, or AIB. In some aspects, the amino acid at position 28 is a charged amino acid, e.g., a negative-charged amino acid, as further described herein. See section entitled "Charged C-terminus." In some aspects, the amino acid at position 28 is Asp.

In exemplary aspects, the amino acid at position 28 is an amino acid of Formula IV as described herein. The amino acid in exemplary embodiments is Lys. Without being bound to any particular theory, such an amino acid modification reduces glucagon activity.

Position 29

In some aspects, the glucagon analog comprises an amino acid modification at position 29, relative to SEQ ID NO: 1. In some aspects, the amino acid at position 29 is an amino acid other than Thr. In some aspects, the amino acid at position 29 is Gly. In some aspects, the amino acid at position 29 is Ala.

In some aspects, the amino acid at position 29 is an amino acid comprising a side chain which is conjugated to a heterologous moiety, as described herein under the section entitled "CONJUGATES.

Charged C-Terminus

In some embodiments, the glucagon analog comprises one or more amino acid substitutions and/or additions that introduce a charged amino acid into the C-terminal portion of the analog, relative to SEQ ID NO: 1. In some embodiments, such modifications enhance stability and solubility. As used herein the term "charged amino acid" or "charged residue" refers to an amino acid that comprises a side chain that is positive-charged or negative-charged (i.e., de-protonated) or positive-charged (i.e., protonated) in aqueous solution at physiological pH. In some aspects, these amino acid substitutions and/or additions that introduce a charged amino acid modifications are at a position C-terminal to position 27 of SEQ ID NO: 1. In some embodiments, one, two or three (and in some instances, more than three) charged amino acids are introduced within the C-terminal portion (e.g., position(s) C-terminal to position 27). In accordance with some embodiments, the native amino acid(s) at positions 28 and/or 29 are substituted with a charged amino acids, and/or in a further embodiment one to three charged amino acids are also added to the C-terminus of the analog. In exemplary embodiments, one, two or all of the charged amino acids are negative-charged. The negative-charged amino acid in some embodiments is aspartic acid, glutamic acid, cysteic acid, homocystcic acid, or homoglutamic acid. In some aspects, these modifications increase solubility or stability. In some embodiments, position 30 is not a charged amino acid. Without being bound to a particular theory, a charged amino acid, e.g., a negative charged amino acid, e.g., Glu, reduced GIP activity.

C-Terminal Truncation

In accordance with some embodiments, the glucagon analogs disclosed herein are modified by truncation of the C-terminus by one or two amino acid residues. Such modified glucagon peptides, retain similar activity and potency at the glucagon receptor and GLP-1 receptor. In this regard, the glucagon peptides can comprise amino acids 1-27 or 1-28 of the native glucagon analog (SEQ ID NO: 1), optionally with any of the additional modifications described herein.

Charge-Neutral C-Terminus

In some embodiments, the glucagon analog comprises a charge-neutral group, such as an amide or ester, at the C-terminus in place of the alpha carboxylate, relative to SEQ ID NO: 1. Without being bound to any particular theory, such modifications in exemplary aspects increases activity of the glucagon analog at the GLP-1 receptor. Accordingly, in some embodiments, the glucagon analog is an amidated peptide, such that the C-terminal residue comprises an amide in place of the alpha carboxylate of an amino acid. As used herein a general reference to a peptide or analog is intended to encompass peptides that have a modified amino terminus, carboxy terminus, or both amino and carboxy termini. For example, an amino acid chain composing an amide group in place of the terminal carboxylic acid is intended to be encompassed by an amino acid sequence designating the standard amino acids.

C-Terminal Extensions

In some embodiments of the present disclosures, the glucagon analogs comprise a C-terminal extension of 1-21 amino acids fused to the amino acid at position 29. The C-terminal extension may comprise 1, 2, 3, 4, 5, 6, 7, 8, 9, 10, 11, 12, 13, 14, 15, 16, 17, 18, 19, 20, or 21 amino acids. In some aspects, the C-terminal extension is any of the heterologous peptides described below in the section "CONJUGATES." For example, in some aspects, the extension comprises an amino acid sequence which forms a Trp cage structure, e.g., the extension comprises the amino acid sequence of GPSSGAPPPS (SEQ ID NO: 5), or a conservatively substituted sequence thereof. In alternative aspects, the extension of 1 to 21 amino acids comprises at least one charged amino acid. In exemplary aspects, the extension comprises an amino acid sequence of: X1-X2, wherein X1 is a charged amino acid and X2 is a small aliphatic amino acid. In some aspects, X1 is a positive charged amino acid, e.g., Arg. In some aspects, extension comprises Arg-Gly.

In some embodiments, the extension comprises an amino acid sequence of SEQ ID NO: 5 (GPSSGAPPPS), SEQ ID NO: 6 (GGPSSGAPPPS), SEQ ID NO: 7 (KRNRNNIA), or SEQ ID NO: 8 (KRNR). In specific aspects, the amino acid sequence is attached through the C-terminal amino acid of the glucagon analog, e.g., amino acid at position 29. In some embodiments, the amino acid sequence of any of SEQ ID NOs: 5-8 is bound to amino acid 29 of the glucagon analog through a peptide bond. In some specific embodiments, the amino acid at position 29 of the glucagon analog is a Gly and the Gly is fused to one of the amino acid sequences of any of SEQ ID NOs: 5-8.

In exemplary aspects, the glucagon analog comprises an extension which forms a forms a structure known in the art as a Trp cage (see, e.g., Paschek et al., *Proc Natl Acad Sci USA* 105 (46): 17754-17759 (2008). In some aspects, the extension comprises the amino acid sequence GPSSGAPPPS (SEQ ID NO: 5) or GGPSSGAPPPS (SEQ ID NO: 6) or GPSSGRPPPS (SEQ ID NO: 183) or a sequence of one of the foregoing with 1, 2, or 3 conservative amino acid substitutions. In exemplary aspects, when the extension comprises the amino acid sequence of SEQ ID NO: 183, the amino acid at position 28 is a negative charged amino acid, e.g., Asp or Glu.

Other Modifications

Descriptions of yet other modifications, relative to SEQ ID NO: 1, of the glucagon analogs of the present disclosures are found throughout this application. The above listing is not exhaustive, but merely exemplary.

In some embodiments, the glucagon analogs described herein are glycosylated, amidated, carboxylated, phosphorylated, esterified, N-acylated, cyclized via, e.g., a disulfide bridge, or converted into a salt (e.g., an acid addition salt, a basic addition salt), and/or optionally dimerized, multimerized, or polymerized, or conjugated.

Excluded Peptides

The glucagon analogs of the present disclosures are structurally distinct from the glucagon analogs which exhibit GIP receptor agonist activity described in International Patent Application No. PCT US2009/47447 (filed on Jun. 16, 2009), U.S. Application No. 61/073,274 (filed Jun. 17, 2008); U.S. Application No. 61/078,171 (filed Jul. 3, 2008); U.S. Application No. 61/090,448 (filed Aug. 20, 2008), U.S. Application No. 61/151,349 (filed Feb. 10, 2009), U.S. Application No. 61/187,578 (filed Jun. 16, 2009), International Patent Application No. PCT/US2010-038825 (filed Jun. 16, 2010); the contents of which are incorporated by reference in their entirety. Accordingly, in any or all embodiments, the glucagon analog of the present disclosures is not any of the glucagon analogs or peptides described in International Patent Application No. PCT/US2009/47447 (filed on Jun. 16, 2009, and published as WO 2010/011439), U.S. Application No. 61/073,274 (filed Jun. 17, 2008); U.S. Application No. 61/078,171 (filed Jul. 3, 2008); U.S. Application No. 61/090,448 (filed Aug. 20, 2008), U.S. Application No. 61/151,349 (filed Feb. 10, 2009), U.S. Application No. 61/187,578 (filed Jun. 16, 2009), International Patent Application No. PCT/US2010/038825 (filed Jun. 16, 2010, and published as WO 2010/148089), U.S. Application No. 61/298,812 (filed Jan. 27, 2010), or International Patent Application No. PCT/US2011/022608 (filed Jan. 26, 2011, and published as WO 2011/094337). In exemplary embodiments, the peptides, glucagon peptides, or glucagon analogs of the present disclosures is not (i.e., excludes) any one or all of the peptides of SEQ ID NOs: 1-262 of WO 2010/011439; SEQ ID NOs: 1-680 of WO 2010/148089, or SEQ ID NOs: 1-1318 of PCT/US2011/022608.).

In exemplary embodiments, the peptides, glucagon peptides, or glucagon analogs of the present disclosures is not (i.e., excludes) any one or all of the peptides of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, and/or 262 of International Patent Application Publication No. WO 2010/011439.

In exemplary embodiments, the peptides, glucagon peptides, or glucagon analogs of the present disclosures is not (i.e., excludes) any one or all of the peptides of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, and/or 680 of International Patent Application Publication No. WO 2010/148089. In exemplary embodiments, the peptides, glucagon peptides, or glucagon analogs of the present disclosures is not (i.e., excludes) any one or all of the peptides of SEQ ID NO: 657, 658, 659, 660, 661, 662, 663, 664, 665, 666, 667, 668, 669 of International Patent Application Publication No. WO 2010/148089, which are presented herein as SEQ ID NOs: 219-229, respectively.

In exemplary embodiments, the peptides, glucagon peptides, or glucagon analogs of the present disclosures is not (i.e., excludes) any one or all of the peptides of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, 989, 990, 991, 992, 993, 994, 995, 996, 997, 998, 999, 1000, 1001, 1002, 1003, 1004, 1005, 1006, 1007, 1008, 1009, 1010, 1011, 1012, 1013, 1014, 1015, 1016, 1017, 1018, 1019, 1020, 1021, 1022, 1023, 1024, 1025, 1026, 1027, 1028, 1029, 1030, 1031, 1032, 1033, 1034, 1035, 1036, 1037, 1038, 1039, 1040, 1041, 1042, 1043, 1044, 1045, 1046, 1047, 1048, 1049, 1050, 1051, 1052, 1053, 1054, 1055, 1056, 1057, 1058, 1059, 1060, 1061, 1062, 1063, 1064, 1065, 1066, 1067, 1068, 1069, 1070, 1071, 1072, 1073, 1074, 1075, 1076, 1077, 1078, 1079, 1080, 1081, 1082, 1083, 1084, 1085, 1086, 1087, 1088, 1089, 1090, 1091, 1092, 1093, 1094, 1095, 1096, 1097, 1098, 1099, 1100, 1101, 1102, 1103, 1104, 1105, 1106, 1107, 1108, 1109, 1110, 1111, 1112, 1113, 1114, 1115, 1116, 1117, 1118, 1119, 1120, 1121, 1122, 1123, 1124, 1125, 1126, 1127, 1128, 1129, 1130, 1131, 1132, 1133, 1134, 1135, 1136, 1137, 1138, 1139, 1140, 1141, 1142, 1143, 1144, 1145, 1146, 1147, 1148, 1149, 1150, 1151, 1152, 1153, 1154, 1155, 1156, 1157, 1158, 1159, 1160, 1161, 1162, 1163, 1164, 1165, 1166, 1167, 1168, 1169, 1170, 1171, 1172, 1173, 1174, 1175, 1176, 1177, 1178, 1179, 1180, 1181, 1182, 1183, 1184, 1185, 1186, 1187, 1188, 1189, 1190, 1191, 1192, 1193, 1194, 1195, 1196, 1197, 1198, 1199, 1200, 1201, 1202, 1203, 1204, 1205, 1206, 1207, 1208, 1209, 1210, 1211, 1212, 1213, 1214, 1215, 1216, 1217, 1218, 1219, 1220, 1221, 1222, 1223, 1224, 1225, 1226, 1227, 1228, 1229, 1230, 1231, 1232, 1233, 1234, 1235, 1236, 1237, 1238, 1239, 1240, 1241, 1242, 1243, 1244, 1245, 1246, 1247, 1248, 1249, 1250, 1251, 1252, 1253, 1254, 1255, 1256, 1257, 1258, 1259, 1260, 1261, 1262, 1263, 1264, 1265, 1266, 1267, 1268, 1269, 1270, 1271, 1272, 1273, 1274, 1275, 1276, 1277, 1278, 1279, 1280, 1281, 1282, 1283, 1284, 1285, 1286, 1287, 1288, 1289, 1290, 1291, 1292, 1293, 1294, 1295, 1296, 1297, 1298, 1299, 1300, 1301, 1302, 1303, 1304, 1305, 1306, 1307, 1308, 1309, 1310, 1311, 1312, 1313, 1314, 1315, 1316, 1317, and/or 1318 of International Application No. Publication No. WO/2011/094337.

Exemplary Embodiments

In exemplary embodiments, the peptide of the present disclosures is an analog of glucagon (SEQ ID NO: 1) comprising (i) an amino acid comprising an imidazole side chain at position 1, (ii) a DPP-IV protective amino acid at position 2, (iii) an acylated amino acid or alkylated amino acid, optionally at any of positions 9, 10, 12, 16, 20, or 37-43, wherein optionally the acyl or alkyl group is linked to the amino acid via a spacer; (iv) an alpha helix stabilizing amino acid at one or more of positions 16-21, and (v) up to ten additional amino acid modifications relative to SEQ ID NO: 1, wherein when the glucagon analog is not conjugated to a heterologous moiety, e.g., a hydrophilic moiety (e.g., PEG), the glucagon analog exhibits at least or about 0.1% (e.g., at least or about 1%, at least or about 10%, at least or about 50%, at least about 80%, at least or about 100%, at least or about 500%) activity of native GIP at the GIP receptor.

The glucagon analogs described here may comprise any activity profile described herein. See, e.g., the section entitled "ACTIVITY OF THE PRESENTLY DISCLOSED PEPTIDES." In exemplary aspects, the glucagon analog exhibits a GIP percentage potency of at least or about 1%, at least or about 10%, at least or about 50%, at least or about 90%, at least or about 100%, at least or about 300%, or at least or about 500%. In some aspects, the glucagon analog also exhibits a GLP-1 percentage potency of at least or about 1%, at least or about 10%, at least or about 50%, at least or about 90%, at least or about 100%, at least or about 300%, or at least or about 500%. In alternative or additional aspects, the glucagon analog exhibits a glucagon percentage potency of at least or about 1%, at least or about 10%, at least or about 50%, at least or about 90%, or at least or about 100%. Accordingly, while the glucagon analogs may be considered as GIP agonist peptides, in some aspects, the glucagon analogs additionally may be considered as a GIP-GLP-1 co-agonist, a GIP-glucagon co-agonist, or a GIP-GLP-1-glucgaon triagonist. For example, the peptide may exhibits agonist activity at each of the human GIP receptor, the human GLP-1 receptor and the human glucagon receptor, wherein the peptide exhibits an EC50 at the GIP receptor which is within 100-fold (e.g., 50-fold, 40-fold, 30-fold, 20-fold, 15-fold, 10-fold, or less) of its EC50 at the GLP-1 receptor and is within 100-fold (e.g., 50-fold, 40-fold, 30-fold, 20-fold, 15-fold, 10-fold, or less) of its EC50 at the glucagon receptor.

In exemplary embodiments, the glucagon analog comprises an amino acid comprising an imidazole side chain at position 1. In exemplary aspects, the amino acid at position 1 comprises a structure of Formula A

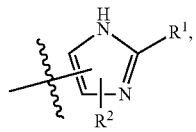
[Formula A]

wherein each of R1 and R2 independently is selected from the group consisting of H, (C1-6)alkyl, O(C1-6)alkyl, (C1-6)alkyl-OH, F, and (C1-C6)alkyl of which at least one H is replaced by F.

In exemplary aspects, the amino acid at position 1 is the native residue of glucagon (SEQ ID NO: 1) L-histidine (His), or is a derivative of His (His derivative), e.g., a derivative of His in which the alpha atoms are modified. As used herein, the term "His derivative" refers to a chemical moiety comprising an imidazole, e.g., comprising a structure of Formula A, or a substituted imidazole, attached to at least one carbon atom. In exemplary embodiments, the His derivative comprises a structure similar to the structure of histidine, except that the alpha amine, alpha carbon, or alpha carboxylate is replaced with another chemical moiety. In exemplary embodiments, the His derivative is an alpha substituted histidine of which the hydrogen atom linked to the alpha carbon is substituted with another chemical moiety, e.g., methyl, ethyl, propyl, isopropyl, hydroxyl, methoxy, ethoxy, and the like. The His derivative in some aspects is D-histidine, desaminohistidine, hydroxyl-histidine, acetyl-histidine, homo-histidine, N-methyl histidine, alpha-methyl histidine, imidazole acetic acid, or alpha, alpha-dimethyl imidiazole acetic acid (DMIA).

In some aspects, the DPP-IV protective amino acid at position 2 at position 2 is one of D-serine, D-alanine, valine, glycine, N-methyl serine, N-methyl alanine, or alpha, aminoisobutyric acid (AIB). In some aspects, the DPP-IV protective amino acid is D-Ser, or a conservative amino acid substitution thereof, or an α,α-disubstituted amino acid. In some aspects, the α,α-disubstituted amino acid comprises R1 and R2, each of which is bonded to the alpha carbon, wherein each of R1 and R2 is independently selected from the group consisting of C1-C4 alkyl, optionally substituted with a hydroxyl, amide, thiol, halo, or R1 and R2 together with the alpha carbon to which they are attached form a ring. In some aspects, the α,α-disubstituted amino acid is AIB. In exemplary aspects, when the DPP-IV protective amino acid is D-Ser, the GIP agonist peptide is not conjugated to a heterologous moiety, e.g., a hydrophilic moiety (e.g., PEG). In other aspects of the present disclosures, the DPP-IV protective amino acid is not D-serine.

In some aspects, the glucagon analog comprises an alpha helix stabilizing amino acid at any of positions 16, 17, 18, 19, 20, or 21. In some aspects, the glucagon analog comprises an alpha helix stabilizing amino acid at one, two, three, four, five, or all of positions 16, 17, 18, 19, 20, or 21. In exemplary aspects, the glucagon analog comprises an alpha helix stabilizing amino acid at positions 16, 17, 20, and 21. In some aspects, the glucagon analog comprises an alpha helix stabilizing amino acid at positions 16 and 20. In alternative or additional aspects, the glucagon analog comprises an alpha helix stabilizing amino acid at positions 17 and 21.

In some aspects, when the glucagon analog comprises an alpha helix stabilizing amino acid at position 20, the amino acid at position 20 is an alpha, alpha disubstituted amino acid. In exemplary aspects, the α,α-disubstituted amino acid comprises R1 and R2, each of which is bonded to the alpha carbon, wherein each of R1 and R2 is independently selected from the group consisting of C1-C4 alkyl, optionally substituted with a hydroxyl, amide, thiol, halo, or R1 and R2 together with the alpha carbon to which they are attached form a ring. In some embodiments, the α,α-disubstituted amino acid is 1-aminocyclopropane-1-carboxylate (ACPC). In some aspects, the α,α-disubstituted at position 20 is AIB. Optionally, in some embodiments, when the amino acid at position 20 is an alpha, alpha disubstituted amino acid, the amino acid at position 16 is an alpha helix stabilizing amino acid other than AIB. In exemplary embodiments, the amino acid at position 16 is a charged amino acid, e.g., a positive-charged amino acid, negative charged amino acid. In some aspects, when the amino acid at position 20 is an alpha, alpha disubstituted amino acid, the amino acid at position 16 is a positive-charged amino acid of Formula IV, e.g., Lys, or is a negative-charged amino acid, e.g., Glu. In some aspects, when the amino acid at position 20 is an alpha, alpha disubstituted amino acid, the amino acid at position 16 is a charge neutral amino acid, e.g., Ser, Ala, Gly.

Accordingly, in exemplary embodiments, the glucagon analog comprises (i) an amino acid comprising an imidazole side chain at position 1, (ii) a DPP-IV protective amino acid at position 2, optionally, aminoisobutyric acid, (iii) an amino acid comprising a non-native acyl or alkyl group, optionally at any of positions 9, 10, 12, 16, 20, or 37-43, optionally wherein the non-native acyl or alkyl group is linked to such amino acid via a spacer; (iv) an alpha, alpha disubstituted amino acid at position 20, and (v) up to ten (e.g., up to 1, 2, 3, 4, 5, 6, 7, 8 or 9) additional amino acid modifications relative to SEQ ID NO: 1.

In exemplary embodiments, when the glucagon analog comprises an alpha, alpha disubstituted amino acid at position 20, and when the glucagon analog lacks a hydrophilic moiety, the glucagon analog exhibits a GIP percentage potency of at least 0.1% (e.g., at least 1%, at least 10%, at least 20%). In exemplary embodiments, the glucagon analog has less than 100-fold (e.g., less than or about 90-fold, less than or about 80-fold, less than or about 70-fold, less than or about 60-fold, less than or about 50-fold, less than or about 40-fold, less than or about 30-fold, less than or about 20-fold, less than or about 15-fold, less than or about 10-fold, less than or about 5-fold) selectivity for the human GLP-1 receptor versus the GIP receptor. In exemplary aspects, the peptide has an EC50 at the GIP receptor which is less than 100-fold (e.g., less than or about 90-fold, less than or about 80-fold, less than or about 70-fold, less than or about 60-fold, less than or about 50-fold, less than or about 40-fold, less than or about 30-fold, less than or about 20-fold, less than or about 15-fold, less than or about 10-fold, less than or about 5-fold) different than its EC50 at the GLP-1 receptor, which, optionally, is less than 100-fold (e.g., less than or about 90-fold, less than or about 80-fold, less than or about 70-fold, less than or about 60-fold, less than or about 50-fold, less than or about 40-fold, less than or about 30-fold, less than or about 20-fold, less than or about 15-fold, less than or about 10-fold, less than or about 5-fold), different from its EC50 at the glucagon receptor.

In exemplary embodiments, when the glucagon analog comprises an alpha, alpha disubstituted amino acid at position 20, the α,α-disubstituted amino acid comprises R1 and R2, each of which is bonded to the alpha carbon, wherein each of R1 and R2 is independently selected from the group consisting of C1-C4 alkyl, optionally substituted with a hydroxyl, amide, thiol, halo, or R1 and R2 together with the alpha carbon to which they are attached form a ring. In exemplary embodiments, the α,α-disubstituted amino acid at position 20 is AIB. Also, in exemplary embodiments, when the glucagon analog comprises an alpha, alpha disubstituted amino acid at position 20, the amino acid at position 16 is an alpha helix stabilizing amino acid other than AIB. In exemplary aspects, the amino acid at position 16 is a charged amino acid, optionally, a negative charged amino acid (e.g., Glu or Asp) or a positive charged amino acid (e.g., Lys or Orn).

In alternative embodiments, the glucagon analog does not comprise an alpha helix stabilizing amino acid at position 20, and one or more of positions 16, 17, 18, 19, or 21 is an alpha helix stabilizing amino acid. In some aspects, the alpha helix stabilizing amino acid is located at position 16. In some embodiments, the alpha helix stabilizing amino acid is a negative charged amino acid (e.g., Glu), a positive-charged amino acid, (e.g., comprising a structure of Formula IV (e.g., Lys)), or an alpha, alpha disubstituted amino acid. In some aspects, the α,α-disubstituted amino acid comprises R1 and R2, each of which is bonded to the alpha carbon, wherein each of R1 and R2 is independently selected from the group consisting of C1-C4 alkyl, optionally substituted with a hydroxyl, amide, thiol, halo, or R1 and R2 together with the alpha carbon to which they are attached form a ring. In specific aspects, the α,α-disubstituted amino acid at position 16 is AIB.

In additional embodiments, when the glucagon analog does not comprise an alpha helix stabilizing amino acid at position 20, and when one or more of positions 16, 17, 18, 19, or 21 is an alpha helix stabilizing amino acid, the glucagon analog comprises (i) an extension of 1 to 21 amino acids C-terminal to the amino acid at position 29 of the peptide analog or (ii) the acylated amino acid or alkylated amino acid is located at position 10, 12, or 16. In some aspects, the glucagon analog comprises an extension of 1 to 21 amino acids C-terminal to the amino acid at position 29 of the peptide analog, and optionally the amino acid at position 29 is Gly. The extension of 1 to 21 amino acids in some aspects is any of those described herein—see, e.g., the section entitled "C-terminal Extensions." In some aspects, the extension comprises an amino acid sequence which forms a Trp cage structure, e.g., the extension comprises the amino acid sequence of GPSSGAPPPS (SEQ ID NO: 5), or a conservatively substituted sequence thereof. In alternative aspects, the extension of 1 to 21 amino acids comprises at least one charged amino acid. In exemplary aspects, the extension comprises an amino acid sequence of: X1-X2, wherein X1 is a charged amino acid and X2 is a small aliphatic amino acid. In some aspects, X1 is a positive charged amino acid, e.g., Arg. In some aspects, extension comprises Arg-Gly.

Accordingly, in alternative exemplary embodiments, the glucagon analog comprises (i) an amino acid comprising an imidazole side chain at position 1, (ii) a DPP-IV protective amino acid at position 2, optionally, aminoisobutyric acid, (iii) an amino acid comprising a non-native acyl or alkyl group, optionally at any of positions 9, 10, 12, 16, 20, or 37-43, optionally wherein the non-native acyl or alkyl group is linked to such amino acid via a spacer; (iv) an alpha helix stability amino acid at one or more of positions 16-21, optionally, position 16, wherein the analog does not comprise an alpha helix stabilizing amino acid at position 20, and (v) up to ten (e.g., up to 1, 2, 3, 4, 5, 6, 7, 8 or 9) additional amino acid modifications relative to SEQ ID NO: 1. In exemplary aspects, the analog does not comprise at position 20 an alpha, alpha di-substituted amino acid, optionally, AIB, or an alpha helix stabilizing amino acid selected from the group consisting of: Leu, Phe, Ala, Met, Gly, Ile, Ser, Asn, Glu, Asp, Lys, and Arg. In exemplary aspects, the glucagon analog is not modified at position 20 compared to SEQ ID NO: 1, and, therefore has Gln residue which is the native amino acid of glucagon at this position.

In exemplary embodiments, when the glucagon analog comprises an alpha helix stability amino acid at one or more of positions 16-21, optionally, position 16, and the analog does not comprise an alpha helix stabilizing amino acid at position 20, and when the glucagon analog lacks a hydrophilic moiety, the glucagon analog exhibits a GIP percentage potency of at least 0.1% (e.g., at least 1%, at least 10%, at least 20%). In exemplary embodiments, the glucagon analog has less than 100-fold (e.g., less than or about 90-fold, less than or about 80-fold, less than or about 70-fold, less than or about 60-fold, less than or about 50-fold, less than or about 40-fold, less than or about 30-fold, less than or about 20-fold, less than or about 15-fold, less than or about 10-fold, less than or about 5-fold) selectivity for the human GLP-1 receptor versus the GIP receptor. In exemplary aspects, the peptide has an EC50 at the GIP receptor which is less than 100-fold (e.g., less than or about 90-fold, less than or about 80-fold, less than or about 70-fold, less than or about 60-fold, less than or about 50-fold, less than or about 40-fold, less than or about 30-fold, less than or about 20-fold, less than or about 15-fold, less than or about 10-fold, less than or about 5-fold) different than its EC50 at the GLP-1 receptor, which, optionally, is less than 100-fold (e.g., less than or about 90-fold, less than or about 80-fold, less than or about 70-fold, less than or about 60-fold, less than or about 50-fold, less than or about 40-fold, less than or about 30-fold, less than or about 20-fold, less than or about 15-fold, less than or about 10-fold, less than or about 5-fold), different from its EC50 at the glucagon receptor.

In exemplary aspects, when the glucagon analog comprises an alpha helix stability amino acid at one or more of positions 16-21 and the analog does not comprise an alpha helix stabilizing amino acid at position 20, the glucagon analog comprises an alpha helix stabilizing amino acid at position 16, optionally, wherein the alpha helix stabilizing amino acid is a negative charged amino acid (e.g., Glu or Asp) or an alpha, alpha disubstituted amino acid. The α,α-disubstituted amino acid at position 16 may comprise R1 and R2, each of which is bonded to the alpha carbon, wherein each of R1 and R2 is independently selected from the group consisting of C1-C4 alkyl, optionally substituted with a hydroxyl, amide, thiol, halo, or R1 and R2 together with the alpha carbon to which they are attached form a ring. In exemplary aspects, the amino acid at position 16 is AIB. In exemplary aspects, the glucagon analog comprises at position 18 a small aliphatic amino acid, optionally, Ala, and an Arg at position 17. In exemplary aspects, the glucagon analog comprises the sequence ERAAQ (SEQ ID NO: 200) as positions 16 through 20 or ERAAQD (SEQ ID NO: 201) as positions 16 through 21.

In exemplary aspects, the glucagon analog comprises an amino acid comprising a non-native acyl or alkyl group at any one of positions 9, 10, 12, 16, 20. In exemplary aspects, the glucagon analog comprises an amino acid covalently attached to a C12 to C18 acyl group or alkyl group at any one or more of positions 9, 10, 12, 13, 14, 16, 17, and 20. In exemplary aspects, the glucagon analog comprises an amino acid covalently attached to a 12 to C18 acyl group or alkyl group at any one or more of positions 10, 14 In some aspects, the glucagon analog comprises an acylated amino acid or alkylated amino acid at position 10, 12, or 16. In exemplary aspects, the acylated amino acid or alkylated amino acid is at position 14. In some aspects, the glucagon analog comprises an extension of 1 to 21 amino acids C-terminal to the amino acid at position 29 and comprises an amino acid comprising a non-native acyl or alkyl group at any of positions 37-43 (e.g., 37, 38, 39, 40, 41, 42, 43). In some aspects, the amino acid comprising a non-native acyl or alkyl group is at position 40.

In exemplary embodiments, the acyl

In exemplary aspects, the glucagon analog comprises an extension of 1 to 21 amino acids C-terminal to the amino acid at position 29 and, in some aspects, the extension forms a structure known in the art as a Trp cage. In some aspects, the extension comprises the amino acid sequence GPSSGAPPPS (SEQ ID NO: 5) or GGPSSGAPPPS (SEQ ID NO: 6) or GPSSGRPPPS (SEQ ID NO: 183) or a sequence of one of the foregoing with 1, 2, or 3 conservative amino acid substitutions. In alternative aspects, the extension comprises at least one charged amino acid, e.g., the extension comprises an amino acid sequence of: X1-X2, wherein X1 is a charged amino acid (e.g., a positive charged amino acid (e.g., Arg)) and X2 is a small aliphatic amino acid. In some aspects, the extension comprises Arg-Gly.

In exemplary aspects, the acylated amino acid or alkylated amino acid comprises a structure of Formula I (optionally, Lys), Formula II, (optionally, Cys), or Formula III, (optionally, Ser). Optionally, in some aspects, the acylated amino acid or alkylated amino acid comprises a structure of Formula I, e.g., Lys.

In some embodiments, the acylated or alkylated amino acid is an aromatic amino acid comprising a side chain amine. In exemplary aspects, the aromatic amino acid comprising a side chain amine is 4-amino-phenylalanine (4-aminoPhe), p-amino phenylglycine, p-amino homophenylalanine, or 3-amino tyrosine. In exemplary aspects, the aromatic amino acid comprising a side chain amine is 4-amino-Phe. In exemplary aspects, the acylated or alkylated amino acid is an amino acid of Formula II, n is 2 (homoserine). In exemplary aspects, the acylated or alkylated amino acid is Thr or homothreonine. In exemplary embodiments, the acylated or alkylated amino acid is an aromatic amino acid comprising a side chain hydroxyl, including but not limited to tyrosine, homotyrosine, methyltyrosine, or 3-amino tyrosine.

In exemplary aspects, the glucagon analog comprises an amino acid covalently attached to a Cx-succinoyl, wherein x is an integer between 10 and 26, optionally, between 12 and 18. In exemplary aspects, the Cx-succinoyl is attached to the peptide or glucagon analog via a spacer. The spacer may be any one of those described herein.

In some aspects, the acylated amino acid or alkylated amino acid is linked to the acyl group or alkyl group via a spacer. In some aspects, the spacer is 3 to 10 atoms in length. In some aspects, the spacer is an amino acid or dipeptide, and, in some aspects, the spacer comprises one or two acidic amino acid residues, e.g., Glu. In some aspects, the acyl or alkyl group is linked to the amino acid via wherein the total length of the spacer and the acyl group is about 14 to about 28 atoms in length. In some aspects, the spacer comprises a Cys. In some aspects, the spacer comprises one or two gamma-Glu. In some aspects, the spacer comprises a Lys. In some aspects, the spacer comprises a combination of two of Cys, gamma-Glu, and Lys, or two gamma-Glu residues.

In particular aspects, the spacer is a Cys residue, which is covalently attached to an alkyl group, e.g., a non-functionalized or functionalized carbon chain. In exemplary aspects, the Cys residue is S-palmityl alkylated (i.e., S-palmitate alkylated), optionally, wherein the Cys residue is attached to a Lys residue which is part of the peptide backbone. In alternative embodiments, the spacer is a dipeptide comprising a Cys residue, which is covalently attached to an alkyl group. In exemplary aspects, the Cys is S-palmityl alkylated, and the Cys is attached to another amino acid of the spacer, which, in turn, is attached to, e.g., a Lys residue which is part of the peptide backbone.

In exemplary aspects, the spacer comprises a small polyethylene glycol moiety (PEG) comprising a structure [—O—CH$_2$—CH$_2$—]$_n$, wherein n is an integer between 2 and 16, (e.g., 2, 3, 4, 5, 6, 7, 8, 9, 10, 11, 12, 13, 14, 15, 16).

With regard to the acylated amino acid, the acyl group in some aspects is a C12 to C18 (e.g., C12, C13, C14, C15, C16, C17, C18) fatty acyl group. In some aspects, the acyl group is a C14 or C16 fatty acyl group. In alternative aspects, the acyl group is a succinic acid or a succinic acid derivative (e.g., a succinic acid derivative of Formula V, VI, or VII). In alternative aspects, the acyl group is a maleic acid or a maleic acid derivative (e.g., a maleic acid derivative of Formula VIII, IX, or X).

With regard to the alkylated amino acid, the non-native alkyl group in some aspects is a carboxy-functionalized carbon chain of structure —Cx-COOH, wherein x is an integer, optionally an integer between 4-30 (e.g., 4, 5, 6, 7, 8, 9, 10, 11, 12, 13, 14, 15, 16, 17, 18, 19, 20, 21, 22, 23, 24, 25, 26, 27, 28, 29, 30).

In exemplary aspect, the peptide or glucagon analog comprises two or more acyl or alkyl groups. In this regard, the peptide or glucagon analog may be a diacylated or dual acylated peptide. The two or more acyl or alkyl groups may be arranged in a linear formation, optionally with intervening spacers. The two or more acyl or alkyl groups may be arranged in a branched formation, as described herein. In exemplary aspects, the two acyl or alkyl groups are attached to a Lys spacer residue.

In some aspects of the present disclosures, the glucagon analog comprises at least one charged amino acid C-terminal to the amino acid at position 27. For example, in some aspects, the glucagon analog comprises a charged amino acid (e.g., a negative charged amino acid) at position 28. The negative charged amino acid in some aspects is Asp. In alternative aspects, the amino acid at position 28 is a positive charged amino acid, e.g., a positive charged amino acid is an amino acid of Formula I, e.g., Lys.

In alternative or additional aspects, the glucagon analog comprises an amino acid modification at position 27, at position 29, or at both positions 27 and 29. For example, the amino acid at position 27 is in some aspects is Leu, Nle, Val, or Lys and/or the amino acid at position 29 is in some aspects Gly or Thr.

The glucagon analogs described herein may comprise additional amino acid modifications, e.g., up to ten (e.g., 0, 1, 2, 3, 4, 5, 6, 7, 8, 9, 10) additional amino acid modifications, relative to SEQ ID NO: 1, as further discussed herein. In exemplary aspects, the glucagon analog comprises one or more of:
  a) a DPP-IV protective amino acid at position 1 of the peptide analog;
  b) an acidic amino acid, optionally, Glu, at position 3;
  c) an Ile at position 7;
  d) an Ile or Arg at position 12;
  e) an acidic amino acid, optionally, Glu, at position 15;
  f) an aliphatic amino acid, optionally, Ala, at position 18;
  g) an acidic amino acid, optionally, Glu, at position 21;
  h) an Asn, Ala, or AIB at position 24;
  i) an aliphatic amino acid, optionally, Ala, or Leu, or Nle, at position 27;
  j) an acidic amino acid, optionally, Glu, or an aliphatic amino acid, optionally, Ala, at position 28;
  k) an aliphatic amino acid, optionally, Ala, at position 29;
  l) amidation at the C-terminus.

In accordance with the foregoing, the glucagon analog in exemplary aspects comprises the amino acid sequence of any of SEQ ID NOs: 27-33, 35-41, 43-46, 76-80, 83-87, 89, and 90 or any of SEQ ID NOs: 94-100, 102-112, 120-124, 127-131. In exemplary aspects, the glucagon analog comprises or consists of any of SEQ ID NOs: 94-100, 102-112, 120-124, 127-131. In exemplary aspects, the glucagon analog comprises or consists of any of SEQ ID NOs: 28, 29, 31, 37-41, 43-46, 76-80, 83-87, 89, and 90. In exemplary aspects, the glucagon analog comprises of consists of any of SEQ ID NOs: 28, 29, 31, 37-41, 79, 80, 89, 90, 95, 130, 145-152, 155-167, 171, 176, 177, 180, 203-207, 212, and 230. In exemplary aspects, the glucagon analog comprises or consists of SEQ ID NO: 27. In exemplary aspects, the glucagon analog comprises or consists of SEQ ID NO: 30. In exemplary aspects, the glucagon analog comprises or consists of SEQ ID NO: 32. In exemplary aspects, the glucagon analog comprises or consists of SEQ ID NO: 33. In exemplary aspects, the glucagon analog comprises or consists of SEQ ID NO: 35. In exemplary aspects, the glucagon analog comprises or consists of SEQ ID NO: 36. In exemplary aspects, the glucagon analog comprises or consists of SEQ ID NO: 28. In exemplary aspects, the glucagon analog comprises or consists of SEQ ID NO: 37.

In exemplary aspects, the glucagon analog comprises or consists of SEQ ID NO: 89. In exemplary aspects, the glucagon analog comprises or consists of SEQ ID NO: 31. In exemplary aspects, the glucagon analog comprises or consists of SEQ ID NO: 180.

The invention further provides a peptide comprising the sequence of SEQ ID NO: 28. In exemplary aspects, the peptide consists of SEQ ID NO: 28.

A peptide comprising the sequence of SEQ ID NO: 31 is also provided by the invention. In exemplary aspects, the peptide consists of SEQ ID NO: 31.

The invention furthermore provides a peptide comprising the sequence of SEQ ID NO: 37. In exemplary aspects, the peptide consists of SEQ ID NO: 37.

The invention moreover provides peptide comprising the sequence of SEQ ID NO: 89. In exemplary aspects, the peptide consists of SEQ ID NO: 89.

The invention moreover provides peptide comprising the sequence of SEQ ID NO: 95. In exemplary aspects, the peptide consists of SEQ ID NO: 95.

The invention moreover provides peptide comprising the sequence of SEQ ID NO: 130. In exemplary aspects, the peptide consists of SEQ ID NO: 130.

Additionally, a peptide comprising the sequence of SEQ ID NO: 31 is provided herein. In exemplary aspects, the peptide consists of SEQ ID NO: 171.

A peptide comprising the sequence of SEQ ID NO: 180 is also provided by the invention. In exemplary aspects, the peptide consists of SEQ ID NO: 180.

The invention provides a peptide comprising the sequence of SEQ ID NO: 184, $$HX_2X_3GTFTSDX_{10}SKYLDX_{16}RX_{18}AX_{20}X_{21}FVQWLX_{27}X_{28}X_{29}GPSSGX_{35}PPPS \quad \text{(SEQ ID NO: 184)}$$

wherein:
$X_2$ is AIB;
$X_3$ is Gln or Gln analog;
$X_{10}$ is Tyr or an amino acid covalently attached to a C12 to C18 acyl or alkyl group;
$X_{16}$ is any amino acid, optionally, any amino acid other than Gly, Pro, and Ser;
$X_{18}$ is Arg or Ala;
$X_{20}$ is negative charged amino acid or a charge-neutral amino acid, optionally, AIB or Gln;
$X_{21}$ is an acidic amino acid, optionally, Asp or Glu;
$X_{27}$ is Leu, Ala, Nle, or Met;
$X_{28}$ is Ala or an acidic amino acid (optionally, Asp or Glu);
$X_{29}$ is Ala or Gly;
$X_{35}$ is Ala or a basic amino acid (optionally, Arg or Lys);
wherein, when $X_{28}$ is an acidic amino acid, $X_{35}$ is a basic amino acid;
wherein, when $X_{10}$ is Tyr, the peptide comprises at position 40 an amino acid covalently attached to a C12 to C18 acyl or alkyl group, and, wherein, optionally, the peptide comprises Gly at position 41, and
wherein the C-terminal amino acid of the peptide is amidated.

In exemplary aspects, X10 of SEQ ID NO: 184 is Tyr, the peptide comprises at position 40 an amino acid covalently attached to a C12 to C18 acyl or alkyl group, and the peptide optionally comprises Gly at position 41. In exemplary aspects, X10 of SEQ ID NO: 184 is an amino acid covalently attached to a C12-C18 acyl or alkyl group.

In exemplary aspects, X20 of SEQ ID NO: 184 is Gln, and optionally, the amino acid at position 16 is a negative charged amino acid (e.g., Glu). In exemplary aspects, X18 of SEQ ID NO: 184 is Ala and the peptide comprises E16, R17, A18, A19, and Q20.

In alternative exemplary aspects, X20 of SEQ ID NO: 184 is AIB. Optionally, $X_{16}$ of SEQ ID NO: 184 is any amino acid other than AIB.

Also, in exemplary aspects, (i) $X_{25}$ of SEQ ID NO: 184 is an acidic amino acid, optionally Asp or Glu, and $X_{35}$ of SEQ ID NO: 184 is a basic amino acid, optionally Arg or Lys, (ii) only one of $X_{27}$, $X_{28}$ and $X_{29}$ of SEQ ID NO: 184 is an Ala, (iii) the peptide comprise an amidated Gly at the C-terminus.

The invention also provides a peptide comprising the sequence of SEQ ID NO: 184 with up to 3 amino acid modifications (e.g., conservative substitutions) relative to SEQ ID NO: 184, wherein the analog exhibits agonist activity at each of the human GIP receptor, the human GLP-1 receptor and the human glucagon receptor. In exemplary embodiments, the activity (e.g., the EC50) at each of the human GIP receptor, the human GLP-1 receptor and the human glucagon receptor of the glucagon analog is within 100-fold (e.g., within 50-fold, within 25-fold, within 10-fold) of one another.

The invention additionally provides a peptide comprising the sequence of SEQ ID NO: 185, $$HX_2QGTFTSDX_{10}SKYLDX_{16}RX_{18}AX_{20}X_{21}FVQWLX_{27}X_{28}X_{29}GPSSGAPPPS \quad \text{(SEQ ID NO: 185)}$$

wherein:
$X_2$ is AIB;
$X_{10}$ is Tyr or an amino acid covalently attached to a C12 to C18 acyl or alkyl group;
$X_{16}$ is Glu, an alpha, alpha disubstituted amino acid, Lys or
$X_{18}$ is Arg or Ala;
$X_{20}$ is AIB or Gln;
$X_{21}$ is Asp or Glu;
$X_{27}$ is Leu, Nle, or Met;
$X_{28}$ is Ala, Asp or Glu;
$X_{29}$ is Gly of Thr;
and
wherein, when $X_{10}$ is Tyr, the peptide comprises at position 40 an amino acid covalently attached to a C12 to C18 acyl or alkyl group, and, wherein, optionally, the peptide comprises Gly at position 41, and
wherein the C-terminal amino acid of the peptide is amidated.

The invention also provides a peptide comprising the sequence of SEQ ID NO: 185 with up to 3 amino acid modifications (e.g., conservative substitutions) relative to SEQ ID NO: 185, wherein the analog exhibits agonist activity at each of the human GIP receptor, the human GLP-1 receptor and the human glucagon receptor. In exemplary embodiments, the activity (e.g., the EC50) at each of the human GIP receptor, the human GLP-1 receptor and the human glucagon receptor of the glucagon analog is within 100-fold (e.g., within 50-fold, within 25-fold, within 10-fold) of one another.

The invention also provides a peptide comprising the sequence of SEQ ID NO: 196, $$HX_2X_3GTFTSDX_{10}SKYLDX_{16}RX_{18}AX_{20}X_{21}FVQWLX_{27}X_{28}X_{29}GPSSGX_{35}PPPS \quad \text{(SEQ ID NO: 196)}$$

wherein:

$X_2$ is AIB;

$X_3$ is Gln or Gln analog or an amino acid that reduces glucagon activity (optionally Glu);

$X_{10}$ is Tyr or an amino acid covalently attached to a C12 to C18 acyl or alkyl group;

$X_{16}$ is any amino acid, optionally, any amino acid other than Gly, Pro, and Ser;

$X_{18}$ is Arg or Ala;

$X_{20}$ is negative charged amino acid or a charge-neutral amino acid, optionally, AIB or Gln;

$X_{21}$ is an acidic amino acid, optionally, Asp or Glu;

$X_{27}$ is Leu, Ala, Nle, or Met;

$X_{28}$ is Ala or an acidic amino acid (optionally, Asp or Glu);

$X_{29}$ is Ala or Gly;

$X_{35}$ is Ala or a basic amino acid (optionally, Arg or Lys);

wherein, when $X_{28}$ is an acidic amino acid, $X_{35}$ is a basic amino acid;

wherein, when $X_{10}$ is Tyr, the peptide comprises at position 40 an amino acid covalently attached to a C12 to C18 acyl or alkyl group, and, wherein, optionally, the peptide comprises Gly at position 41, and wherein the C-terminal amino acid of the peptide is amidated.

Additional amino acids that reduce glucagon activity are described herein. See section entitled "Position 3." In exemplary aspects, $X_3$ is an acidic, basic, or hydrophobic amino acid (e.g., glutamic acid, ornithine, norleucine). In exemplary aspects, $X_3$ is Glu.

Furthermore provided is a peptide comprising the sequence of SEQ ID NO: 186:

(SEQ ID NO: 186)
$HX_2X_3GTFTSDX_{10}SKYLDX_{16}RX_{18}AX_{20}X_{21}FVQWLX_{27}X_{28}X_{29}$ wherein:

$X_2$ is AIB;

$X_3$ is Gln or Gln analog;

$X_{10}$ is Tyr or an amino acid covalently attached to a C10 to C26 acyl or alkyl group;

$X_{16}$ is any amino acid, optionally, any amino acid other than Gly, Pro, and Ser;

$X_{18}$ is Arg or Ala;

$X_{20}$ is a negative charged amino acid or a charge-neutral amino acid, optionally, AIB or Gln;

$X_{21}$ is $X_{21}$ is an acidic amino acid, optionally, Asp or Glu;

$X_{27}$ is Leu, Ala, Nle, or Met;

$X_{28}$ is Ala or an acidic amino acid (optionally, Asp or Glu);

$X_{29}$ is Ala, Gly or Thr; and wherein the peptide comprises an amino acid covalently attached to a C10 to C26 acyl or alkyl group, optionally, at position 10, and the C-terminal amino acid of the peptide is amidated.

In exemplary aspects, $X_{20}$ of SEQ ID NO: 186 is AIB. In exemplary aspects, $X_{29}$ is Thr and the peptide does not comprise GPSSGAPPPS (SEQ ID NO: 5). In some aspects, $X_{20}$ of SEQ ID NO: 186 is AIB and $X_{16}$ is an amino acid other than AIB.

In exemplary aspects, $X_{20}$ is Gln. In some aspects, $X_{16}$ is a negative charged amino acid, optionally, Glu. In exemplary aspects, $X_{18}$ is Ala, and optionally, the peptide comprises E16, R17, A18, A19, and Q20.

In some aspects, the peptide of SEQ ID NO: 186 comprises an extension of 1 to 21 amino acids C-terminal to the amino acid at position 29, and optionally the amino acid at position 29 is Gly. In exemplary aspects, the extension comprises the amino acid sequence GPSSGAPPPS (SEQ ID NO: 5), or a conservatively substituted sequence thereof, or wherein the extension comprises the sequence X1-X2, wherein X1 is a charged amino acid and X2 is a small aliphatic amino acid, optionally, wherein X1 is a positive charged amino acid. In some aspects, the positive charged amino acid is Arg and optionally the peptide comprises or consists of Arg-Gly. In certain aspects, the extension comprises the amino acid sequence GPSSGAPPPS (SEQ ID NO: 5) followed by Lys or Lys-Gly, wherein the Lys is covalently attached to an C10 to C26 acyl group.

In exemplary aspects, the peptide comprises SEQ ID NO: 186, wherein $X_2$ is AIB, $X_3$ is Gln, $X_{10}$ is an amino acid covalently attached to a C10 to C26 acyl or alkyl group, $X_{18}$ is Arg or Ala, $X_{20}$ is AIB or Gln, $X_{21}$ is Asp or Glu, $X_{29}$ is Gly, and the C-terminal amino acid is amidated, wherein Gly at position 29 is fused to GPSSGAPPPS followed by Lys or Lys-Gly, wherein the Lys is covalently attached to a C10-C26 acyl group.

The invention also provides a peptide comprising the sequence of SEQ ID NO: 186 with up to 3 amino acid modifications (e.g., conservative substitutions) relative to SEQ ID NO: 186, wherein the analog exhibits agonist activity at each of the human GIP receptor, the human GLP-1 receptor and the human glucagon receptor. In exemplary embodiments, the activity (e.g., the EC50) at each of the human GIP receptor, the human GLP-1 receptor and the human glucagon receptor of the glucagon analog is within 100-fold (e.g., within 50-fold, within 25-fold, within 10-fold) of one another.

The invention provides a peptide comprising the sequence of SEQ ID NO: 187:

(SEQ ID NO: 187)
$HX_2QGTFTSDX_{10}SKYLDX_{16}RX_{18}AX_{20}X_{21}FVQWLX_{27}X_{28}X_{29}$ wherein:

$X_2$ is AIB;

$X_{10}$ is Tyr or an amino acid covalently attached to a C10 to C26 acyl or alkyl group;

$X_{16}$ is Glu, alpha, alpha-disubstituted amino acid, or Lys;

$X_{18}$ is Arg or Ala;

$X_{20}$ is a negative charged amino acid or a charge-neutral amino acid, optionally, AIB or Gln;

$X_{21}$ is Asp or Glu;

$X_{27}$ is Leu, Ala, Nle, or Met;

$X_{28}$ is Ala, Asp or Glu;

$X_{29}$ is Gly or Thr; and wherein the peptide comprises an amino acid covalently attached to a C12 to C18 acyl or alkyl group, optionally, at position 10, and the C-terminal amino acid of the peptide is amidated.

The invention also provides a peptide comprising the sequence of SEQ ID NO: 187 with up to 3 amino acid modifications (e.g., conservative substitutions) relative to SEQ ID NO: 187, wherein the analog exhibits agonist activity at each of the human GIP receptor, the human GLP-1 receptor and the human glucagon receptor. In exemplary embodiments, the activity (e.g., the EC50) at each of the human GIP receptor, the human GLP-1 receptor and the human glucagon receptor of the glucagon analog is within 100-fold (e.g., within 50-fold, within 25-fold, within 10-fold) of one another.

The invention provides a peptide comprising the sequence of SEQ ID NO: 198:

(SEQ ID NO: 198)
$HX_2X_3GTFTSDX_{10}SKYLDX_{16}RX_{18}AX_{20}X_{21}FVQWLX_{27}X_{28}X_{29}$ wherein:
$X_2$ is AIB;
$X_3$ is Gln or Gln analog or an amino acid that reduces glucagon activity (e.g., Glu);
$X_{10}$ is Tyr or an amino acid covalently attached to a C10 to C26 acyl or alkyl group;
$X_{16}$ is any amino acid, optionally, any amino acid other than Gly, Pro, and Ser;
$X_{18}$ is Arg or Ala;
$X_{20}$ is a negative charged amino acid or a charge-neutral amino acid, optionally, AIB or Gln;
$X_{21}$ is $X_{21}$ is an acidic amino acid, optionally, Asp or Glu;
$X_{27}$ is Leu, Ala, Nle, or Met;
$X_{28}$ is Ala or an acidic amino acid (optionally, Asp or Glu);
$X_{29}$ is Ala, Gly or Thr; and
wherein the peptide comprises an amino acid covalently attached to a C10 to C26 acyl or alkyl group, optionally, at position 10, and the C-terminal amino acid of the peptide is amidated.

Additional amino acids that reduce glucagon activity are described herein. See section entitled "Position 3." In exemplary aspects, $X_3$ is an acidic, basic, or hydrophobic amino acid (e.g., glutamic acid, ornithine, norleucine). In exemplary aspects, $X_3$ is Glu.

The invention provides a peptide comprising SEQ ID NO: 184. The invention provides a peptide comprising SEQ ID NO: 185. The invention provides a peptide comprising SEQ ID NO: 196. The invention provides a peptide comprising SEQ ID NO: 186. The invention provides a peptide comprising SEQ ID NO: 187. The invention provides a peptide comprising SEQ ID NO: 198.

Furthermore provided herein is an analog of glucagon (SEQ ID NO: 1) having GIP agonist activity, comprising:
(a) an amino acid comprising an imidazole side chain at position 1,
(b) at position 16, an amino acid of Formula IV:

[Formula IV]

wherein n is 1 to 7, wherein each of R1 and R2 is independently selected from the group consisting of H, C1-C18 alkyl, (C1-C18 alkyl)OH, (C1-C18 alkyl)NH2, (C1-C18 alkyl)SH, (C0-C4 alkyl)(C3-C6)cycloalkyl, (C0-C4 alkyl)(C2-C5 heterocyclic), (C0-C4 alkyl)(C6-C10 aryl)R7, and (C1-C4 alkyl)(C3-C9 heteroaryl), wherein R7 is H or OH, wherein optionally the side chain of the amino acid of Formula IV comprises a free amino group,
(c) an α,α-disubstituted amino acid at position 20,
(d) up to ten additional amino acid modifications relative to SEQ ID NO: 1,
wherein, when the analog lacks a hydrophilic moiety, the glucagon analog exhibits at least 0.1% activity of native GIP at the GIP receptor, wherein the glucagon analog has less than 100-fold selectivity for the human GLP-1 receptor versus the GIP receptor.

In exemplary embodiments, the analog of glucagon (SEQ ID NO: 1) having GIP agonist activity, comprises one or more of:
(a) an amino acid comprising an imidazole side chain at position 1,
(b) at position 16, an amino acid of Formula IV:

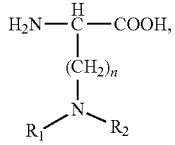

[Formula IV]

wherein n is 1 to 7, wherein each of R1 and R2 is independently selected from the group consisting of H, $C_1$-$C_{18}$ alkyl, ($C_1$-$C_{18}$ alkyl)OH, ($C_1$-$C_{18}$ alkyl)$NH_2$, (C1-C18 alkyl)SH, ($C_0$-$C_4$ alkyl)($C_3$-$C_6$)cycloalkyl, ($C_0$-$C_4$ alkyl)($C_2$-$C_5$ heterocyclic), ($C_0$-$C_4$ alkyl)($C_6$-$C_{10}$ aryl)$R_7$, and ($C_1$-$C_4$ alkyl)($C_3$-$C_9$ heteroaryl), wherein $R_7$ is H or OH, optionally, wherein the side chain of the amino acid of Formula IV comprises a free amino group,
(c) an α,α-disubstituted amino acid at position 20,
(d) up to ten additional amino acid modifications relative to SEQ ID NO: 1,
wherein, when the analog lacks a heterologous moiety, e.g., a hydrophilic moiety (e.g., PEG), the glucagon analog exhibits at least or about 0.1% (e.g., at least or about 1%, at least or about 10%, at least or about 50%, at least or about 80%, at least or about 100%, at least or about 500%) activity of native GIP at the GIP receptor. In exemplary aspects, the peptide has an EC50 at the GIP receptor which is less than 100-fold (e.g., less than or about 90-fold, less than or about 80-fold, less than or about 70-fold, less than or about 60-fold, less than or about 50-fold, less than or about 40-fold, less than or about 30-fold, less than or about 20-fold, less than or about 15-fold, less than or about 10-fold, less than or about 5-fold), different than its EC50 at the GLP-1 receptor, which, optionally, is less than 100-fold (e.g., less than or about 90-fold, less than or about 80-fold, less than or about 70-fold, less than or about 60-fold, less than or about 50-fold, less than or about 40-fold, less than or about 30-fold, less than or about 20-fold, less than or about 15-fold, less than or about 10-fold, less than or about 5-fold), different from its EC50 at the glucagon receptor.

In exemplary embodiments, the glucagon analog comprises at position 1 an amino acid comprising a structure of Formula A

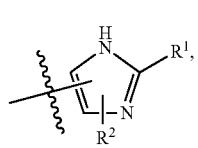

[Formula A]

wherein each of R1 and R2 independently is selected from the group consisting of H, (C1-6)alkyl, O(C1-6)alkyl, (C1-6)alkyl-OH, F, and (C1-C6)alkyl of which at least one H is replaced by F.

In exemplary aspects, the amino acid at position 1 is the native residue of glucagon (SEQ ID NO: 1) L-histidine (His), or is a derivative of His (His derivative), e.g., D-histidine, desaminohistidine, hydroxyl-histidine, acetyl-histidine, homo-histidine, N-methyl histidine, alpha-methyl histidine, imidazole acetic acid, or alpha, alpha-dimethyl imidiazole acetic acid (DMIA).

In exemplary aspects, the glucagon analog comprises the amino acid of Formula IV at position 16 in (b) is homoLys, Lys, Orn, or 2,4-diaminobutyric acid (Dab).

In exemplary aspects, the amino acid at position 20, e.g., the α,α-disubstituted amino acid, comprises R1 and R2, each of which is bonded to the alpha carbon, wherein each of R1 and R2 is independently selected from the group consisting of C1-C4 alkyl, optionally substituted with a hydroxyl, amide, thiol, halo, or R1 and R2 together with the alpha carbon to which they are attached form a ring. In exemplary aspects, the α,α-disubstituted at position 20 is AIB. In other exemplary aspects, the α,α-disubstituted at position 20 is ACPC.

In exemplary aspects, the glucagon analog comprises up to ten additional modifications, relative to SEQ ID NO: 1. In exemplary aspects, the glucagon analog comprises an amino acid substitution, relative to SEQ ID NO: 1, at one or more of positions 2, 12, 17, 18, 21, 24, 27, 28, and 29. In exemplary aspects, the glucagon analog comprises one or more of:
  i. a DPP-IV protective amino acid at position 2; optionally AIB or D-Ser;
  ii. a large, aliphatic, nonpolar amino acid at position 12, optionally Ile;
  iii. an amino acid other than Arg at position 17, optionally Gln;
  iv. a small aliphatic amino acid at position 18, optionally Ala;
  v. an amino acid other than Asp at position 21, optionally Glu;
  vi. an amino acid other than Gln at position 24, optionally Asn or Ala;
  vii. an amino acid other than Met at position 27, optionally Leu;
  viii. an amino acid other than Asn at position 28, optionally Ala;
  ix. an amino acid other than Thr at position 29, optionally Gly; and
  x. an extension of 1 to 21 amino acids C-terminal to the amino acid at position 29.

In exemplary aspects, the glucagon analog comprises an extension of GPSSGAPPPS or GPSSGAPPPSC.

In exemplary aspects, the glucagon analog comprising a His at position 1, Lys at position 16 and AIB at position 20 does not comprise Gln-Ala at positions 17-18.

In other exemplary embodiments, the glucagon analog comprises an amino acid sequence of any of SEQ ID NOs: 48, 52, 53, and 74. Such glucagon analogs are similar in structure to those of SEQ ID NOs: 27-33, 35-41, 43-46, 76-80, 83-87, 89, and 90, except that the former glucagon analogs (SEQ ID NOs: 48, 52, 53, and 74) do not comprise an acylated amino acid or alkylated amino acid.

In yet other exemplary embodiments, the glucagon analog comprises an amino acid sequence of any of SEQ ID NOs: 50, 51, 54, 56, 58-60, 62-66, 68-70, 72, 73, 75, 81, 82, 88, and 92 or any of SEQ ID NOs: 114-119, 125, 126, and 133, or any of SEQ ID NOs: 139-144, 150-153, 208, 210, and 211. Such glucagon analogs comprise a large, aromatic amino acid at position 1, e.g., Tyr.

In some embodiments, the GIP agonist peptides comprise an amino acid sequence of any of SEQ ID NOs: 27-33, 35-41, 43-46, 76-80, 83-87, 89, 90, 94-100, 102-112, 120-124, and 127-131, or any of SEQ ID NOs: 48, 52, 53, and 74, or any of SEQ ID NOs: 50, 51, 54, 56, 58-60, 62-66, 68-70, 72, 73, 75, 81, 82, 88, 92, 114-119, 125, 126, and 133. In some embodiments, the GIP agonist peptide comprises an amino acid sequence of any of SEQ ID NOs: 28, 29, 31, 37-41, 79, 80, 89, 90, 95, 130, 145-152, 155-167, 171, 176, 177, 180, 203-207, 212, and 230.

In some embodiments, the GIP agonist peptides comprise a structure based on a parent sequence comprising any of SEQ ID NOs: 27-33, 35-41, 43-46, 76-80, 83-87, 89, 90, 94-100, 102-112, 120-124, and 127-131, or any of SEQ ID NOs: 48, 52, 53, and 74, or any of SEQ ID NOs: 50, 51, 54, 56, 58-60, 62-66, 68-70, 72, 73, 75, 81, 82, 88, 92, 114-119, 125, 126, and 133, or any of SEQ ID NOs: 28, 29, 31, 37-41, 79, 80, 89, 90, 95, 130, 145-152, 155-167, 171, 176, 177, 180, 203-207, 212, and 230, but differs from the parent sequence at one or more positions.

In some or any embodiments, the peptide of the present disclosures is an analog of a parent sequence comprising any of SEQ ID NOs: 27-33, 35-41, 43-46, 76-80, 83-87, 89, 90, 94-100, 102-112, 120-124, and 127-131, or any of SEQ ID NOs: 48, 52, 53, and 74, or any of SEQ ID NOs: 50, 51, 54, 56, 58-60, 62-66, 68-70, 72, 73, 75, 81, 82, 88, 92, 114-119, 125, 126, and 133, or any of SEQ ID NOs: 28, 29, 31, 37-41, 79, 80, 89, 90, 95, 130, 145-152, 155-167, 171, 176, 177, 180, 203-207, 212, and 230 comprising an amino acid sequence based on the amino acid sequence of the parent sequence but differs from the parent sequence inasmuch as the amino acid sequence of the analog comprises one or more (e.g., 1, 2, 3, 4, 5, 6, 7, 8, 9, 10, 11, 12, 13, 14, 15, and in some instances, 16 or more (e.g., 17, 18, 19, 20, 21, 22, 23, 24, 25, etc.), specified or optional amino acid modifications. In some or any embodiments, the peptide of the present disclosures comprises a total of 1, up to 2, up to 3, up to 4, up to 5, up to 6, up to 7, up to 8, up to 9, or up to 10 additional amino acid modifications relative to the parent sequence comprising any of SEQ ID NOs: 27-33, 35-41, 43-46, 76-80, 83-87, 89, 90, 94-100, 102-112, 120-124, and 127-131, or any of SEQ ID NOs: 48, 52, 53, and 74, or any of SEQ ID NOs: 50, 51, 54, 56, 58-60, 62-66, 68-70, 72, 73, 75, 81, 82, 88, 92, 114-119, 125, 126, and 133, or any of SEQ ID NOs: 28, 29, 31, 37-41, 79, 80, 89, 90, 95, 130, 145-152, 155-167, 171, 176, 177, 180, 203-207, 212, and 230. In some or any embodiments, the modifications are any of those described herein with regard to glucagon analogs, e.g., acylation, alkylation, pegylation, truncation at C-terminus, substitution of the amino acid at one or more of positions 1, 2, 3, 7, 10, 12, 15, 16, 17, 18, 19, 20, 21, 23, 24, 27, 28, and 29.

In some or any embodiments, the modification is an amino acid substitution or replacement, e.g., a conservative amino acid substitution. In some aspects, the conservative substitution is a replacement of the amino acid at one or more of positions 2, 5, 7, 10, 11, 12, 13, 14, 16, 17, 18, 19, 20, 21, 24, 27, 28 or 29. In alternative embodiments, the amino acid substitution is not a conservative amino acid substitution, e.g., is a non-conservative amino acid substitution.

In some embodiments, the peptide of the present disclosures comprises an amino acid sequence which has at least 25% sequence identity to the amino acid sequence of the parent sequence, which comprises any of SEQ ID NOs: 27-33, 35-41, 43-46, 76-80, 83-87, 89, 90, 94-100, 102-112, 120-124, and 127-131, or any of SEQ ID NOs: 48, 52, 53, and 74, or any of SEQ ID NOs: 50, 51, 54, 56, 58-60, 62-66, 68-70, 72, 73, 75, 81, 82, 88, 92, 114-119, 125, 126, and 133, or any of SEQ ID NOs: 28, 29, 31, 37-41, 79, 80, 89, 90, 95, 130, 145-152, 155-167, 171, 176, 177, 180, 203-207, 212, and 230. In some embodiments, the peptide of the present disclosures comprises an amino acid sequence which is at least 30%, at least 40%, at least 50%, at least 60%, at least 70%, at least 80%, at least 85%, at least 90% or has greater than 90% sequence identity to the parent sequence. In some embodiments, the amino acid sequence of the presently disclosed peptide which has the above-referenced % sequence identity is the full-length amino acid sequence of the presently disclosed peptide. In some embodiments, the amino acid sequence of the peptide of the present disclosures which has the above-referenced % sequence identity is only a portion of the amino acid sequence of the presently disclosed peptide. In some embodiments, the presently disclosed peptide comprises an amino acid sequence which has about A % or greater sequence identity to a reference amino acid sequence of at least 5 contiguous amino acids (e.g., at least 6, at least 7, at least 8, at least 9, at least 10 amino acids) of the parent sequence, wherein the reference amino acid sequence begins with the amino acid at position C of SEQ ID NO: 1 and ends with the amino acid at position D of SEQ ID NO: 1, wherein A is 25, 30, 35, 40, 45, 50, 55, 60, 65, 70, 75, 80, 85, 90, 91, 92, 93, 94, 95, 96, 97, 98, 99; C is 1, 2, 3, 4, 5, 6, 7, 8, 9, 10, 11, 12, 13, 14, 15, 16, 17, 18, 19, 20, 21, 22, 23, 24, 25, 26, 27, or 28 and D is 5, 6, 7, 8, 9, 10, 11, 12, 13, 14, 15, 16, 17, 18, 19, 20, 21, 22, 23, 24, 25, 26, 27, 28 or 29. Any and all possible combinations of the foregoing parameters are envisioned, including but not limited to, e.g., wherein A is 90% and C and D are 1 and 27, or 6 and 27, or 8 and 27, or 10 and 27, or 12 and 27, or 16 and 27.

The analogs of the parent sequence comprising any of SEQ ID NOs: 27-33, 35-41, 43-46, 76-80, 83-87, 89, and 90, or any of SEQ ID NOs: 48, 52, 53, and 74, or any of SEQ ID NOs: 50, 51, 54, 56, 58-60, 62-66, 68-70, 72, 73, 75, 81, 82, 88, and 92, or any of comprising any of SEQ ID NOs: 28, 29, 31, 37-41, 79, 80, 89, 90, 95, 130, 145-152, 155-167, 171, 176, 177, 180, 203-207, 212, and 230 described herein may comprise a peptide backbone of any number of amino acids, i.e., can be of any peptide length. In some embodiments, the peptides described herein are the same length as SEQ ID NO: 1, i.e., are 29 amino acids in length. In some embodiments, the presently disclosed peptide is longer than 29 amino acids in length, e.g., the presently disclosed peptide comprises a C-terminal extension of 1-21 amino acids, as further described herein. Accordingly, the peptide of the present disclosures in some embodiments, is 30, 31, 32, 33, 34, 35, 36, 37, 38, 39, 40, 41, 42, 43, 44, 45, 46, 47, 48, 49, or 50 amino acids in length. In some embodiments, the presently disclosed peptide is up to 50 amino acids in length. In some embodiments, the presently disclosed peptide is longer than 29 amino acids in length (e.g., greater than 50 amino acids, (e.g., at least or about 60, at least or about 70, at least or about 80, at least or about 90, at least or about 100, at least or about 150, at least or about 200, at least or about 250, at least or about 300, at least or about 350, at least or about 400, at least or about 450, at least or about 500 amino acids in length) due to fusion with another peptide. In other embodiments, the presently disclosed peptide is less than 29 amino acids in length, e.g., 28, 27, 26, 25, 24, 23, amino acids.

In accordance with the foregoing, in some aspects, the peptide of the present disclosures is an analog of a parent sequence comprising any of SEQ ID NOs: 27-33, 35-41, 43-46, 76-80, 83-87, 89, 90, 94-100, 102-112, 120-124, and 127-131, or any of SEQ ID NOs: 48, 52, 53, and 74, or any of SEQ ID NOs: 50, 51, 54, 56, 58-60, 62-66, 68-70, 72, 73, 75, 81, 82, 88, 92, 114-119, 125, 126, and 133, or any of SEQ ID NOs: 28, 29, 31, 37-41, 79, 80, 89, 90, 95, 130, 145-152, 155-167, 171, 176, 177, 180, 203-207, 212, and 230 which sequence of the analog comprises one or more amino acid modifications which affect GIP activity, glucagon activity, and/or GLP-1 activity, enhance stability, e.g., by reducing degradation of the peptide (e.g., by improving resistance to DPP-IV proteases), enhance solubility, increase half-life, delay the onset of action, extend the duration of action at the GIP, glucagon, or GLP-1 receptor, or a combination of any of the foregoing. Such amino acid modifications, in addition to other modifications, are further described herein with regard to glucagon analogs, and any of these modifications can be applied individually or in combination.

Methods of Making Peptides

The glucagon analogs of the disclosure can be obtained by methods known in the art. Suitable methods of de novo synthesizing peptides are described in, for example, Chan et al., Fmoc Solid Phase Peptide Synthesis, Oxford University Press, Oxford, United Kingdom, 2005; Peptide and Protein Drug Analysis, ed. Reid, R., Marcel Dekker, Inc., 2000; Epitope Mapping, ed. Westwood et al., Oxford University Press, Oxford, United Kingdom, 2000; and U.S. Pat. No. 5,449,752. Additional exemplary methods of making the peptides of the present disclosures are set forth in Example 1.

In some embodiments, the peptides described herein are commercially synthesized by companies, such as Synpep (Dublin, Calif.), Peptide Technologies Corp. (Gaithersburg, Md.), and Multiple Peptide Systems (San Diego, Calif.). In this respect, the peptides can be synthetic, recombinant, isolated, and/or purified.

Also, in the instances in which the analogs of the disclosure do not comprise any non-coded or non-natural amino acids, the glucagon analog can be recombinantly produced using a nucleic acid encoding the amino acid sequence of the analog using standard recombinant methods. See, for instance, Sambrook et al., Molecular Cloning: A Laboratory Manual. 3rd ed., Cold Spring Harbor Press, Cold Spring Harbor, N.Y. 2001; and Ausubel et al., Current Protocols in Molecular Biology, Greene Publishing Associates and John Wiley & Sons, NY, 1994.

In some embodiments, the glucagon analogs of the disclosure are isolated. The term "isolated" as used herein means having been removed from its natural environment. In exemplary embodiments, the analog is made through recombinant methods and the analog is isolated from the host cell.

In some embodiments, the glucagon analogs of the disclosure are purified. The term "purified," as used herein relates to the isolation of a molecule or compound in a form that is substantially free of contaminants which in some aspects are normally associated with the molecule or compound in a native or natural environment and means having been increased in purity as a result of being separated from other components of the original composition. The purified peptide or compound include, for example, peptides substantially free of nucleic acid molecules, lipids, and carbohydrates, or other starting materials or intermediates which are used or formed during chemical synthesis of the peptides. It is recognized that "purity" is a relative term, and not to be necessarily construed as absolute purity or absolute enrichment or absolute selection. In some aspects, the purity is at least or about 50%, is at least or about 60%, at least or about 70%, at least or about 80%, or at least or about 90% (e.g., at least or about 91%, at least or about 92%, at least or about 93%, at least or about 94%, at least or about 95%, at least or about 96%, at least or about 97%, at least or about 98%, at least or about 99% or is approximately 100%.

Conjugates

The invention further provides conjugates comprising one or more of the glucagon analogs described herein conjugated to a heterologous moiety. As used herein, the term "heterologous moiety" is synonymous with the term "conjugate moiety" and refers to any molecule (chemical or biochemical, naturally-occurring or non-coded) which is different from the glucagon analogs described herein. Exemplary conjugate moieties that can be linked to any of the analogs described herein include but are not limited to a heterologous peptide or polypeptide (including for example, a plasma protein), a targeting agent, an immunoglobulin or portion thereof (e.g., variable region, CDR, or Fc region), a diagnostic label such as a radioisotope, fluorophore or enzymatic label, a polymer including water soluble polymers, or other therapeutic or diagnostic agents. In some embodiments a conjugate is provided comprising an analog of the present invention and a plasma protein, wherein the plasma protein is selected from the group consisting of albumin, transferin, fibrinogen and globulins. In some embodiments the plasma protein moiety of the conjugate is albumin or transferin. The conjugate in some embodiments comprises one or more of the glucagon analogs described herein and one or more of: a peptide (which is distinct from the glucagon and/or GLP-1 receptor active glucagon analogs described herein), a polypeptide, a nucleic acid molecule, an antibody or fragment thereof, a polymer, a quantum dot, a small molecule, a toxin, a diagnostic agent, a carbohydrate, an amino acid.

In some embodiments, the heterologous moiety is a peptide which is distinct from the glucagon analogs described herein and the conjugate is a fusion peptide or a chimeric peptide. In some embodiments, the heterologous moiety is a peptide extension of 1-21 amino acids. In specific embodiments, the extension is attached to the C-terminus of the glucagon analog, e.g., to amino acid at position 29.

In some specific aspects, the extension is a single amino acid or dipeptide. In specific embodiments, the extension comprises an amino acid selected from the group consisting of: a charged amino acid (e.g., a negative-charged amino acid (e.g., Glu), a positive-charged amino acid), an amino acid comprising a hydrophilic moiety. In some aspects, the extension is Gly, Glu, Cys, Gly-Gly, Gly-Glu.

In some embodiments, the extension comprises an amino acid sequence of SEQ ID NO: 5 (GPSSGAPPPS), SEQ ID NO: 6 (GGPSSGAPPPS), SEQ ID NO: 7 (KRNRNNIA), or SEQ ID NO: 8 (KRNR). In specific aspects, the amino acid sequence is attached through the C-terminal amino acid of the glucagon analog, e.g., amino acid at position 29. In some embodiments, the amino acid sequence of any of SEQ ID NOs: 5-8 is bound to amino acid 29 of the glucagon analog through a peptide bond. In some specific embodiments, the amino acid at position 29 of the glucagon analog is a Gly and the Gly is fused to one of the amino acid sequences of any of SEQ ID NOs: 5-8.

In some embodiments, the heterologous moiety is a polymer. In some embodiments, the polymer is selected from the group consisting of: polyamides, polycarbonates, polyalkylenes and derivatives thereof including, polyalkylene glycols, polyalkylene oxides, polyalkylene terephthalates, polymers of acrylic and methacrylic esters, including poly(methyl methacrylate), poly(ethyl methacrylate), poly (butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate), polyvinyl polymers including polyvinyl alcohols, polyvinyl ethers, polyvinyl esters, polyvinyl halides, poly(vinyl acetate), and polyvinylpyrrolidone, polyglycolides, polysiloxanes, polyurethanes and co-polymers thereof, celluloses including alkyl cellulose, hydroxyalkyl celluloses, cellulose ethers, cellulose esters, nitro celluloses, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, and cellulose sulphate sodium salt, polypropylene, polyethylenes including poly(ethylene glycol), poly(ethylene oxide), and poly(ethylene terephthalate), and polystyrene.

In some aspects, the polymer is a biodegradable polymer, including a synthetic biodegradable polymer (e.g., polymers of lactic acid and glycolic acid, polyanhydrides, poly(ortho) esters, polyurethanes, poly(butic acid), poly(valeric acid), and poly(lactide-cocaprolactone)), and a natural biodegradable polymer (e.g., alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins (e.g., zein and other prolamines and hydrophobic proteins)), as well as any copolymer or mixture thereof. In general, these materials degrade either by enzymatic hydrolysis or exposure to water in vivo, by surface or bulk erosion.

In some aspects, the polymer is a bioadhesive polymer, such as a bioerodible hydrogel described by H. S. Sawhney, C. P. Pathak and J. A. Hubbell in Macromolecules, 1993, 26, 581-587, the teachings of which are incorporated herein, polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly (octadecyl acrylate).

In some embodiments, the polymer is a water-soluble polymer or a hydrophilic polymer. Hydrophilic polymers are further described herein under "Hydrophilic Moieties." Suitable water-soluble polymers are known in the art and include, for example, polyvinylpyrrolidone, hydroxypropyl cellulose (HPC; Klucel), hydroxypropyl methylcellulose (HPMC; Methocel), nitrocellulose, hydroxypropyl ethylcellulose, hydroxypropyl butylcellulose, hydroxypropyl pentylcellulose, methyl cellulose, ethylcellulose (Ethocel), hydroxyethyl cellulose, various alkyl celluloses and hydroxyalkyl celluloses, various cellulose ethers, cellulose acetate, carboxymethyl cellulose, sodium carboxymethyl cellulose, calcium carboxymethyl cellulose, vinyl acetate/ crotonic acid copolymers, poly-hydroxyalkyl methacrylate, hydroxymethyl methacrylate, methacrylic acid copolymers, polymethacrylic acid, polymethylmethacrylate, maleic anhydride/methyl vinyl ether copolymers, poly vinyl alcohol, sodium and calcium polyacrylic acid, polyacrylic acid, acidic carboxy polymers, carboxypolymethylene, carboxyvinyl polymers, polyoxyethylene polyoxypropylene copolymer, polymethylvinylether co-maleic anhydride, carboxymethylamide, potassium methacrylate divinylbenzene co-polymer, polyoxyethyleneglycols, polyethylene oxide, and derivatives, salts, and combinations thereof.

In specific embodiments, the polymer is a polyalkylene glycol, including, for example, polyethylene glycol (PEG).

In some embodiments, the heterologous moiety is a carbohydrate. In some embodiments, the carbohydrate is a monosaccharide (e.g., glucose, galactose, fructose), a disaccharide (e.g., sucrose, lactose, maltose), an oligosaccharide (e.g., raffinose, stachyose), or a polysaccharide (e.g., starch, amylase, amylopectin, cellulose, chitin, callose, laminarin, xylan, mannan, fucoidan, or galactomannan).

In some embodiments, the heterologous moiety is a lipid. The lipid, in some embodiments, is a fatty acid, eicosanoid, prostaglandin, leukotriene, thromboxane, N-acyl ethanolamine), glycerolipid (e.g., mono-, di-, tri-substituted glycerols), glycerophospholipid (e.g., phosphatidylcholine, phosphatidylinositol, phosphatidylethanolamine, phosphatidylserine), sphingolipid (e.g., sphingosine, ceramide), sterol lipid (e.g., steroid, cholesterol), prenol lipid, saccharolipid, or a polyketide, oil, wax, cholesterol, sterol, fat-soluble vitamin, monoglyceride, diglyceride, triglyceride, a phospholipid.

In some embodiments, the heterologous moiety is attached via non-covalent or covalent bonding to the analog of the present disclosure. In exemplary aspects, the heterologous moiety is attached to the analog of the present disclosure via a linker. Linkage can be accomplished by covalent chemical bonds, physical forces such electrostatic, hydrogen, ionic, van der Waals, or hydrophobic or hydrophilic interactions. A variety of non-covalent coupling systems may be used, including biotin-avidin, ligand/receptor, enzyme/substrate, nucleic acid/nucleic acid binding protein, lipid/lipid binding protein, cellular adhesion molecule partners; or any binding partners or fragments thereof which have affinity for each other.

The glucagon analog in some embodiments is linked to conjugate moieties via direct covalent linkage by reacting targeted amino acid residues of the analog with an organic derivatizing agent that is capable of reacting with selected side chains or the N- or C-terminal residues of these targeted amino acids. Reactive groups on the analog or conjugate moiety include, e.g., an aldehyde, amino, ester, thiol, α-haloacetyl, maleimido or hydrazino group. Derivatizing agents include, for example, maleimidobenzoyl sulfosuccinimide ester (conjugation through cysteine residues), N-hydroxysuccinimide (through lysine residues), glutaraldehyde, succinic anhydride or other agents known in the art. Alternatively, the conjugate moieties can be linked to the analog indirectly through intermediate carriers, such as polysaccharide or polypeptide carriers. Examples of polysaccharide carriers include aminodextran. Examples of suitable polypeptide carriers include polylysine, polyglutamic acid, polyaspartic acid, co-polymers thereof, and mixed polymers of these amino acids and others, e.g., serines, to confer desirable solubility properties on the resultant loaded carrier.

Cysteinyl residues are most commonly reacted with α-haloacetates (and corresponding amines), such as chloroacetic acid, chloroacetamide to give carboxymethyl or carboxyamidomethyl derivatives. Cysteinyl residues also are derivatized by reaction with bromotrifluoroacetone, alpha-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5-7.0 because this agent is relatively specific for the histidyl side chain. Para-bromophenacyl bromide also is useful; the reaction is preferably performed in 0.1 M sodium cacodylate at pH 6.0.

Lysinyl and amino-terminal residues are reacted with succinic or other carboxylic acid anhydrides. Derivatization with these agents has the effect of reversing the charge of the lysinyl residues. Other suitable reagents for derivatizing alpha-amino-containing residues include imidoesters such as methyl picolinimidate, pyridoxal phosphate, pyridoxal, chloroborohydride, trinitrobenzenesulfonic acid, O-methylisourea, 2,4-pentanedione, and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high pKa of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively.

Carboxyl side groups (aspartyl or glutamyl) are selectively modified by reaction with carbodiimides (R—N=C=N—R'), where R and R' are different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Other modifications include hydroxylation of proline and lysine, phosphorylation of hydroxyl groups of seryl or threonyl residues, methylation of the alpha-amino groups of lysine, arginine, and histidine side chains (T. E. Creighton, Proteins: Structure and Molecular Properties, W.H. Freeman & Co., San Francisco, pp. 79-86 (1983)), deamidation of asparagine or glutamine, acetylation of the N-terminal amine, and/or amidation or esterification of the C-terminal carboxylic acid group.

Another type of covalent modification involves chemically or enzymatically coupling glycosides to the analog. Sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of tyrosine, or tryptophan, or (f) the amide group of glutamine. These methods are described in WO87/05330 published 11 Sep. 1987, and in Aplin and Wriston, CRC Crit. Rev. Biochem., pp. 259-306 (1981).

In some embodiments, the glucagon analog is conjugated to a heterologous moiety via covalent linkage between a side chain of an amino acid of the glucagon analog and the heterologous moiety. In some embodiments, the glucagon analog is conjugated to a heterologous moiety via the side chain of an amino acid at position 16, 17, 21, 24, or 29, a position within a C-terminal extension, or the C-terminal amino acid, or a combination of these positions. In some aspects, the amino acid covalently linked to a heterologous moiety (e.g., the amino acid comprising a heterologous moiety) is a Cys, Lys, Orn, homo-Cys, or Ac-Phe, and the side chain of the amino acid is covalently bonded to a heterologous moiety.

In some embodiments, the conjugate comprises a linker that joins the glucagon analog to the heterologous moiety. In some aspects, the linker comprises a chain of atoms from 1 to about 60, or 1 to 30 atoms or longer, 2 to 5 atoms, 2 to 10 atoms, 5 to 10 atoms, or 10 to 20 atoms long. In some embodiments, the chain atoms are all carbon atoms. In some embodiments, the chain atoms in the backbone of the linker are selected from the group consisting of C, O, N, and S. Chain atoms and linkers may be selected according to their expected solubility (hydrophilicity) so as to provide a more soluble conjugate. In some embodiments, the linker provides a functional group that is subject to cleavage by an enzyme or other catalyst or hydrolytic conditions found in the target tissue or organ or cell. In some embodiments, the length of the linker is long enough to reduce the potential for steric hindrance. If the linker is a covalent bond or a peptidyl bond and the conjugate is a polypeptide, the entire conjugate can be a fusion protein. Such peptidyl linkers may be any length. Exemplary linkers are from about 1 to 50 amino acids in length, 5 to 50, 3 to 5, 5 to 10, 5 to 15, or 10 to 30 amino acids in length. Such fusion proteins may alternatively be produced by recombinant genetic engineering methods known to one of ordinary skill in the art.

Conjugates: Fc Fusions

As noted above, in some embodiments, the analogs are conjugated, e.g., fused to an immunoglobulin or portion thereof (e.g., variable region, CDR, or Fc region). Known types of immunoglobulins (Ig) include IgG, IgA, IgE, IgD or IgM. The Fc region is a C-terminal region of an Ig heavy chain, which is responsible for binding to Fc receptors that carry out activities such as recycling (which results in prolonged half-life), antibody dependent cell-mediated cytotoxicity (ADCC), and complement dependent cytotoxicity (CDC).

For example, according to some definitions the human IgG heavy chain Fc region stretches from Cys226 to the C-terminus of the heavy chain. The "hinge region" generally extends from Glu216 to Pro230 of human IgG1 (hinge regions of other IgG isotypes may be aligned with the IgG1 sequence by aligning the cysteines involved in cysteine bonding). The Fc region of an IgG includes two constant domains, CH2 and CH3. The CH2 domain of a human IgG Fc region usually extends from amino acids 231 to amino acid 341. The CH3 domain of a human IgG Fc region usually extends from amino acids 342 to 447. References made to amino acid numbering of immunoglobulins or immunoglobulin fragments, or regions, are all based on Kabat et al. 1991, Sequences of Proteins of Immunological Interest, U.S. Department of Public Health, Bethesda, Md. In a related embodiments, the Fc region may comprise one or more native or modified constant regions from an immunoglobulin heavy chain, other than CH1, for example, the CH2 and CH3 regions of IgG and IgA, or the CH3 and CH4 regions of IgE.

Suitable conjugate moieties include portions of immunoglobulin sequence that include the FcRn binding site. FcRn, a salvage receptor, is responsible for recycling immunoglobulins and returning them to circulation in blood. The region of the Fc portion of IgG that binds to the FcRn receptor has been described based on X-ray crystallography (Burmeister et al. 1994, Nature 372:379). The major contact area of the Fc with the FcRn is near the junction of the CH2 and CH3 domains. Fc-FcRn contacts are all within a single Ig heavy chain. The major contact sites include amino acid residues 248, 250-257, 272, 285, 288, 290-291, 308-311, and 314 of the CH2 domain and amino acid residues 385-387, 428, and 433-436 of the CH3 domain.

Some conjugate moieties may or may not include FcγR binding site(s). FcγR are responsible for ADCC and CDC. Examples of positions within the Fc region that make a direct contact with FcγR are amino acids 234-239 (lower hinge region), amino acids 265-269 (B/C loop), amino acids 297-299 (C'/E loop), and amino acids 327-332 (F/G) loop (Sondermann et al., Nature 406: 267-273, 2000). The lower hinge region of IgE has also been implicated in the FcRI binding (Henry, et al., Biochemistry 36, 15568-15578, 1997). Residues involved in IgA receptor binding are described in Lewis et al., (J Immunol. 175:6694-701, 2005). Amino acid residues involved in IgE receptor binding are described in Sayers et al. (J Biol Chem. 279(34):35320-5, 2004).

Amino acid modifications may be made to the Fc region of an immunoglobulin. Such variant Fc regions comprise at least one amino acid modification in the CH3 domain of the Fc region (residues 342-447) and/or at least one amino acid modification in the CH2 domain of the Fc region (residues 231-341). Mutations believed to impart an increased affinity for FcRn include T256A, T307A, E380A, and N434A (Shields et al. 2001, J. Biol. Chem. 276:6591). Other mutations may reduce binding of the Fc region to FcγRI, FcγRIIA, FcγRIIB, and/or FcγRIIIA without significantly reducing affinity for FcRn. For example, substitution of the Asn at position 297 of the Fc region with Ala or another amino acid removes a highly conserved N-glycosylation site and may result in reduced immunogenicity with concomitant prolonged half-life of the Fc region, as well as reduced binding to FcγRs (Routledge et al. 1995, Transplantation 60:847; Friend et al. 1999, Transplantation 68:1632; Shields et al. 1995, J. Biol. Chem. 276:6591). Amino acid modifications at positions 233-236 of IgG1 have been made that reduce binding to FcγRs (Ward and Ghetie 1995, Therapeutic Immunology 2:77 and Armour et al. 1999, Eur. J. Immunol. 29:2613). Some exemplary amino acid substitutions are described in U.S. Pat. Nos. 7,355,008 and 7,381,408, each incorporated by reference herein in its entirety.

Conjugates: Hydrophilic Moieties

The glucagon analogs described herein can be further modified to improve its solubility and stability in aqueous solutions at physiological pH, while retaining the high biological activity relative to native glucagon. Hydrophilic moieties such as PEG groups can be attached to the analogs under any suitable conditions used to react a protein with an activated polymer molecule. Any means known in the art can be used, including via acylation, reductive alkylation, Michael addition, thiol alkylation or other chemoselective conjugation/ligation methods through a reactive group on the PEG moiety (e.g., an aldehyde, amino, ester, thiol, α-haloacetyl, maleimido or hydrazino group) to a reactive group on the target compound (e.g., an aldehyde, amino, ester, thiol, α-haloacetyl, maleimido or hydrazino group). Activating groups which can be used to link the water soluble polymer to one or more proteins include without limitation sulfone, maleimide, sulfhydryl, thiol, triflate, tresylate, azidirine, oxirane, 5-pyridyl, and alpha-halogenated acyl group (e.g., alpha-iodo acetic acid, alpha-bromoacetic acid, alpha-chloroacetic acid). If attached to the analog by reductive alkylation, the polymer selected should have a single reactive aldehyde so that the degree of polymerization is controlled. See, for example, Kinstler et al., *Adv. Drug. Delivery Rev.* 54: 477-485 (2002); Roberts et al., *Adv. Drug*

Delivery Rev. 54: 459-476 (2002); and Zalipsky et al., *Adv. Drug Delivery Rev.* 16: 157-182 (1995).

In specific aspects, an amino acid residue of the analog having a thiol is modified with a hydrophilic moiety such as PEG. In some embodiments, the thiol is modified with maleimide-activated PEG in a Michael addition reaction to result in a PEGylated analog comprising the thioether linkage shown below:

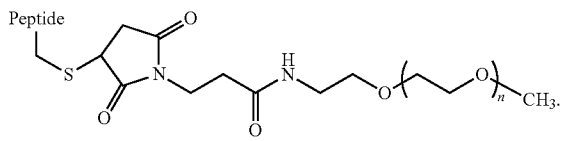

In some embodiments, the thiol is modified with a haloacetyl-activated PEG in a nucleophilic substitution reaction to result in a PEGylated analog comprising a thioether linkage.

Suitable hydrophilic moieties include polyethylene glycol (PEG), polypropylene glycol, polyoxyethylated polyols (e.g., POG), polyoxyethylated sorbitol, polyoxyethylated glucose, polyoxyethylated glycerol (POG), polyoxyalkylenes, polyethylene glycol propionaldehyde, copolymers of ethylene glycol/propylene glycol, monomethoxy-polyethylene glycol, mono-(C1-C10) alkoxy- or aryloxy-polyethylene glycol, carboxymethylcellulose, polyacetals, polyvinyl alcohol (PVA), polyvinyl pyrrolidone, poly-1,3-dioxolane, poly-1,3,6-trioxane, ethylene/maleic anhydride copolymer, poly (β-amino acids) (either homopolymers or random copolymers), poly(n-vinyl pyrrolidone)polyethylene glycol, propropylene glycol homopolymers (PPG) and other polyakylene oxides, polypropylene oxide/ethylene oxide copolymers, colonic acids or other polysaccharide polymers, Ficoll or dextran and mixtures thereof. Dextrans are polysaccharide polymers of glucose subunits, predominantly linked by al-6 linkages. Dextran is available in many molecular weight ranges, e.g., about 1 kD to about 100 kD, or from about 5, 10, 15 or 20 kD to about 20, 30, 40, 50, 60, 70, 80 or 90 kD. Linear or branched polymers are contemplated. Resulting preparations of conjugates may be essentially monodisperse or polydisperse, and may have about 0.5, 0.7, 1, 1.2, 1.5 or 2 polymer moieties per analog.

In some or any embodiments, the glucagon analog is conjugated to a hydrophilic moiety via covalent linkage between a side chain of an amino acid of the glucagon analog and the hydrophilic moiety. In some or any embodiments, the glucagon analog is conjugated to a hydrophilic moiety via the side chain of an amino acid at position 16, 17, 21, 24, or 29, a position within a C-terminal extension, or the C-terminal amino acid, or a combination of these positions. In some aspects, the amino acid covalently linked to a hydrophilic moiety (e.g., the amino acid comprising a hydrophilic moiety) is a Cys, Lys, Orn, homo-Cys, or Ac-Phe, and the side chain of the amino acid is covalently bonded to a hydrophilic moiety (e.g., PEG).

Conjugates: rPEG

In some or any embodiments, the conjugate of the present disclosure comprises the glucagon analog having GIP receptor agonist activity fused to an accessory analog which is capable of forming an extended conformation similar to chemical PEG (e.g., a recombinant PEG (rPEG) molecule), such as those described in International Patent Application Publication No. WO2009/023270 and U.S. Patent Application Publication No. US20080286808. The rPEG molecule in some aspects is a polypeptide comprising one or more of glycine, serine, glutamic acid, aspartic acid, alanine, or proline. In some aspects, the rPEG is a homopolymer, e.g., poly-glycine, poly-serine, poly-glutamic acid, poly-aspartic acid, poly-alanine, or poly-proline. In other embodiments, the rPEG comprises two types of amino acids repeated, e.g., poly(Gly-Ser), poly(Gly-Glu), poly(Gly-Ala), poly(Gly-Asp), poly(Gly-Pro), poly(Ser-Glu), etc. In some aspects, the rPEG comprises three different types of amino acids, e.g., poly(Gly-Ser-Glu). In specific aspects, the rPEG increases the half-life of the Glucagon and/or GLP-1 agonist analog. In some aspects, the rPEG comprises a net positive or net negative charge. The rPEG in some aspects lacks secondary structure. In some embodiments, the rPEG is greater than or equal to 10 amino acids in length and in some embodiments is about 40 to about 50 amino acids in length. The accessory peptide in some aspects is fused to the N- or C-terminus of the analog of the present disclosure through a peptide bond or a proteinase cleavage site, or is inserted into the loops of the analog of the present disclosure. The rPEG in some aspects comprises an affinity tag or is linked to a PEG that is greater than 5 kDa. In some embodiments, the rPEG confers the analog of the present disclosure with an increased hydrodynamic radius, serum half-life, protease resistance, or solubility and in some aspects confers the analog with decreased immunogenicity.

Conjugates: Multimers

The invention further provides multimers or dimers of the analogs disclosed herein, including homo- or hetero-multimers or homo- or hetero-dimers. Two or more of the analogs can be linked together using standard linking agents and procedures known to those skilled in the art. For example, dimers can be formed between two peptides through the use of bifunctional thiol crosslinkers and bi-functional amine crosslinkers, particularly for the analogs that have been substituted with cysteine, lysine ornithine, homocysteine or acetyl phenylalanine residues. The dimer can be a homodimer or alternatively can be a heterodimer. In exemplary embodiments, the linker connecting the two (or more) analogs is PEG, e.g., a 5 kDa PEG, 20 kDa PEG. In some embodiments, the linker is a disulfide bond. For example, each monomer of the dimer may comprise a Cys residue (e.g., a terminal or internally positioned Cys) and the sulfur atom of each Cys residue participates in the formation of the disulfide bond. In exemplary aspects, each monomer of the dimer is linked via a thioether bond. In exemplary aspects, an epsilon amine of a Lys residue of one monomer is bonded to a Cys residue, which, in turn, is connected via a chemical moiety to the epsilon amine of a Lys residue of the other monomer. Methods of making such thioether bonded dimers are further described herein. In some aspects, the monomers are connected via terminal amino acids (e.g., N-terminal or C-terminal), via internal amino acids, or via a terminal amino acid of at least one monomer and an internal amino acid of at least one other monomer. In specific aspects, the monomers are not connected via an N-terminal amino acid. In some aspects, the monomers of the multimer are attached together in a "tail-to-tail" orientation in which the C-terminal amino acids of each monomer are attached together.

Prodrugs

Further provided by the invention are prodrugs of the peptides and analogs described herein. As used herein, the term "prodrug" is defined as any compound that undergoes chemical modification before exhibiting its full pharmacological effects.

In exemplary embodiments, the prodrug is an amide-based peptide prodrug, similar to those described in International Patent Application Publication No. WO/2010/071807, which published on Jun. 24, 2010. Such prodrugs are intended to delay onset of action and extend the half life of the drug. The delayed onset of action is advantageous in that it allows systemic distribution of the prodrug prior to its activation. Accordingly, the administration of prodrugs eliminates complications caused by peak activities upon administration and increases the therapeutic index of the parent drug.

In exemplary aspects, the prodrug comprises the structure: A-B-Q; wherein Q is a peptide or analog described herein; A is an amino acid or a hydroxy acid; B is an N-alkylated amino acid linked to Q through an amide bond between A-B and an amine of Q; wherein A, B, or the amino acid of Q to which A-B is linked is a non-coded amino acid, further wherein chemical cleavage half-life (t½) of A-B from Q is at least about 1 hour to about 1 week in PBS under physiological conditions. As used herein the term "hydroxy acid" refers to an amino acid that has been modified to replace the alpha carbon amino group with a hydroxyl group.

In some embodiments the dipeptide prodrug element has the general structure of Formula I:

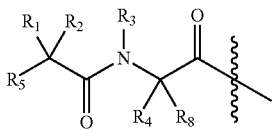

wherein $R_1$, $R_2$, $R_4$ and $R_8$ are independently selected from the group consisting of H, $C_1$-$C_{18}$ alkyl, $C_2$-$C_{18}$ alkenyl, ($C_1$-$C_{18}$ alkyl)OH, ($C_1$-$C_{18}$ alkyl)SH, ($C_2$-$C_3$ alkyl)SCH$_3$, ($C_1$-$C_4$ alkyl)CONH$_2$, ($C_1$-$C_4$ alkyl)COOH, ($C_1$-$C_4$ alkyl)NH$_2$, ($C_1$-$C_4$ alkyl)NHC(NH$_2^+$)NH$_2$, ($C_0$-$C_4$ alkyl)($C_3$-$C_6$ cycloalkyl), ($C_0$-$C_4$ alkyl)($C_2$-$C_5$ heterocyclic), ($C_0$-$C_4$ alkyl)($C_6$-$C_{10}$ aryl)$R_7$, ($C_1$-$C_4$ alkyl)($C_3$-$C_9$ heteroaryl), and $C_1$-$C_{12}$ alkyl (A)(W$_1$)$C_1$-$C_{12}$ alkyl, wherein W$_1$ is a heteroatom selected from the group consisting of N, S and O, or $R_1$ and $R_2$ together with the atoms to which they are attached form a $C_3$-$C_{12}$ cycloalkyl or aryl; or $R_4$ and $R_8$ together with the atoms to which they are attached form a $C_3$-$C_6$ cycloalkyl;

$R_3$ is selected from the group consisting of $C_1$-$C_{18}$ alkyl, ($C_1$-$C_{18}$ alkyl)OH, ($C_1$-$C_{18}$ alkyl)NH$_2$, ($C_1$-$C_{18}$ alkyl)SH, ($C_0$-$C_4$ alkyl)($C_3$-$C_6$)cycloalkyl, ($C_0$-$C_4$ alkyl)($C_2$-$C_5$ heterocyclic), ($C_0$-$C_4$ alkyl)($C_6$-$C_{10}$ aryl)$R_7$, and ($C_1$-$C_4$ alkyl)($C_3$-$C_9$ heteroaryl) or $R_4$ and $R_3$ together with the atoms to which they are attached form a 4, 5 or 6 member heterocyclic ring;

$R_5$ is NHR$_6$ or OH;

$R_6$ is H, $C_1$-$C_8$ alkyl or $R_6$ and $R_2$ together with the atoms to which they are attached form a 4, 5 or 6 member heterocyclic ring; and $R_7$ is selected from the group consisting of H and OH.

In other embodiments the dipeptide prodrug element has the general structure of Formula I:

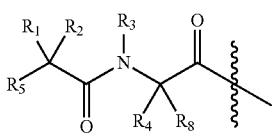

wherein $R_1$, $R_2$, $R_4$ and $R_8$ are independently selected from the group consisting of H, $C_1$-$C_{18}$ alkyl, $C_2$-$C_{18}$ alkenyl, ($C_1$-$C_{18}$ alkyl)OH, ($C_1$-$C_{18}$ alkyl)SH, ($C_2$-$C_3$ alkyl)SCH$_3$, ($C_1$-$C_4$ alkyl)CONH$_2$, ($C_1$-$C_4$ alkyl)COOH, ($C_1$-$C_4$ alkyl)NH$_2$, ($C_1$-$C_4$ alkyl)NHC(NH$_2^+$)NH$_2$, ($C_0$-$C_4$ alkyl)($C_3$-$C_6$ cycloalkyl), ($C_0$-$C_4$ alkyl)($C_2$-$C_5$ heterocyclic), ($C_0$-$C_4$ alkyl)($C_6$-$C_{10}$ aryl)$R_7$, ($C_1$-$C_4$ alkyl)($C_3$-$C_9$ heteroaryl), and $C_1$-$C_{12}$ alkyl (W$_1$)$C_1$-$C_{12}$ alkyl, wherein W$_1$ is a heteroatom selected from the group consisting of N, S and O, or $R_1$ and $R_2$ together with the atoms to which they are attached form a $C_3$-$C_{12}$ cycloalkyl; or $R_4$ and $R_8$ together with the atoms to which they are attached form a $C_3$-$C_6$ cycloalkyl;

$R_3$ is selected from the group consisting of $C_1$-$C_{18}$ alkyl, ($C_1$-$C_{18}$ alkyl)OH, ($C_1$-$C_{18}$ alkyl)NH$_2$, ($C_1$-$C_{18}$ alkyl)SH, ($C_0$-$C_4$ alkyl)($C_3$-$C_6$)cycloalkyl, ($C_0$-$C_4$ alkyl)($C_2$-$C_5$ heterocyclic), ($C_0$-$C_4$ alkyl)($C_6$-$C_{10}$ aryl)$R_7$, and ($C_1$-$C_4$ alkyl)($C_3$-$C_9$ heteroaryl) or $R_4$ and $R_3$ together with the atoms to which they are attached form a 4, 5 or 6 member heterocyclic ring;

$R_5$ is NHR$_6$ or OH;

$R_6$ is H, $C_1$-$C_8$ alkyl or $R_6$ and $R_1$ together with the atoms to which they are attached form a 4, 5 or 6 member heterocyclic ring; and $R_7$ is selected from the group consisting of hydrogen, $C_1$-$C_{18}$ alkyl, $C_2$-$C_{18}$ alkenyl, ($C_0$-$C_4$ alkyl)CONH$_2$, ($C_0$-$C_4$ alkyl)COOH, ($C_0$-$C_4$ alkyl)NH$_2$, ($C_0$-$C_4$ alkyl)OH, and halo.

In some embodiments $R_8$ is H and $R_5$ is NHR$_6$.

In some embodiments the dipeptide prodrug element has the structure of Formula I, wherein $R_1$ and $R_8$ are independently H or $C_1$-$C_8$ alkyl;

$R_2$ and $R_4$ are independently selected from the group consisting of H, $C_1$-$C_8$ alkyl, $C_2$-$C_8$ alkenyl, ($C_1$-$C_4$ alkyl)OH, ($C_1$-$C_4$ alkyl)SH, ($C_2$-$C_3$ alkyl)SCH$_3$, ($C_1$-$C_4$ alkyl)CONH$_2$, ($C_1$-$C_4$ alkyl)COOH, ($C_1$-$C_4$ alkyl)NH$_2$, ($C_1$-$C_4$ alkyl)NHC(NH$_2$+) NH$_2$, ($C_0$-$C_4$ alkyl)($C_3$-$C_6$ cycloalkyl), ($C_0$-$C_4$ alkyl)($C_2$-$C_5$ heterocyclic), ($C_0$-$C_4$ alkyl)($C_6$-$C_{10}$ aryl)$R_7$, and CH$_2$($C_3$-$C_9$ heteroaryl), or $R_1$ and $R_2$ together with the atoms to which they are attached form a $C_3$-$C_{12}$ cycloalkyl or aryl;

$R_5$ is NHR$_6$; and $R_6$ is H or $C_1$-$C_8$ alkyl.

In other embodiments the dipeptide prodrug element has the structure of Formula I, wherein $R_1$ and $R_8$ are independently H or $C_1$-$C_8$ alkyl;

$R_2$ and $R_4$ are independently selected from the group consisting of H, $C_1$-$C_8$ alkyl, $C_2$-$C_8$ alkenyl, ($C_1$-$C_4$ alkyl)OH, ($C_1$-$C_4$ alkyl)SH, ($C_2$-$C_3$ alkyl)SCH$_3$, ($C_1$-$C_4$ alkyl)CONH$_2$, ($C_1$-$C_4$ alkyl)COOH, ($C_1$-$C_4$ alkyl)NH$_2$, ($C_1$-$C_4$ alkyl)NHC(NH$_2$+) NH$_2$, ($C_0$-$C_4$ alkyl)($C_3$-$C_6$ cycloalkyl), ($C_0$-$C_4$ alkyl)($C_2$-$C_5$ heterocyclic), ($C_0$-$C_4$ alkyl)($C_6$-$C_{10}$ aryl)$R_7$, and CH$_2$($C_3$-$C_9$ heteroaryl), or $R_1$ and $R_2$ together with the atoms to which they are attached form a $C_3$-$C_{12}$ cycloalkyl;

$R_3$ is $C_1$-$C_{18}$ alkyl;

$R_5$ is NHR$_6$;

$R_6$ is H or $C_1$-$C_8$ alkyl; and $R_7$ is selected from the group consisting of hydrogen, $C_1$-$C_{18}$ alkyl, $C_2$-$C_{18}$ alkenyl, ($C_0$-$C_4$ alkyl)CONH$_2$, ($C_0$-$C_4$ alkyl)COOH, ($C_0$-$C_4$ alkyl)NH$_2$, ($C_0$-$C_4$ alkyl)OH, and halo.

The half life of the prodrug formed in accordance with the present disclosure is determined by the substituents of the dipeptide prodrug element, its location, and the amino acid to which it is attached. For example, the prodrug may comprise a peptide or analog described herein, wherein the dipeptide prodrug element is linked through the alpha amino group of the N-terminal amino acid of the peptide or analog described herein. In this embodiment prodrugs having a $t_{1/2}$ of, e.g., about 1 hour comprise a dipeptide prodrug element with the structure:

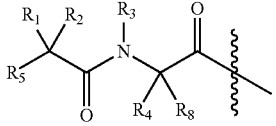

wherein $R_1$ and $R_2$ are independently $C_1$-$C_{18}$ alkyl or aryl; or $R_1$ and $R_2$ are linked through —$(CH_2)_p$, wherein p is 2-9;

$R_3$ is $C_1$-$C_{18}$ alkyl;

$R_4$ and $R_8$ are each hydrogen; and $R_5$ is an amine.

In other embodiments, prodrugs having a $t_{1/2}$ of, e.g., about 1 hour comprise a dipeptide prodrug element with the structure:

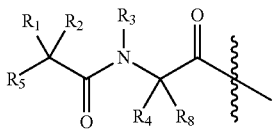

wherein $R_1$ and $R_2$ are independently $C_1$-$C_{18}$ alkyl or ($C_0$-$C_4$ alkyl)($C_0$-$C_{10}$ aryl)$R_7$; or $R_1$ and $R_2$ are linked through —$(CH_2)_p$, wherein p is 2-9;

$R_3$ is $C_1$-$C_{18}$ alkyl;

$R_4$ and $R_8$ are each hydrogen;

$R_5$ is $NH_2$; and $R_7$ is selected from the group consisting of hydrogen, $C_1$-$C_{18}$ alkyl, $C_2$-$C_{18}$ alkenyl, ($C_0$-$C_4$ alkyl)$CONH_2$, ($C_0$-$C_4$ alkyl)COOH, ($C_0$-$C_4$ alkyl)$NH_2$, ($C_0$-$C_4$ alkyl)OH, and halo.

Furthermore, prodrugs having the dipeptide prodrug element linked to the N-terminal alpha amino acid of the peptide or analog described herein and having a $t_{1/2}$, e.g., between about 6 to about 24 hours, comprise a dipeptide prodrug element with the structure:

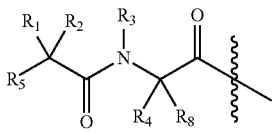

wherein $R_1$ and $R_2$ are independently selected from the group consisting of hydrogen, $C_1$-$C_{18}$ alkyl and aryl, or $R_1$ and $R_2$ are linked through $(CH_2)_p$, wherein p is 2-9;

$R_3$ is $C_1$-$C_{18}$ alkyl or $R_3$ and $R_4$ together with the atoms to which they are attached form a 4-12 heterocyclic ring;

$R_4$ and $R_8$ are independently selected from the group consisting of hydrogen, $C_1$-$C_8$ alkyl and aryl; and $R_5$ is an amine;

with the proviso that both $R_1$ and $R_2$ are not hydrogen and provided that one of $R_4$ or $R_8$ is hydrogen.

In some embodiments, prodrugs having the dipeptide prodrug element linked to the N-terminal alpha amino acid of the peptide or analog described herein and having a $t_{1/2}$, e.g., between about 12 to about 72 hours, or in some embodiments between about 12 to about 48 hours, comprise a dipeptide prodrug element with the structure:

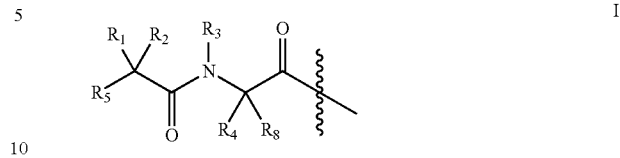

wherein $R_1$ and $R_2$ are independently selected from the group consisting of hydrogen, $C_1$-$C_{18}$ alkyl, ($C_1$-$C_{18}$ alkyl)OH, ($C_1$-$C_4$ alkyl)$NH_2$, and ($C_0$-$C_4$ alkyl)($C_6$-$C_{10}$ aryl)$R_7$, or $R_1$ and $R_2$ are linked through $(CH_2)_p$, wherein p is 2-9;

$R_3$ is $C_1$-$C_{18}$ alkyl or $R_3$ and $R_4$ together with the atoms to which they are attached form a 4-12 heterocyclic ring;

$R_4$ and $R_8$ are independently selected from the group consisting of hydrogen, $C_1$-$C_8$ alkyl and ($C_0$-$C_4$ alkyl)($C_6$-$C_{10}$ aryl)$R_7$;

$R_5$ is $NH_2$; and $R_7$ is selected from the group consisting of H, $C_1$-$C_{18}$ alkyl, $C_2$-$C_{18}$ alkenyl, ($C_0$-$C_4$ alkyl)$CONH_2$, ($C_0$-$C_4$ alkyl)COOH, ($C_0$-$C_4$ alkyl)$NH_2$, ($C_0$-$C_4$ alkyl)OH, and halo;

with the proviso that both $R_1$ and $R_2$ are not hydrogen and provided that at least one of $R_4$ or $R_8$ is hydrogen.

In some embodiments, prodrugs having the dipeptide prodrug element linked to the N-terminal amino acid of the peptide or analog described herein and having a $t_{1/2}$, e.g., between about 12 to about 72 hours, or in some embodiments between about 12 to about 48 hours, comprise a dipeptide prodrug element with the structure:

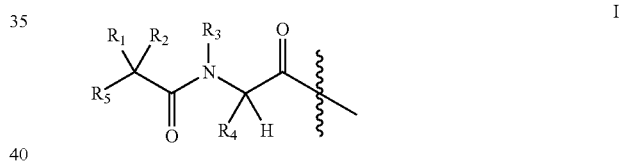

wherein $R_1$ and $R_2$ are independently selected from the group consisting of hydrogen, $C_1$-$C_8$ alkyl and ($C_1$-$C_4$ alkyl)$NH_2$, or $R_1$ and $R_2$ are linked through $(CH_2)_p$, wherein p is 2-9;

$R_3$ is $C_1$-$C_8$ alkyl or $R_3$ and $R_4$ together with the atoms to which they are attached form a 4-6 heterocyclic ring;

$R_4$ is selected from the group consisting of hydrogen and $C_1$-$C_8$ alkyl; and $R_5$ is $NH_2$;

with the proviso that both $R_1$ and $R_2$ are not hydrogen.

In other embodiments, prodrugs having the dipeptide prodrug element linked to the N-terminal amino acid of the peptide or analog described here and having a $t_{1/2}$, e.g., between about 12 to about 72 hours, or in some embodiments between about 12 to about 48 hours, comprise a dipeptide prodrug element with the structure:

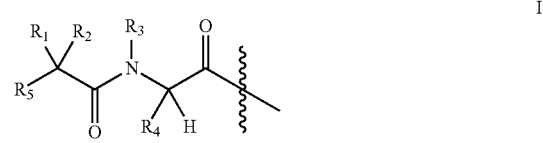

wherein
$R_1$ and $R_2$ are independently selected from the group consisting of hydrogen, $C_1$-$C_8$ alkyl and ($C_1$-$C_4$ alkyl)$NH_2$;
$R_3$ is $C_1$-$C_6$ alkyl;
$R_4$ is hydrogen; and
$R_5$ is $NH_2$;
with the proviso that both $R_1$ and $R_2$ are not hydrogen.

In some embodiments, prodrugs having the dipeptide prodrug element linked to the N-terminal amino acid of the peptide or analog described herein and having a $t_{1/2}$, e.g., between about 12 to about 72 hours, or in some embodiments between about 12 to about 48 hours, comprise a dipeptide prodrug element with the structure:

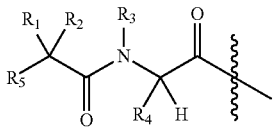

I wherein
$R_1$ and $R_2$ are independently selected from the group consisting of hydrogen and $C_1$-$C_8$ alkyl, ($C_1$-$C_4$ alkyl)$NH_2$, or $R_1$ and $R_2$ are linked through $(CH_2)_p$, wherein p is 2-9;
$R_3$ is $C_1$-$C_5$ alkyl;
$R_4$ is ($C_0$-$C_4$ alkyl)($C_6$-$C_{10}$ aryl)$R_7$;
$R_5$ is $NH_2$; and
$R_7$ is selected from the group consisting of hydrogen, $C_1$-$C_8$ alkyl and ($C_0$-$C_4$ alkyl)OH;
with the proviso that both $R_1$ and $R_2$ are not hydrogen.

In addition a prodrug having the dipeptide prodrug element linked to the N-terminal alpha amino acid of the peptide and analog described herein and having a $t_{1/2}$, e.g., of about 72 to about 168 hours is provided wherein the dipeptide prodrug element has the structure:

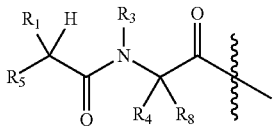

wherein $R_1$ is selected from the group consisting of hydrogen, $C_1$-$C_8$ alkyl and aryl;
$R_3$ is $C_1$-$C_{18}$ alkyl;
$R_4$ and $R_8$ are each hydrogen; and
$R_5$ is an amine or N-substituted amine or a hydroxyl;
with the proviso that, if $R_1$ is alkyl or aryl, then $R_1$ and $R_5$ together with the atoms to which they are attached form a 4-11 heterocyclic ring.

In some embodiments, the dipeptide prodrug element has the structure:

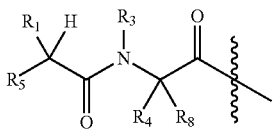

I wherein $R_1$ is selected from the group consisting of hydrogen, $C_1$-$C_8$ alkyl and ($C_0$-$C_4$ alkyl)($C_6$-$C_{10}$ aryl)$R_7$;

$R_3$ is $C_1$-$C_{18}$ alkyl;
$R_4$ and $R_8$ are each hydrogen;
$R_5$ is $NHR_6$ or OH;
$R_6$ is H, $C_1$-$C_8$ alkyl, or $R_6$ and $R_1$ together with the atoms to which they are attached form a 4, 5 or 6 member heterocyclic ring; and
$R_7$ is selected from the group consisting of hydrogen, $C_1$-$C_{18}$ alkyl, $C_2$-$C_{18}$ alkenyl, ($C_0$-$C_4$ alkyl)$CONH_2$, ($C_0$-$C_4$ alkyl)COOH, ($C_0$-$C_4$ alkyl)$NH_2$, ($C_0$-$C_4$ alkyl)OH, and halo;
with the proviso that, if $R_1$ is alkyl or ($C_0$-$C_4$ alkyl)($C_6$-$C_{10}$ aryl)$R_7$, then $R_1$ and $R_5$ together with the atoms to which they are attached form a 4-11 heterocyclic ring.

In some embodiments the dipeptide prodrug element is linked to a side chain amine of an internal amino acid of the peptide or analog described herein. In this embodiment prodrugs having a $t_{1/2}$, e.g., of about 1 hour have the structure:

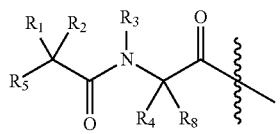

wherein
$R_1$ and $R_2$ are independently $C_1$-$C_8$ alkyl or aryl; or $R_1$ and $R_2$ are linked through $(CH_2)_p$, wherein p is 2-9;
$R_3$ is $C_1$-$C_{18}$ alkyl;
$R_4$ and $R_8$ are each hydrogen; and $R_5$ is an amine In some embodiments, prodrugs having a $t_{1/2}$, e.g., of about 1 hour have the structure:

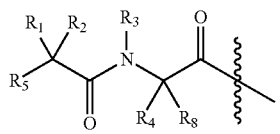

wherein
$R_1$ and $R_2$ are independently $C_1$-$C_8$ alkyl or ($C_0$-$C_4$ alkyl)($C_6$-$C_{10}$ aryl)$R_7$; or $R_1$ and $R_2$ are linked through —$(CH_2)_p$—, wherein p is 2-9;
$R_3$ is $C_1$-$C_{18}$ alkyl;
$R_4$ and $R_8$ are each hydrogen;
$R_5$ is $NH_2$; and
$R_7$ is selected from the group consisting of hydrogen, $C_1$-$C_{18}$ alkyl, $C_2$-$C_{18}$ alkenyl, ($C_0$-$C_4$ alkyl)$CONH_2$, ($C_0$-$C_4$ alkyl)COOH, ($C_0$-$C_4$ alkyl)$NH_2$, ($C_0$-$C_4$ alkyl)OH, and halo.

Furthermore, prodrugs having a $t_{1/2}$, e.g., between about 6 to about 24 hours and having the dipeptide prodrug element linked to a internal amino acid side chain comprise a dipeptide prodrug element with the structure:

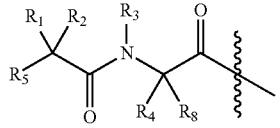

wherein $R_1$ and $R_2$ are independently selected from the group consisting of hydrogen, $C_1$-$C_8$ alkyl and aryl, or $R_1$ and $R_2$ are linked through —$(CH_2)_p$—, wherein p is 2-9;

$R_3$ is $C_1$-$C_{18}$ alkyl or $R_3$ and $R_4$ together with the atoms to which they are attached form a 4-12 heterocyclic ring;

$R_4$ and $R_8$ are independently $C_1$-$C_{18}$ alkyl or aryl; and $R_5$ is an amine or N-substituted amine;

with the proviso that both $R_1$ and $R_2$ are not hydrogen and provided that one of $R_4$ or $R_8$ is hydrogen.

In some embodiments, prodrugs having a $t_{1/2}$, e.g., between about 12 to about 72 hours, or in some embodiments between about 12 to about 48 hours, and having the dipeptide prodrug element linked to a internal amino acid side chain comprise a dipeptide prodrug element with the structure:

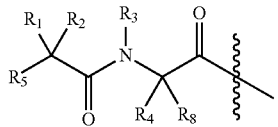

wherein $R_1$ and $R_2$ are independently selected from the group consisting of hydrogen, $C_1$-$C_8$ alkyl, and ($C_0$-$C_4$ alkyl)($C_6$-$C_{10}$ aryl)$R_7$, or $R_1$ and $R_2$ are linked through —(CH$_2$)$_p$—, wherein p is 2-9;

$R_3$ is $C_1$-$C_{18}$ alkyl or $R_3$ and $R_4$ together with the atoms to which they are attached form a 4-12 heterocyclic ring;

$R_4$ and $R_8$ are independently hydrogen, $C_1$-$C_{18}$ alkyl or ($C_0$-$C_4$ alkyl)($C_6$-$C_{10}$ aryl)$R_7$;

$R_5$ is NHR$_6$;

$R_6$ is H or $C_1$-$C_8$ alkyl, or $R_6$ and $R_2$ together with the atoms to which they are attached form a 4, 5 or 6 member heterocyclic ring; and $R_7$ is selected from the group consisting of hydrogen, $C_1$-$C_{18}$ alkyl, $C_2$-$C_{18}$ alkenyl, ($C_0$-$C_4$ alkyl)CONH$_2$, ($C_0$-$C_4$ alkyl)COOH, ($C_0$-$C_4$ alkyl)NH$_2$, ($C_0$-$C_4$ alkyl)OH, and halo;

with the proviso that both $R_1$ and $R_2$ are not hydrogen and provided that at least one of $R_4$ or $R_8$ is hydrogen.

In addition a prodrug having a $t_{1/2}$, e.g., of about 72 to about 168 hours and having the dipeptide prodrug element linked to a internal amino acid side chain of the peptide or analog described herein is provided wherein the dipeptide prodrug element has the structure:

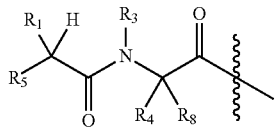

wherein $R_1$ and $R_2$ are independently selected from the group consisting of hydrogen, $C_1$-$C_{18}$ alkyl and aryl;

$R_3$ is $C_1$-$C_{18}$ alkyl;

$R_4$ and $R_8$ are each hydrogen; and $R_5$ is an amine or N-substituted amine or a hydroxyl;

with the proviso that, if $R_1$ and $R_2$ are both independently an alkyl or aryl, either $R_1$ or $R_2$ is linked through (CH2)$_p$ to $R_5$, wherein p is 2-9.

In some embodiments, a prodrug having a $t_{1/2}$, e.g., of about 72 to about 168 hours and having the dipeptide prodrug element linked to a internal amino acid side chain of the peptide or analog described herein is provided wherein the dipeptide prodrug element has the structure:

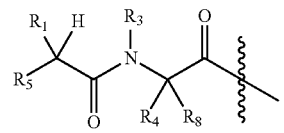

wherein $R_1$ is selected from the group consisting of hydrogen, $C_1$-$C_{18}$ alkyl and ($C_0$-$C_4$ alkyl)($C_6$-$C_{10}$ aryl)$R_7$;

$R_3$ is $C_1$-$C_{18}$ alkyl;

$R_4$ and $R_8$ are each hydrogen;

$R_5$ is NHR$_6$ or OH;

$R_6$ is H or $C_1$-$C_8$ alkyl, or $R_6$ and $R_1$ together with the atoms to which they are attached form a 4, 5 or 6 member heterocyclic ring; and $R_7$ is selected from the group consisting of hydrogen, $C_1$-$C_{18}$ alkyl, $C_2$-$C_{18}$ alkenyl, ($C_0$-$C_4$ alkyl)CONH$_2$, ($C_0$-$C_4$ alkyl)COOH, ($C_0$-$C_4$ alkyl)NH$_2$, ($C_0$-$C_4$ alkyl)OH, and halo;

with the proviso that, if $R_1$ and $R_2$ are both independently an alkyl or ($C_0$-$C_4$ alkyl)($C_6$-$C_{10}$ aryl)$R_7$, either $R_1$ or $R_2$ is linked through (CH$_2$)$_p$ to $R_5$, wherein p is 2-9.

In some embodiments the dipeptide prodrug element is linked to a side chain amine of an internal amino acid of the peptide or analog described herein wherein the internal amino acid comprises the structure of Formula II:

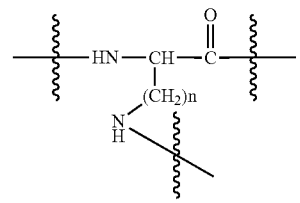

wherein
n is an integer selected from 1 to 4. In some embodiments n is 3 or 4 and in some embodiments the internal amino acid is lysine. In some embodiments the dipeptide prodrug element is linked to a primary amine on a side chain of an amino acid located at position 12, 16, 17, 18, 20, 28, or 29 of the peptide or analog described herein. In some embodiments the amino acid at 12, 16, 17, 18, 20, 28, or 29 comprises the structure of Formula II:

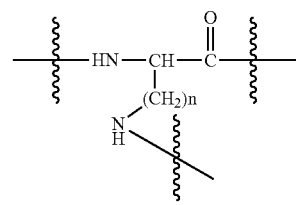

wherein n is an integer selected from 1 to 4 and the dipeptide prodrug element is linked to the amino acid side chain via an amide bond. In some embodiments n is 4 and the amino acid is located at position 20.

In a further embodiment the dipeptide prodrug element is linked to the peptide or analog thereof via an amine present on an aryl group of an aromatic amino acid. In some embodiments the aromatic amino acid is an internal amino acid of the peptide or analog described herein, however the aromatic amino acid can also be the N-terminal amino acid. In some embodiments the aromatic amino acid is selected from the group consisting of amino-Phe, amino-napthyl alanine, amino tryptophan, amino-phenyl-glycine, amino-homo-Phe, and amino tyrosine. In some embodiments the primary amine that forms an amide bond with the dipeptide prodrug element is in the para-position on the aryl group. In some embodiments the aromatic amine comprises the structure of Formula III:

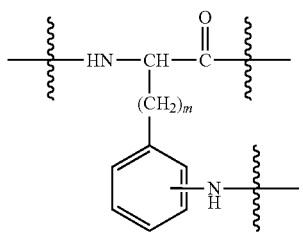

wherein m is an integer from 1 to 3.

For those embodiments wherein the dipeptide prodrug element is linked to the peptide or analog described herein via an amine present on an aryl group of an aromatic amino acid, prodrugs having a $t_{1/2}$, e.g., of about 1 hour have a dipeptide structure of:

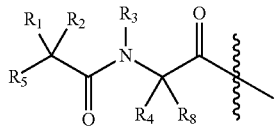

wherein $R_1$ and $R_2$ are independently $C_1$-$C_{18}$ alkyl or aryl;
$R_3$ is $C_1$-$C_{18}$ alkyl or $R_3$ and $R_4$ together with the atoms to which they are attached form a 4-12 heterocyclic ring;
$R_4$ and $R_8$ are independently selected from the group consisting of hydrogen, $C_1$-$C_{18}$ alkyl and aryl; and $R_5$ is an amine or a hydroxyl.

In some embodiments, the dipeptide prodrug element is linked to the peptide or analog described herein via an amine present on an aryl group of an aromatic amino acid, prodrugs having a $t_{1/2}$, e.g., of about 1 hour have a dipeptide structure of:

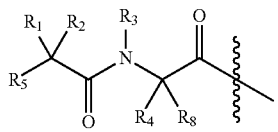

wherein $R_1$ and $R_2$ are independently $C_1$-$C_{18}$ alkyl or $(C_0$-$C_4$ alkyl)$(C_6$-$C_{10}$ aryl)$R_7$;
$R_3$ is $C_1$-$C_{18}$ alkyl or $R_3$ and $R_4$ together with the atoms to which they are attached form a 4-12 heterocyclic ring;
$R_4$ and $R_8$ are independently selected from the group consisting of hydrogen, $C_1$-$C_{18}$ alkyl and $(C_0$-$C_4$ alkyl)$(C_6$-$C_{10}$ aryl)$R_7$;
$R_5$ is $NH_2$ or OH; and
$R_7$ is selected from the group consisting of hydrogen, $C_1$-$C_{18}$ alkyl, $C_2$-$C_{18}$ alkenyl, $(C_0$-$C_4$ alkyl)$CONH_2$, $(C_0$-$C_4$ alkyl)$COOH$, $(C_0$-$C_4$ alkyl)$NH_2$, $(C_0$-$C_4$ alkyl)$OH$, and halo.

Furthermore, prodrugs having the dipeptide prodrug element is linked via an aromatic amino acid and having a $t_{1/2}$, e.g., of about 6 to about 24 hours are provided wherein the dipeptide comprises a structure of:

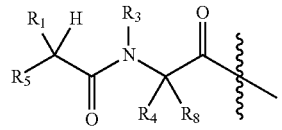

wherein
$R_1$ is selected from the group consisting of hydrogen, $C_1$-$C_{18}$ alkyl and aryl, or $R_1$ and $R_2$ are linked through —$(CH_2)_p$—, wherein p is 2-9;
$R_3$ is $C_1$-$C_{18}$ alkyl or $R_3$ and $R_4$ together with the atoms to which they are attached form a 4-6 heterocyclic ring;
$R_4$ and $R_8$ are independently selected from the group consisting of hydrogen, $C_1$-$C_{18}$ alkyl and aryl; and $R_5$ is an amine or N-substituted amine In some embodiments, prodrugs having the dipeptide prodrug element linked via an aromatic amino acid and having a $t_{1/2}$, e.g., of about 6 to about 24 hours are provided wherein the dipeptide comprises a structure of:

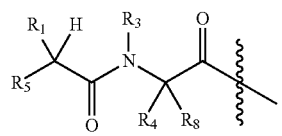

wherein
$R_1$ is selected from the group consisting of hydrogen, $C_1$-$C_{18}$ alkyl, $(C_1$-$C_{18}$ alkyl)$OH$, $(C_1$-$C_4$ alkyl)$NH_2$, and $(C_0$-$C_4$ alkyl)$(C_6$-$C_{10}$ aryl)$R_7$;
$R_3$ is $C_1$-$C_{18}$ alkyl or $R_3$ and $R_4$ together with the atoms to which they are attached form a 4-6 heterocyclic ring;
$R_4$ and $R_8$ are independently selected from the group consisting of hydrogen, $C_1$-$C_{18}$ alkyl and $(C_0$-$C_4$ alkyl)$(C_6$-$C_{10}$ aryl)$R_7$;
$R_5$ is $NHR_6$;
$R_6$ is H, $C_1$-$C_8$ alkyl, or $R_6$ and $R_1$ together with the atoms to which they are attached form a 4, 5 or 6 member heterocyclic ring; and
$R_7$ is selected from the group consisting of hydrogen, $C_1$-$C_{18}$ alkyl, $C_2$-$C_{18}$ alkenyl, $(C_0$-$C_4$ alkyl)$CONH_2$, $(C_0$-$C_4$ alkyl)$COOH$, $(C_0$-$C_4$ alkyl)$NH_2$, $(C_0$-$C_4$ alkyl)$OH$, and halo.

In addition, prodrugs having the dipeptide prodrug element is linked via an aromatic amino acid and having a $t_{1/2}$, e.g., of about 72 to about 168 hours are provided wherein the dipeptide comprises a structure of:

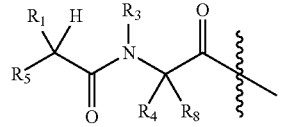

wherein $R_1$ and $R_2$ are independently selected from the group consisting of hydrogen, $C_1$-$C_8$ alkyl and aryl;
$R_3$ is $C_1$-$C_{18}$ alkyl or $R_3$ and $R_4$ together with the atoms to which they are attached form a 4-6 heterocyclic ring;
$R_4$ and $R_8$ are each hydrogen; and $R_5$ is selected from the group consisting of amine, N-substituted amine and hydroxyl.

In some embodiments, prodrugs having the dipeptide prodrug element linked via an aromatic amino acid and having a $t_{1/2}$, e.g., of about 72 to about 168 hours are provided wherein the dipeptide comprises a structure of:

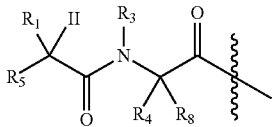

wherein $R_1$ and $R_2$ are independently selected from the group consisting of hydrogen, $C_1$-$C_8$ alkyl, ($C_1$-$C_4$ alkyl)COOH, and ($C_0$-$C_4$ alkyl)($C_6$-$C_{10}$ aryl)$R_7$, or $R_1$ and $R_5$ together with the atoms to which they are attached form a 4-11 heterocyclic ring;

$R_3$ is $C_1$-$C_{18}$ alkyl or $R_3$ and $R_4$ together with the atoms to which they are attached form a 4-6 heterocyclic ring;

$R_4$ is hydrogen or forms a 4-6 heterocyclic ring with $R_3$;

$R_8$ is hydrogen;

$R_5$ is $NHR_6$ or OH;

$R_6$ is H or $C_1$-$C_8$ alkyl, or $R_6$ and $R_1$ together with the atoms to which they are attached form a 4, 5 or 6 member heterocyclic ring; and $R_7$ is selected from the group consisting of hydrogen, $C_1$-$C_{18}$ alkyl, $C_2$-$C_{18}$ alkenyl, ($C_0$-$C_4$ alkyl)CONH$_2$, ($C_0$-$C_4$ alkyl)COOH, ($C_0$-$C_4$ alkyl)NH$_2$, ($C_0$-$C_4$ alkyl)OH, and halo.

In some embodiments the dipeptide prodrug element is linked to an aromatic amino acid via a primary amine present as an aryl substituent of the aromatic amino acid, wherein the aromatic amino acid is located at position 10, 13, 22, or 25 of the peptide or analog described herein (based on the numbering for native glucagon, see e.g., SEQ ID NO: 1). In some embodiments the dipeptide prodrug element linked aromatic amino acid amino acid is located at position 22 of the peptide or analog described herein.

In accordance with some embodiments the dipeptide prodrug element is linked at the N-terminal amine of the peptide or analog described herein, including for example a glucagon related peptide, or osteocalcin, as well as analogs, derivatives and conjugates of the foregoing, wherein the dipeptide prodrug element comprises the structure:

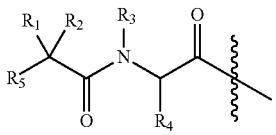

wherein $R_1$ is selected from the group consisting of H and $C_1$-$C_8$ alkyl;

$R_2$ and $R_4$ are independently selected from the group consisting of H, $C_1$-$C_8$ alkyl, $C_2$-$C_8$ alkenyl, ($C_1$-$C_4$ alkyl)OH, ($C_1$-$C_4$ alkyl)SH, ($C_2$-$C_3$ alkyl)SCH$_3$, ($C_1$-$C_4$ alkyl)CONH$_2$, ($C_1$-$C_4$ alkyl)COOH, ($C_1$-$C_4$ alkyl)NH$_2$, ($C_1$-$C_4$ alkyl)NHC(NH$_2^+$) NH$_2$, ($C_0$-$C_4$ alkyl)($C_3$-$C_6$ cycloalkyl), ($C_0$-C4 alkyl)($C_6$-$C_{10}$ aryl)$R_7$, CH$_2$($C_5$-$C_9$ heteroaryl), or $R_1$ and $R_2$ together with the atoms to which they are attached form a $C_3$-$C_6$ cycloalkyl;

$R_3$ is selected from the group consisting of $C_1$-$C_8$ alkyl, ($C_3$-$C_6$)cycloalkyl or $R_4$ and $R_3$ together with the atoms to which they are attached form a 5 or 6 member heterocyclic ring;

$R_5$ is $NHR_6$ or OH;

$R_6$ is H, or $R_6$ and $R_2$ together with the atoms to which they are attached form a 5 or 6 member heterocyclic ring; and $R_7$ is selected from the group consisting of H and OH. In some embodiments $R_1$ is H or $C_1$-$C_8$ alkyl, $R_2$ is selected from the group consisting of H, $C_1$-$C_6$ alkyl, CH$_2$OH, ($C_1$-$C_4$ alkyl)NH$_2$, ($C_3$-$C_6$ cycloalkyl) and CH$_2$($C_6$ aryl)$R_7$ or $R_6$ and $R_2$ together with the atoms to which they are attached form a 5 member heterocyclic ring, $R_3$ is $C_1$-$C_6$ alkyl, and $R_4$ is selected from the group consisting of H, $C_1$-$C_4$ alkyl, ($C_3$-$C_6$)cycloalkyl, ($C_1$-$C_4$ alkyl)OH, ($C_1$-$C_4$ alkyl)SH and ($C_0$-C4 alkyl)($C_6$ aryl)$R_7$, or $R_3$ and $R_4$ together with the atoms to which they are attached form a 5 member heterocyclic ring. In a further embodiment $R_3$ is CH$_3$, $R_5$ is NHR$_6$, and in an alternative further embodiment $R_3$ and $R_4$ together with the atoms to which they are attached form a 5 member heterocyclic ring and $R_5$ is NHR$_6$.

In accordance with another embodiment the dipeptide prodrug element is linked at the N-terminal amine of the peptide or analog described herein, wherein the dipeptide prodrug element comprises the structure:

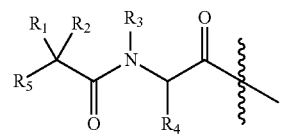

wherein $R_1$ is selected from the group consisting of H and $C_1$-$C_8$ alkyl;

$R_2$ and $R_4$ are independently selected from the group consisting of H, $C_1$-$C_8$ alkyl, $C_2$-$C_8$ alkenyl, ($C_1$-$C_4$ alkyl)OH, ($C_1$-$C_4$ alkyl)SH, ($C_2$-$C_3$ alkyl)SCH$_3$, ($C_1$-$C_4$ alkyl)CONH$_2$, ($C_1$-$C_4$ alkyl)COOH, ($C_1$-$C_4$ alkyl)NH$_2$, ($C_1$-$C_4$ alkyl)NHC(NH$_2^+$) NH$_2$, ($C_0$-$C_4$ alkyl)($C_3$-$C_6$ cycloalkyl), ($C_0$-$C_4$ alkyl)($C_6$-$C_{10}$ aryl)$R_7$, CH$_2$($C_5$-$C_9$ heteroaryl), or $R_1$ and $R_2$ together with the atoms to which they are attached form a $C_3$-$C_6$ cycloalkyl;

$R_3$ is selected from the group consisting of $C_1$-$C_8$ alkyl, ($C_3$-$C_6$)cycloalkyl or $R_4$ and $R_3$ together with the atoms to which they are attached form a 5 or 6 member heterocyclic ring;

$R_5$ is $NHR_6$ or OH;

$R_6$ is H, or $R_6$ and $R_2$ together with the atoms to which they are attached form a 5 or 6 member heterocyclic ring; and $R_7$ is selected from the group consisting of hydrogen, $C_1$-$C_{18}$ alkyl, $C_2$-$C_{18}$ alkenyl, ($C_0$-$C_4$ alkyl)CONH$_2$, ($C_0$-$C_4$ alkyl)COOH, ($C_0$-$C_4$ alkyl)NH$_2$, ($C_0$-$C_4$ alkyl)OH, and halo. In some embodiments $R_1$ is H or $C_1$-$C_8$ alkyl, $R_2$ is selected from the group consisting of H, $C_1$-$C_6$ alkyl, CH$_2$OH, ($C_1$-$C_4$ alkyl)NH$_2$, ($C_3$-$C_6$ cycloalkyl) and CH$_2$($C_6$ aryl)$R_7$ or $R_6$ and $R_2$ together with the atoms to which they are attached form a 5 member heterocyclic ring, $R_3$ is $C_1$-$C_6$ alkyl, and $R_4$ is selected from the group consisting of H, $C_1$-$C_4$ alkyl, ($C_3$-$C_6$)cycloalkyl, ($C_1$-$C_4$ alkyl)OH, ($C_1$-$C_4$ alkyl)SH and ($C_0$-$C_4$ alkyl)($C_6$ aryl)$R_7$, or $R_3$ and $R_4$ together with the atoms to which they are attached form a 5 member heterocyclic ring. In a further embodiment $R_3$ is CH$_3$, $R_5$ is NHR$_6$, and in an alternative further embodiment $R_3$ and $R_4$ together with the atoms to which they are attached form a 5 member heterocyclic ring and $R_5$ is NHR$_6$.

Pharmaceutical Compositions, Uses and Kits

Salts

In some embodiments, the glucagon analog is in the form of a salt, e.g., a pharmaceutically acceptable salt. As used herein the term "pharmaceutically acceptable salt" refers to salts of compounds that retain the biological activity of the parent compound, and which are not biologically or otherwise undesirable. Such salts can be prepared in situ during the final isolation and purification of the analog, or separately prepared by reacting a free base function with a suitable acid. Many of the compounds disclosed herein are capable of forming acid and/or base salts by virtue of the presence of amino and/or carboxyl groups or groups similar thereto.

Pharmaceutically acceptable acid addition salts may be prepared from inorganic and organic acids. Representative acid addition salts include, but are not limited to acetate, adipate, alginate, citrate, aspartate, benzoate, benzenesulfonate, bisulfate, butyrate, camphorate, camphor sulfonate, digluconate, glycerophosphate, hemisulfate, heptanoate, hexanoate, fumarate, hydrochloride, hydrobromide, hydroiodide, 2-hydroxyethansulfonate (isothionate), lactate, maleate, methane sulfonate, nicotinate, 2-naphthalene sulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate, and undecanoate. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like. Examples of acids which can be employed to form pharmaceutically acceptable acid addition salts include, for example, an inorganic acid, e.g., hydrochloric acid, hydrobromic acid, sulphuric acid, and phosphoric acid, and an organic acid, e.g., oxalic acid, maleic acid, succinic acid, and citric acid.

Basic addition salts also can be prepared in situ during the final isolation and purification of the source of salicylic acid, or by reacting a carboxylic acid-containing moiety with a suitable base such as the hydroxide, carbonate, or bicarbonate of a pharmaceutically acceptable metal cation or with ammonia or an organic primary, secondary, or tertiary amine. Pharmaceutically acceptable salts include, but are not limited to, cations based on alkali metals or alkaline earth metals such as lithium, sodium, potassium, calcium, magnesium, and aluminum salts, and the like, and nontoxic quaternary ammonia and amine cations including ammonium, tetramethylammonium, tetraethylammonium, methylammonium, dimethylammonium, trimethylammonium, triethylammonium, diethylammonium, and ethylammonium, amongst others. Other representative organic amines useful for the formation of base addition salts include, for example, ethylenediamine, ethanolamine, diethanolamine, piperidine, piperazine, and the like. Salts derived from organic bases include, but are not limited to, salts of primary, secondary and tertiary amines.

Further, basic nitrogen-containing groups can be quaternized with the analog of the present disclosure as lower alkyl halides such as methyl, ethyl, propyl, and butyl chlorides, bromides, and iodides; long chain halides such as decyl, lauryl, myristyl, and stearyl chlorides, bromides, and iodides; arylalkyl halides like benzyl and phenethyl bromides and others. Water or oil-soluble or dispersible products are thereby obtained.

Formulations

In accordance with some embodiments, a pharmaceutical composition is provided wherein the composition comprises a glucagon analog of the present disclosure, or pharmaceutically acceptable salt thereof, and a pharmaceutically acceptable carrier. As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

The pharmaceutical composition can comprise any pharmaceutically acceptable ingredient, including, for example, acidifying agents, additives, adsorbents, aerosol propellants, air displacement agents, alkalizing agents, anticaking agents, anticoagulants, antimicrobial preservatives, antioxidants, antiseptics, bases, binders, buffering agents, chelating agents, coating agents, coloring agents, desiccants, detergents, diluents, disinfectants, disintegrants, dispersing agents, dissolution enhancing agents, dyes, emollients, emulsifying agents, emulsion stabilizers, fillers, film forming agents, flavor enhancers, flavoring agents, flow enhancers, gelling agents, granulating agents, humectants, lubricants, mucoadhesives, ointment bases, ointments, oleaginous vehicles, organic bases, pastille bases, pigments, plasticizers, polishing agents, preservatives, sequestering agents, skin penetrants, solubilizing agents, solvents, stabilizing agents, suppository bases, surface active agents, surfactants, suspending agents, sweetening agents, therapeutic agents, thickening agents, tonicity agents, toxicity agents, viscosity-increasing agents, water-absorbing agents, water-miscible cosolvents, water softeners, or wetting agents.

In some embodiments, the pharmaceutical composition comprises any one or a combination of the following components: acacia, acesulfame potassium, acetyltributyl citrate, acetyltriethyl citrate, agar, albumin, alcohol, dehydrated alcohol, denatured alcohol, dilute alcohol, aleuritic acid, alginic acid, aliphatic polyesters, alumina, aluminum hydroxide, aluminum stearate, amylopectin, α-amylose, ascorbic acid, ascorbyl palmitate, aspartame, bacteriostatic water for injection, bentonite, bentonite magma, benzalkonium chloride, benzethonium chloride, benzoic acid, benzyl alcohol, benzyl benzoate, bronopol, butylated hydroxyanisole, butylated hydroxytoluene, butylparaben, butylparaben sodium, calcium alginate, calcium ascorbate, calcium carbonate, calcium cyclamate, dibasic anhydrous calcium phosphate, dibasic dehydrate calcium phosphate, tribasic calcium phosphate, calcium propionate, calcium silicate, calcium sorbate, calcium stearate, calcium sulfate, calcium sulfate hemihydrate, canola oil, carbomer, carbon dioxide, carboxymethyl cellulose calcium, carboxymethyl cellulose sodium, β-carotene, carrageenan, castor oil, hydrogenated castor oil, cationic emulsifying wax, cellulose acetate, cellulose acetate phthalate, ethyl cellulose, microcrystalline cellulose, powdered cellulose, silicified microcrystalline cellulose, sodium carboxymethyl cellulose, cetostearyl alcohol, cetrimide, cetyl alcohol, chlorhexidine, chlorobutanol, chlorocresol, cholesterol, chlorhexidine acetate, chlorhexidine gluconate, chlorhexidine hydrochloride, chlorodifluoroethane (HCFC), chlorodifluoromethane, chlorofluorocarbons (CFC) chlorophenoxyethanol, chloroxylenol, corn syrup solids, anhydrous citric acid, citric acid monohydrate, cocoa butter, coloring agents, corn oil, cottonseed oil, cresol, m-cresol, o-cresol, p-cresol, croscarmellose sodium, crospovidone, cyclamic acid, cyclodextrins, dextrates, dextrin, dextrose, dextrose anhydrous, diazolidinyl urea, dibutyl phthalate, dibutyl sebacate, diethanolamine, diethyl phthalate, difluoroethane (HFC), dimethyl-β-cyclodextrin, cyclodextrin-type compounds such as Captisol®, dimethyl ether, dimethyl phthalate, dipotassium edentate, disodium edentate, disodium hydrogen phosphate, docusate calcium, docusate potassium, docusate sodium, dodecyl gallate, dodecyltrimethylammonium bromide, edentate calcium disodium, edtic acid, eglumine, ethyl alcohol, ethylcellulose, ethyl gallate, ethyl laurate, ethyl maltol, ethyl oleate, ethylparaben, ethylparaben potassium, ethylparaben sodium, ethyl vanillin, fructose, fructose liquid, fructose milled, fructose pyrogen-free, powdered fructose, fumaric acid, gelatin, glucose, liquid glucose, glyceride mixtures of saturated vegetable fatty acids, glycerin, glyceryl behenate, glyceryl monooleate, glyceryl monostearate, self-emulsifying glyceryl monostearate, glyceryl palmitostearate, glycine, glycols, glycofurol, guar gum, heptafluoropropane (HFC), hexadecyltrimethylammonium bromide, high fructose syrup, human serum albumin, hydrocarbons (HC), dilute hydrochloric acid, hydrogenated vegetable oil type TI, hydroxyethyl cellulose, 2-hydroxyethyl-β-cyclodextrin, hydroxypropyl cellulose, low-substituted hydroxypropyl cellulose, 2-hydroxypropyl-β-cyclodextrin, hydroxypropyl methylcellulose, hydroxypropyl methylcellulose phthalate, imidurea, indigo carmine, ion exchangers, iron oxides, isopropyl alcohol, isopropyl myristate, isopropyl palmitate, isotonic saline, kaolin, lactic acid, lactitol, lactose, lanolin, lanolin alcohols, anhydrous lanolin, lecithin, magnesium aluminum silicate, magnesium carbonate, normal magnesium carbonate, magnesium carbonate anhydrous, magnesium carbonate hydroxide, magnesium hydroxide, magnesium lauryl sulfate, magnesium oxide, magnesium silicate, magnesium stearate, magnesium trisilicate, magnesium trisilicate anhydrous, malic acid, malt, maltitol, maltitol solution, maltodextrin, maltol, maltose, mannitol, medium chain triglycerides, meglumine, menthol, methylcellulose, methyl methacrylate, methyl oleate, methylparaben, methylparaben potassium, methylparaben sodium, microcrystalline cellulose and carboxymethylcellulose sodium, mineral oil, light mineral oil, mineral oil and lanolin alcohols, oil, olive oil, monoethanolamine, montmorillonite, octyl gallate, oleic acid, palmitic acid, paraffin, peanut oil, petrolatum, petrolatum and lanolin alcohols, pharmaceutical glaze, phenol, liquified phenol, phenoxyethanol, phenoxypropanol, phenylethyl alcohol, phenylmercuric acetate, phenylmercuric borate, phenylmercuric nitrate, polacrilin, polacrilin potassium, poloxamer, polydextrose, polyethylene glycol, polyethylene oxide, polyacrylates, polyethylene-polyoxypropylene-block polymers, polymethacrylates, polyoxyethylene alkyl ethers, polyoxyethylene castor oil derivatives, polyoxyethylene sorbitol fatty acid esters, polyoxyethylene stearates, polyvinyl alcohol, polyvinyl pyrrolidone, potassium alginate, potassium benzoate, potassium bicarbonate, potassium bisulfite, potassium chloride, potassium citrate, potassium citrate anhydrous, potassium hydrogen phosphate, potassium metabisulfite, monobasic potassium phosphate, potassium propionate, potassium sorbate, povidone, propanol, propionic acid, propylene carbonate, propylene glycol, propylene glycol alginate, propyl gallate, propylparaben, propylparaben potassium, propylparaben sodium, protamine sulfate, rapeseed oil, Ringer's solution, saccharin, saccharin ammonium, saccharin calcium, saccharin sodium, safflower oil, saponite, serum proteins, sesame oil, colloidal silica, colloidal silicon dioxide, sodium alginate, sodium ascorbate, sodium benzoate, sodium bicarbonate, sodium bisulfite, sodium chloride, anhydrous sodium citrate, sodium citrate dehydrate, sodium chloride, sodium cyclamate, sodium edentate, sodium dodecyl sulfate, sodium lauryl sulfate, sodium metabisulfite, sodium phosphate, dibasic, sodium phosphate, monobasic, sodium phosphate, tribasic, anhydrous sodium propionate, sodium propionate, sodium sorbate, sodium starch glycolate, sodium stearyl fumarate, sodium sulfite, sorbic acid, sorbitan esters (sorbitan fatty esters), sorbitol, sorbitol solution 70%, soybean oil, spermaceti wax, starch, corn starch, potato starch, pregelatinized starch, sterilizable maize starch, stearic acid, purified stearic acid, stearyl alcohol, sucrose, sugars, compressible sugar, confectioner's sugar, sugar spheres, invert sugar, Sugartab, Sunset Yellow FCF, synthetic paraffin, talc, tartaric acid, tartrazine, tetrafluoroethane (HFC), theobroma oil, thimerosal, titanium dioxide, alpha tocopherol, tocopheryl acetate, alpha tocopheryl acid succinate, beta-tocopherol, delta-tocopherol, gamma-tocopherol, tragacanth, triacetin, tributyl citrate, triethanolamine, triethyl citrate, trimethyl-β-cyclodextrin, trimethyltetradecylammonium bromide, tris buffer, trisodium edentate, vanillin, type I hydrogenated vegetable oil, water, soft water, hard water, carbon dioxide-free water, pyrogen-free water, water for injection, sterile water for inhalation, sterile water for injection, sterile water for irrigation, waxes, anionic emulsifying wax, carnauba wax, cationic emulsifying wax, cetyl ester wax, microcrystalline wax, nonionic emulsifying wax, suppository wax, white wax, yellow wax, white petrolatum, wool fat, xanthan gum, xylitol, zein, zinc propionate, zinc salts, zinc stearate, or any excipient in the *Handbook of Pharmaceutical Excipients*, Third Edition, A. H. Kibbe (Pharmaceutical Press, London, UK, 2000), which is incorporated by reference in its entirety. *Remington's Pharmaceutical Sciences*, Sixteenth Edition, E. W. Martin (Mack Publishing Co., Easton, Pa., 1980), which is incorporated by reference in its entirety, discloses various components used in formulating pharmaceutically acceptable compositions and known techniques for the preparation thereof. Except insofar as any conventional agent is incompatible with the pharmaceutical compositions, its use in pharmaceutical compositions is contemplated. Supplementary active ingredients also can be incorporated into the compositions.

In some embodiments, the foregoing component(s) may be present in the pharmaceutical composition at any concentration, such as, for example, at least A, wherein A is 0.0001% w/v, 0.001% w/v, 0.01% w/v, 0.1% w/v, 1% w/v, 2% w/v, 5% w/v, 10% w/v, 20% w/v, 30% w/v, 40% w/v, 50% w/v, 60% w/v, 70% w/v, 80% w/v, or 90% w/v. In some embodiments, the foregoing component(s) may be present in the pharmaceutical composition at any concentration, such as, for example, at most B, wherein B is 90% w/v, 80% w/v, 70% w/v, 60% w/v, 50% w/v, 40% w/v, 30% w/v, 20% w/v, 10% w/v, 5% w/v, 2% w/v, 1% w/v, 0.1% w/v, 0.001% w/v, or 0.0001%. In other embodiments, the foregoing component(s) may be present in the pharmaceutical composition at any concentration range, such as, for example from about A to about B. In some embodiments, A is 0.0001% and B is 90%.

In some embodiments, the pharmaceutically acceptable ingredient is selected from the group consisting of a sugar (e.g., glucose, sucrose, trehalose, lactose, fructose, maltose, dextran, glycerin, dextran, mellibiose, melezitose, raffinose, mannotriose, stachyose, maltose, lactulose, maltulose, or iso-maltulose, or combinations of these sugars), a sugar alcohol (e.g., glycol, glycerol, erythritol, threitol, arabitol, xylitol, ribitol, mannitol, sorbitol, dulcitol, iditol, isomalt, maltitol, lactitol, or glucitol, or combinations of these sugar alcohols), a salt (e.g., sodium chloride), an emulsifier or surfactant (e.g., polysorbates, such as polyoxyethylene 20 sorbitan monooleate, or other block copolymers of ethylene oxide and propylene oxide), lyoprotectants, and mixtures thereof. For example, excipients such as sugars or sugar alcohols are present, e.g., in a concentration of about 20 mg/mL to about 40 mg/mL, or 25 to 45 mg/mL, such as 35 mg/mL.

The pharmaceutical compositions may be formulated to achieve a physiologically compatible pH. In some embodiments, the pH of the pharmaceutical composition may be at least 5, at least 5.5, at least 6, at least 6.5, at least 7, at least 7.5, at least 8, at least 8.5, at least 9, at least 9.5, at least 10, or at least 10.5 up to and including pH 11, depending on the formulation and route of administration, for example between 4 and 7, or 4.5 and 5.5. In exemplary embodiments, the pharmaceutical compositions may comprise buffering agents to achieve a physiological compatible pH. The buffering agents may include any compounds capable of buffering at the desired pH such as, for example, phosphate buffers (e.g., PBS), triethanolamine, Tris, bicine, TAPS, tricine, HEPES, TES, MOPS, PIPES, cacodylate, MES, acetate, citrate, succinate, histidine or other pharmaceutically acceptable buffers. In exemplary embodiments, the strength of the buffer is at least 0.5 mM, at least 1 mM, at least 5 mM, at least 10 mM, at least 20 mM, at least 30 mM, at least 40 mM, at least 50 mM, at least 60 mM, at least 70 mM, at least 80 mM, at least 90 mM, at least 100 mM, at least 120 mM, at least 150 mM, or at least 200 mM. In some embodiments, the strength of the buffer is no more than 300 mM (e.g., at most 200 mM, at most 100 mM, at most 90 mM, at most 80 mM, at most 70 mM, at most 60 mM, at most 50 mM, at most 40 mM, at most 30 mM, at most 20 mM, at most 10 mM, at most 5 mM, at most 1 mM). For example, the buffer concentration can be about 2 mM to about 100 mM, or about 10 mM to about 50 mM.

Routes of Administration

The following discussion on routes of administration is merely provided to illustrate exemplary embodiments and should not be construed as limiting the scope in any way.

Formulations suitable for oral administration can consist of (a) liquid solutions, such as an effective amount of the analog of the present disclosure dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and other pharmacologically compatible excipients. Lozenge forms can comprise the analog of the present disclosure in a flavor, usually sucrose and acacia or tragacanth, as well as pastilles comprising the analog of the present disclosure in an inert base, such as gelatin and glycerin, or sucrose and acacia, emulsions, gels, and the like containing, in addition to, such excipients as are known in the art.

The analogs of the disclosure, alone or in combination with other suitable components, can be delivered via pulmonary administration and can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer. Such spray formulations also may be used to spray mucosa. In some embodiments, the analog is formulated into a powder blend or into microparticles or nanoparticles. Suitable pulmonary formulations are known in the art. See, e.g., Qian et al., Int J Pharm 366: 218-220 (2009); Adjei and Garren, Pharmaceutical Research, 7(6): 565-569 (1990); Kawashima et al., J Controlled Release 62(1-2): 279-287 (1999); Liu et al., Pharm Res 10(2): 228-232 (1993); International Patent Application Publication Nos. WO 2007/133747 and WO 2007/141411.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The term, "parenteral" means not through the alimentary canal but by some other route such as subcutaneous, intramuscular, intraspinal, or intravenous. The analog of the present disclosure can be administered with a physiologically acceptable diluent in a pharmaceutical carrier, such as a sterile liquid or mixture of liquids, including water, saline, aqueous dextrose and related sugar solutions, an alcohol, such as ethanol or hexadecyl alcohol, a glycol, such as propylene glycol or polyethylene glycol, dimethylsulfoxide, glycerol, ketals such as 2,2-dimethyl-1,3-dioxolane-4-methanol, ethers, poly(ethyleneglycol) 400, oils, fatty acids, fatty acid esters or glycerides, or acetylated fatty acid glycerides with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl-imidazoline quaternary ammonium salts, and (e) mixtures thereof.

The parenteral formulations will typically contain from about 0.5% to about 25% by weight of the analog of the present disclosure in solution. Preservatives and buffers may be used. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5% to about 15% by weight. Suitable surfactants include polyethylene glycol sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Injectable formulations are in accordance with the invention. The requirements for effective pharmaceutical carriers for injectable compositions are well-known to those of ordinary skill in the art (see, e.g., *Pharmaceutics and Pharmacy Practice*, J. B. Lippincott Company, Philadelphia, Pa., Banker and Chalmers, eds., pages 238-250 (1982), and *ASHP Handbook on Injectable Drugs*, Toissel, 4th ed., pages 622-630 (1986)).

Additionally, the analog of the present disclosures can be made into suppositories for rectal administration by mixing with a variety of bases, such as emulsifying bases or water-soluble bases. Formulations suitable for vaginal administration can be presented as pessaries, tampons, creams, gels, pastes, foams, or spray formulas containing, in addition to the active ingredient, such carriers as are known in the art to be appropriate.

It will be appreciated by one of skill in the art that, in addition to the above-described pharmaceutical compositions, the analog of the disclosure can be formulated as inclusion complexes, such as cyclodextrin inclusion complexes, or liposomes.

Dose

The analogs of the disclosure are believed to be useful in methods of treating a disease or medical condition in which GIP receptor agonism, GIP/GLP-1 receptor co-agonism, GIP/glucagon receptor co-agonism, or GIP/GLP-1/glucagon receptor triagonism plays a role. For purposes of the disclosure, the amount or dose of the analog of the present disclosure administered should be sufficient to effect, e.g., a therapeutic or prophylactic response, in the subject or animal over a reasonable time frame. For example, the dose of the analog of the present disclosure should be sufficient to stimulate cAMP secretion from cells as described herein or sufficient to decrease blood glucose levels, fat levels, food intake levels, or body weight of a mammal, in a period of from about 1 to 4 minutes, 1 to 4 hours or 1 to 4 weeks or longer, e.g., 5 to 20 or more weeks, from the time of administration. In exemplary embodiments, the time period could be even longer. The dose will be determined by the efficacy of the particular analog of the present disclosure and the condition of the animal (e.g., human), as well as the body weight of the animal (e.g., human) to be treated.

Many assays for determining an administered dose are known in the art. For purposes herein, an assay, which comprises comparing the extent to which blood glucose levels are lowered upon administration of a given dose of the analog of the present disclosure to a mammal among a set of mammals of which is each given a different dose of the analog, could be used to determine a starting dose to be administered to a mammal. The extent to which blood glucose levels are lowered upon administration of a certain dose can be assayed by methods known in the art, including, for instance, the methods described herein as Example 11.

The dose of the analog of the present disclosure also will be determined by the existence, nature and extent of any adverse side effects that might accompany the administration of a particular analog of the present disclosure. Typically, the attending physician will decide the dosage of the analog of the present disclosure with which to treat each individual patient, taking into consideration a variety of factors, such as age, body weight, general health, diet, sex, analog of the present disclosure to be administered, route of administration, and the severity of the condition being treated. By way of example and not intending to limit the invention, the dose of the analog of the present disclosure can be about 0.0001 to about 1 g/kg body weight of the subject being treated/day, from about 0.0001 to about 0.001 g/kg body weight/day, or about 0.01 mg to about 1 g/kg body weight/day. In exemplary embodiments, the dose can be a total weekly dose of about 1 mg to about 40 mg, or about 4 mg to about 30 mg, or about 4 to about 20 mg, or about 10 to about 20 mg, or about 12 mg to about 30 mg.

In some embodiments, the pharmaceutical composition comprises any of the analogs disclosed herein at a purity level suitable for administration to a patient. In some embodiments, the analog has a purity level of at least about 90%, about 91%, about 92%, about 93%, about 94%, about 95%, about 96%, about 97%, about 98% or about 99%, and a pharmaceutically acceptable diluent, carrier or excipient. The pharmaceutical composition in some aspects comprise the analog of the present disclosure at a concentration of at least A, wherein A is about about 0.001 mg/ml, about 0.01 mg/ml, 0 about 1 mg/ml, about 0.5 mg/ml, about 1 mg/ml, about 2 mg/ml, about 3 mg/ml, about 4 mg/ml, about 5 mg/ml, about 6 mg/ml, about 7 mg/ml, about 8 mg/ml, about 9 mg/ml, about 10 mg/ml, about 11 mg/ml, about 12 mg/ml, about 13 mg/ml, about 14 mg/ml, about 15 mg/ml, about 16 mg/ml, about 17 mg/ml, about 18 mg/ml, about 19 mg/ml, about 20 mg/ml, about 21 mg/ml, about 22 mg/ml, about 23 mg/ml, about 24 mg/ml, about 25 mg/ml or higher. In some embodiments, the pharmaceutical composition comprises the analog at a concentration of at most B, wherein B is about 30 mg/ml, about 25 mg/ml, about 24 mg/ml, about 23, mg/ml, about 22 mg/ml, about 21 mg/ml, about 20 mg/ml, about 19 mg/ml, about 18 mg/ml, about 17 mg/ml, about 16 mg/ml, about 15 mg/ml, about 14 mg/ml, about 13 mg/ml, about 12 mg/ml, about 11 mg/ml, about 10 mg/ml, about 9 mg/ml, about 8 mg/ml, about 7 mg/ml, about 6 mg/ml, about 5 mg/ml, about 4 mg/ml, about 3 mg/ml, about 2 mg/ml, about 1 mg/ml, or about 0.1 mg/ml. In some embodiments, the compositions may contain an analog at a concentration range of A to B mg/ml, for example, about 0.001 to about 30.0 mg/ml.

Targeted Forms

One of ordinary skill in the art will readily appreciate that the analogs of the disclosure can be modified in any number of ways, such that the therapeutic or prophylactic efficacy of the analog of the present disclosures is increased through the modification. For instance, the analog of the present disclosure can be conjugated either directly or indirectly through a linker to a targeting moiety. The practice of conjugating compounds, e.g., glucagon analogs described herein, to targeting moieties is known in the art. See, for instance, Wadhwa et al., *J Drug Targeting*, 3, 111-127 (1995) and U.S. Pat. No. 5,087,616. The term "targeting moiety" as used herein, refers to any molecule or agent that specifically recognizes and binds to a cell-surface receptor, such that the targeting moiety directs the delivery of the analog of the present disclosures to a population of cells on which surface the receptor (the glucagon receptor, the GLP-1 receptor) is expressed. Targeting moieties include, but are not limited to, antibodies, or fragments thereof, peptides, hormones, growth factors, cytokines, and any other natural or non-natural ligands, which bind to cell surface receptors (e.g., Epithelial Growth Factor Receptor (EGFR), T-cell receptor (TCR), B-cell receptor (BCR), CD28, Platelet-derived Growth Factor Receptor (PDGF), nicotinic acetylcholine receptor (nAChR), etc.). As used herein a "linker" is a bond, molecule or group of molecules that binds two separate entities to one another. Linkers may provide for optimal spacing of the two entities or may further supply a labile linkage that allows the two entities to be separated from each other. Labile linkages include photocleavable groups, acid-labile moieties, base-labile moieties and enzyme-cleavable groups. The term "linker" in some embodiments refers to any agent or molecule that bridges the analog of the present disclosures to the targeting moiety. One of ordinary skill in the art recognizes that sites on the analog of the present disclosures, which are not necessary for the function of the analog of the present disclosures, are ideal sites for attaching a linker and/or a targeting moiety, provided that the linker and/or targeting moiety, once attached to the analog of the present disclosures, do(es) not interfere with the function of the analog of the present disclosures, i.e., the ability to stimulate cAMP secretion from cells, to treat diabetes or obesity.

Controlled Release Formulations

Alternatively, the glucagon analogs described herein can be modified into a depot form, such that the manner in which the analog of the present disclosures is released into the body to which it is administered is controlled with respect to time and location within the body (see, for example, U.S. Pat. No. 4,450,150). Depot forms of analog of the present disclosures can be, for example, an implantable composition comprising the analog of the present disclosures and a porous or non-porous material, such as a polymer, wherein the analog of the present disclosures is encapsulated by or diffused throughout the material and/or degradation of the non-porous material. The depot is then implanted into the desired location within the body and the analog of the present disclosures are released from the implant at a predetermined rate.

The pharmaceutical composition in exemplary aspects is modified to have any type of in vivo release profile. In some aspects, the pharmaceutical composition is an immediate release, controlled release, sustained release, extended release, delayed release, or bi-phasic release formulation. Methods of formulating peptides for controlled release are known in the art. See, for example, Qian et al., *J Pharm* 374: 46-52 (2009) and International Patent Application Publication Nos. WO 2008/130158, WO2004/033036; WO2000/032218; and WO 1999/040942.

The instant compositions may further comprise, for example, micelles or liposomes, or some other encapsulated form, or may be administered in an extended release form to provide a prolonged storage and/or delivery effect. The disclosed pharmaceutical formulations may be administered according to any regime including, for example, daily (1 time per day, 2 times per day, 3 times per day, 4 times per day, 5 times per day, 6 times per day), three times a week, twice a week, every two days, every three days, every four days, every five days, every six days, weekly, bi-weekly, every three weeks, monthly, or bi-monthly.

Combinations

The glucagon analogs described herein may be administered alone or in combination with other therapeutic agents which aim to treat or prevent any of the diseases or medical conditions described herein. For example, the glucagon analogs described herein may be co-administered with (simultaneously or sequentially) an anti-diabetic or anti-obesity agent. Anti-diabetic agents known in the art or under investigation include insulin, leptin, Peptide YY (PYY), Pancreatic Peptide (PP), fibroblast growth factor 21 (FGF21), Y2Y4 receptor agonists, sulfonylureas, such as tolbutamide (Orinase), acetohexamide (Dymelor), tolazamide (Tolinase), chlorpropamide (Diabinese), glipizide (Glucotrol), glyburide (Diabeta, Micronase, Glynase), glimepiride (Amaryl), or gliclazide (Diamicron); meglitinides, such as repaglinide (Prandin) or nateglinide (Starlix); higuanides such as metformin (Glucophage) or phenformin; thiazolidinediones such as rosiglitazone (Avandia), pioglitazone (Actos), or troglitazone (Rezulin), or other PPARγ inhibitors; alpha glucosidase inhibitors that inhibit carbohydrate digestion, such as miglitol (Glyset), acarbose (Precose/Glucobay); exenatide (Byetta) or pramlintide; Dipeptidyl peptidase-4 (DPP-4) inhibitors such as vildagliptin or sitagliptin; SGLT (sodium-dependent glucose transporter 1) inhibitors; glucokinase activators (GKA); glucagon receptor antagonists (GRA); or FBPase (fructose 1,6-bisphosphatase) inhibitors.

Anti-obesity agents known in the art or under investigation include appetite suppressants, including phenethylamine type stimulants, phentermine (optionally with fenfluramine or dexfenfluramine), diethylpropion (Tenuate®), phendimetrazine (Prelu-2®, Bontril®), benzphetamine (Didrex®), sibutramine (Meridia®, Reductil®); rimonabant (Acomplia®), other cannabinoid receptor antagonists; oxyntomodulin; fluoxetine hydrochloride (Prozac); Qnexa (topiramate and phentermine), Excalia (bupropion and zonisamide) or Contrave (bupropion and naltrexone); or lipase inhibitors, similar to XENICAL (Orlistat) or Cetilistat (also known as ATL-962), or GT 389-255.

The peptides described herein in some embodiments are co-administered with an agent for treatment of non-alcoholic fatty liver disease or NASH. Agents used to treat non-alcoholic fatty liver disease include ursodeoxycholic acid (a.k.a., Actigall, URSO, and Ursodiol), Metformin (Glucophage), rosiglitazone (Avandia), Clofibrate, Gemfibrozil, Polymixin B, and Betaine.

The peptides described herein in some embodiments are co-administered with an agent for treatment of a neurodegenerative disease, e.g., Parkinson's Disease. Anti-Parkinson's Disease agents are furthermore known in the art and include, but not limited to, levodopa, carbidopa, anticholinergics, bromocriptine, pramipexole, and ropinirole, amantadine, and rasagiline.

In view of the foregoing, the invention further provides pharmaceutical compositions and kits additionally comprising one of these other therapeutic agents. The additional therapeutic agent may be administered simultaneously or sequentially with the analog of the present disclosure. In some aspects, the analog is administered before the additional therapeutic agent, while in other aspects, the analog is administered after the additional therapeutic agent.

Uses

Based on the information provided for the first time herein, it is contemplated that the compositions (e.g., related pharmaceutical compositions) of the present disclosures are useful for treatment of a disease or medical condition, in which e.g., the lack of activity at the GIP receptor, the GLP-1 receptor, or at both receptors, is a factor in the onset and/or progression of the disease or medical condition. Accordingly, the present disclosures provides a method of treating or preventing a disease or medical condition in a patient, wherein the disease or medical condition is a disease of medical condition in which a lack of GIP receptor activation and/or GLP-1 receptor activation is associated with the onset and/or progression of the disease of medical condition. The method comprises providing to the patient a composition or conjugate in accordance with any of those described herein in an amount effective to treat or prevent the disease or medical condition.

In some embodiments, the disease or medical condition is metabolic syndrome. Metabolic Syndrome, also known as metabolic syndrome X, insulin resistance syndrome or Reaven's syndrome, is a disorder that affects over 50 million Americans. Metabolic Syndrome is typically characterized by a clustering of at least three or more of the following risk factors: (1) abdominal obesity (excessive fat tissue in and around the abdomen), (2) atherogenic dyslipidemia (blood fat disorders including high triglycerides, low HDL cholesterol and high LDL cholesterol that enhance the accumulation of plaque in the artery walls), (3) elevated blood pressure, (4) insulin resistance or glucose intolerance, (5) prothrombotic state (e.g., high fibrinogen or plasminogen activator inhibitor-1 in blood), and (6) pro-inflammatory state (e.g., elevated C-reactive protein in blood). Other risk factors may include aging, hormonal imbalance and genetic predisposition.

Metabolic Syndrome is associated with an increased the risk of coronary heart disease and other disorders related to the accumulation of vascular plaque, such as stroke and peripheral vascular disease, referred to as atherosclerotic cardiovascular disease (ASCVD). Patients with Metabolic Syndrome may progress from an insulin resistant state in its early stages to full blown type II diabetes with further increasing risk of ASCVD. Without intending to be bound by any particular theory, the relationship between insulin resistance, Metabolic Syndrome and vascular disease may involve one or more concurrent pathogenic mechanisms including impaired insulin-stimulated vasodilation, insulin resistance-associated reduction in NO availability due to enhanced oxidative stress, and abnormalities in adipocyte-derived hormones such as adiponectin (Lteif and Mather, Can. J. Cardiol. 20 (suppl. B):66B-76B (2004)).

According to the 2001 National Cholesterol Education Program Adult Treatment Panel (ATP III), any three of the following traits in the same individual meet the criteria for Metabolic Syndrome: (a) abdominal obesity (a waist circumference over 102 cm in men and over 88 cm in women); (b) serum triglycerides (150 mg/dl or above); (c) HDL cholesterol (40 mg/dl or lower in men and 50 mg/dl or lower in women); (d) blood pressure (130/85 or more); and (e) fasting blood glucose (110 mg/dl or above). According to the World Health Organization (WHO), an individual having high insulin levels (an elevated fasting blood glucose or an elevated post meal glucose alone) with at least two of the following criteria meets the criteria for Metabolic Syndrome: (a) abdominal obesity (waist to hip ratio of greater than 0.9, a body mass index of at least 30 kg/m2, or a waist measurement over 37 inches); (b) cholesterol panel showing a triglyceride level of at least 150 mg/dl or an HDL cholesterol lower than 35 mg/dl; (c) blood pressure of 140/90 or more, or on treatment for high blood pressure).

(Mathur, Ruchi, "Metabolic Syndrome," ed. Shiel, Jr., William C., MedicineNet.com, May 11, 2009).

For purposes herein, if an individual meets the criteria of either or both of the criteria set forth by the 2001 National Cholesterol Education Program Adult Treatment Panel or the WHO, that individual is considered as afflicted with Metabolic Syndrome.

Without being bound to any particular theory, compositions and conjugates described herein are useful for treating Metabolic Syndrome. Accordingly, the invention provides a method of preventing or treating Metabolic Syndrome, or reducing one, two, three or more risk factors thereof, in a subject, comprising providing to the subject a composition described herein in an amount effective to prevent or treat Metabolic Syndrome, or the risk factor thereof.

In some embodiments, the method treats a hyperglycemic medical condition. In exemplary aspects, the hyperglycemic medical condition is diabetes, diabetes mellitus type I, diabetes mellitus type II, or gestational diabetes, either insulin-dependent or non-insulin-dependent. In some aspects, the method treats the hyperglycemic medical condition by reducing one or more complications of diabetes including nephropathy, retinopathy and vascular disease.

In some aspects, the disease or medical condition is obesity. In some aspects, the obesity is drug-induced obesity. In some aspects, the method treats obesity by preventing or reducing weight gain or increasing weight loss in the patient. In some aspects, the method treats obesity by reducing appetite, decreasing food intake, lowering the levels of fat in the patient, or decreasing the rate of movement of food through the gastrointestinal system.

Because obesity is associated with the onset or progression of other diseases, the methods of treating obesity are further useful in methods of reducing complications associated with obesity including vascular disease (coronary artery disease, stroke, peripheral vascular disease, ischemia reperfusion, etc.), hypertension, onset of diabetes type II, hyperlipidemia and musculoskeletal diseases. The present disclosures accordingly provides methods of treating or preventing these obesity-associated complications.

In some embodiments, the disease or medical condition is Nonalcoholic fatty liver disease (NAFLD). NAFLD refers to a wide spectrum of liver disease ranging from simple fatty liver (steatosis), to nonalcoholic steatohepatitis (NASH), to cirrhosis (irreversible, advanced scarring of the liver). All of the stages of NAFLD have in common the accumulation of fat (fatty infiltration) in the liver cells (hepatocytes). Simple fatty liver is the abnormal accumulation of a certain type of fat, triglyceride, in the liver cells with no inflammation or scarring. In NASH, the fat accumulation is associated with varying degrees of inflammation (hepatitis) and scarring (fibrosis) of the liver. The inflammatory cells can destroy the liver cells (hepatocellular necrosis). In the terms "steatohepatitis" and "steatonecrosis", steato refers to fatty infiltration, hepatitis refers to inflammation in the liver, and necrosis refers to destroyed liver cells. NASH can ultimately lead to scarring of the liver (fibrosis) and then irreversible, advanced scarring (cirrhosis). Cirrhosis that is caused by NASH is the last and most severe stage in the NAFLD spectrum. (Mendler, Michel, "Fatty Liver: Nonalcoholic Fatty Liver Disease (NAFLD) and Nonalcoholic Steatohepatitis (NASH)," ed. Schoenfield, Leslie J., MedicineNet. com, Aug. 29, 2005).

Alcoholic Liver Disease, or Alcohol-Induced Liver Disease, encompasses three pathologically distinct liver diseases related to or caused by the excessive consumption of alcohol: fatty liver (steatosis), chronic or acute hepatitis, and cirrhosis. Alcoholic hepatitis can range from a mild hepatitis, with abnormal laboratory tests being the only indication of disease, to severe liver dysfunction with complications such as jaundice (yellow skin caused by bilirubin retention), hepatic encephalopathy (neurological dysfunction caused by liver failure), ascites (fluid accumulation in the abdomen), bleeding esophageal varices (varicose veins in the esophagus), abnormal blood clotting and coma. Histologically, alcoholic hepatitis has a characteristic appearance with ballooning degeneration of hepatocytes, inflammation with neutrophils and sometimes Mallory bodies (abnormal aggregations of cellular intermediate filament proteins). Cirrhosis is characterized anatomically by widespread nodules in the liver combined with fibrosis. (Worman, Howard J., "Alcoholic Liver Disease", Columbia University Medical Center website).

Without being bound to any particular theory, the compositions and conjugates described herein are useful for the treatment of Alcoholic Liver Disease, NAFLD, or any stage thereof, including, for example, steatosis, steatohepatitis, hepatitis, hepatic inflammation, NASH, cirrhosis, or complications thereof. Accordingly, the present disclosures provides a method of preventing or treating Alcoholic Liver Disease, NAFLD, or any stage thereof, in a subject comprising providing to a subject a composition described herein in an amount effective to prevent or treat Alcoholic Liver Disease, NAFLD, or the stage thereof. Such treatment methods include reduction in one, two, three or more of the following: liver fat content, incidence or progression of cirrhosis, incidence of hepatocellular carcinoma, signs of inflammation, e.g., abnormal hepatic enzyme levels (e.g., aspartate aminotransferase AST and/or alanine aminotransferase ALT, or LDH), elevated serum ferritin, elevated serum bilirubin, and/or signs of fibrosis, e.g., elevated TGF-beta levels. In exemplary embodiments, the compositions are used treat patients who have progressed beyond simple fatty liver (steatosis) and exhibit signs of inflammation or hepatitis. Such methods may result, for example, in reduction of AST and/or ALT levels.

GLP-1 and exendin-4 have been shown to have some neuroprotective effect. The present disclosures also provides uses of the compositions described herein in treating neurodegenerative diseases, including but not limited to Alzheimer's disease, Parkinson's disease, Multiple Sclerosis, Amylotrophic Lateral Sclerosis, other demyelination related disorders, senile dementia, subcortical dementia, arteriosclerotic dementia, AIDS-associated dementia, or other dementias, a central nervous system cancer, traumatic brain injury, spinal cord injury, stroke or cerebral ischemia, cerebral vasculitis, epilepsy, Huntington's disease, Tourette's syndrome, Guillain Barre syndrome, Wilson disease, Pick's disease, neuroinflammatory disorders, encephalitis, encephalomyelitis or meningitis of viral, fungal or bacterial origin, or other central nervous system infections, prion diseases, cerebellar ataxias, cerebellar degeneration, spinocerebellar degeneration syndromes, Friedreichs ataxia, ataxia telangiectasia, spinal dysmyotrophy, progressive supranuclear palsy, dystonia, muscle spasticity, tremor, retinitis pigmentosa, striatonigral degeneration, mitochondrial encephalo-myopathies, neuronal ceroid lipofuscinosis, hepatic encephalopathies, renal encephalopathies, metabolic encephalopathies, toxin-induced encephalopathies, and radiation-induced brain damage.

In some embodiments, the compositions are used in conjunction with parenteral administration of nutrients to non-diabetic patients in a hospital setting, e.g., to patients receiving parenteral nutrition or total parenteral nutrition. Nonlimiting examples include surgery patients, patients in comas, patients with digestive tract illness, or a nonfunctional gastrointestinal tract (e.g. due to surgical removal, blockage or impaired absorptive capacity, Crohn's disease, ulcerative colitis, gastrointestinal tract obstruction, gastrointestinal tract fistula, acute pancreatitis, ischemic bowel, major gastrointestinal surgery, certain congenital gastrointestinal tract anomalies, prolonged diarrhea, or short bowel syndrome due to surgery, patients in shock, and patients undergoing healing processes often receive parenteral administration of carbohydrates along with various combinations of lipids, electrolytes, minerals, vitamins and amino acids. The compositions comprising the GIP agonist peptide and glucagon antagonist peptide, as described herein, and the parenteral nutrition composition can be administered at the same time, at different times, before, or after each other, provided that the composition is exerting the desired biological effect at the time that the parenteral nutrition composition is being digested. For example, the parenteral nutrition may be administered, 1, 2 or 3 times per day, while the composition is administered once every other day, three times a week, two times a week, once a week, once every 2 weeks, once every 3 weeks, or once a month.

As used herein, the term "treating" includes prophylaxis of the specific disorder or condition, or alleviation of the symptoms associated with a specific disorder or condition and/or preventing or eliminating said symptoms. For example, as used herein the term "treating diabetes" will refer in general to altering glucose blood levels in the direction of normal levels and may include increasing or decreasing blood glucose levels depending on a given situation.

As used herein an "effective" amount or a "therapeutically effective amount" of a glucagon peptide refers to a nontoxic but sufficient amount of the peptide to provide the desired effect. For example one desired effect would be the prevention or treatment of hypoglycemia, as measured, for example, by an increase in blood glucose level. An alternative desired effect for the glucagon peptides of the present disclosure would include treating hyperglycemia, e.g., as measured by a change in blood glucose level closer to normal, or inducing weight loss/preventing weight gain, e.g., as measured by reduction in body weight, or preventing or reducing an increase in body weight, or normalizing body fat distribution. The amount that is "effective" will vary from subject to subject, depending on the age and general condition of the individual, mode of administration, and the like. Thus, it is not always possible to specify an exact "effective amount." However, an appropriate "effective" amount in any individual case may be determined by one of ordinary skill in the art using routine experimentation.

Subjects

With regard to the above methods of treatment, the patient is any host. In some embodiments, the host is a mammal. As used herein, the term "mammal" refers to any vertebrate animal of the mammalia class, including, but not limited to, any of the monotreme, marsupial, and placental taxas. In some embodiments, the mammal is one of the mammals of the order Rodentia, such as mice and hamsters, and mammals of the order Logomorpha, such as rabbits. In exemplary embodiments, the mammals are from the order Carnivora, including Felines (cats) and Canines (dogs). In exemplary embodiments, the mammals are from the order Artiodactyla, including Bovines (cows) and S wines (pigs) or of the order Perssodactyla, including Equines (horses). In some instances, the mammals are of the order Primates, Ceboids, or Simoids (monkeys) or of the order Anthropoids (humans and apes). In particular embodiments, the mammal is a human.

Kits

The glucagon analogs of the present disclosure can be provided in accordance with one embodiment as part of a kit. Accordingly, in some embodiments, a kit for administering a glucagon analog to a patient in need thereof is provided wherein the kit comprises a glucagon analog as described herein.

In one embodiment the kit is provided with a device for administering the glucagon analog to a subject. The device in some aspects is a syringe needle, pen device, jet injector or other needle-free injector. The kit may alternatively or in addition include one or more containers, e.g., vials, tubes, bottles, single or multi-chambered pre-filled syringes, cartridges, infusion pumps (external or implantable), jet injectors, pre-filled pen devices and the like, optionally containing the glucagon analog in a lyophilized form or in an aqueous solution. The kits in some embodiments comprise instructions for use. In accordance with one embodiment the device of the kit is an aerosol dispensing device, wherein the composition is prepackaged within the aerosol device. In another embodiment the kit comprises a syringe and a needle, and in one embodiment the sterile glucagon composition is prepackaged within the syringe.

The kits in some embodiments comprise instructions for use. The instructions in some aspects include instructions for use in accordance with any of the methods described herein. The instructions may additionally include instructions for maintaining a healthy diet and/or a physical exercise program. The instructions may be in the form of a paper pamphlet, or in electronic form, e.g., a computer readable storage device comprising the instructions.

The following examples are given merely to illustrate the present invention and not in any way to limit its scope.

EXAMPLES

Example 1

The following provides exemplary methods of synthesizing the peptide analogs of the present disclosures.

Synthesis of Peptide Fragments of Glucagon

Materials:

All peptides described herein in the EXAMPLES were amidated unless specified otherwise.

MBHA resin (4-methylbenzhydrylamine polystyrene resin was used during peptide synthesis. MBHA resin, 100-180 mesh, 1% DVB cross-linked polystyrene; loading of 0.7-1.0 mmol/g), Boc-protected and Fmoc protected amino acids were purchased from Midwest Biotech. The solid phase peptide syntheses using Boc-protected amino acids were performed on an Applied Biosystem 430A Peptide Synthesizer. Fmoc protected amino acid synthesis was performed using the Applied Biosystems Model 433 Peptide Synthesizer.

Peptide Synthesis (Boc Amino Acids/HF Cleavage):

Synthesis of these analogs was performed on the Applied Biosystem Model 430A Peptide Synthesizer. Synthetic peptides were constructed by sequential addition of amino acids to a cartridge containing 2 mmol of Boc protected amino acid. Specifically, the synthesis was carried out using Boc DEPBT-activated single couplings. At the end of the coupling step, the peptidyl-resin was treated with TFA to remove the N-terminal Boc protecting group. It was washed repeatedly with dimethylformamide (DMF) and this repetitive cycle was repeated for the desired number of coupling steps. After the assembly, the sidechain protection, Fmoc, was removed by 20% piperidine treatment and acylation was conducted using DIC. The peptidyl-resin at the end of the entire synthesis was dried by using dichloromethane (DCM), and the peptide was cleaved from the resin with anhydrous HF.

For the lactamization, orthogonal protecting groups were selected for Glu and Lys (e.g., Glu(Fm), Lys(Fmoc)). After removal of the protecting groups and before HF cleavage, cyclization was performed as described previously (see, e.g., International Patent Application Publication No. WO2008/101017).

HF Treatment of the Peptidyl-Resin

The peptidyl-resin was treated with anhydrous hydrogen fluoride (HF), and this typically yielded approximately 350 mg (~50% yield) of a crude deprotected-peptide. Specifically, the peptidyl-resin (30 mg to 200 mg) was placed in the HF reaction vessel for cleavage. 500 µL of p-cresol was added to the vessel as a carbonium ion scavenger. The vessel was attached to the HF system and submerged in the methanol/dry ice mixture. The vessel was evacuated with a vacuum pump and 10 ml of HF was distilled to the reaction vessel. This reaction mixture of the peptidyl-resin and the HF was stirred for one hour at 0° C., after which a vacuum was established and the HF was quickly evacuated (10-15 min). The vessel was removed carefully and filled with approximately 35 ml of ether to precipitate the peptide and to extract the p-cresol and small molecule organic protecting groups resulting from HF treatment. This mixture was filtered utilizing a teflon filter and repeated twice to remove all excess cresol. This filtrate was discarded. The precipitated peptide dissolves in approximately 20 ml of 10% acetic acid (aq). This filtrate, which contained the desired peptide, was collected and lyophilized.

An analytical HPLC analysis of the crude solubilized peptide was conducted under the following conditions [4.6× 30 mm Xterra C8, 1.50 mL/min, 220 nm, A buffer 0.1% trifluoroacetic acid (TFA)/10% acrylonitrile (CAN), B buffer 0.1% TFA/100% ACN, gradient 5-95% B over 15 minutes]. The extract was diluted twofold with water and loaded onto a 2.2×25 cm Vydac C4 preparative reverse phase column and eluted using an acetonitrile gradient on a Waters HPLC system (A buffer of 0.1% TFA/10% ACN, B buffer of 0.1% TFA/10% ACN and a gradient of 0-100% B over 120 minutes at a flow of 15.00 ml/min HPLC analysis of the purified peptide demonstrated greater than 95% purity and electrospray ionization mass spectral analysis was used to confirm the identity of the peptide.

Peptide Acylation

Acylated peptides were prepared as follows. Peptides were synthesized on a solid support resin using either a CS Bio 4886 Peptide Synthesizer or Applied Biosystems 430A Peptide Synthesizer. In situ neutralization chemistry was used as described by Schnolzer et al., Int. J. Peptide Protein Res. 40: 180-193 (1992). For acylated peptides, the target amino acid residue to be acylated (e.g., position ten, relative to the amino acid position numbering of SEQ ID NO: 3) was substituted with an Nε-FMOC lysine residue. Treatment of the completed N-terminally BOC protected peptide with 20% piperidine in DMF for 30 minutes removed FMOC/formyl groups. Coupling to the free ε-amino Lys residue was achieved by coupling a ten-fold molar excess of either an FMOC-protected spacer amino acid (ex. FMOC-Glu-OtBu) or acyl chain (ex. $CH_3(CH_2)_{14}$—COOH) and PyBOP or DEPBT coupling reagent in DMF/N,N-diisopropylethylamine (DIEA). Subsequent removal of the spacer amino acid's FMOC group is followed by repetition of coupling with an acyl chain. Final treatment with 100% TFA resulted in removal of any side chain protecting groups and the N-terminal BOC group. Peptide resins were neutralized with 5% DIEA/DMF, dried, and then cleaved from the support using HF/p-cresol, 95:5, at 0° C. for one hour. Following ether extraction, a 5% acetic acid (HOAc) solution was used to solvate the crude peptide. A sample of the solution was then verified to contain the correct molecular weight peptide by ESI-MS. Correct peptides were purified by RP-HPLC using a linear gradient of 10% acetonitrile (CH3CN)/0.1% TFA to 0.1% TFA in 100% CH3CN. A Vydac C18 22 mm×250 mm protein column was used for the purification. Acylated peptide analogs generally completed elution by a buffer ratio of 20:80. Portions were pooled together and checked for purity on an analytical RP-HPLC. Pure fractions were lyophilized yielding white, solid peptides.

If a peptide comprised a lactam bridge and target residues to be acylated, acylation is carried out as described above upon addition of that amino acid to the peptide backbone.

Dual acylations or di-acylations are prepared as follows. Peptides are synthesized on a solid support resin using either a CS Bio 4886 Peptide Synthesizer or Applied Biosystems 430A Peptide Synthesizer. In situ neutralization chemistry is used as described by Schnolzer et al., Int. J. Peptide Protein Res. 40: 180-193 (1992). For two site double acylated peptides, the target amino acid residues to be acylated (e.g., position ten and 40, relative to the amino acid position numbering of SEQ ID NO: 3) are substituted with an Nε-FMOC lysine residue. Treatment of the completed N-terminally BOC protected peptide with 20% piperidine in DMF for 30 minutes removes FMOC/formyl groups. Coupling to the free ε-amino Lys residue is achieved by coupling a ten-fold molar excess of either an FMOC-protected spacer amino acid (ex. FMOC-Glu-OtBu) or acyl chain (ex. $CH_3(CH_2)_{14}$—COOH) and PyBOP or DEPBT coupling reagent in DMF/DIEA. Subsequent removal of the spacer amino acid's FMOC group is followed by repetition of coupling with an acyl chain. Final treatment with 100% TFA results in removal of any side chain protecting groups and the N-terminal BOC group. Peptide resins are neutralized with 5% DIEA/DMF, dried, and then are cleaved from the support using HF/p-cresol, 95:5, at 0° C. for one hour. Following ether extraction, a 5% HOAc solution is used to solvate the crude peptide. A sample of the solution is then verified to contain the correct molecular weight peptide by ESI-MS. Correct peptides are purified by RP-HPLC using a linear gradient of 10% CH3CN/0.1% TFA to 0.1% TFA in 100% CH3CN. A Vydac C18 22 mm×250 mm protein column was used for the purification. Acylated peptide analogs generally complete elution by a buffer ratio of 20:80. Portions are pooled together and checked for purity on an analytical RP-HPLC. Pure fractions are lyophilized yielding white, solid peptides.

One site branch double acylations are prepared as follows. Peptides are synthesized on a solid support resin using either a CS Bio 4886 Peptide Synthesizer or Applied Biosystems 430A Peptide Synthesizer. In situ neutralization chemistry is used as described by Schnolzer et al., Int. J. Peptide Protein Res. 40: 180-193 (1992). For acylated peptides, the target amino acid residue to be acylated (e.g., position ten relative to the amino acid position numbering of SEQ ID NO: 3) is substituted with an Nε-FMOC lysine residue. Treatment of the completed N-terminally BOC protected peptide with 20% piperidine in DMF for 30 minutes removes FMOC/formyl groups. Coupling to a Lys residue through the C-terminus is achieved by coupling a ten-fold molar excess of an ε-amino and α-amino FMOC-protected spacer amino acid (ex. FMOC-Lys(FMOC)-OH) and PyBOP or DEPBT coupling reagent in DMF/DIEA. Subsequent removal of the spacer amino acid's FMOC groups is followed by coupling each of the ε-amino and α-amino groups with an acyl chain. Final treatment with 100% TFA results in removal of any side chain protecting groups and the N-terminal BOC group. Peptide resins are neutralized with 5% DIEA/DMF, dried, and then are cleaved from the support using HF/p-cresol, 95:5, at 0° C. for one hour. Following ether extraction, a 5% HOAc solution is used to solvate the crude peptide. A sample of the solution is then verified to contain the correct molecular weight peptide by ESI-MS. Correct peptides are purified by RP-HPLC using a linear gradient of 10% CH3CN/0.1% TFA to 0.1% TFA in 100% CH3CN. A Vydac C18 22 mm×250 mm protein column was used for the purification. Acylated peptide analogs generally complete elution by a buffer ratio of 20:80. Portions are pooled together and checked for purity on an analytical RP-HPLC. Pure fractions were lyophilized yielding white, solid peptides.

One site linear double acylations are prepared as follows. Peptides are synthesized on a solid support resin using either a CS Bio 4886 Peptide Synthesizer or Applied Biosystems 430A Peptide Synthesizer. In situ neutralization chemistry is used as described by Schnolzer et al., Int. J. Peptide Protein Res. 40: 180-193 (1992). For acylated peptides, the target amino acid residue to be acylated (e.g., position ten, relative to the amino acid position numbering of SEQ ID NO: 3) is substituted with an Nε-FMOC lysine residue. Treatment of the completed N-terminally BOC protected peptide with 20% piperidine in DMF for 30 minutes removes FMOC/formyl groups. Coupling to the free ε-amino Lys residue is achieved by coupling a ten-fold molar excess of either an FMOC-protected spacer amino acid (ex. FMOC-Glu-OtBu) or acyl chain (ex. $CH_3(CH_2)_{14}$—COOH) and PyBOP or DEPBT coupling reagent in DMF/DIEA. Subsequent removal of the spacer amino acid's FMOC group is followed by coupling with an acyl chain functionalized at the end of the fatty acid tail with a protected amino acid such a as FmocNH—$(CH_2)_{11}$—COOH. The resulting single acylated amino acid is treated with 20% piperidine in DMF to remove the FMOC protecting group, followed by coupling with an acyl chain. Final treatment with 100% TFA results in the removal of any side chain protecting groups and the N-terminal BOC group. Peptide resins are neutralized with 5% DIEA/DMF, dried, and then cleaved from the support using HF/p-cresol, 95:5, at 0° C. for one hour. Following ether extraction, a 5% HOAc solution is used to solvate the crude peptide. A sample of the solution is then verified to contain the correct molecular weight peptide by ESI-MS. Correct peptides are purified by RP-HPLC using a linear gradient of 10% CH3CN/0.1% TFA to 0.1% TFA in 100% CH3CN. A Vydac C18 22 mm×250 mm protein column is used for the purification. Acylated peptide analogs generally complete elution by a buffer ratio of 20:80. Portions are pooled together and checked for purity on an analytical RP-HPLC. Pure fractions are lyophilized yielding white, solid peptides.

In the instances of two site or single site double acylations, the two acyl chains to be coupled to the peptide can be the same or different. In the case of two different acyl chains, the target amino acid(s) to be acylated are substituted with two different protecting groups. For example an Nε-FMOC lysine residue and an Nε-ivDde lysine residue (two site double acylation) or an FMOC Lys (ivDde)-OH (single site double acylation, 852082 Novabiochem). Treatment of the completed N-terminally BOC protected peptide with 20% piperidine in DMF for 30 minutes removed FMOC/formyl groups. The free ε-amino Lys residue is coupled with either an acyl group or spacer amino acid followed by coupling to an acyl group. The resulting single acylated peptide is treated with 2% hydrazine/DMF to remove the(ivDde) protecting group. The free amino Lys residue is coupled with either an acyl group or a spacer amino acid followed by coupling to an acy group. The double acylated peptide is isolated as described above.

Figure 5B:
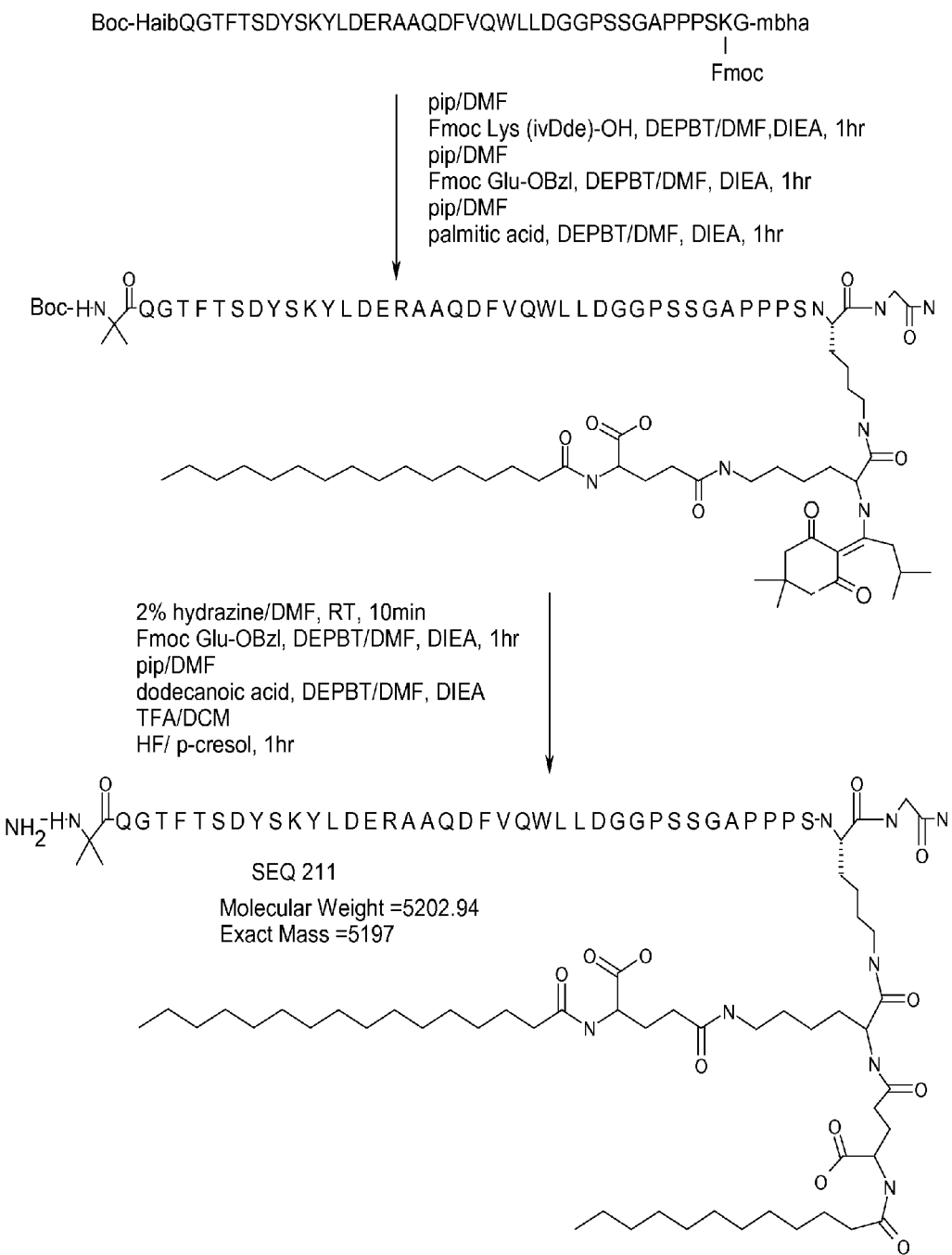
Figure 5C:
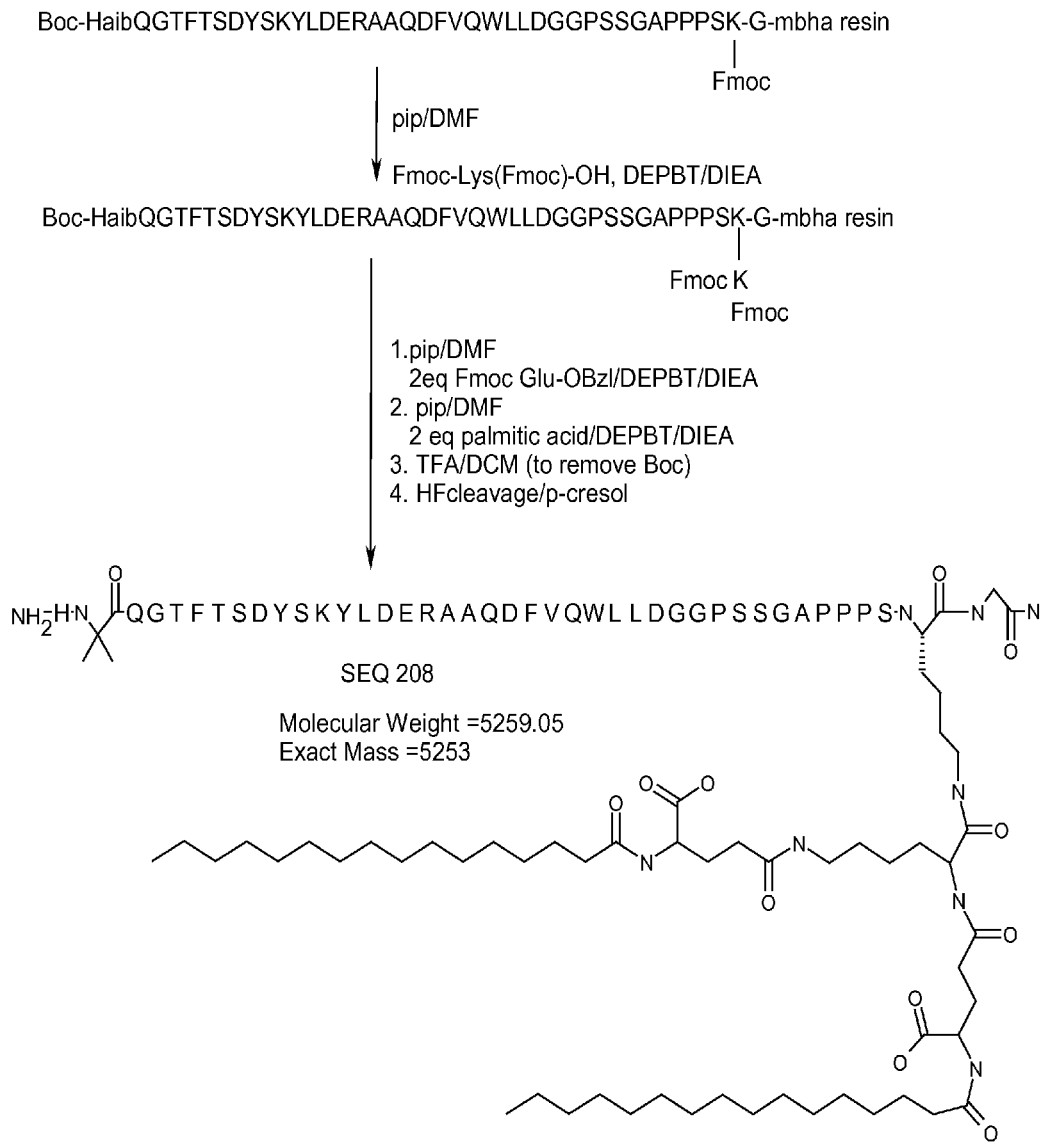
Figure 5D:
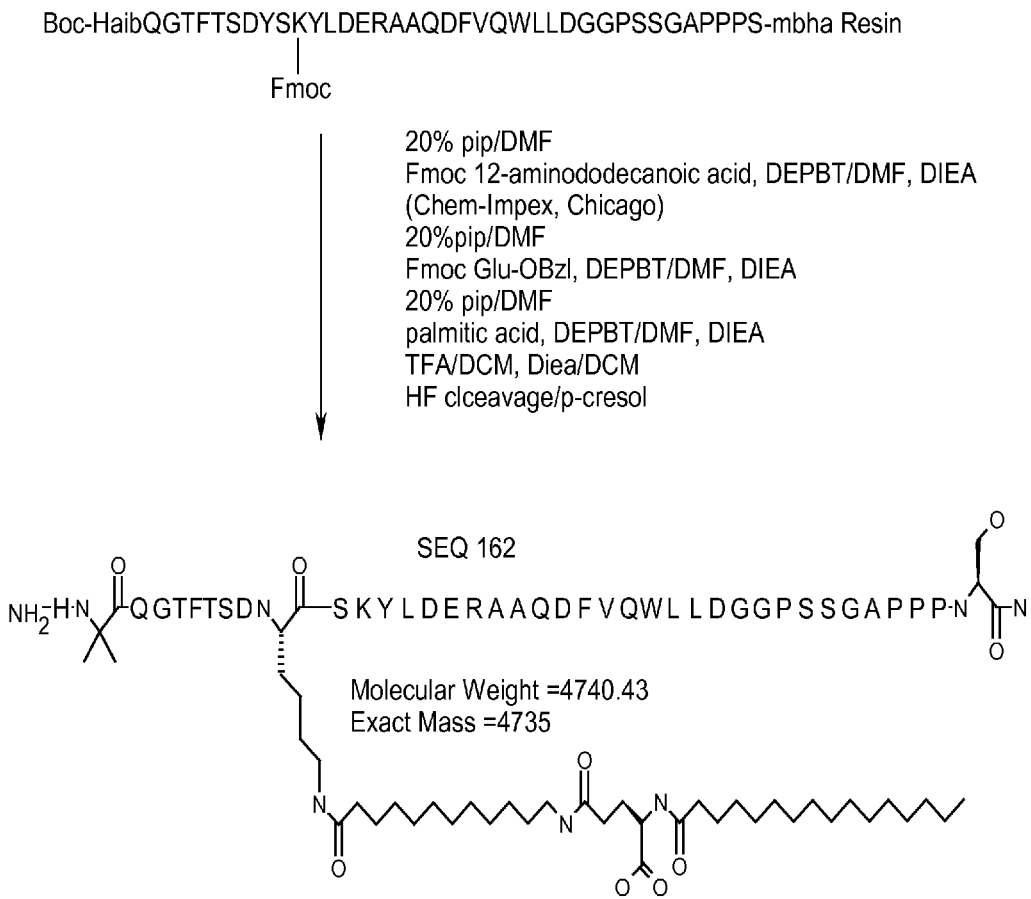

An example synthesis of a dual acylated peptide (Glucagon Aib2 E16 A18 L27 D28 Cex K40(C16γE-K-γEC12) G41-amide, having the amino acid sequence of SEQ ID NO: 211) is shown in FIG. 5B and is further described below:

0.28 gm (0.2 mmole) mbha-resin (Midwest Biotech) was placed in a reaction vessel and the following sequence was assembled on a CSBio336 synthesizer using DEPBT/DIEA activated single couplings of Boc amino acids.

```
Boc-HaibQGTFTSDYSKYLDERAAQDFVQWLLDGGPSSGAPP
PSK(Fmoc)G-mbha resin
```

The Boc protected peptide resin was transferred to a manual reaction vessel and was treated with 20% piperidine/DMF at room temp for 10 min. The resin was filtered, washed with DMF 3 times, and an activated solution of Fmoc Lys(ivDde)-OH (EMD-Novabiochem) was added (previously prepared by dissolving 2 mmole Fmoc Lys (ivDde) in 4.0 ml 0.5M DEPBT/DMF and 0.35 ml (2 mmole) DIEA wad added.

The peptide resin was mixed at room temp for 16 hrs, then filtered, washed with DMF and was treated with 20% piperidine/DMF for 10 min. The resin was filtered, washed with DMF several times, and an activated solution of Fmoc Glu-OBzl was added (previously prepared by dissolving 2 mmole Fmoc Glu-OBzl in 4.0 ml 0.5M DEPBT/DMF and 0.35 ml DIEA was added). The reaction was mixed 1 hr at room temp then filtered and the resin washed with DMF. After another treatment with 20% pip/DMF, the resin was washed with DMF several times, and an activated solution of palmitic acid was added to complete the acylation of the α-amine of the side chain Lys at position 40 (previously prepared by dissolving 2 mmole palmitic acid in 4.0 ml 0.5M DEPBT/DMF and adding 0.35 ml DIEA). The reaction was mixed for 1 hr.

The peptide resin was filtered, washed with DMF and treated with 2% hydrazine/DMF at room temp for 15 min, the filtered and was washed with DMF several times. An activated solution of Fmoc Glu-OBzl was added (same as above) and the reaction mixed for 1 hr at rt. The resin was divided into three portions for final acylation at the ε-lysine amine. In this case, to one portion an activated solution of docecanoic acid was added. Previously prepared by dissolving 1 mmole dodecanoic acid (Aldrich) in 2.0 ml 0.5M DEPBT/DMF and 0.175 ml DIEA was added. The reaction was mixed 1 hr, the filtered, washed with DMF, then with dichloromethane. The N-terminal Boc group was removed on treatment with 50% TFA/DCM, and after neutralization with 5% DIEA/DCM, an HF cleavage was run in an ice bath for 1 hrs using p-cresol as a scavenger. After evaporation of the HF, the residue was suspended in ethyl ether and the peptide/resin mixture was filtered and washed with ether. The peptide was extracted into aqueous acetic acid and analyzed on HPLC. (4.6×50 mm Zorbax SB-C8, 1 ml/min, 45° C., 214 nm (0.5 A) A=0.1% TFA, B=0.1% TFA/90% ACN. The remaining cleavage extract was loaded onto a 21.2×250 mm Amberchrom XT20 column and a 0.1% TFA/acetonitrile gradient was run on a Pharmacia FPLC for purification.

Fractions 83-86 were combined, frozen and lyophilized to give 22.3 mg of the peptide of SEQ ID NO: 211 with a purity of 90%+. Theoretical mol. wt.=5202.9, ESI observed mass=5202.0

Peptide Acylation Via Succinoylation

Succinoylated peptides are prepared as follows. Peptides are synthesized on a solid support resin using either a CS Bio 4886 Peptide Synthesizer or Applied Biosystems 430A Peptide Synthesizer. In situ neutralization chemistry is used as described by Schnolzer et al., Int. J. Peptide Protein Res. 40: 180-193 (1992). For succincoylated peptides, the target amino acid residue to be acylated (e.g., position ten, relative to the amino acid position numbering of SEQ ID NO: 3) is substituted with an Nε-FMOC lysine residue. Treatment of the completed N-terminally BOC protected peptide with 20% piperidine in DMF for 10 minutes removed FMOC/formyl groups. The resin is filtered, washed with DMF/DCM and re-suspended in DCM. Coupling to the free ε-amino Lys residue is achieved by coupling a ten-fold molar excess of n-hexadecylsuccinic anhydride (TCI) along with 4-dimethylaminopyridine. The resin is mixed overnight, filtered, washed with DCM and treated with 50% TFA/DCM to remove any side chain protecting groups and the N-terminal BOC. Peptide resins are neutralized with 5% DIEA/DMF, dried, and then are cleaved from the support using HF/p-cresol, 95:5, at 0° C. for one hour. Following ether extraction, a 5% HOAc solution is used to solvate the crude peptide. A sample of the solution is then verified by HPLC analysis. The remaining acetic acid solution is loaded onto a 10×250 mm Amberchrom XT20 column for purification. An aqueous TFA/ACN gradient is run while collecting fraction and monitoring the UV at 214 nm. Pure fractions are lyophilized, yielding solid peptides.

Figure 3B:
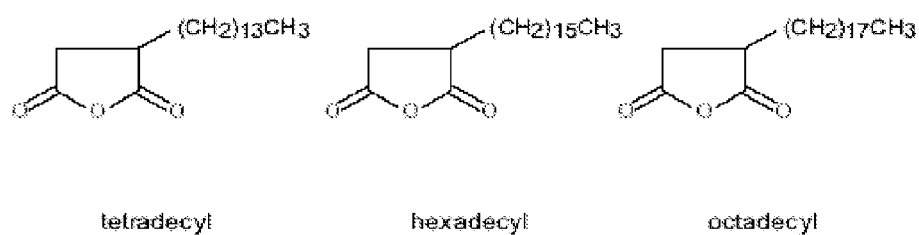
Figure 3C:
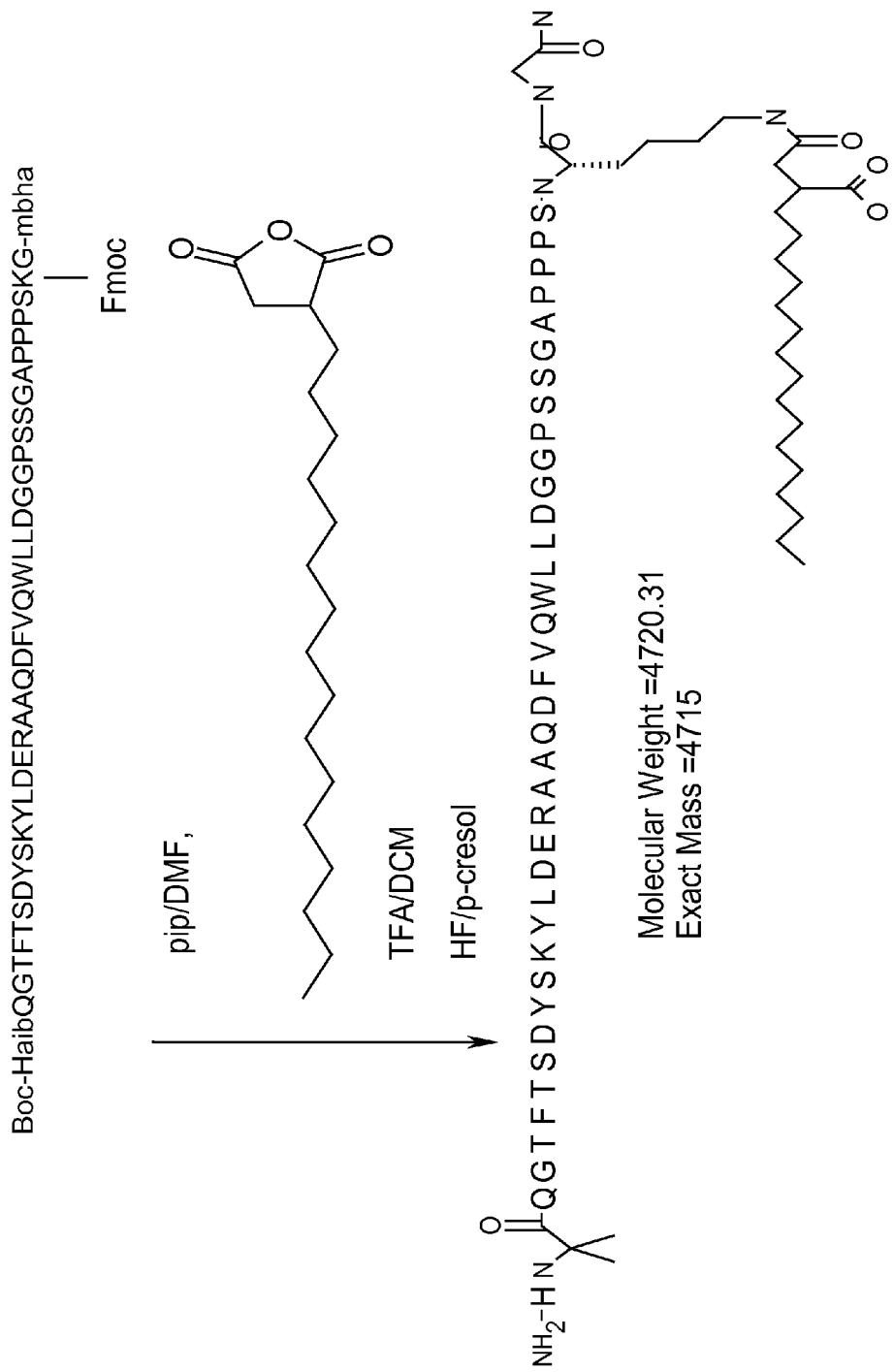

An example synthesis of a succinoylated peptide (Glucagon Aib2 E16 A18 L27 D28 Cex K40(C16 succinoyl)G41-amide having the amino acid sequence of SEQ ID NO: 156) is shown in Figure FIG. 3C and is further described below:

0.28 gm (0.2 mmole) mbha-resin (Midwest Biotech) was placed in a reaction vessel and the following sequence was assembled on a CSBio336 synthesizer using DEPBT/DIEA activated single couplings.

```
Boc-HaibQGTFTSDYSKYLDERAAQDFVQWLLDGGPSSGAPP
PSK(Fmoc)G-mbha resin
```

Approximately, one third of the Boc protected peptide resin was transferred to a manual reaction vessel and was treated with 20% piperidine/DMF at room temp for 10 min. The resin was filtered, washed with DMF 3 times, with dichloromethane twice and re-suspended in 10 ml DCM. 324 mg (1 mmole) n-hexadecylsuccinic anhydride (TCI) was added along with 2-3 mg of 4-dimethylaminopyridine (Aldrich).

The resin was mixed overnight at room temp before filtering, washing with DCM twice, and treating with 50% TFA/DCM for 1-2 min. The resin was filtered, washed several times with DCM, neutralized by washing with 5% DIEA/DCM and transferred to a HF reaction vessel. An HF cleavage was run using 5 ml liquid hydrogen fluoride and 0.5 ml p-cresol scavenger. After stirring 1 hr in an ice bath, the HF was removed in vacuo and the residue suspended in ethyl ether. The suspension was filtered using a sintered glass funnel, the solids washed with ether, and the peptide extracted into 15 ml 50% aqueous acetic acid. After analysis on HPLC (4.6×50 mm Zorbax SB-C8, 1 ml/min, 45° C., 214 nm, A=0.1% TFA, B=0.1% TFA/90% ACN, gradient=30% B to 90% B over 10 min), the cleavage extract was loaded onto a 21.2×250 mm Amberchrom XT20 column for purification. An aq TFA/acetonitrile gradient was run while collecting fractions and monitoring the UV absorbance. Fractions 55-56 were identified as being single component and were frozen and lyophilized. 32.5 mg was recovered with a purity of 90%+(DLS-027-68B). Theoretical mol. wt.=4720.3, ESI observed mass=4717.0

Peptide Alkylation (e.g., S-Alkylation)

An example synthesis of an alkylated (e.g., S-alkylated) peptide (Glucagon Aib2 E16 A18 L27 D29 Cex Cys40(S-2 palmityl)amide having an amino acid sequence of SEQ ID NO: 164) is shown in FIG. 6 and is further described below:

0.28 gm 0.2 mmole mbha-resin (Midwest Biotech) was placed in a CSBio reaction vessel and the following sequence was assembled on a CSBio336 synthesizer using Boc amino acids and DEPBT/DIEA activated single couplings.

HaibQGTFTSDYSKYLDERAAQDFVQWLLDGGPSSGAPPPSC-amide

The peptide resin was transferred to an HF reaction vessel and an HF cleavage was run using 10 ml liquid hydrogen fluoride and 1 ml p-cresol scavenger in an ice bath for 1 hr. After evaporating the HF, the residue was suspended in ethyl ether and the peptide and resin were filtered into a sintered glass funnel. After washing with ethyl ether and quickly air drying, the peptide was extracted into 50% aqueous acetic acid. After analysis via HPLC (4.6×50 mm Zorbax SB-C8, 1 ml/min, 45° C., 214 nm, A=0.1% TFA, B=0.1% TFA/90% ACN, 30% to 90% B over 10 min), the cleavage extract was diluted 3-4 with water and was loaded onto a 22.2×250 mm Amberchrom XT20 column for purification using aq TFA/CAN gradient. An initial pool was re-purified over the same column to give 79 mg of 95% purity. Theoretical mol. wt.=4313.7, ESI observed mass=4312.0

16 mg (3.7 µmole) of the above free thiol peptide was suspended in 1 ml methanol and with stirring under a stream of nitrogen, 1.5 ul of tetramethylguanidine in 1 ml methanol (MeOH) was added followed by 3 mg (7.4 µmole) 2-iodo-hexadecanoic acid (2-iodopalmitic acid) in 0.5 mg tetrahydrofuran (THF). 2-iodohexadecanoic acid was previously prepared by treating 2-bromohexadecanoic acid with potassium iodide in acetone (DLS-027-52). The alkylation reaction was warmed in a bath for 10 min during which most of the solvent evaporated. The residue was dissolved in aqueous acetic acid, analyzed by HPLC and was found to be more hydrophobic than the starting peptide. The remaining acetic acid solution was loaded onto a 10×250 mm Amberchrom XT20 column for purification. An aq. TFA/ACN gradient was run while collecting fractions and monitoring the UV at 214 nm. Fractions 64-68 were combined, frozen and lyophilized to give 6.1 mg of material (the peptide of SEQ ID NO: 164) with a purity of 90%+. Theoretical mol. wt=4568.1, MALDI observed mass=4568.79

When the peptide comprises a Lys residue instead of the Cys residue at the C-terminus, the peptide may be made with the backbone Lys first. The target amino acid residue to be N-alkylated is substituted with an Nε-FMOC lysine residue. Treating of the completed N-terminally BOC protected peptide with 20% piperidine in DMF for 30 minutes removes FMOC/formyl groups from the Lys residue. A Cys residue is coupled to the free ε-amino Lys residue. The Cys residue is then alkylated by reaction with 2-iodopalmitic acid as described above.

Peptide Acylation with "miniPEG" Spacers

An example synthesis of an acylated peptide via a mini-PEG spacer (the peptide having an amino acid sequence of SEQ ID NO: 89) is described below:

0.28 gm (0.2 mmole) 4-methylbenzhydrylamine (mbha) resin (Midwest Biotech, Inc., Fishers, Ind.) was placed in a reaction vessel and the following sequence was assembled on a CSBio336 synthesizer using Boc amino acids and 3-(diethoxyphosphoryloxy)-3H-benzo[d][1,2,3]triazine-4-one/N,N-Diisopropylethylamine (DEPBT/DIEA) activated single couplings.

Boc-HaibQGTFTSDYSKYLDERAAQDFVQWLLDGGPSSGAPP
PSK(Fmoc)G-mbha

Approximately, one third of the Boc protected peptide resin was transferred to a manual reaction vessel and was treated with 20% piperidine/dimethylformamide at room temperature for 10 min. The resin was filtered, washed with dimethylformamide (DMF) several times and an activated solution of Fmoc amidoPEG4 was added (previously prepared by dissolving 487.5 mg 1.0 mmole N-Fmoc Amido dPEG4 Acid (Peptides International, Louisville, Ky.) in 2.0 ml 0.5M DEPBT/DMF and adding 0.175 ml 1 mmole diisopropylethylamine). The reaction was mixed at room temp for approx. 1 hr.

The peptide resin was filtered washed with DMF, and again treated with 20% piperidine/DMF for 10 min. The resin was filtered, washed with DMF several times, and an activated solution of Fmoc Glu-OBzl was added (previously prepared by dissolving 470 mg 1 mmole of Fmoc Glu-γ-OBzl (Aapptec, Louisville, Ky.) in 2.0 ml 0.5M DEPBT/DMF and adding by 0.175 ml 1 mmole DIEA). The reaction was mixed at room temp for 1 hr.

The peptide resin was again filtered, washed with DMF, and treated with 20% piperidine/DMF at room temp for 10 min. The resin was filtered, washed with DMF several times, and an activated solution of palmitic acid was added (previously prepared by dissolving 256 mg 1 mmole palmitic acid (Sigma-Aldrich, St. Louis, Mo.) in 2.0 ml 0.5M DEPBT/DMF and adding 0.175 ml DIEA. The reaction was mixed at room temp for 1 hr.

Finally, the peptide resin was filtered, washed with DMF followed by dichloromethane and was treated with 50% TFA/DCM to remove the N-terminal Boc group. After 1-2 min, the resin was filtered, washed with DCM several times followed by a solution of 5% DIEA/DCM. The air dried peptide resin was transferred to an HF reaction vessel and an HF cleavage was conducted using 5 ml liquid hydrogen fluoride and 0.5 ml p-cresol scavenger. After mixing 1 hr in an ice bath, the HF was removed in vacuo and the residue was suspended in ethyl ether. The peptide/resin mixture was filtered in a sintered glass funnel, washed with ethyl ether, and quickly air dried. The peptide was extracted into 10 ml 50% aqueous acetic acid which was analyzed by HPLC (4.6×50 mm Zorbax SB-C8, 1 ml/min, 214 nm, A=0.1% TFA, B=0.1% TFA/90% ACN, gradient=30% B to 90% B over 10 min). The remaining crude extract was diluted 3× with water and was loaded onto a 22.2×250 mm Amberchrom XT20 column for purification using an aqueous TFA/ACN gradient. An initial purification pool was re-purified over the same column to give 19 mg of product with a purity of 90%+. Theoretical mass=5010.6, ESI observed mass was 5008.0.

Figure 12A:
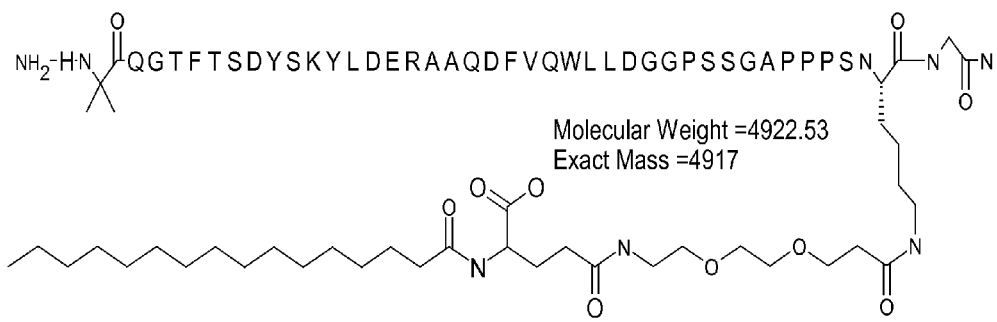
FIGS. 12A-12C represent a collection of schematics of acylated peptides each comprising an acylated amino acid covalently attached to an acyl group via a "miniPEG" spacer.
Figure 12B:
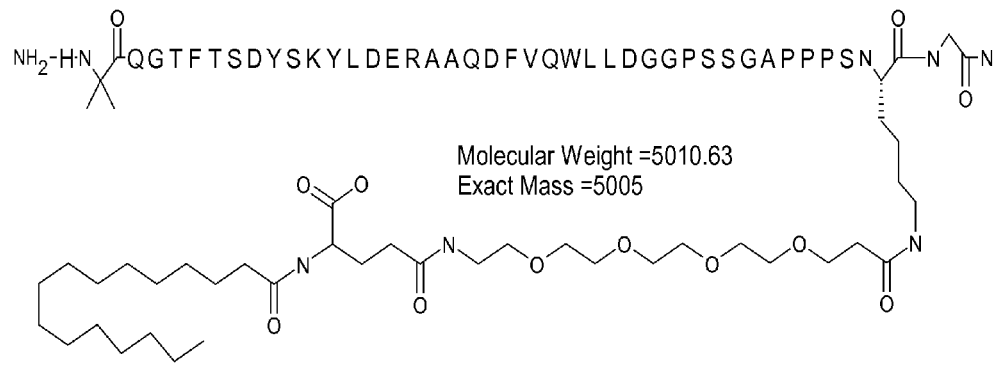
Figure 12C:
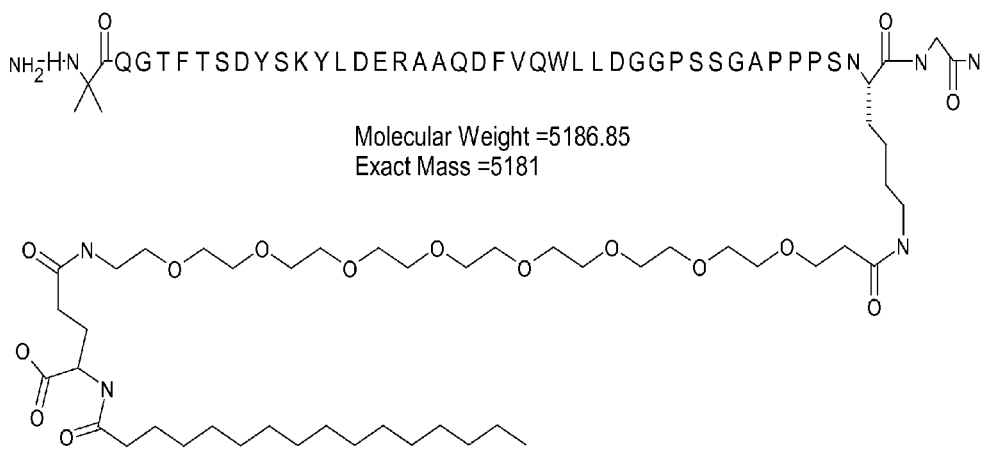

The same procedure was repeated using different N-Fmoc Amido dPEG Acids. In one instance, N-Fmoc Amido dPEG8 Acid (Peptides International, Louisville, Ky.) was used and in another instance, N-Fmoc Amido dPEG2 Acid (Peptides International, Louisville, Ky.) was used. The structures of the acylated peptides are shown in FIGS. 12A-12C.

Peptide Dimerization-Disulfide Dimerization

An example synthesis of a disulfide dimer peptide is described below:

0.28 gm (0.2 mmole) mbha-resin (Midwest Biotech) was placed in a CSBio reaction vessel and the following sequence was assembled on a CSBio336 synthesizer using Boc amino acids and DEPBT/DIEA activated single couplings.

```
Boc-HaibQGTFTSDYSKYLDERAAQDFVQWLLDGGPSSGAPP
PSK(Fmoc)G-amide
```

The Boc protected peptide resin was transferred to a manual reaction vessel and was treated with 20% piperidine/DMF at room temp for 10 min. The resin was filtered, thoroughly washed with DMF, then acylated with an activated solution of Fmoc Cys(Trt) (previously prepared by dissolving 1.17 gm 2 mmole Fmoc Cys(Trt)-OH (Aapptec) in 4.0 ml 0.5M DEPBT/DMF and adding 0.35 ml 2 mmole diisopropylethylamine). The reaction was mixed at room temp for 2 hrs, then filtered washed with DMF and the same procedure was used to add Fmoc Glu-OBzl followed by palmitic acid.

Finally, the resin was filtered, washed with DMF, with dichlorormethane, and was treated with 50% TFA/DCM for 1-2 min. After neutralization with 5% DIEA/DCM, the peptide resin was transferred to and HF reaction vessel and an HF cleavage was run using 10 ml liquid hydrogen fluoride and 1 ml p-cresol scavenger in an ice bath for 1 hr. After evaporating the HF, the residue was suspended in ethyl ether and the peptide and resin were filtered into a sintered glass funnel. After washing with ethyl ether and quickly air drying, the peptide was extracted into 50% aqueous acetic acid. After analysis via HPLC (4.6×50 mm Zorbax SB-C8, 1 ml/min, 45° C., 214 nm, A=0.1% TFA, B=0.1% TFA/90% ACN, 30% to 90% B over 10 min), the cleavage extract was diluted 3-4 with water and was loaded onto a 21.2×250 mm Amberchrom XT20 column for purification using aq TFA/acetonitrile gradient. Purification fractions 64-67 were combined, frozen, and lyophilized to give 58.7 mg of material with a HPLC purity of 90%+.

DLS-027-97A Theoretical mol. wt.=4866.48, ESI observed mass=4864.0

```
HaibQGTFTSDYSKYLDERAAQDFVQWLLDGGPSSGAPPPSK
(Cys(SH)γE-C16)G-amide
```

18.6 mg (3.8 μmole) of the above peptide was dissolved in 2.0 ml 3M guanidine/0.05M tris (pH8.5) and 1 ml dimethylsulfoxide was added. The reaction was stirred at room temp exposed to the air. After 6 hrs, an analytical HPLC compared to the starting peptide showed the presence of a more hydrophobic peak.

The reaction mixture was diluted with 20 ml 0.1% TFA and was loaded onto a 10×250 mm Amberchrom XT20 column A purification was run using a 0.1% TFA/acetonitrile gradient while monitoring the UV absorbance at 220 nm Fractions 68-72 were combined and lyophilized to give 5.5 mg of purified dimer.

Figure 9A:
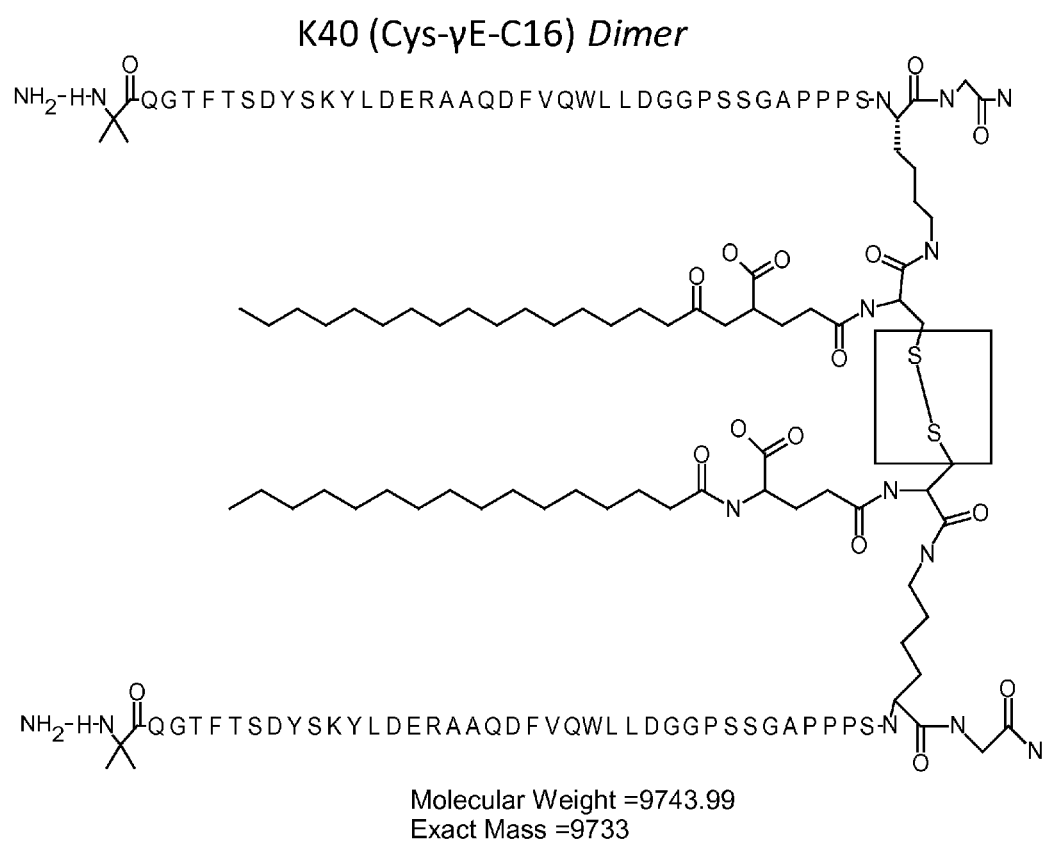
FIGS. 9A and 9B relate to dimers comprising two peptides wherein at least one comprises an acyl group.

HPLC purity was 90%+. Theoretical mol. wt.=9743.99, MALDI observed mass=9745.1. DLS-027-98B. The structure of the resulting dimer is shown in FIG. 9A.

Peptide Dimerization-Thioether Dimerization

An example synthesis of a thioether dimer is described below:

0.28 gm (0.2 mmole) mbha-resin (Midwest Biotech) was placed in a reaction vessel and the following sequence was assembled on a CSBio336 synthesizer using DEPBT/DIEA activated single couplings.

```
Boc-HaibQGTFTSDYSKYLDERAAQDFVQWLLDCXPSSGAPP
PSK(Fmoc)G-mbha
```

One third of the Boc protected peptide resin was transferred to a manual reaction vessel and was treated with 20% piperidine/DMF at room temp for 10 min. After washing several time with DMF, an activated solution of Boc Dap (Fmoc) was added (previously prepared by dissolving 426 mg 1 mmole Boc Dap(Fmoc)-OH (Chem-Impex) in 2.0 ml 0.5M DEPBT/DMF and 0.175 ml 1 mmole DIEA was added). The reaction was mixed at room temp for 2 hrs, the filtered, washed with DMF and re-treated with 20% piperidine/DMF as above. After washing with DMF, the resin was acylated with an activated solution of bromoacetic acid (previously prepared by dissolving 139 mg 1 mmole bromoacetic acid (Aldrich) in 2.0 ml 0.5M DEPBT/DMF and adding 0.175 ml DIEA). The reaction was mixed at room temp for 1-2 hrs, then filtered and the resin washed with DMF followed by DCM. The peptide resin was treated with 50% TFA/DCM at room temp for 2 min, then filtered, washed with DCM and neutralized with 5% DIEA/DCM. The completed peptide resin was transferred to an HF reaction vessel and an HF cleavage was conducted using 5 ml liquid hydrogen fluoride/0.5 ml p-cresol. After stirring 1 hr in an ice bath, the HF was evaporated and the residue suspended in ethyl ether. The resin/peptide mixture was filtered into a sintered glass funnel and washed with ether. The peptide was extracted into 50% aqueous acetic acid and the crude product was analyzed via HPLC: 4.6×50 mm Zorbax SB-C8, 1 ml/min, 45° C., 214 nm, A=0.1% TFA, B=0.1% TFA/90% ACN, gradient=30% B to 90% B over 10 min. The cleavage extract was loaded onto a 21.2×250 mm Amberchrom XT20 column and a purification was run using an aqueous TFA/acetonitrile gradient while monitoring the UV absorbance at 220 nm. Fractions 48-53 were combine frozen, and lyophilized to give 18 mg of the peptide of SEQ ID NO: 89 with K40(Dap-BrAcetyl), purity=90%+. Theoretical mol. wt.=4602.8, ESI observed mass=4616.0

```
HaibQGTFTSDYSKYLDERAAQDFVQWLLDGGPSSGAPPPSK
(Dap-BrAcetyl)G-amide
```

Figure 9B:
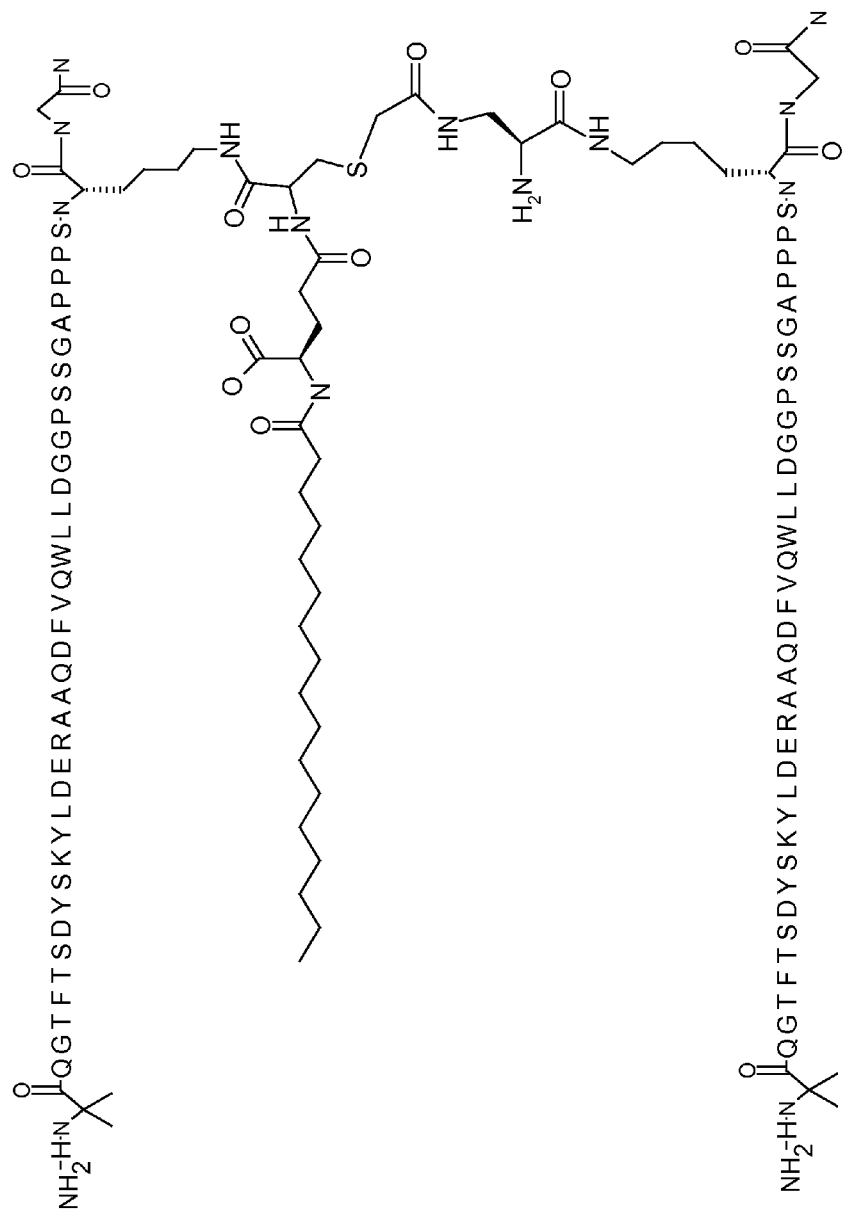

15 mg (3.2 μmole) of the above K40(Dap-BrAcetyl) peptide and 15 mg of the peptide of SEQ ID NO: 89 K40(Cys γE-C16) were dissolved in 3.0 ml 7M urea/0.05M tris (pH8.6) and was mixed at room temp while monitoring the HPLC of the reaction progress. After 30 min, most of the starting materials were reduced in peak height while a new peak was the major component. The reaction mixture was diluted with 25 ml 0.1% TFA and was loaded onto a 10×250 mm Amberchrom XT20 column for purification. An aqueous TFA/acetonitrile gradient was run while monitoring the UV absorbance at 220 nm. Fractions 57-61 were combined, frozen, and lyophilized to give 7.1 mg of thioether dimer. HPLC purity=90%+, Theoretical mol. wt.=9401.4, MALDI observed mass=9402.8. The structure of the dimer is shown in FIG. 9B.

Peptide PEGylation

For peptide PEGylation, 40 kDa methoxy poly(ethylene glycol) idoacetamide (NOF) was reacted with a molar equivalent of peptide in 7M Urea, 50 mM Tris-HCl buffer using the minimal amount of solvent needed to dissolve both peptide and PEG into a clear solution (generally less than 2 mL for a reaction using 2-3 mg peptide). Vigorous stirring at room temperature commenced for 4-6 hours and the reaction analyzed by analytical RP-HPLC. PEGylated products appeared distinctly from the starting material with decreased retention times. Purification was performed on a Vydac C4 column with conditions similar to those used for the initial peptide purification. Elution occurred around buffer ratios of 50:50. Fractions of pure PEGylated peptide were found and lyophilized. Yields were above 50%, varying per reaction.

Analysis Using Mass Spectrometry

The mass spectra were obtained using a Sciex API-III electrospray quadrapole mass spectrometer with a standard ESI ion source. Ionization conditions that were used are as follows: ESI in the positive-ion mode; ion spray voltage, 3.9 kV; orifice potential, 60 V. The nebulizing and curtain gas used was nitrogen flow rate of 0.9 L/min. Mass spectra were recorded from 600-1800 Thompsons at 0.5 Th per step and 2 msec dwell time. The sample (about 1 mg/mL) was dissolved in 50% aqueous acetonitrile with 1% acetic acid and introduced by an external syringe pump at the rate of 5 μL/min.

When the peptides were analyzed in PBS solution by ESI MS, they were first desalted using a ZipTip solid phase extraction tip containing 0.6 μL C4 resin, according to instructions provided by the manufacturer (Millipore Corporation, Billerica, Mass., see the Millipore website of the world wide web at millipore.com/catalogue.nsf/docs/C5737).

High Performance Liquid Chromatography (HPLC) Analysis:

Preliminary analyses were performed with these crude peptides to get an approximation of their relative conversion rates in Phosphate Buffered Saline (PBS) buffer (pH, 7.2) using high performance liquid chromatography (HPLC) and MALDI analysis. The crude peptide samples were dissolved in the PBS buffer at a concentration of 1 mg/ml. 1 ml of the resulting solution was stored in a 1.5 ml HPLC vial which was then sealed and incubated at 37° C. Aliquots of 100 μl were drawn out at various time intervals, cooled to room temperature and analyzed by HPLC.

The HPLC analyses were performed using a Beckman System Gold Chromatography system using a UV detector at 214 nm HPLC analyses were performed on a 150 mm×4.6 mm C18 Vydac column. The flow rate was 1 ml/min. Solvent A contained 0.1% TFA in distilled water, and solvent B contained 0.1% TFA in 90% CH3CN. A linear gradient was employed (40% to 70% B in 15 minutes). The data were collected and analyzed using Peak Simple Chromatography software.

The initial rates of hydrolysis were used to measure the rate constant for the dissociation of the respective prodrugs. The concentrations of the prodrug and the drug were estimated from their peak areas respectively. The first order dissociation rate constants of the prodrugs were determined by plotting the logarithm of the concentration of the prodrug at various time intervals. The slope of this plot gives the rate constant 'k'. The half lives of the degradation of the various prodrugs were then calculated by using the formula t½=0.693/k.

Example 2

This example describes an exemplary method of testing the biological activity of the peptides of the present disclosures, which method involves assaying cAMP synthesis.

The ability of glucagon analogs to induce cAMP was measured in a firefly luciferase-based reporter assay. HEK293 cells co-transfected with a receptor (glucagon receptor, GLP-1 receptor or GIP receptor) and luciferase gene linked to cAMP responsive element were serum deprived by culturing 16 h in DMEM (Invitrogen, Carlsbad, Calif.) supplemented with 0.25% Bovine Growth Serum (HyClone, Logan, Utah) and then incubated with serial dilutions of either glucagon, GLP-1, GIP or novel glucagon analogs for 5 h at 37° C., 5% $CO_2$ in 96 well poly-D-Lysine-coated "Biocoat" plates (BD Biosciences, San Jose, Calif.). At the end of the incubation 100 microliters of LucLite luminescence substrate reagent (Perkin-Elmer, Wellesley, Mass.) were added to each well. The plate was shaken briefly, incubated 10 min in the dark and light output was measured on MicroBeta-1450 liquid scintillation counter (Perkin-Elmer, Wellesley, Mass.). Effective 50% concentrations were calculated by using Origin software (OriginLab, Northampton, Mass.

Example 3

This example describes an exemplary method of assaying the stability of peptides of the present disclosures.

Each glucagon analog is dissolved in water or PBS and an initial HPLC analysis is conducted. After adjusting the pH (4, 5, 6, 7), the samples are incubated over a specified time period at 37° C. and are re-analyzed by HPLC to determine the integrity of the peptide. The concentration of the specific peptide of interest is determined and the percent remaining intact is calculated relative to the initial analysis.

Example 4

This example describes an exemplary method of assaying solubility of peptides.

A solution (1 mg/ml or 3 mg/ml) of glucagon (or an analog) is prepared in 0.01N HCl. 100 ul of stock solution is diluted to 1 ml with 0.01N HCl and the UV absorbance (276 nm) is determined. The pH of the remaining stock solution is adjusted to pH7 using 200-250 ul 0.1M $Na_2HPO_4$ (pH9.2). The solution is allowed to stand overnight at 4° C. then centrifuged. 100 ul of supernatant is then diluted to 1 ml with 0.01N HCl, and the UV absorbance is determined (in duplicate).

The initial absorbance reading is compensated for the increase in volume and the following calculation is used to establish percent solubility:

$$\frac{\text{Final Absorbance}}{\text{Initial Absorbance}} \times 100 = \text{percent soluble}$$

Example 5

This example describes an exemplary method of assaying peptides for binding to a receptor.

The affinity of peptides to the glucagon receptor is measured in a competition binding assay utilizing scintillation proximity assay technology. Serial 3-fold dilutions of the peptides made in scintillation proximity assay buffer (0.05 M Tris-HCl, pH 7.5, 0.15 M NaCl, 0.1% w/v bovine serum albumin) are mixed in 96 well white/clear bottom plate (Corning Inc., Acton, Mass.) with 0.05 nM (3-[$^{125}$I]-iodotyrosyl) Tyr10 glucagon (Amersham Biosciences, Piscataway, N.J.), 1-6 micrograms per well, plasma membrane fragments prepared from cells over-expressing human glucagon receptor, and 1 mg/well polyethyleneimine-treated wheat germ agglutinin type A scintillation proximity assay beads (Amersham Biosciences, Piscataway, N.J.). Upon 5 min shaking at 800 rpm on a rotary shaker, the plate is incubated 12 h at room temperature and then is read on MicroBeta1450 liquid scintillation counter (Perkin-Elmer, Wellesley, Mass.). Non-specifically bound (NSB) radioactivity is measured in the wells with 4 times greater concentration of "cold" native ligand than the highest concentration in test samples and total bound radioactivity is detected in the wells with no competitor. Percent specific binding is calculated as following: % Specific Binding=((Bound−NSB)/(Total bound−NSB))×100. IC$_{50}$ values were determined by using Origin software (OriginLab, Northampton, Mass.).

Example 6

The following peptides comprising at least Tyr at position 1, AIB at position 2 (for DPP-IV resistance), Lys at position 16, AIB at position 20, and Leu, Ala and Gly at positions 27-29 were made as essentially described in Example 1 and tested in vitro for agonist activity at each of the GLP-1 receptor, glucagon receptor, and GIP receptor as essentially described in Example 2:
The EC50s at the GLP-1 receptor (GLP-1R), the glucagon receptor (GR), and the GIP receptor (GIPR) are provided in Table 1.

TABLE 1

| Peptide | SEQ ID NO: | GLP-1 Receptor | | Glucagon Receptor | | GIP Receptor | |
|---|---|---|---|---|---|---|---|
| | | EC$_{50}$, nM [Std Dev] | relative activity | EC$_{50}$, nM [Std Dev] | relative activity | EC$_{50}$, nM [Std Dev] | relative activity |
| mt-263 | 10 | 0.0100 [0.0154] | 154.20% | 4.0450 [0.0762] | 1.88% | 0.0054 [0.0166] | 305.91% |
| mt-402 | 11 | 0.0070 [0.0154] | 220.60% | 0.0298 [0.0762] | 256.00% | 0.0185 [0.0166] | 89.46% |
| mt-403 | 12 | 0.0027 [0.154] | 581.89% | 0.0077 [0.0762] | 987.18% | 0.0061 [0.0166] | 273.10% |
| mt-404 | 13 | 0.0060 [0.0154] | 258.29% | 0.1076 [0.0762] | 70.80% | 0.0327 [0.0166] | 50.57% |
| mt-405 | 14 | 0.0022 [0.0154] | 717.21% | 0.0096 [0.0762] | 797.18% | 0.0039 [0.0166] | 425.45% |

Relative activity is activity of peptide relative to the activity of the native hormone Example 7

Additional peptides mt-395 (SEQ ID NO: 15), mt-396 (SEQ ID NO: 16), mt-397 (SEQ ID NO: 17), and mt-398 (SEQ TD NO: 18) which were based on the structure of mt-263 were made as essentially described in Example 1 and tested in vitro as essentially described in Example 2. The EC50s at each of the GLP-1R, GR, and GIPR are shown in Table 2.

TABLE 2

| Peptide | SEQ ID NO: | GLP-1 Receptor | | Glucagon Receptor | | GIP Receptor | |
|---|---|---|---|---|---|---|---|
| | | EC$_{50}$, nM [Std. Dev] | relative activity | EC$_{50}$, nM [Std. Dev] | relative activity | EC$_{50}$, nM [Std. Dev] | relative activity |
| mt-263 | 10 | 0.0081 [0.0245] | 300.61% | 3.1371 [0.0298] | 0.95% | 0.0033 [0.0135] | 403.89% |
| mt-395 | 15 | 0.0076 [0.0245] | 321.55% | 3.4095 [0.0298] | 0.87% | 0.0025 [0.0135] | 537.45% |
| mt-396 | 16 | 0.0093 [0.0245] | 262.27% | 2.9033 [0.0298] | 1.03% | 0.0034 [0.0135] | 402.69% |
| mt-397 | 17 | 0.0085 [0.0245] | 287.88% | 5.3528 [0.0298] | 0.56% | 0.0029 [0.0135] | 470.03% |
| mt-398 | 18 | 0.0078 [0.0245] | 314.93% | 3.7352 [0.0298] | 0.80% | 0.0031 [0.0135] | 433.76% |

Relative activity is activity of peptide relative to the activity of the native hormone

Example 8

Additional peptides comprising a Tyr at position 1, AIB at position 2 (for DPP-IV resistance), Glu at position 16 and Lys at position 20 (bridged by a lactam between positions 16 and 20), Leu-Ala-Gly at positions 27-29, and GPSSGAP-PS at positions 30-39 were made as essentially described in Example 1 and tested for agonist activity at each of the GLP-1R, GR, and GIPR as essentially described in Example 2. Other peptides lacking a lactam were made and tested. The results of the activity assays are shown in Table 3.

TABLE 3

| Code | SEQ ID NO: | GLP-1R EC$_{50}$, nM | GLP-1R Std Dev | GLP-1R relative activity | GR EC$_{50}$, nM | GR Std Dev | GR relative activity | GIPR EC$_{50}$, nM | GIPR Std Dev | GIPR relative activity |
|---|---|---|---|---|---|---|---|---|---|---|
| mt-217 | 19 | 0.222 | 0.025 | 11.26% | 13.886 | 0.114 | 0.82% | 9.574 | 0.019 | 0.20% |
| mt-218 | 20 | 0.338 | 0.025 | 7.40% | 16.298 | 0.114 | 0.70% | 14.283 | 0.019 | 0.13% |
| mt-219 | 21 | 0.151 | 0.025 | 16.56% | 17.628 | 0.114 | 0.65% | 6.165 | 0.019 | .31% |
| mt-220 | 22 | 0.180 | 0.025 | 13.89% | 9.670 | 0.114 | 1.18% | 10.268 | 0.019 | 0.19% |
| mt-225 | 23 | 0.098 | 0.029 | 29.59% | 2.712 | 0.054 | 1.99% | 1.899 | 0.017 | 0.90% |
| mt-226 | 24 | 0.097 | 0.029 | 29.90% | 3.462 | 0.054 | 1.56% | 1.467 | 0.017 | 1.16% |
| mt-227 | 25 | 0.080 | 0.029 | 36.25% | 4.244 | 0.054 | 1.27% | 1.320 | 0.017 | 1.29% |
| mt-228 | 26 | 0.146 | 0.029 | 19.86% | 5.364 | 0.054 | 1.01% | 2.266 | 0.017 | 0.75% |

Relative activity is activity of peptide relative to the activity of the native hormone

Example 9

Exemplary peptide analogs of the present disclosures were made as essentially described in Example 1. Each of the peptide analogs comprised an amino acid sequence based on native glucagon (SEQ ID NO: 1) with the native His at position 1, a DPP-IV protective amino acid at position 2, an acylated amino acid at position 10, one or more alpha helix stabilizing amino acids within positions 16-21 of the peptide analog, and other modifications. All peptides were amidated at the C-terminus. The peptides were then tested for activity at each of the glucagon, GLP-1, and GIP receptors, as described in Example 2. A composite of the results from multiple different activity assays are shown in Table 4.

TABLE 4

| SEQ ID NO: | Analog No. | Shorthand Notation of amino acid changes | EC50 (nM) at Glucagon Receptor | EC50 (nM) at GLP-1 Receptor | EC50 (nM) at GIP Receptor |
|---|---|---|---|---|---|
| 1 | | Native glucagon | 0.025 | ND | ND |
|  | | Native GLP-1 | ND | 0.025 | ND |
| 2 | | Native GIP | ND | ND | 0.01 |
| 27 | 29 | dSer2, K10acyl, E16, A18, L27, D28, G29 + CEX | 0.003 | 0.002 | 0.085 |
| 28 | 30 | Aib2, K10acyl, E16, A18, L27, D28, G29 + CEX | 0.002 | 0.002 | 0.003 |
| 29 | 34 | Aib2, K10acyl, E16, A18, L27, D28, GRG29-31 | 0.007 | 0.003 | 0.064 |
| 30 | 36 | dSer2, K10acyl, E16, Aib20, E21, L27, D28 | 0.008 | 0.0031 | 0.25 |
| 31 | 37 | Aib2, K10acyl, E16, Aib20, E21, L27, D28 | 0.008 | 0.0044 | 0.008 |
| 32 | 44 | DMIA1, dSer2, K10acyl, E16, A18, L27, D28 | 0.004 | 0.003 | 0.103 |
| 33 | 49 | Aib2, K10acyl, Aib16, A10, D28, G29 + CEX | 0.005 | 0.004 | 0.248 |
| 35 | 53 | Aib2, K10acyl, Aib16, A18, V27, K28, G29 + CEX | 0.011 | 0.005 | 0.073 |
| 36 | 54 | Aib2, K10acyl, Aib16, A18, K27, D28, G29 + CEX | 0.008 | 0.004 | 0.171 |

TABLE 4-continued

| SEQ ID NO: | Analog No. | Shorthand Notation of amino acid changes | EC50 (nM) at Glucagon Receptor | EC50 (nM) at GLP-1 Receptor | EC50 (nM) at GIP Receptor |
|---|---|---|---|---|---|
| 37 | 61 | Aib2, K10acyl, E16, Aib20, E21, L27, D28, G29 + CEX | 0.004 | 0.006 | 0.002 |
| 38 | 62 | Aib2, E3, K10acyl, E16, Aib20, E21, L27, D28, G29 + CEX | 0.127 | 0.008 | 0.012 |
| 39 | 63 | Aib2, E3, K10acyl, E16, L27, D28, G29 + CEX | 1.276 | 0.008 | 0.026 |
| 40 | 64 | Aib2, E3, K10acyl, E16, Aib20, E21, L27, D28 | 0.042 | 0.006 | 0.024 |
| 41 | 65 | Aib2, E3, K10acyl, E16, Aib20, L27, D28, G29 + CEX | 0.221 | 0.006 | 0.013 |

CEX = GPSSGAPPPS (SEQ ID NO: 5)
acyl = C16 acyl

Each of the peptide analogs of Table 4 demonstrated potent activity at each of the glucagon, GLP-1, and GIP receptors. Notably, each of the peptide analogs exhibited an EC50 at the GIP receptor of <0.5 nM, and most of the peptide analogs exhibited an EC50 at the GIP receptor of <0.1 nM. These peptide analogs also exhibited potent activity at the GLP-1 receptor, each peptide analog exhibiting an EC50<0.008 nM. The peptide analogs lacking a Glu at position 3 demonstrated potent activity at the glucagon receptor, each peptide analog of which exhibited an EC50<0.03 nM.

In general, peptide analogs comprising an AIB at position 20 or a combination of Glu at position 16 and a C-terminal extension exhibited highly potent activity at the GIP receptor. Also, peptide analogs comprising AIB at position 2 generally exhibited greater activity at the GIP receptor, as compared to a corresponding peptide analog comprising d-Ser at position 2 (e.g., compare EC50s at GIP receptor between SEQ ID NOs: 2 and 3 or SEQ ID NOs: 5 and 6)

Example 10

Exemplary peptide analogs of the present disclosures were made as essentially described in Example 1. The peptide analogs were similar in structure, comprising an amino acid sequence based on native glucagon (SEQ ID NO: 1) with the native His at position 1, a DPP-IV protective amino acid at position 2, and an alpha helix stabilizing amino acid at position 16, except that the position at which an acylated amino acid occurred varied among this set of peptide analogs. All peptides were amidated at the C-terminus. The peptides were then tested for activity at each of the glucagon, GLP-1, and GIP receptors, as described in Example 2. A composite of the results from multiple different activity assays are shown in Table 5 for some of the peptides made and tested.

As shown in Table 5, peptide analogs comprising an acylated amino acid at any of positions 9 and 12, demonstrated an improvement in GIP activity, as compared to the unacylated peptide analog of SEQ ID NO: 42. Not all of the acylated peptide analogs that were made and tested demonstrated an improved GIP activity, however. One of the peptide analogs which was acylated at a position other than position 9 and 12 demonstrated a reduced activity at the GIP receptor.

Example 11

This example describes the in vivo activities of exemplary glucagon analogs of the present disclosures.

The in vivo activities of GIP receptor-active glucagon analogs having an amino acid sequence of one of SEQ ID NOs: 28, 37-39 and 134 were tested in diet-induced obese (DIO) mice and compared to the in vivo activities of mice that were administered a glucagon agonist analog or a vehicle control. Each test group of mice was made of nineteen mice and each mouse was subcutaneously injected with a 10 nmol/kg dose of peptide or a vehicle control. Body weight and food intake were measured on days 0, 1, 3, 5, and 7 post administration, while fasting blood glucose levels were measured on days 0 and 7. The mice were fasted for 6 hours prior to the measurement of blood glucose on days 0 and 7. Ad lib blood glucose levels were additionally measured on day 5 post-administration.

All of the mice injected with a GIP receptor-active glucagon analog demonstrated a significant reduction (a reduction between about 11% and about 27%) in body weight seven days following administration, as compared to the mice administered a vehicle control. Additionally all of the mice injected with a GIP receptor-active glucagon analog exhibited a substantial reduction (a reduction between about 43% and about 65%) in blood glucose levels seven days post-administration.

TABLE 5

| SEQ ID NO: | Shorthand Notation of amino acid changes | EC50 (nM) at Glucagon Receptor | EC50 (nM) at GLP-1 Receptor | EC50 (nM) at GIP Receptor |
|---|---|---|---|---|
| 1 | Native Glucagon | 0.10048 | ND | ND |
|  | Native GLP-1 | ND | 0.01593 | ND |
| 2 | Native GIP | ND | ND | 0.05665 |
| 42 | Glucagon Aib2, Aib16, amide | 0.30892 | 0.43695 | 103.93715 |
| 43 | Glucagon Aib2, K9(rErEC16), Aib16, amide | 1.15223 | 0.23172 | 15.14376 |
| 45 | Glucagon Aib2, K12(rErEC16), Aib16, amide | 0.04254 | 0.02049 | 0.65062 |

Another study was carried out in male db/db mice to analyze the in vivo activities of GIP receptor-active glucagon analogs. In this study, a 20 nmol/kg dose of a GIP receptor-active glucagon analog having an amino acid sequence of one of SEQ ID NOs: 28, 31, 37, 135 and 136 was administered to the mice via subcutaneous injection. A vehicle control was administered to a control group of mice. Blood glucose levels were assayed prior to administration and 1, 2, 4, 8, 24, 48, and 72 hours after dosing. Body weight was measured before dosing and 72 hours after dosing. Consistent with the results observed in the DIO mice study, all mice that were administered a GIP receptor-active glucagon analog demonstrated a substantial reduction in body weight (a reduction between about 2% and about 5%), as compared to the vehicle control group. Also, all mice that received a GIP receptor-active glucagon analog exhibited a reduction in blood glucose levels.

Example 12

This example describes the structures of additional exemplary peptides.

Glucagon analogs are made as essentially described in Example 1 and Table 6 describes the structure of these analogs. The glucagon analogs are tested for activity at each of the glucagon receptor, GLP-1 receptor, and the GIP receptor as essentially described in Example 2.

TABLE 6

| SEQ ID NO: | Structure | EC50 (nM) at Glucagon Receptor | EC50 (nM) at GLP-1 Receptor | EC50 (nM) at GIP Receptor |
|---|---|---|---|---|
| 48 | H(D-Ser)QGTFTSDYSIYLDKQAA(aib)EFVNWLLAGGPSSGAPPPSC(-SH)-amide | 0.026 | 0.01 | 0.433 |
| 50 | Y(D-ser)QGTFTSDYSIYLDKQAA(aib)EFVNWLLAGGPSSGAPPPSC-amide | 0.041 | 0.108 | 0.072 |
| 51 | Y(D-ser)QGTFTSDYSIYLDKQAA(aib)EFVNWLLAGGPSSGAPPPSC(40K-TE)-amide | 0.255 | 0.572 | 0.433 |
| 52 | H(aib)QGTFTSDYSIYLDKQAA(aib)EFVNWLLAGGPSSGAPPPSC-amide | 0.2 | 0.005 | 0.006 |
| 53 | H(aib)QGTFTSDYSIYLDKQAA(aib)EFVNWLLAGGPSSGAPPPSC(40K-TE)-amide | 3.511 | 0.027 | 0.232 |
| 54 | Y(aib)QGTFTSDYSIYLDKQAA(aib)EFV(aib)WLLAGGPSSGAPPPSC-amide | 0.566 | 0.091 | 0.467 |
| 56 | Y(aib)QGTFTSDYSIYLDEQAAKEEV(aib)WLLAGGPSSGAPPPS C-amide, (underlined residues bridged via lactam) | 1.266 | 0.096 | 1.981 |
| 58 | Y(aib)QGTFTSDYSIYLDKEAA(aib)KFVNWLLAGGPSSGAPPPSC-amide, (underlined residues bridged via lactam) | 0.063 | 0.014 | 0.005 |
| 59 | Y(aib)QGTFTSDYSIYLDKEAA(aib)KFVNWLLAGGPSSGAPPPSC(40K-TE)-amide, (underlined residues bridged via lactam) | 0.432 | 0.063 | 0.122 |
| 60 | Y(aib)QGTFTSDYSIYLDKQAA(acpc)EFVNWLLAGGPSSGAPPPSC-amide | 0.047 | 0.0028 | 0.025 |
| 68 | Y(aib)QGTFTSD(K(γE-C14-acyl))SIYLDKQAA(aib)EFVNWLLAGGPSSGAPPPSC(40K-ME)-amide | 50.1 | 0.612 | 0.862 |
| 69 | Y(aib)QGTFTSD(K(γE-C16-acyl))SIYLDKQAA(aib)EFVNWLLAGGPSSGAPPPSC(40K-ME)-amide | 0.055 | 0.02 | 0.015 |
| 70 | Y(aib)QGTFTSDYSIYLDKQAA(aib)EFVC(40K-ME)WLLAGGPSSGAPPPS(K(C16-acyl))-amide | 0.018 | 0.007 | 0.014 |
| 72 | Y(aib)EGTFTSDYSIYLDKQAA(aib)EFVNWLLAGGPSSGAPPPSC(40K-TE)-NH2 | 1.676 | 2.686 | 0.035 |
| 73 | Y(aib)EGTFTSDYSIYLDKQAA(acpc)EFVNWLLAGGPSSGAPPPSC(40K-TE)-NH2 | ~10 | 0.91 | 1.56 |
| 74 | H(aib)QGTFTSDYSIYLDKQAA(acpc)EFVNWLLAGGPSSGAPPPSC(40K-TE)-NH2 | 2.519 | 6.42 | 2.541 |
| 75 | Y(aib)QGTFTSDYSIYLDKQAA(acpc)EFVNW | 3.116 | 17.7 | 2.438 |

TABLE 6-continued

| SEQ ID NO: | Structure | EC50 (nM) at Glucagon Receptor | EC50 (nM) at GLP-1 Receptor | EC50 (nM) at GIP Receptor |
|---|---|---|---|---|
|  | LLAGGPSSGAPPPSC(40K-TE)-NH2 |  |  |  |
| 79 | H(aib)QGTFTSDK(γE-C16)SKYLDERRA(aib)EFVQWLLDGGPSSGAPPPS-NH2 | 0.004 | 0.006 | 0.003 |
| 80 | H(aib)EGTFTSDK(γE-C16)SKYLDERAAQDFVQWLLDGGPSSGAPPPS-NH2 | 1.276 | 0.008 | 0.026 |
| 81 | Y(aib)QGTFTSDK(γE-γE-C16)SIYLDKQAA(aib)EFVNWLLAGGPSSGAPPPS-NH2 | 0.073 | 0.008 | 0.005 |
| 175 | Y(aib)EGTFTSDYSIYLDKQAA(aib)EEVNWLLAGGPSSGAPPPSC-NH₂, wherein the C at the C-terminus is covalently attached to 40 kDa PEG | 0.62 | 0.066 | 0.100 |
| 172 | YaibQGTFTSDYSIYLDKQAAaibEFVC(40K-TEPEG)WLLAGGPSSGAPPPSK(C8)-amide | 3.06 | 0.108 | 0.487 |
| 173 | YaibQGTFTSDYSIYLDKQAAaibEFVC(40K-TEPEG)WLLAGGPSSGAPPPSK(C12)-amide | 0.190 | 0.011 | 0.089 |
| 174 | YaibQGTFTSDYSIYLDKQAAaibEFVC(40K-TEPEG)WLLAGGPSSGAPPPSK(C14)-amide | 0.025 | 0.010 | 0.019 |

Example 13

Glucagon analogs were made as essentially described in Example 1 and Table 7 describes the structure of these analogs. The glucagon analogs were tested for activity at each of the glucagon receptor, GLP-1 receptor, and the GIP receptor as essentially described in Example 2.

TABLE 7

| SEQ ID NO | Amino Acid Sequence | EC50 (nM) at Glucagon Receptor | EC50 (nM) at GLP-1 Receptor | EC50 (nM) at GIP Receptor |
|---|---|---|---|---|
| 28 | HAibQGTFTSDK(γE-C16)SKYLDERAAQDFVQWLLDGGPSSGAPPPS-amide | 0.002 | 0.002 | 0.003 |

TABLE 7-continued

| SEQ ID NO | Amino Acid Sequence | EC50 (nM) at Glucagon Receptor | EC50 (nM) at GLP-1 Receptor | EC50 (nM) at GIP Receptor |
|---|---|---|---|---|
| 89 | HAibQGTFTSDYSKYLDERAAQDFVQWLLDGGPSSGAPPPSKG(γEγE-C16)-amide | 0.0041 | 0.0021 | 0.024 |
| 90 | HAibQGTFTSDKSK(γEγE-C16)YLDERAAQDFVQWLLDGGPSSGAPPPS-amide | 0.0056 | 0.0027 | 0.017 |
| 91 | YAibQGTFTSDK(γEγE-C16)SIYLDKQAAAibEFVNWLLDGGPSSGAPPPS-amide | 0.073 | 0.008 | 0.005 |
| 92 | YAibQGTFTSDK(γEγE-C16)SIYLDKQAAAibEFVNWLLDT-amide | 0.0105 | 0.0031 | 0.021 |
| 31 | IIAibQGTFTSDK(γE-C16)SKYLDERRAAibEFVQWLLDT-amide | 0.008 | 0.0044 | 0.008 |

Example 14

Glucagon analogs were made as essentially described in Example 1 and Table 8 describes the structure of these analogs. Full descriptions of these analogs are provided in the sequence listing and the SEQ ID NO: for each is provided in Table 8. The glucagon analogs were tested for activity at each of the glucagon receptor, GLP-1 receptor, and the GIP receptor as essentially described in Example 2.

TABLE 8

|  |  | Glu (0.025) | GLP (0.025) | GIP (0.01) |
|---|---|---|---|---|
| SEQ ID NO: 28 | GIP/GLP-1/glucagon triagonist peptide: HaibQGTFTSDK(γE-C16)SKYLDFRAAQDFVQWLLDGGPSSGAPPPS-NH₂ | 0.002 | 0.002 | 0.003 |
| SEQ ID NO: 39 | GIP/GLP-1 co-agonist peptide: HaibEGTFTSDK(γE-C16)SKYLDERAAQDFVQWLLDGGPSSGAPPPS-NH₂ | 1.276 | 0.008 | 0.026 |
| SEQ ID NO: 37 | GIP/GLP-1/glucagon triagonist peptide: IIaibQGTFTSDK(γE-C16)SKYLDERRAaibEFVQWLLDGGPSSGAPPPS-NH₂ | 0.004 | 0.006 | 0.003 |
| SEQ ID NO: 262 | GIP/GLP-1 co-agonist peptide: HaibEGTFTSDK(γE-C16)SKYLDERRAaibEFVQWLLDGGPSSGAPPPS-NH₂ | 0.127 | 0.008 | 0.012 |

To test in vivo activities of these peptides, the peptides of Table 8 (excluding native peptides) were subcutaneously injected into DIO mice (C57B66 mice) at either 5 or 10 and the GIP receptor as essentially described in Example 2. Table 9 summarizes the structure and activities of each peptide.

TABLE 9

| Acylated amino acid (position thereof) | Acyl type | Acyl Spacer | Amino Acid at 41st position | Structure (SEQ ID NO:) | EC50 (nM) at Glucagon Receptor | EC50 (nM) at GLP-1 Receptor | EC50 (nM) at GIP Receptor |
|---|---|---|---|---|---|---|---|
| Lys(40) | C16 | None | n/a | Y aib E GTFTSDYSIYLDKQAA aib EFVNWLLAGGPSSGAPPPS K(-C16)-NH₂ (SEQ ID NO: 138) | 0.085 | 0.002 | 0.001 |
| Lys(40) | C16 | None | Gly | Y aib E GTFTSDYSIYLDKQAA aib EFVNWLLAGGPSSGAPPPS K(-C16)G-NH₂ (SEQ ID NO: 139) | 0.203 | 0.005 | 0.001 |
| Lys(40) | SuccinoylC16 | None | Gly | Y aib E GTFTSDYSIYLDKQAA aib EFVNWLLAGGPSSGAPPPS K(-SuccinoylC16)G-NH₂ (SEQ ID NO: 140) | 0.077 | 0.001 | 0.001 |
| Lys(40) | SuccinoylC16 | β-Ala | Gly | Y aib E GTFTSDYSIYLDKQAA aib EFVNWLLAGGPSSGAPPPS K(-βAlaSuccinoylC16) G-NH₂ (SEQ ID NO: 141) | 0.058 | 0.001 | 0.002 |
| Lys(40) | SuccinoylC18 | None | Gly | Y aib E GTFTSDYSIYLDKQAA aib EFVNWLLAGGPSSGAPPPS K(-SuccinoylC18) G-NH₂ (SEQ ID NO: 142) | 0.121 | 0.004 | 0.001 |
| 4-aminoPhe (10) | C16 | γE γE | n/a | Y aib E GTFTSDF (4-aminoγEγEC16) SIYLDKQAA aib EFVNW LLAGGPSSGAPPPS-NH₂ (SEQ ID NO: 143) | 0.165 | 0.002 | 0.003 |
| 4-aminoPhe (10) | SuccinoylC16 | None | n/a | Y aib E GTFTSDF (4amino-succinoylC16) SIYLDKQAA aib EFVNW LLAGGPSSGAPPPS-NH₂ (SEQ ID NO: 144) | >0.500 | 0.004 | 0.013 | nmol/kg every Monday, Wednesday, and Friday, for 4 weeks. The mice were fed a high fat, diabetogenic diet. As shown in FIG. 1, the body weight of the mice which received injections of one of these peptides was lowered, as compared to vehicle control.

Example 15

Acylated peptides comprising the amino acid sequence of SEQ ID NO: 1 (native glucagon) with a Tyr at position 1, AIB at position 2, Glu at position 3, Ile at position 12, Lys at position 16, Gln at position 17, Ala at position 18, AIB at position 20, Glu at position 21, Asn at position 24, Leu at position 27, Ala at position 28, Gly at position 29, followed by the amino acid sequence GPSSGSPPPS (SEQ ID NO: 5), and a C-terminal amidation were made as essentially described in Example 1. The peptides differed by the type of acylation, type of acylation spacer, and/or position of acylated amino acid. The different acylated residues are depicted in FIG. 3. The peptides were then tested for in vitro activity at each of the glucagon receptor, GLP-1 receptor, The in vivo activities of the peptides listed in Table 9 were tested by injecting into DIO mice (each having an average body weight of 49.0 g) at a dose of 10 nmol/kg on Monday, Wednesday, and Friday for 1 week. The body weight and food intake of the mice were measured on Days 0, 2, 4, 6, and 7, while blood glucose levels were measured on Days 0 and 7.

Figure 2:
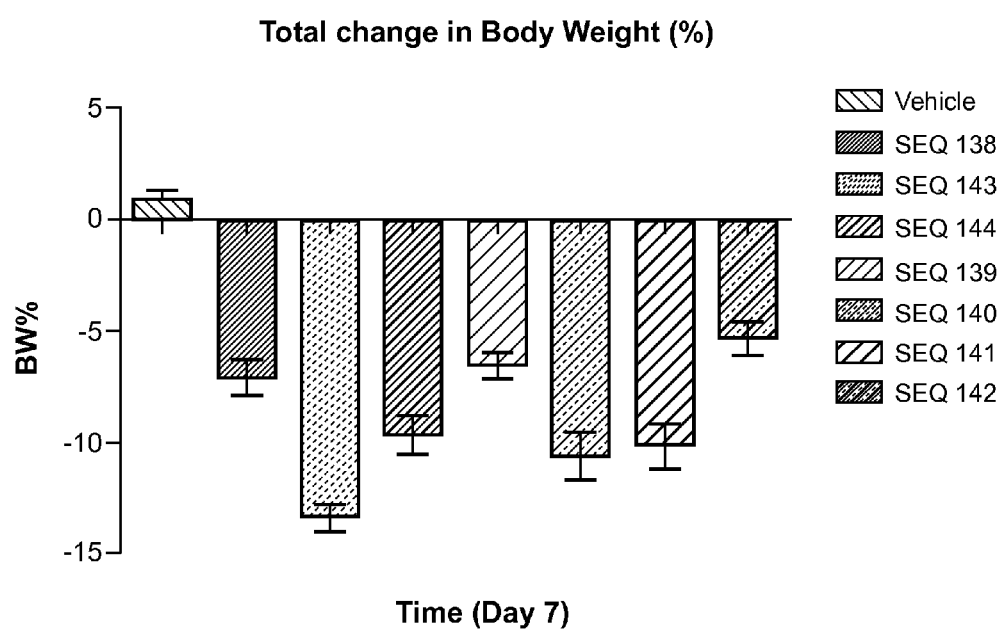
FIG. 2 depicts a graph of the total change in body weight (%), as measured on Day 7) of mice injected with a vehicle control, or with one of the following peptides: a peptide of SEQ ID NO: 138 which peptide is directly attached to a C16 fatty acyl group on Lys at position 40, a peptide of SEQ ID NO: 143 which peptide is acylated via a gamma-Glu-gamma-Glu dipeptide spacer on an 4-amino-Phe residue at position 10, a peptide of SEQ ID NO: 144 which peptide is C16-succinoylated on a 4-aminoPhe at position 10, a peptide of SEQ ID NO: 139 which peptide is directly attached to a C16 fatty acyl group on Lys at position 40 (which is followed by a Gly at position 41), a peptide of SEQ ID NO: 140 which peptide is C16-succinoylated on a Lys at position 40 (which is followed by a Gly at position 41), a peptide of SEQ ID NO: 141 which peptide is C16-succinoylated on a Lys at position 40 via a beta-Ala spacer (which Lys is followed by a Gly at position 41), or a peptide of SEQ ID NO: 142 which peptide is directly attached to a C18 fatty acyl group on a Lys at position 40 (which is followed by a Gly at position 41).

As shown in FIG. 2, the body weight of mice that received injections of the acylated peptides demonstrated at least a 5% decrease in total body weight by Day 7.

Example 16

Acylated peptides comprising the amino acid sequence of native glucagon (SEQ ID NO: 1) with a AIB at position 2, Glu at position 16 (except when position 16 is acylated), Ala at position 18, Leu at position 27, Asp at position 28, Gly at position 29, followed by the amino acid sequence GPSSGSPPPS (SEQ ID NO: 5), and a C-terminal amidation were made as essentially described in Example 1. The peptides differed by the type of acylation, type of acylation spacer, and/or position of acylated amino acid. The peptides were then tested for in vitro activity at each of the glucagon receptor, GLP-1 receptor, and the GIP receptor as essentially described in Example 2. Table 10 summarizes the structure and activities of each peptide.

TABLE 10

| Structure | | | | | Glucagon Receptor | | GLP-1 Receptor | | GIP-1 Receptor | |
|---|---|---|---|---|---|---|---|---|---|---|
| Acylated amino acid (position thereof) | Acyl type | Acyl Spacer | Amino Acid at 41st position | Amino acid sequence (SEQ ID NO:) | $EC_{50}$ ST Dev | n* | $EC_{50}$ ST Dev | n* | $EC_{50}$ ST Dev | n* |
| Lys(10) | C16 | γE | n/a | HaibQGTFTSDK(γE-C16)SKYLDERAAQDFVQWLLDGGPSSGAPPPS-amide (SEQ ID NO: 28) | 0.006 (0.003) | 1 | 0.007 (0.0020) | 1 | 0.003 (0.001) | 1 |
| 4-aminoPhe (40) | C16 | γEγE | Gly | HaibQGTFTSDYSKYLDERAAQDFVQWLLDGGPSSGAPPPSK(C16)G-amide (SEQ ID NO: 177) | 0.010 (0.001) | | 0.014 (0.002) | | 0.021 (0.002) | |
| 4-aminoPhe (40) | succinoyl C16 | n/a | Gly | HaibQGTFTSDYSKYLDERAAQDFVQWLLDGGPSSGAPPPSK(SuccinoylC14)G-amide (SEQ ID NO: 176) | 0.012 (0.002) | | 0.014 (0.011) | | 0.101 (0.002) | |
| 4-aminoPhe (6) | C16 | γE | n/a | HaibQGTFTSDYSKYLDERAAQDFVQWLLDGGPSSGAPPPSaF(γEγE-C16)G-amide (SEQ ID NO: 145) | 0.002 (0.001) | 2 | 0.002 (0.0011) | 2 | 0.017 (0.0057) | 2 |
| 4-aminoPhe (10) | C16 | γE | n/a | HaibQGTFTSDYSKYLDERAAQDFVQWLLDGGPSSGAPPPSaF(C16succinoyl)G-amide (SEQ ID NO: 146) | 0.007 0.001) | 2 | 0.007 (0.003) | 2 | 0.052 (0.0205) | 2 |
| 4-aminoPhe (13) | C16 | γE | n/a | HaibQGTaF(γE-C16)TSDYSKYLDERAAQDFVQWLLDGGPSSGAPPPS-amide (SEQ ID NO: 147) | 0.246 (0.079) | 2 | 0.004 (0.0013) | 2 | 3.131 (N/A) | 1 |
| 4-aminoPhe (10) | succinoyl C16 | n/a | n/a | HaibQGTFTSDaF(γE-C16)SKYLDERAAQDFVQWLLDGGPSSGAPPPS-amide (SEQ ID NO: 148) | 0.008 0.008) | 2 | 0.009 (0.0036) | 2 | 0.009 (0.0020) | 2 |
| Lys(13) | C16 | γE | n/a | HaibQGTLISDYSKaF(γE-C16)LDERAAQDFVQWLLDGGPSSGAPPPS-amide (SEQ ID NO: 149) | 0.011 (0.004) | 2 | 0.007 (0.0036) | 2 | 0.395 (0.2630) | 2 |
| Lys(14) | C16 | γE | n/a | HaibQGTFTSDaF(C16succinoyl)SKYLDERAAQDFVQWLLDGGPSSGAPPPS-amide (SEQ ID NO: 150) | 0.006 (0.002) | 2 | 0.004 (0.0018) | 2 | 0.141 (0.046) | 2 |
| Lys(16) | C16 | γE | n/a | HaibQGTFTSDYSKK(γE-C16)LDERAAQDFVQWLLDGGPSSGAPPPS-amide (SEQ ID NO: 151) | 0.008 0.001) | 2 | 0.004 (0.0013) | 2 | 0.309 (0.0884) | 2 |
| Lys(17) | C16 | γE | n/a | HaibQGTFTSDYSKYK(γE-C16)DERAAQDFVQWLLDGGPSSGAPPPS-amide (SEQ ID NO: 152) | 0.004 (0.001) | 2 | 0.004 (0.0013) | 2 | 0.011 | 2 |
| Lys(10) | C16 | γE | n/a | HaibQGTFTSDYSKYLDK(γE-C16)RAAQDFVQWLLDGGPSSGAPPPS-amide (SEQ ID NO: 153) | 0.012 (0.006) | 2 | 0.007 (0.0006) | 2 | 0.276 | 2 |

TABLE 10-continued

| Acylated amino acid (position thereof) | Acyl type | Acyl Spacer | Amino Acid at 41st position | Amino acid sequence (SEQ ID NO:) | Glucagon Receptor EC$_{50}$ ST Dev | n* | GLP-1 Receptor EC$_{50}$ ST Dev | n* | GIP-1 Receptor EC$_{50}$ ST Dev | n* |
|---|---|---|---|---|---|---|---|---|---|---|
| 4-aminoPhe (40) | C16 | γEγE | Gly | HaibQGEFTSDYSKYLDEK(γE-C16)AAQDFVQWLLDGGPSSGAPPPS-amide (SEQ ID NO: 154) | 0.008 (0.001) | 2 | 0.004 (0.0019) | 2 | 0.175 | 2 |

*number of experiments; different fractions of SEQ ID NOs: 147 and 149 were used in the experiments. Data may be from different experiments.

Example 17

Select peptides from Tables 10 (peptides of SEQ ID NOs: 145, 148, and 152) and peptides of SEQ ID NOs: 28 and 89 were tested for in vivo activities in DIO mice (having an original average body weight of 58.0 g) on a high fat, diabetogenic diet. The peptides at a dose of 10 nmol/kg (of the original average body weight) were subcutaneously injected on Days 0 and 3. The body weight and food intake of the mice were measured on Days 0, 1, 3, 5, and 7, while blood glucose levels were measured on Days 0 and 7.

Figure 4:
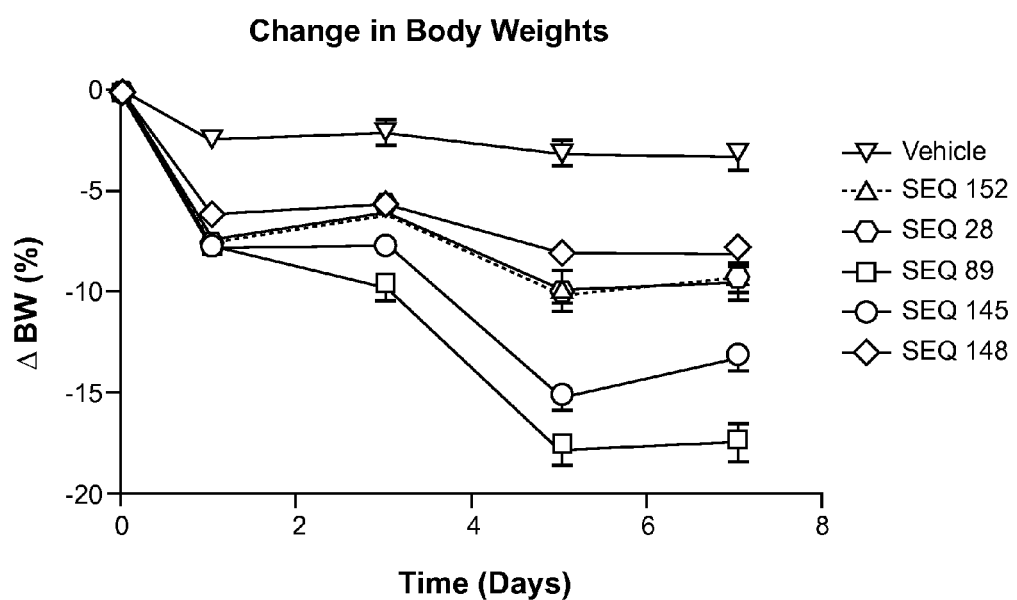
FIG. 4 is a graph of the change in body weight (%) of mice injected with vehicle control (▽), or with a peptide of SEQ ID NO: 152 which peptide comprises a Lys residue at position 16 covalently attached to a C16 fatty acyl group via a gammGlu acid spacer (Δ), a peptide of SEQ ID NO: 28 which peptide comprises a Lys residue at position 10 covalently attached to a C16 fatty acyl group via a gammaGlu (open hexagon), a peptide of SEQ ID NO: 89 which peptide comprises a Lys at position 40 covalently attached to a C16 fatty acyl group via a gammaGlu-gammaGlu dipeptide spacer (□), a peptide of SEQ ID NO: 145 which peptide comprises a 4-aminoPhe at position 40 covalently attached to C16 fatty acyl group via a gammaGlu-gammaGlu dipeptide spacer (○), or a peptide of SEQ ID NO: 148 which peptide comprises an 4-aminoPhe at position 10 covalently attached to a C16 fatty acyl group via a gammaGlu spacer (◊).

As shown in FIG. 4, the mice that received an injection of one of these peptides demonstrated a decreased body weight over the course of 7 days, as compared to vehicle controls. The mice that received injections of the peptides demonstrated at least a 5% decrease in total body weight by Day 7 of which two demonstrated at least a 10% decrease in total body weight by Day 7.

Example 18

Acylated peptides comprising a "mini-PEG" spacer were made as essentially described in Example 1. FIG. 12 represents a schematic of the structures of these acylated peptides. The peptides comprising a mini-PEG spacer were tested for in vitro activity at each of the glucagon receptor, GLP-1 receptor, and the GIP receptor as essentially described in Example 2, and compared to the activities of acylated peptides comprising no spacer or a E spacer. All peptides of this experiment comprised the amino acid sequence of native glucagon (SEQ ID NO: 1) with AIB at position 2, Glu at position 16, Ala at position 18, Leu at position 28, Asp at position 28, Gly at position 29, followed by the amino acid sequence GPSSGSPPPSK (SEQ ID NO: 9), wherein K was an acylated amino acid, and a C-terminal amidation. Table 11 summarizes the structure and activities of each peptide.

TABLE 11

| Acylated amino acid (position thereof) | Acyl type | Acyl Spacer | Amino Acid at 41st position | Amino Acid Sequence | Glucagon Receptor EC$_{50}$ (ST Dev) | n* | GLP-1 Receptor EC$_{50}$ (ST Dev) | n* | GIP Receptor EC$_{50}$ (ST Dev) | n* |
|---|---|---|---|---|---|---|---|---|---|---|
| Lys(40) | C16 | E | Gly | HaibQGTFTSDYSKYLDERAAQDFVQWLLDGGPSSGSPPPSK(γE-C16)G-amide (SEQ ID NO: 155) | 0.004 (0.0004) | 2 | 0.003 (0.0003) | 2 | 0.008 (0.001) | 1 |
| Lys(40) | Succinoyl C16 | None | Gly | HaibQGTFTSDYSKYLDERAAQDFVQWLLDGGPSSGAPPPSK(C16succinoyl)G-amide (SEQ ID NO: 156) | 0.003 (0.0003) | 2 | 0.003 (0.0008) | 2 | 0.006 (0.0009) | 1 |
| Lys(40) | C16 | PEG2-E | Gly | HaibQGTFTSDYSKYLDERAAQDFVQWLLDDGASSGAPPPSK(Peg2-γE-C16)G-amide (SEQ ID NO: 157) | 0.011 (0.001) | 1 | 0.009 (0.0005) | 1 | 0.021 (0.004) | 1 |
| Lys(40) | C16 | PEG4-E | Gly | HaibQGTFTSDYSKYLDERAAQDFVQWLLDGGPSSGAPPPSK(Peg4-γE-C16)G-amide (SEQ ID NO: 158) | 0.004 (0.0005) | 2 | 0.003 (0.0005) | 2 | 0.005 0.0005) | 2 |
| Lys(40) | C16 | PEG8-E | Gly | HaibQGTFTSDYSKYLDERAAQDFVQWLLDGGPSSGAPPPSK(Peg8-γE-C16)G-amide (SEQ ID NO: 159) | 0.006 (0.0009) | 1 | 0.005 (0.001) | 1 | 0.002 (0.0004) | 2 |

Example 19

Dual acylated peptides were made. Two peptides comprised a single acylated amino acid residue carrying two acylations in a branched formation: one peptide had the branched acylation at position 10, and a 2nd peptide had the branched acylation at position 40. FIG. 5 (at the top) depicts the structure of the single acylated Lys residue carrying two acylations in a branched formation. In another instance, a peptide comprised one acylated amino acid residue carrying two acylations in a linear formation. FIG. 5A (middle) depicts the structure of the single acylated Lys residue carrying a C12 acylation attached to a C16 acylation via a E spacer in a linear formation. In yet another instance, a peptide comprised two acylated amino acid residues: one at position 10 and another at position 40. FIG. 5 (at the bottom) depicts the structure of each acylated Lys residue carrying a C16 acylation via a E spacer. The parentheses denote that the Lys residues are connected via the backbone amino acids at positions 11-39.

The peptides carrying two acylations were tested for in vitro activity at each of the glucagon receptor, GLP-1 receptor, and the GIP receptor as essentially described in Example 2 and the results are shown in Table 12.

TABLE 12

| Dual Acylated Peptides | EC$_{50}$ (cAMP, nmole)* | | |
|---|---|---|---|
| | GCGR | GLPR | GIPR |
| HaibQGTFTSD **K\*(rEC16)** SKYLDERAAQDFVQWLLDGGP SSGAPPPS-amide (SEQ ID NO: 28) | 0.004 | 0.003 | 0.007 |
| HaibQGTFTSD **K\*K(rEC16)$_2$** SKYLDERAAQDFVQWLLDGGPS SGAPPPS-amide (SEQ ID NO: 160) | 0.024 | 0.007 | 0.015 |
| HaibQGTFTSDYSKYLDERAA QDFVQWLLDGGPSSGAPPPS **K\*K(rEC16)$_2$**-amide (SEQ ID NO: 161) | 0.011 | 0.007 | 0.010 |
| HaibQGTFTSD **K\*(C12-rEC16)** SKYLDERAAQDFVQWLLDGGP SSGAPPPS-amide (SEQ ID NO: 162) | 0.008 | 0.003 | 0.033 |
| HaibQGTFTSD **K\*(rEC16)** YSKYLDERAAQDFVQWLLDGG PSSGAPPPS **K\*(rEC16)**-amide (SEQ ID NO: 163) | 0.018 | 0.011 | 0.024 |

On Day 0, the peptides of Table 12, as well as two dimers (described in Example 22 and FIG. 9) and two additional peptides (a peptide of SEQ ID NO: 28 and a peptide of SEQ ID NO: 89) were subcutaneously injected once into DIO mice (at a dose of 10 nmol/kg). The DIO mice had been given a diabetogenic diet prior to injection and the average body weight of the mice was 60 g. The body weight and food intake of the mice were measured on Days 0, 1, 3, 5, and 7, while fasted blood glucose levels were measured on Days 0 and 7.

Figure 5E:
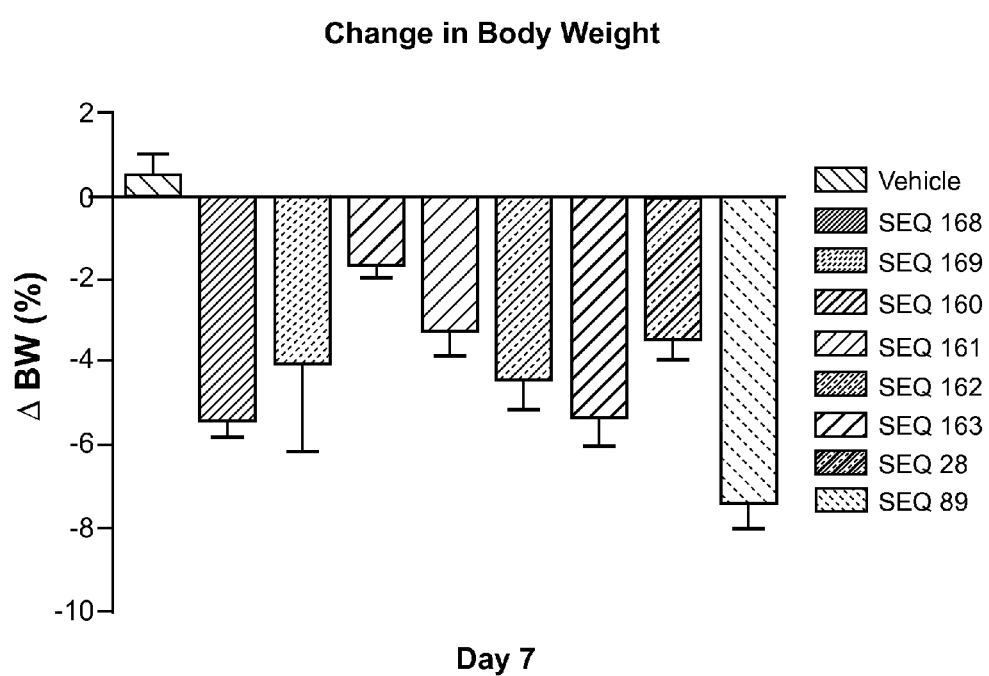

As shown in FIG. 5E, mice that received a peptide injection exhibited decreased body weight on Day 7 of this study, as compared to mice that were injected with a vehicle control.

Figure 5F:
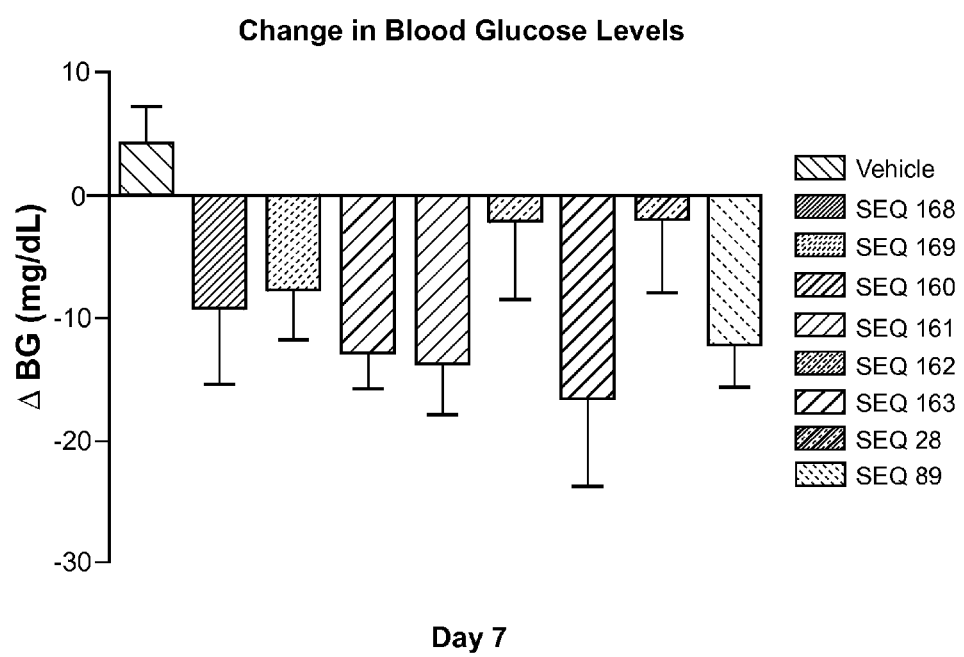

As shown in FIG. 5F, blood glucose levels decreased in mice that received a peptide injection, as compared to mice that were injected with a vehicle control.

Example 20

Peptides were S-alkylated in three different ways. In a first way, an S-palmityl akylated Cys residue was part of the peptide backbone. The akylated Cys residue was located at position 40. The structure is shown in FIG. 6 (bottom) and is listed as SEQ ID NO: 164 in the sequence listing. In a second way, an S-palmityl akylated Cys residue was attached to a Lys residue, which Lys residue was located at position 40 of the peptide. The resulting structure is shown in FIG. 7 (Cys-S—Palmitic) and is listed as SEQ ID NO: 165 in the sequence listing. In a third way, an S-palmityl akylated Cys residue was attached to a spacer residue (gamma-glutamic acid) which was in turn attached to a Lys residue located at position 40 of the peptide. The resulting structure is shown in FIG. 7 (γE-Cys-S-palmitic) and is listed as SEQ ID NO: 166 in the sequence listing. The S-alkylated peptides were made as described in Example 1.

The peptides were tested for in vitro activity at each of the glucagon receptor, GLP-1 receptor, and GIP receptor, as essentially described in Example 2. The EC50s at each receptor for each peptide are listed below in Table 13.

TABLE 13

| Structure | Glucagon Receptor | | | GLP-1 Receptor | | | GIP Receptor | | |
|---|---|---|---|---|---|---|---|---|---|
| HaibQGTFTSDYSKYLDE RAAQDFVQWLLDGGPSSG APPPSC**(S-palmityl)** G-amide (SEQ ID NO: 163) | 0.006 | 0.0008 | 2 | 0.003 | 0.0003 | 2 | 0.051 | 0.007 | 1 |
| HaibQGTFTSDYSKYLDE RAAQDFVQWLLDGGPSSG APPPSK**(Cys S-palmityl)**G-amide (SEQ ID NO: 164) | 0.006 | 0.0013 | 1 | 0.003 | 0.0003 | 1 | 0.028 | 0.001 | 1 |
| HaibQGTFTSDYSKYKLD ERAAQDFVQWELDGGPSS GAPPPSK**(γE-Cys S-palmityl)**Gamide (SEQ ID NO: 165) | 0.009 | 0.0013 | 1 | 0.003 | 0.0003 | 1 | 0.043 | 0.001 | 1 |

Example 21

The in vivo activities of selected peptides from the previous Examples were tested by subcutaneously injecting 10 nmol/kg of body weight into DIO mice. The average body weight of the mice was 60 g and there were 8 mice per group.

Among the peptides tested were an acylated peptide with a gamma-glutamic acid spacer, an acylated peptide with a dipeptide spacer of two gamma-glutamic acids, a C16-succinoylated peptide, an acylated peptide with a miniPEG spacer comprising the structure $(-O-CH_2-CH_2-)_n$, wherein n is 2, an acylated peptide with a miniPEG spacer comprising the structure $(-O-CH_2-CH_2-)_n$, wherein n is 4, an acylated peptide with a miniPEG spacer comprising the structure $(-O-CH_2-CH_2-)_n$, wherein n is 8, an S-palmityl akylated peptide, wherein Lys is the backbone residue and Cys is a spacer between the Lys and the acyl group, and an S-palmityl alkylated peptide, wherein Lys is the backbone residue and gamma-glutamic acid-Cys is a dipeptide spacer between the Lys and the acyl group. Body weight and food intake were measured on Days 0, 1, 3, 5, and 7, while blood glucose measurements were taken on Days 0 and 7.

Figure 8:
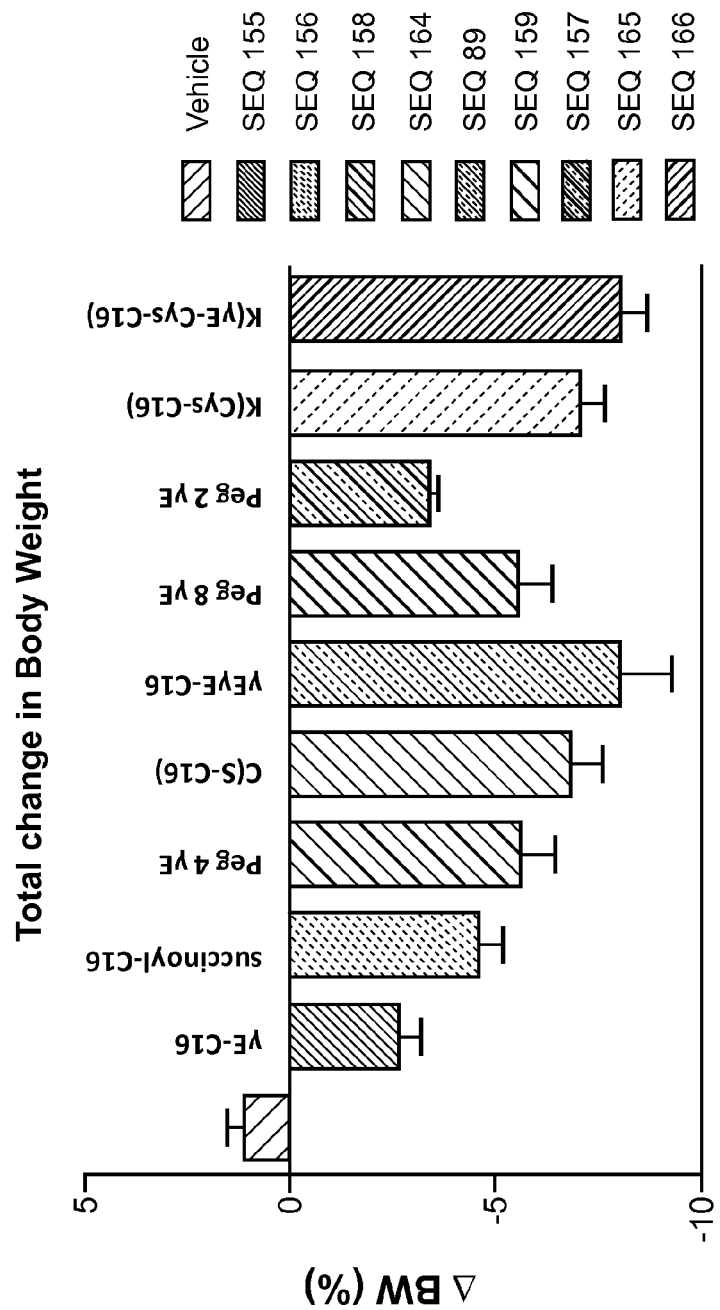
FIG. 8 represents a graph of change in body weight (%) as measured on Day 7 of mice injected with vehicle control or with one of nine different acylated peptides: SEQ ID NO: 155, SEQ ID NO: 156, SEQ ID NO: 158, SEQ ID NO: 164, SEQ ID NO: 89, SEQ ID NO: 159, SEQ ID NO: 157, SEQ ID NO: 165, SEQ ID NO: 166.

As shown in FIG. 8, many of the tested peptides demonstrated at least a 5% decrease in total change in body weight as measured on Day 7.

Example 22

Three homodimers were made, wherein each homodimer comprised two peptides of SEQ ID NO: 167. The C-terminal Lys residue (at position 40) of each peptide of SEQ ID NO: 167 was amidated (instead of containing an alpha carboxylate) and the epsilon NH2 group of this Lys residue was peptide bonded to a Cys reside, which in turn was bound to a gamma-glutamic acid residue. The gamma-glutamic acid residue was bound to a C16 acyl group. Each half of the dimer was either attached to the other half via a disulfide linkage or a thioether linkage. Example 1 details the synthesis of the homodimers.

The structures of the resulting products are shown in FIGS. 9A and 9B.

The homodimers were tested for in vitro activity at each of the glucagon receptor, GLP-1 receptor, and GIP receptor, as essentially described in Example 2. The EC50s at each receptor for each peptide are listed below in Table 14.

TABLE 14

| Structure of each monomer | Glucagon Receptor | | | GLP-1 Receptor | | | GIP Receptor | | |
| --- | --- | --- | --- | --- | --- | --- | --- | --- | --- |
| | EC50 | STDev | n* | EC50 | STDev | n* | EC50 | STDev | n* |
| Disulfide dimer (disulfide with two C16 acylations) HaibQGTFTSDYSKYLDERAAQD FVQWLLDGGPSSGAPPPSK(Cysr E-C16)G-amide (SEQ ID NO: 168) | 0.004 | 0.0007 | 2 | 0.002 | 0.0003 | 2 | 0.004 | 0.0002 | 2 |
| S-acetylDap K40 dimer (thioether with one C16 acylation) HaibQGTFTSDYSKYLDERAAQD EVQWLLDEGGPSSGAPPPSK(Cysr E-C16)G-amide (SEQ ID NO: 169) | 0.003 | 0.0003 | 2 | 0.002 | 0.0003 | 2 | 0.009 | 0.0005 | 2 |
| Cys-K40 disulfide dimer (disulfide with one C16 acylation) HaibQGTFTSDYSKYLDERAAQD FVQWLLDGGPSSGAPPPSK(Cysr EC16)G-amide (SEQ ID NO: 170) | 0.003 | 0.0003 | 1 | 0.001 | 0.0003 | 1 | 0.014 | 0.001 | 1 |

Example 23

DIO mice (8 animals per group, average body weight of 54 g) were subcutaneously injected with one of 4 peptides described in the table below at either 1 nmol/kg/day or 3 nmol/kg/day, or was given a vehicle control every day. The structures and their in vitro activities at each of the glucagon receptor, GLP-1 receptor, and GIP receptor are provided in Table 15.

TABLE 15

| Structure | EC50 (nM) at glucagon receptor [STDev] | EC50 (nM) at GLP-1 receptor [STDev] | EC50 (nM) at GIP receptor [STDev] |
| --- | --- | --- | --- |
| HaibQGTFTSDK(γE-C16)SKYLDERAAQDF VQWLLDGGPSSGAPPP S-amide (SEQ ID NO: 28) | 0.002 [0.001] | 0.002 [0.001] | 0.002 [0.001] |
| HaibQGTFTSDYSKYL DERAAQDFQVWLLDGG PSSGAPPPSK(γEγE-C16)G-amide (SEQ ID NO: 89) | 0.004 [0.001] | 0.004 [0.001] | 0.020 [0.006] |
| YaibEGTFTSDYSIYL DKQAAaibEFVNWELA GGPSSGAPPPSK (C16)-amide (SEQ ID NO: 138) | 0.053 [0.015] | 0.003 [0.001] | 0.002 [0.001] |

TABLE 15-continued

| Structure | EC50 (nM) at glucagon receptor [STDev] | EC50 (nM) at GLP-1 receptor [STDev] | EC50 (nM) at GIP receptor [STDev] |
|---|---|---|---|
| HaibEGTFTSDYSKYL DERAAQDFVQWLLDGG PSSGAPPPSK(γEγE-C16)G-amide (SEQ ID NO: 171) | 0.455 [0.137] | 0.005 [0.001] | 0.038 [0.005] |

Body weight and food intake was measured on every other day, beginning with Day 0 (the day of first administration). Body composition was measured on Days 0 and 19, while ad lib blood glucose levels were measured on Days 0, 7, 14, and 20. ipGTT (1 g/kg) was measured on Day 20 at 0, 15, 20, 60, 120 minutes post-glucose injection). Necropsy (liver and pancreas) and a final bleed was measured on day 22 (after an overnight fast).

Figure 10:
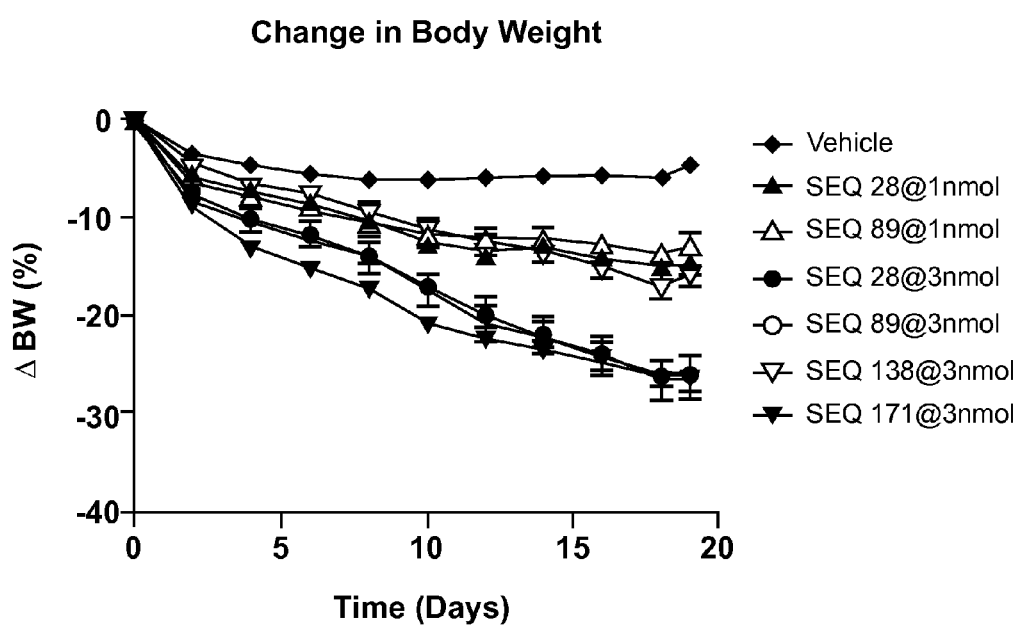
FIG. 10 represents a graph of the change in body weight (%) of mice injected with a vehicle control or with a peptide of SEQ ID NO: 28 (at 1 or 3 nmol/kg), a peptide of SEQ ID NO: 89 (at 1 or 3 nmol/kg), a peptide of SEQ ID NO: 138 (at 3 nmol/kg), or a peptide of SEQ ID NO: 171 (at 3 nmol/kg), as a function of time post-injection.
Figure 11:
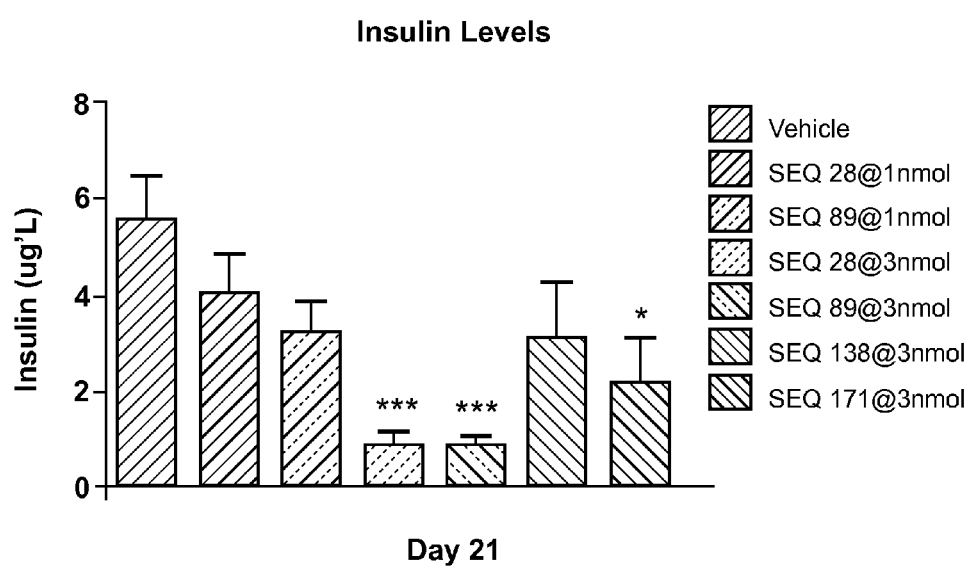
FIG. 11 represents a graph of the insulin levels, as measured on Day 21, of mice injected with a vehicle control or with a peptide of SEQ ID NO: 28 (at 1 or 3 nmol/kg), a peptide of SEQ ID NO: 89 (at 1 or 3 nmol/kg), a peptide of SEQ ID NO: 138 (at 3 nmol/kg), or a peptide of SEQ ID NO: 171 (at 3 nmol/kg).

As shown in FIG. 10, body weight decreased in all animals given a peptide of Table 15. Food intake as measured on Day 19 was decreased in all animals that were given a peptide of Table 15, as compared to mice given a vehicle control. As shown in FIG. 11, the insulin levels (as measured on Day 21) also decreased in animals that were given a peptide, as compared to a vehicle. Notably, the mice that had demonstrated the greatest amount of weight loss were also the mice that demonstrated the lowest insulin levels Example 24

Peptides demonstrating body weight lowering capability as assessed in Example 21 were selected for additional mutation studies in which amino acids within the C-terminal half of the peptide were modified in one of several ways. In a first way, the peptide having the sequence of SEQ ID NO: 89 was altered such that the amino acid at position 27, 28, or 29 was substituted with an alanine residue. In another way, the peptide having the sequence of SEQ ID NO: 28 was modified to have a Glu at position 28 and an Arg at position 35. It was theorized that a salt bridge between these two amino acids would form a salt bridge to stabilize the Trp cage structure in the C-terminal portion of the peptide. Lastly, the peptide having the sequence of SEQ ID NO: 28 was modified to include a Gly as the C-terminal amino acid. The peptides, as well as other peptides that look similar to the peptide of SEQ ID NO: 89 or the peptide of SEQ ID NO: 28, were tested for in vitro activities at each of the glucagon receptor, GLP-1 receptor, and G11) receptor as essentially described in Example 2 and the results are provided in Table 16.

TABLE 16

| Structure | EC50 (nM) at glucagon receptor | EC50 (nM) at GLP-1 receptor | EC50 (nM) at GIP receptor |
|---|---|---|---|
| HaibQGTFTSDYSKYL DERAAQDFVQWLLDGG PSSGAPPPSK (γEC16)G-NH$_2$ (SEQ ID NO: 89) | 0.006 | 0.005 | 0.028 |
| HaibQGTFTSDK(γE-C16ac)SKYLDERAAQ DFVQWLLDGGPSSGAP PPS-amide (SEQ ID NO: 28) | 0.003 | 0.004 | 0.004 |
| HaibQGTFTSDYSKYL DERAAQDFVQWLLAGG PSSGAPPPSK (γE7E-C16)G-NH$_2$ (SEQ ID NO: 203) | 0.003 | 0.001 | 0.007 |
| HaibQGTFTSDYSKYL DERAAQDFVQWLLDAG PSSGAPPPSK (γEγE-C16)G-NH$_2$ (SEQ ID NO: 204) | 0.003 | 0.001 | 0.069 |
| HaibQGTFTSDK(γE-C16)SKYLDERAAQDF VQWLLDGGPSSGAPPP SG-NH$_2$ (SEQ ID NO: 205) | 0.005 | 0.002 | 0.004 |
| YaibQGTFTSDYSKYL DERAAQDFVQWLLDGG PSSGAPPPSK (K-bisγEC16)G-NH$_2$ (SEQ ID NO: 208) | 0.031 | 0.025 | 0.079 |
| YaibQGTFTSDYSKYL DERAAQDFVQWLLDGG PSSGAPPPSK (K-γEC16,γEC8)G-NH$_2$ (SEQ ID NO: 210) | 0.010 | 0.005 | 0.359 |
| YaibQGTFTSDYSKYL DERAAQDFVQWLLDGG PSSGAPPPSK (K-γEC16,γEC12) G-NH$_2$ (SEQ ID NO: 211) | 0.010 | 0.006 | 0.038 |
| HaibQGTFTSDYSKYL DERAAQDFVQWLLDGG PSSGAPPPSY (O-2palmitic acid) G-NH$_2$ (SEQ ID NO: 212) | 0.007 | 0.004 | 0.339 |
| HaibQGTFTSDK (γEγE-C16)SKYLDE RAAQDFVQWLLDGGPS SGAPPPSG-NH$_2$ (SEQ ID NO: 207) | 0.005 | 0.002 | 0.015 |

Example 25

Peptides were made as essentially described in Example 1 and tested for in vitro activity at each of the glucagon, GLP-1, and GIP receptors as essentially described herein. The structures and EC50 values (nM) of each peptide are provided below in Table 17.

TABLE 17

| Peptide | Glucagon EC50 (nM) [STDev] | GLP-1 EC50 (nM) [STDev] | GIP EC50 (nM) [STDev] |
|---|---|---|---|
| Glucagon | 0.025 [0.003] | | |
| GLP-1 | | 0.025 [0.003] | |
| GIP | | | 0.0065 [0.0001] |
| HaibQGTFTSDYSIYL DEKRAKEFVCWLLAGG PSSGAPPPSK-amide (SEQ ID NO: 230) | 1.644 [0.302] | 0.222 [0.034] | 0.164 [0.010] |

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted.

Recitation of ranges of values herein are merely intended to serve as a shorthand method of referring individually to each separate value falling within the range and each endpoint, unless otherwise indicated herein, and each separate value and endpoint is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

SEQUENCE LISTING

```
<160> NUMBER OF SEQ ID NOS: 270

<210> SEQ ID NO 1
<211> LENGTH: 29
<212> TYPE: PRT
<213> ORGANISM: Homo sapiens
<220> FEATURE:
<221> NAME/KEY: MISC_FEATURE
<223> OTHER INFORMATION: Wild type glucagon

<400> SEQUENCE: 1

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 2
<211> LENGTH: 42
<212> TYPE: PRT
<213> ORGANISM: Homo sapiens
<220> FEATURE:
<221> NAME/KEY: mat_peptide
<222> LOCATION: (1)..(42)
<223> OTHER INFORMATION: Gastric Inhibitory Polypeptide

<400> SEQUENCE: 2

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
            35                  40
```

```
<210> SEQ ID NO 3
<211> LENGTH: 30
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (1)..(30)
<223> OTHER INFORMATION: GLP-1(7-36) amidated
<220> FEATURE:
<221> NAME/KEY: MISC_FEATURE
<222> LOCATION: (30)..(30)
<223> OTHER INFORMATION: C-terminal amidation

<400> SEQUENCE: 3

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 4
<211> LENGTH: 31
<212> TYPE: PRT
<213> ORGANISM: Homo sapiens
<220> FEATURE:
<221> NAME/KEY: MISC_FEATURE
<222> LOCATION: (1)..(31)
<223> OTHER INFORMATION: GLP-1(7-37)

<400> SEQUENCE: 4

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 5
<211> LENGTH: 10
<212> TYPE: PRT
<213> ORGANISM: Artificial Sequence
<220> FEATURE:
<223> OTHER INFORMATION: Synthetic peptide

<400> SEQUENCE: 5

Gly Pro Ser Ser Gly Ala Pro Pro Pro Ser
1               5                   10

<210> SEQ ID NO 6
<211> LENGTH: 11
<212> TYPE: PRT
<213> ORGANISM: Artificial Sequence
<220> FEATURE:
<223> OTHER INFORMATION: Synthetic peptide

<400> SEQUENCE: 6

Gly Gly Pro Ser Ser Gly Ala Pro Pro Pro Ser
1               5                   10

<210> SEQ ID NO 7
<211> LENGTH: 8
<212> TYPE: PRT
<213> ORGANISM: Artificial Sequence
<220> FEATURE:
<223> OTHER INFORMATION: Synthetic peptide
```

```
<400> SEQUENCE: 7

Lys Arg Asn Arg Asn Asn Ile Ala
1               5

<210> SEQ ID NO 8
<211> LENGTH: 4
<212> TYPE: PRT
<213> ORGANISM: Artificial Sequence
<220> FEATURE:
<223> OTHER INFORMATION: Synthetic peptide

<400> SEQUENCE: 8

Lys Arg Asn Arg
1

<210> SEQ ID NO 9
<211> LENGTH: 11
<212> TYPE: PRT
<213> ORGANISM: Artificial Sequence
<220> FEATURE:
<223> OTHER INFORMATION: Synthetic peptide

<400> SEQUENCE: 9

Gly Pro Ser Ser Gly Ala Pro Pro Pro Ser Lys
1               5                   10

<210> SEQ ID NO 10
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: mt-263
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (20)..(20)
<223> OTHER INFORMATION: Xaa is AIB
<220> FEATURE:
<221> NAME/KEY: MISC_FEATURE
<222> LOCATION: (40)..(40)
<223> OTHER INFORMATION: C-terminal amidation

<400> SEQUENCE: 10

Tyr Xaa Glu Gly Thr Phe Thr Ser Asp Tyr Ser Ile Tyr Leu Asp Lys
1               5                   10                  15

Gln Ala Ala Xaa Glu Phe Val Asn Trp Leu Leu Ala Gly Gly Pro Ser
            20                  25                  30

Ser Gly Ala Pro Pro Pro Ser Lys
        35                  40

<210> SEQ ID NO 11
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: mt-402
<220> FEATURE:
<221> NAME/KEY: misc_feature
<222> LOCATION: (2)..(2)
```

```
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid

<400> SEQUENCE: 11

Tyr Xaa Gln Gly Thr Phe Thr Ser Asp Tyr Ser Ile Tyr Leu Asp Lys
1               5                   10                  15

Lys Ala Ala Xaa Glu Phe Val Asn Trp Leu Leu Ala Gly Gly Pro Ser
            20                  25                  30

Ser Gly Ala Pro Pro Pro Ser Lys
        35                  40

<210> SEQ ID NO 12
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: mt-403
<220> FEATURE:
<221> NAME/KEY: MISC_FEATURE
<222> LOCATION: (16)..(20)
<223> OTHER INFORMATION: Lactam bridge between residues 16 and 20

<400> SEQUENCE: 12

His Ser Gln Gly Thr Phe Ile Ser Asp Tyr Ser Lys Tyr Leu Asp Glu
1               5                   10                  15

Ile His Gln Lys Glu Phe Ile Ala Trp Leu Met Asn Thr
            20                  25

<210> SEQ ID NO 13
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: mt-404
<220> FEATURE:
<221> NAME/KEY: MISC_FEATURE
<222> LOCATION: (16)..(20)
<223> OTHER INFORMATION: Lactam bridge between residues 16 and 20

<400> SEQUENCE: 13

His Ser Gln Gly Thr Phe Ile Ser Asp Tyr Ser Lys Ala Leu Asp Glu
1               5                   10                  15

Ile His Gln Lys Glu Phe Ile Ala Trp Leu Met Asn Thr
            20                  25

<210> SEQ ID NO 14
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: mt-405
<220> FEATURE:
<221> NAME/KEY: MISC_FEATURE
<222> LOCATION: (16)..(20)
<223> OTHER INFORMATION: Lactam bridge between residues 16 and 20

<400> SEQUENCE: 14
```

```
Tyr Ser Gln Gly Thr Phe Thr Ser Asp Tyr Ser Lys Tyr Leu Asp Glu
1               5                   10                  15

Ile His Gln Lys Asp Phe Val Asn Trp Leu Leu Ala Gln
            20                  25

<210> SEQ ID NO 15
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: mt-395
<220> FEATURE:
<221> NAME/KEY: MISC_FEATURE
<222> LOCATION: (16)..(20)
<223> OTHER INFORMATION: Lactam bridge between residues 16 and 20

<400> SEQUENCE: 15

His Ser Gln Gly Thr Phe Thr Ser Asp Tyr Ser Lys Tyr Leu Asp Glu
1               5                   10                  15

Ile His Gln Lys Asp Phe Val Asn Trp Leu Leu Ala Gly Gly Pro Ser
            20                  25                  30

Ser Gly Ala Pro Pro Pro Ser
        35

<210> SEQ ID NO 16
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: mt-396
<220> FEATURE:
<221> NAME/KEY: MISC_FEATURE
<222> LOCATION: (16)..(20)
<223> OTHER INFORMATION: Lactam bridge between residues 16 and 20

<400> SEQUENCE: 16

Tyr Ser Gln Gly Thr Phe Thr Ser Asp Tyr Ser Lys Tyr Leu Asp Glu
1               5                   10                  15

Ile His Gln Lys Asp Phe Val Asn Trp Leu Leu Ala Gly Gly Pro Ser
            20                  25                  30

Ser Gly Ala Pro Pro Pro Ser
        35

<210> SEQ ID NO 17
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: mt-397
<220> FEATURE:
<221> NAME/KEY: MISC_FEATURE
<222> LOCATION: (16)..(20)
<223> OTHER INFORMATION: Lactam bridge between residues 16 and 20

<400> SEQUENCE: 17

Tyr Ser Gln Gly Thr Phe Thr Ser Asp Tyr Ser Lys Tyr Leu Asp Glu
1               5                   10                  15
```

-continued

Ile His Gln Lys Glu Phe Val Asn Trp Leu Leu Ala Gln
            20                  25

<210> SEQ ID NO 18
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: mt-398
<220> FEATURE:
<221> NAME/KEY: MISC_FEATURE
<222> LOCATION: (16)..(20)
<223> OTHER INFORMATION: Lactam bridge between residues 16 and 20

<400> SEQUENCE: 18

Tyr Ser Gln Gly Thr Phe Thr Ser Asp Tyr Ser Lys Tyr Leu Asp Glu
1               5                   10                  15

Gln Ala Ala Lys Glu Phe Ile Ala Trp Leu Met Asn Gly Gly Pro Ser
            20                  25                  30

Ser Gly Ala Pro Pro Pro Ser
        35

<210> SEQ ID NO 19
<211> LENGTH: 42
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: mt-217

<400> SEQUENCE: 19

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Trp Leu Lys His Asn Ile Thr Gln
        35                  40

<210> SEQ ID NO 20
<211> LENGTH: 42
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: mt-218
<220> FEATURE:
<221> NAME/KEY: MISC_FEATURE
<222> LOCATION: (2)..(2)
<223> OTHER INFORMATION: Xaa is AIB

<400> SEQUENCE: 20

Tyr Xaa Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Trp Leu Lys His Asn Ile Thr Gln
        35                  40

<210> SEQ ID NO 21

```
<211> LENGTH: 42
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: mt-219

<400> SEQUENCE: 21

Tyr Ala Pro Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Trp Leu Lys His Asn Ile Thr Gln
        35                  40

<210> SEQ ID NO 22
<211> LENGTH: 42
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: mt-220
<220> FEATURE:
<221> NAME/KEY: MISC_FEATURE
<222> LOCATION: (2)..(2)
<223> OTHER INFORMATION: Xaa is AIB

<400> SEQUENCE: 22

Tyr Xaa Glu Gly Thr Phe Ile Ser Asp Tyr Ser Ile Ala Met Asp Lys
1               5                   10                  15

Ile His Gln Gln Asp Phe Val Cys Trp Leu Leu Ala Gln Lys Gly Lys
            20                  25                  30

Lys Asn Trp Leu Lys His Asn Ile Thr Gln
        35                  40

<210> SEQ ID NO 23
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: mt-225
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (16)..(20)
<223> OTHER INFORMATION: Lactam bridge links Glu16 and Lys20
<220> FEATURE:
<221> NAME/KEY: MISC_FEATURE
<222> LOCATION: (40)..(40)
<223> OTHER INFORMATION: Epsilon amine of Lys is attached to
      Ala-Ac-Cys(PEG), wherein the Ac-Cys(PEG) is a Cys residue
      comprising an alpha amino group capped with an acetyl group
      (CH3CO) and comprising a 40 kDa PEG covalently attached to its
      side chain

<400> SEQUENCE: 23

Tyr Xaa Gln Gly Thr Phe Thr Ser Asp Tyr Ser Ile Tyr Leu Asp Glu
1               5                   10                  15
```

```
Gln Ala Ala Lys Glu Phe Val Asn Trp Leu Leu Ala Gly Gly Pro Ser
            20                  25                  30

Ser Gly Ala Pro Pro Ser Lys
        35                  40

<210> SEQ ID NO 24
<211> LENGTH: 42
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: mt-226

<400> SEQUENCE: 24

Tyr Ala Pro Gly Thr Phe Ile Ser Asp Tyr Ser Ile Ala Met Asp Lys
1               5                   10                  15

Ile His Gln Gln Asp Phe Val Cys Trp Leu Leu Ala Gln Lys Gly Lys
            20                  25                  30

Lys Asn Trp Leu Lys His Asn Ile Thr Gln
        35                  40

<210> SEQ ID NO 25
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: mt-227
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (16)..(20)
<223> OTHER INFORMATION: Lactam bridge links Glu16 and Lys20
<220> FEATURE:
<221> NAME/KEY: MISC_FEATURE
<222> LOCATION: (40)..(40)
<223> OTHER INFORMATION: Epsilon amine of Lys is attached to
      Arg-Ac-Cys(PEG), wherein the Ac-Cys(PEG) is a Cys residue
      comprising an alpha amino group capped with an acetyl group
      (CH3CO) and comprising a 40 kDa PEG covalently attached to its
      side chain

<400> SEQUENCE: 25

Tyr Xaa Gln Gly Thr Phe Thr Ser Asp Tyr Ser Ile Tyr Leu Asp Glu
1               5                   10                  15

Gln Ala Ala Lys Glu Phe Val Asn Trp Leu Leu Ala Gly Gly Pro Ser
            20                  25                  30

Ser Gly Ala Pro Pro Ser Lys
        35                  40

<210> SEQ ID NO 26
<211> LENGTH: 42
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: mt-228
<220> FEATURE:
<221> NAME/KEY: MISC_FEATURE
```

-continued

```
<222> LOCATION: (24)..(24)
<223> OTHER INFORMATION: PEG (40kDa) bound to Cysteine

<400> SEQUENCE: 26

Tyr Ala Pro Gly Thr Phe Ile Ser Asp Tyr Ser Ile Ala Met Asp Lys
1               5                   10                  15

Ile His Gln Gln Asp Phe Val Cys Trp Leu Leu Ala Lys Gly Lys
            20                  25                  30

Lys Asn Trp Leu Lys His Asn Ile Thr Gln
        35                  40

<210> SEQ ID NO 27
<211> LENGTH: 39
<212> TYPE: PRT
<213> ORGANISM: Artificial Sequence
<220> FEATURE:
<223> OTHER INFORMATION: Sythetic peptide
<220> FEATURE:
<221> NAME/KEY: MISC_FEATURE
<223> OTHER INFORMATION: Analog #29
<220> FEATURE:
<221> NAME/KEY: MISC_FEATURE
<222> LOCATION: (2)..(2)
<223> OTHER INFORMATION: d-Ser
<220> FEATURE:
<221> NAME/KEY: MISC_FEATURE
<222> LOCATION: (10)..(10)
<223> OTHER INFORMATION: Acylated with a C16 fatty acyl group via
      gamma-Glu spacer
<220> FEATURE:
<221> NAME/KEY: MISC_FEATURE
<222> LOCATION: (39)..(39)
<223> OTHER INFORMATION: C-terminal amidation

<400> SEQUENCE: 27

His Ser Gln Gly Thr Phe Thr Ser Asp Lys Ser Lys Tyr Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Pro Ser
        35

<210> SEQ ID NO 28
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Analog #30
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Acylated with a C16 fatty acyl group via
      gamma-Glu spacer
<220> FEATURE:
<221> NAME/KEY: MISC_FEATURE
<222> LOCATION: (39)..(39)
<223> OTHER INFORMATION: C-terminal amidation

<400> SEQUENCE: 28

His Xaa Gln Gly Thr Phe Thr Ser Asp Lys Ser Lys Tyr Leu Asp Glu
1               5                   10                  15
```

```
Arg Ala Ala Gln Asp Phe Val Gln Trp Leu Leu Asp Gly Gly Pro Ser
            20                  25                  30

Ser Gly Ala Pro Pro Ser
        35

<210> SEQ ID NO 29
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Analog #34
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Acylated with a C16 fatty acyl group via
      gamma-Glu spacer
<220> FEATURE:
<221> NAME/KEY: MISC_FEATURE
<222> LOCATION: (31)..(31)
<223> OTHER INFORMATION: C-terminal amidation

<400> SEQUENCE: 29

His Xaa Gln Gly Thr Phe Thr Ser Asp Lys Ser Lys Tyr Leu Asp Glu
1               5                   10                  15

Arg Ala Ala Gln Asp Phe Val Gln Trp Leu Leu Asp Gly Arg Gly
            20                  25                  30

<210> SEQ ID NO 30
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Analog #36
<220> FEATURE:
<221> NAME/KEY: MISC_FEATURE
<222> LOCATION: (2)..(2)
<223> OTHER INFORMATION: d-Ser
<220> FEATURE:
<221> NAME/KEY: MISC_FEATURE
<222> LOCATION: (10)..(10)
<223> OTHER INFORMATION: Acylated with a C16 fatty acyl group via
      gamma-Glu spacer
<220> FEATURE:
<221> NAME/KEY: MISC_FEATURE
<222> LOCATION: (20)..(20)
<223> OTHER INFORMATION: Xaa is AIB
<220> FEATURE:
<221> NAME/KEY: MISC_FEATURE
<222> LOCATION: (29)..(29)
<223> OTHER INFORMATION: C-terminal amidation

<400> SEQUENCE: 30

His Ser Gln Gly Thr Phe Thr Ser Asp Lys Ser Lys Tyr Leu Asp Glu
1               5                   10                  15

Arg Arg Ala Xaa Glu Phe Val Gln Trp Leu Leu Asp Thr
            20                  25

<210> SEQ ID NO 31
<211> LENGTH: 29
<212> TYPE: PRT
```

```
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Analog #37
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Acylated with a C16 fatty acyl group via
      gamma-Glu spacer
<220> FEATURE:
<221> NAME/KEY: MISC_FEATURE
<222> LOCATION: (20)..(20)
<223> OTHER INFORMATION: Xaa is AIB
<220> FEATURE:
<221> NAME/KEY: MISC_FEATURE
<222> LOCATION: (29)..(29)
<223> OTHER INFORMATION: C-terminal amidation

<400> SEQUENCE: 31

His Xaa Gln Gly Thr Phe Thr Ser Asp Lys Ser Lys Tyr Leu Asp Glu
1               5                   10                  15

Arg Arg Ala Xaa Glu Phe Val Gln Trp Leu Leu Asp Thr
            20                  25

<210> SEQ ID NO 32
<211> LENGTH: 29
<212> TYPE: PRT
<213> ORGANISM: Artificial Sequence
<220> FEATURE:
<223> OTHER INFORMATION: Sythetic peptide
<220> FEATURE:
<221> NAME/KEY: MISC_FEATURE
<223> OTHER INFORMATION: Analog #44
<220> FEATURE:
<221> NAME/KEY: MISC_FEATURE
<222> LOCATION: (1)..(1)
<223> OTHER INFORMATION: Xaa is DMIA
<220> FEATURE:
<221> NAME/KEY: MISC_FEATURE
<222> LOCATION: (2)..(2)
<223> OTHER INFORMATION: d-Ser
<220> FEATURE:
<221> NAME/KEY: MISC_FEATURE
<222> LOCATION: (10)..(10)
<223> OTHER INFORMATION: Acylated with C16 fatty acyl group via
      gamma-Glu spacer
<220> FEATURE:
<221> NAME/KEY: MISC_FEATURE
<222> LOCATION: (29)..(29)
<223> OTHER INFORMATION: C-terminal amidation

<400> SEQUENCE: 32

Xaa Ser Gln Gly Thr Phe Thr Ser Asp Lys Ser Lys Tyr Leu Asp Glu
1               5                   10                  15

Arg Ala Ala Gln Asp Phe Val Gln Trp Leu Leu Asp Thr
            20                  25

<210> SEQ ID NO 33
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Analog #49
<220> FEATURE:
```

```
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Acylated with a C16 fatty acyl group via
      gamma-Glu-gamma-Glu spacer
<220> FEATURE:
<221> NAME/KEY: MISC_FEATURE
<222> LOCATION: (16)..(16)
<223> OTHER INFORMATION: Xaa is AIB
<220> FEATURE:
<221> NAME/KEY: MISC_FEATURE
<222> LOCATION: (39)..(39)
<223> OTHER INFORMATION: C-terminal amidation

<400> SEQUENCE: 33

His Xaa Gln Gly Thr Phe Thr Ser Asp Lys Ser Lys Tyr Leu Asp Xaa
1               5                   10                  15

Arg Ala Ala Gln Asp Phe Val Gln Trp Leu Met Asp Gly Gly Pro Ser
            20                  25                  30

Ser Gly Ala Pro Pro Pro Ser
        35

<210> SEQ ID NO 34

<400> SEQUENCE: 34

000

<210> SEQ ID NO 35
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Analog #53
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Acylated with a C16 fatty acyl group via
      gamma-Glu-gamma-Glu spacer
<220> FEATURE:
<221> NAME/KEY: MISC_FEATURE
<222> LOCATION: (16)..(16)
<223> OTHER INFORMATION: Xaa is AIB
<220> FEATURE:
<221> NAME/KEY: MISC_FEATURE
<222> LOCATION: (39)..(39)
<223> OTHER INFORMATION: C-terminal amidation

<400> SEQUENCE: 35

His Xaa Gln Gly Thr Phe Thr Ser Asp Lys Ser Lys Tyr Leu Asp Xaa
1               5                   10                  15

Arg Ala Ala Gln Asp Phe Val Gln Trp Leu Val Lys Gly Gly Pro Ser
            20                  25                  30

Ser Gly Ala Pro Pro Pro Ser
        35

<210> SEQ ID NO 36
<211> LENGTH: 39
<212> TYPE: PRT
<213> ORGANISM: Artificial Sequence
```

```
<220> FEATURE:
<223> OTHER INFORMATION: Synthetic peptide
<220> FEATURE:
<221> NAME/KEY: MISC_FEATURE
<223> OTHER INFORMATION: Analog #54
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (10)..(10)
<223> OTHER INFORMATION: Acylated with C16 fatty acyl group via
      gamma-Glu-gamma-Glu spacer
<220> FEATURE:
<221> NAME/KEY: MISC_FEATURE
<222> LOCATION: (16)..(16)
<223> OTHER INFORMATION: Xaa is AIB
<220> FEATURE:
<221> NAME/KEY: MISC_FEATURE
<222> LOCATION: (16)..(16)
<223> OTHER INFORMATION: Xaa is AIB
<220> FEATURE:
<221> NAME/KEY: MISC_FEATURE
<222> LOCATION: (39)..(39)
<223> OTHER INFORMATION: C-terminal amidation

<400> SEQUENCE: 36

His Xaa Gln Gly Thr Phe Thr Ser Asp Lys Ser Lys Tyr Leu Asp Xaa
1               5                   10                  15

Arg Ala Ala Gln Asp Phe Val Gln Trp Leu Lys Asp Gly Gly Pro Ser
                20                  25                  30

Ser Gly Ala Pro Pro Pro Ser
        35

<210> SEQ ID NO 37
<211> LENGTH: 39
<212> TYPE: PRT
<213> ORGANISM: Artificial Sequence
<220> FEATURE:
<223> OTHER INFORMATION: Sythetic peptide
<220> FEATURE:
<221> NAME/KEY: MISC_FEATURE
<223> OTHER INFORMATION: Analog #61
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Acylated with a C16 fatty acyl group via
      gamma-Glu spacer
<220> FEATURE:
<221> NAME/KEY: MISC_FEATURE
<222> LOCATION: (20)..(20)
<223> OTHER INFORMATION: Xaa is AIB
<220> FEATURE:
<221> NAME/KEY: MISC_FEATURE
<222> LOCATION: (39)..(39)
<223> OTHER INFORMATION: C-terminal amidation

<400> SEQUENCE: 37

His Xaa Gln Gly Thr Phe Thr Ser Asp Lys Ser Lys Tyr Leu Asp Glu
1               5                   10                  15

Arg Arg Ala Xaa Glu Phe Val Gln Trp Leu Leu Asp Gly Gly Pro Ser
                20                  25                  30

Ser Gly Ala Pro Pro Pro Ser
        35

<210> SEQ ID NO 38
```

```
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Analog #62
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Acylated with a C16 fatty acyl group via
      gamma-Glu spacer
<220> FEATURE:
<221> NAME/KEY: MISC_FEATURE
<222> LOCATION: (20)..(20)
<223> OTHER INFORMATION: Xaa is AIB
<220> FEATURE:
<221> NAME/KEY: MISC_FEATURE
<222> LOCATION: (39)..(39)
<223> OTHER INFORMATION: C-terminal amidation

<400> SEQUENCE: 38

His Xaa Glu Gly Thr Phe Thr Ser Asp Lys Ser Lys Tyr Leu Asp Glu
1               5                   10                  15

Arg Arg Ala Xaa Glu Phe Val Gln Trp Leu Leu Asp Gly Gly Pro Ser
            20                  25                  30

Ser Gly Ala Pro Pro Pro Ser
        35

<210> SEQ ID NO 39
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Analog #63
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Acylated with a C16 fatty acyl group via
      gamma-Glu spacer
<220> FEATURE:
<221> NAME/KEY: MISC_FEATURE
<222> LOCATION: (39)..(39)
<223> OTHER INFORMATION: C-terminal amidation

<400> SEQUENCE: 39

His Xaa Glu Gly Thr Phe Thr Ser Asp Lys Ser Lys Tyr Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Pro Ser
        35

<210> SEQ ID NO 40
<211> LENGTH: 29
<212> TYPE: PRT
<213> ORGANISM: Artificial Sequence
<220> FEATURE:
<223> OTHER INFORMATION: Synthetic peptide
```

```
<220> FEATURE:
<221> NAME/KEY: MISC_FEATURE
<223> OTHER INFORMATION: Analog #64
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Acylated with a C16 fatty acyl group via
      gamma-Glu spacer
<220> FEATURE:
<221> NAME/KEY: MISC_FEATURE
<222> LOCATION: (20)..(20)
<223> OTHER INFORMATION: Xaa is AIB
<220> FEATURE:
<221> NAME/KEY: MISC_FEATURE
<222> LOCATION: (29)..(29)
<223> OTHER INFORMATION: C-terminal amidation

<400> SEQUENCE: 40

His Xaa Glu Gly Thr Phe Thr Ser Asp Lys Ser Lys Tyr Leu Asp Glu
1               5                   10                  15

Arg Arg Ala Xaa Glu Phe Val Gln Trp Leu Leu Asp Thr
            20                  25

<210> SEQ ID NO 41
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Analog #65
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Acylated with a C16 fatty acyl group via
      gamma-Glu spacer
<220> FEATURE:
<221> NAME/KEY: MISC_FEATURE
<222> LOCATION: (20)..(20)
<223> OTHER INFORMATION: Xaa is AIB
<220> FEATURE:
<221> NAME/KEY: MISC_FEATURE
<222> LOCATION: (39)..(39)
<223> OTHER INFORMATION: C-terminal amidation

<400> SEQUENCE: 41

His Xaa Glu Gly Thr Phe Thr Ser Asp Lys Ser Lys Tyr Leu Asp Glu
1               5                   10                  15

Arg Arg Ala Xaa Asp Phe Val Gln Trp Leu Leu Asp Gly Gly Pro Ser
            20                  25                  30

Ser Gly Ala Pro Pro Pro Ser
        35

<210> SEQ ID NO 42
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
```

```
<220> FEATURE:
<221> NAME/KEY: MISC_FEATURE
<222> LOCATION: (16)..(16)
<223> OTHER INFORMATION: Xaa is AIB
<220> FEATURE:
<221> NAME/KEY: MISC_FEATURE
<222> LOCATION: (29)..(29)
<223> OTHER INFORMATION: C-terminal amidation

<400> SEQUENCE: 42

His Xaa Gln Gly Thr Phe Thr Ser Asp Tyr Ser Lys Tyr Leu Asp Xaa
1               5                   10                  15

Arg Arg Ala Gln Asp Phe Val Gln Trp Leu Met Asn Thr
            20                  25

<210> SEQ ID NO 43
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (9)..(9)
<223> OTHER INFORMATION: Acylated with a C16 fatty acyl group via
      gamma-Glu-gamma-Glu spacer
<220> FEATURE:
<221> NAME/KEY: MISC_FEATURE
<222> LOCATION: (16)..(16)
<223> OTHER INFORMATION: Xaa is AIB
<220> FEATURE:
<221> NAME/KEY: MISC_FEATURE
<222> LOCATION: (29)..(29)
<223> OTHER INFORMATION: C-terminal amidation

<400> SEQUENCE: 43

His Xaa Gln Gly Thr Phe Thr Ser Lys Tyr Ser Lys Tyr Leu Asp Xaa
1               5                   10                  15

Arg Arg Ala Gln Asp Phe Val Gln Trp Leu Met Asn Thr
            20                  25

<210> SEQ ID NO 44
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Acylated with a C16 fatty acyl group via
      gamma-Glu-gamma-Glu spacer
<220> FEATURE:
<221> NAME/KEY: MISC_FEATURE
<222> LOCATION: (16)..(16)
<223> OTHER INFORMATION: Xaa is AIB
<220> FEATURE:
<221> NAME/KEY: MISC_FEATURE
<222> LOCATION: (29)..(29)
<223> OTHER INFORMATION: C-terminal amidation

<400> SEQUENCE: 44

His Xaa Gln Gly Thr Phe Thr Ser Asp Lys Ser Lys Tyr Leu Asp Xaa
1               5                   10                  15
```

Arg Arg Ala Gln Asp Phe Val Gln Trp Leu Met Asn Thr
            20                  25

<210> SEQ ID NO 45
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (12)..(12)
<223> OTHER INFORMATION: Acylated with a C16 fatty acyl group via
      gamma-Glu-gamma-Glu spacer
<220> FEATURE:
<221> NAME/KEY: MISC_FEATURE
<222> LOCATION: (16)..(16)
<223> OTHER INFORMATION: Xaa is AIB
<220> FEATURE:
<221> NAME/KEY: MISC_FEATURE
<222> LOCATION: (29)..(29)
<223> OTHER INFORMATION: C-terminal amidation

<400> SEQUENCE: 45

His Xaa Gln Gly Thr Phe Thr Ser Asp Tyr Ser Lys Tyr Leu Asp Xaa
1               5                   10                  15

Arg Arg Ala Gln Asp Phe Val Gln Trp Leu Met Asn Thr
            20                  25

<210> SEQ ID NO 46
<211> LENGTH: 29
<212> TYPE: PRT
<213> ORGANISM: Artificial Sequence
<220> FEATURE:
<223> OTHER INFORMATION: Sythetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (16)..(16)
<223> OTHER INFORMATION: Acylated with a C16 fatty acyl group via
      gamma-Glu-gamma-Glu spacer
<220> FEATURE:
<221> NAME/KEY: MISC_FEATURE
<222> LOCATION: (29)..(29)
<223> OTHER INFORMATION: C-terminal amidation

<400> SEQUENCE: 46

His Xaa Gln Gly Thr Phe Thr Ser Asp Tyr Ser Lys Tyr Leu Asp Lys
1               5                   10                  15

Arg Arg Ala Gln Asp Phe Val Gln Trp Leu Met Asn Thr
            20                  25

<210> SEQ ID NO 47
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE

```
<222> LOCATION: (16)..(16)
<223> OTHER INFORMATION: Xaa is AIB
<220> FEATURE:
<221> NAME/KEY: MISC_FEATURE
<222> LOCATION: (20)..(20)
<223> OTHER INFORMATION: Acylated with a C16 fatty acyl group via
      gamma-Glu-gamma-Glu spacer
<220> FEATURE:
<221> NAME/KEY: MISC_FEATURE
<222> LOCATION: (29)..(29)
<223> OTHER INFORMATION: C-terminal amidation

<400> SEQUENCE: 47

His Xaa Gln Gly Thr Phe Thr Ser Asp Tyr Ser Lys Tyr Leu Asp Xaa
1               5                   10                  15

Arg Arg Ala Lys Asp Phe Val Gln Trp Leu Met Asn Thr
            20                  25

<210> SEQ ID NO 48
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: d-Ser
<220> FEATURE:
<221> NAME/KEY: MISC_FEATURE
<222> LOCATION: (20)..(20)
<223> OTHER INFORMATION: Xaa is AIB
<220> FEATURE:
<221> NAME/KEY: MISC_FEATURE
<222> LOCATION: (40)..(40)
<223> OTHER INFORMATION: C-terminal amidation

<400> SEQUENCE: 48

His Ser Gln Gly Thr Phe Thr Ser Asp Tyr Ser Ile Tyr Leu Asp Lys
1               5                   10                  15

Gln Ala Ala Xaa Glu Phe Val Asn Trp Leu Leu Ala Gly Gly Pro Ser
            20                  25                  30

Ser Gly Ala Pro Pro Pro Ser Cys
        35                  40

<210> SEQ ID NO 49

<400> SEQUENCE: 49

000

<210> SEQ ID NO 50
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: d-Ser
<220> FEATURE:
<221> NAME/KEY: MISC_FEATURE
<222> LOCATION: (20)..(20)
<223> OTHER INFORMATION: Xaa is AIB
<220> FEATURE:
<221> NAME/KEY: MISC_FEATURE
<222> LOCATION: (40)..(40)
<223> OTHER INFORMATION: C-terminal amidation

<400> SEQUENCE: 50
```

```
Tyr Ser Gln Gly Thr Phe Thr Ser Asp Tyr Ser Ile Tyr Leu Asp Lys
1               5                   10                  15

Gln Ala Ala Xaa Glu Phe Val Asn Trp Leu Leu Ala Gly Gly Pro Ser
            20                  25                  30

Ser Gly Ala Pro Pro Pro Ser Cys
        35                  40

<210> SEQ ID NO 51
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: d-Ser
<220> FEATURE:
<221> NAME/KEY: MISC_FEATURE
<222> LOCATION: (20)..(20)
<223> OTHER INFORMATION: Xaa is AIB
<220> FEATURE:
<221> NAME/KEY: MISC_FEATURE
<222> LOCATION: (40)..(40)
<223> OTHER INFORMATION: Covalently bound to PEG
<220> FEATURE:
<221> NAME/KEY: MISC_FEATURE
<222> LOCATION: (40)..(40)
<223> OTHER INFORMATION: C-terminal amidation

<400> SEQUENCE: 51

Tyr Ser Gln Gly Thr Phe Thr Ser Asp Tyr Ser Ile Tyr Leu Asp Lys
1               5                   10                  15

Gln Ala Ala Xaa Glu Phe Val Asn Trp Leu Leu Ala Gly Gly Pro Ser
            20                  25                  30

Ser Gly Ala Pro Pro Pro Ser Cys
        35                  40

<210> SEQ ID NO 52
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (20)..(20)
<223> OTHER INFORMATION: Xaa is AIB
<220> FEATURE:
<221> NAME/KEY: MISC_FEATURE
<222> LOCATION: (40)..(40)
<223> OTHER INFORMATION: C-terminal amidation

<400> SEQUENCE: 52

His Xaa Gln Gly Thr Phe Thr Ser Asp Tyr Ser Ile Tyr Leu Asp Lys
1               5                   10                  15

Gln Ala Ala Xaa Glu Phe Val Asn Trp Leu Leu Ala Gly Gly Pro Ser
            20                  25                  30

Ser Gly Ala Pro Pro Pro Ser Cys
        35                  40

<210> SEQ ID NO 53
<211> LENGTH: 40
```

```
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (20)..(20)
<223> OTHER INFORMATION: Xaa is AIB
<220> FEATURE:
<221> NAME/KEY: MISC_FEATURE
<222> LOCATION: (40)..(40)
<223> OTHER INFORMATION: Covalently bound to PEG
<220> FEATURE:
<221> NAME/KEY: MISC_FEATURE
<222> LOCATION: (40)..(40)
<223> OTHER INFORMATION: C-terminal amidation

<400> SEQUENCE: 53

His Xaa Gln Gly Thr Phe Thr Ser Asp Tyr Ser Ile Tyr Leu Asp Lys
1               5                   10                  15

Gln Ala Ala Xaa Glu Phe Val Asn Trp Leu Leu Ala Gly Gly Pro Ser
            20                  25                  30

Ser Gly Ala Pro Pro Pro Ser Cys
        35                  40

<210> SEQ ID NO 54
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (20)..(20)
<223> OTHER INFORMATION: Xaa is AIB
<220> FEATURE:
<221> NAME/KEY: MISC_FEATURE
<222> LOCATION: (24)..(24)
<223> OTHER INFORMATION: Xaa is AIB
<220> FEATURE:
<221> NAME/KEY: MISC_FEATURE
<222> LOCATION: (40)..(40)
<223> OTHER INFORMATION: C-terminal amidation

<400> SEQUENCE: 54

Tyr Xaa Gln Gly Thr Phe Thr Ser Asp Tyr Ser Ile Tyr Leu Asp Lys
1               5                   10                  15

Gln Ala Ala Xaa Glu Phe Val Xaa Trp Leu Leu Ala Gly Gly Pro Ser
            20                  25                  30

Ser Gly Ala Pro Pro Pro Ser Cys
        35                  40

<210> SEQ ID NO 55

<400> SEQUENCE: 55

000

<210> SEQ ID NO 56
<211> LENGTH: 40
<212> TYPE: PRT
<213> ORGANISM: Artificial Sequence
```

```
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (16)..(20)
<223> OTHER INFORMATION: Linked via lactam bridge
<220> FEATURE:
<221> NAME/KEY: MISC_FEATURE
<222> LOCATION: (24)..(24)
<223> OTHER INFORMATION: Xaa is AIB
<220> FEATURE:
<221> NAME/KEY: MISC_FEATURE
<222> LOCATION: (40)..(40)
<223> OTHER INFORMATION: C-terminal amidation

<400> SEQUENCE: 56

Tyr Xaa Gln Gly Thr Phe Thr Ser Asp Tyr Ser Ile Tyr Leu Asp Glu
1               5                   10                  15

Gln Ala Ala Lys Glu Phe Val Xaa Trp Leu Leu Ala Gly Gly Pro Ser
            20                  25                  30

Ser Gly Ala Pro Pro Pro Ser Cys
        35                  40

<210> SEQ ID NO 57

<400> SEQUENCE: 57

000

<210> SEQ ID NO 58
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (17)..(21)
<223> OTHER INFORMATION: Linked via lactam bridge
<220> FEATURE:
<221> NAME/KEY: MISC_FEATURE
<222> LOCATION: (20)..(20)
<223> OTHER INFORMATION: Xaa is AIB
<220> FEATURE:
<221> NAME/KEY: MISC_FEATURE
<222> LOCATION: (40)..(40)
<223> OTHER INFORMATION: C-terminal amidation

<400> SEQUENCE: 58

Tyr Xaa Gln Gly Thr Phe Thr Ser Asp Tyr Ser Ile Tyr Leu Asp Lys
1               5                   10                  15

Glu Ala Ala Xaa Lys Phe Val Asn Trp Leu Leu Ala Gly Gly Pro Ser
            20                  25                  30

Ser Gly Ala Pro Pro Pro Ser Cys
        35                  40

<210> SEQ ID NO 59
<211> LENGTH: 40
<212> TYPE: PRT
<213> ORGANISM: Artificial Sequence
<220> FEATURE:
<223> OTHER INFORMATION: Synthetic peptide
```

```
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (17)..(21)
<223> OTHER INFORMATION: Linked via lactam bridge
<220> FEATURE:
<221> NAME/KEY: MISC_FEATURE
<222> LOCATION: (21)..(21)
<223> OTHER INFORMATION: Xaa is AIB
<220> FEATURE:
<221> NAME/KEY: MISC_FEATURE
<222> LOCATION: (40)..(40)
<223> OTHER INFORMATION: Covalently bound to PEG
<220> FEATURE:
<221> NAME/KEY: MISC_FEATURE
<222> LOCATION: (40)..(40)
<223> OTHER INFORMATION: C-terminal amidation

<400> SEQUENCE: 59

Tyr Xaa Gln Gly Thr Phe Thr Ser Asp Tyr Ser Ile Tyr Leu Asp Lys
 1               5                  10                  15

Glu Ala Ala Xaa Lys Phe Val Asn Trp Leu Leu Ala Gly Gly Pro Ser
            20                  25                  30

Ser Gly Ala Pro Pro Pro Ser Cys
        35                  40

<210> SEQ ID NO 60
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (20)..(20)
<223> OTHER INFORMATION: Xaa is 1-aminocyclopropane-1-carboxylate
<220> FEATURE:
<221> NAME/KEY: MISC_FEATURE
<222> LOCATION: (40)..(40)
<223> OTHER INFORMATION: C-terminal amidation

<400> SEQUENCE: 60

Tyr Xaa Gln Gly Thr Phe Thr Ser Asp Tyr Ser Ile Tyr Leu Asp Lys
 1               5                  10                  15

Gln Ala Ala Xaa Glu Phe Val Asn Trp Leu Leu Ala Gly Gly Pro Ser
            20                  25                  30

Ser Gly Ala Pro Pro Pro Ser Cys
        35                  40

<210> SEQ ID NO 61

<400> SEQUENCE: 61

000

<210> SEQ ID NO 62
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
```

```
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Acylated with a C14 acyl group via gamma-Glu
      spacer
<220> FEATURE:
<221> NAME/KEY: MISC_FEATURE
<222> LOCATION: (20)..(20)
<223> OTHER INFORMATION: Xaa is AIB
<220> FEATURE:
<221> NAME/KEY: MISC_FEATURE
<222> LOCATION: (40)..(40)
<223> OTHER INFORMATION: C-terminal amidation

<400> SEQUENCE: 62

Tyr Xaa Gln Gly Thr Phe Thr Ser Asp Lys Ser Ile Tyr Leu Asp Lys
1               5                   10                  15

Gln Ala Ala Xaa Glu Phe Val Asn Trp Leu Leu Ala Gly Gly Pro Ser
            20                  25                  30

Ser Gly Ala Pro Pro Pro Ser
        35

<210> SEQ ID NO 63
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Acylated with a C14 fatty acyl group via
      gamma-Glu spacer
<220> FEATURE:
<221> NAME/KEY: MISC_FEATURE
<222> LOCATION: (20)..(20)
<223> OTHER INFORMATION: Xaa is AIB
<220> FEATURE:
<221> NAME/KEY: MISC_FEATURE
<222> LOCATION: (40)..(40)
<223> OTHER INFORMATION: Covalently bound to PEG
<220> FEATURE:
<221> NAME/KEY: MISC_FEATURE
<222> LOCATION: (40)..(40)
<223> OTHER INFORMATION: C-terminal amidation

<400> SEQUENCE: 63

Tyr Xaa Gln Gly Thr Phe Thr Ser Asp Lys Ser Ile Tyr Leu Asp Lys
1               5                   10                  15

Gln Ala Ala Xaa Glu Phe Val Asn Trp Leu Leu Ala Gly Gly Pro Ser
            20                  25                  30

Ser Gly Ala Pro Pro Pro Ser Cys
        35                  40

<210> SEQ ID NO 64
<211> LENGTH: 41
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
```

```
<221> NAME/KEY: MISC_FEATURE
<222> LOCATION: (20)..(20)
<223> OTHER INFORMATION: Xaa is AIB
<220> FEATURE:
<221> NAME/KEY: MISC_FEATURE
<222> LOCATION: (40)..(40)
<223> OTHER INFORMATION: Acylated with a C14 fatty acyl group via
      gamma-Glu spacer
<220> FEATURE:
<221> NAME/KEY: MISC_FEATURE
<222> LOCATION: (41)..(41)
<223> OTHER INFORMATION: C-terminal amidation

<400> SEQUENCE: 64

Tyr Xaa Gln Gly Thr Phe Thr Ser Asp Tyr Ser Ile Tyr Leu Asp Lys
 1               5                  10                  15

Gln Ala Ala Xaa Glu Phe Val Asn Trp Leu Leu Ala Gly Gly Pro Ser
            20                  25                  30

Ser Gly Ala Pro Pro Pro Ser Lys Gly
        35                  40

<210> SEQ ID NO 65
<211> LENGTH: 41
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (20)..(20)
<223> OTHER INFORMATION: Xaa is AIB
<220> FEATURE:
<221> NAME/KEY: MISC_FEATURE
<222> LOCATION: (40)..(40)
<223> OTHER INFORMATION: Acylated with a C14 fatty acyl group via
      gamma-Glu spacer
<220> FEATURE:
<221> NAME/KEY: MISC_FEATURE
<222> LOCATION: (41)..(41)
<223> OTHER INFORMATION: Covalently bound to a PEG
<220> FEATURE:
<221> NAME/KEY: MISC_FEATURE
<222> LOCATION: (41)..(41)
<223> OTHER INFORMATION: C-terminal amidation

<400> SEQUENCE: 65

Tyr Xaa Gln Gly Thr Phe Thr Ser Asp Tyr Ser Ile Tyr Leu Asp Lys
 1               5                  10                  15

Gln Ala Ala Xaa Glu Phe Val Asn Trp Leu Leu Ala Gly Gly Pro Ser
            20                  25                  30

Ser Gly Ala Pro Pro Pro Ser Lys Cys
        35                  40

<210> SEQ ID NO 66
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (20)..(20)
<223> OTHER INFORMATION: Xaa is AIB
```

<220> FEATURE:
<221> NAME/KEY: MISC_FEATURE
<222> LOCATION: (40)..(40)
<223> OTHER INFORMATION: Covalently bound to PEG
<220> FEATURE:
<221> NAME/KEY: MISC_FEATURE
<222> LOCATION: (40)..(40)
<223> OTHER INFORMATION: C-terminal amidation

<400> SEQUENCE: 66

Tyr Xaa Glu Gly Thr Phe Thr Ser Asp Tyr Ser Ile Tyr Leu Asp Lys
1               5                   10                  15

Gln Ala Ala Xaa Glu Phe Val Asn Trp Leu Leu Ala Gly Gly Pro Ser
            20                  25                  30

Ser Gly Ala Pro Pro Pro Ser Cys
        35                  40

<210> SEQ ID NO 67

<400> SEQUENCE: 67

000

<210> SEQ ID NO 68
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Acylated with a C14 fatty acyl group via
      gamma-Glu spacer
<220> FEATURE:
<221> NAME/KEY: MISC_FEATURE
<222> LOCATION: (20)..(20)
<223> OTHER INFORMATION: Xaa is AIB
<220> FEATURE:
<221> NAME/KEY: MISC_FEATURE
<222> LOCATION: (40)..(40)
<223> OTHER INFORMATION: Covalently bound to PEG
<220> FEATURE:
<221> NAME/KEY: MISC_FEATURE
<222> LOCATION: (40)..(40)
<223> OTHER INFORMATION: C-terminal amidation

<400> SEQUENCE: 68

Tyr Xaa Gln Gly Thr Phe Thr Ser Asp Lys Ser Ile Tyr Leu Asp Lys
1               5                   10                  15

Gln Ala Ala Xaa Glu Phe Val Asn Trp Leu Leu Ala Gly Gly Pro Ser
            20                  25                  30

Ser Gly Ala Pro Pro Pro Ser Cys
        35                  40

<210> SEQ ID NO 69
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:

<221> NAME/KEY: MISC_FEATURE
<222> LOCATION: (10)..(10)
<223> OTHER INFORMATION: Acylated with a C16 fatty acyl group via gamma-Glu spacer
<220> FEATURE:
<221> NAME/KEY: MISC_FEATURE
<222> LOCATION: (20)..(20)
<223> OTHER INFORMATION: Xaa is AIB
<220> FEATURE:
<221> NAME/KEY: MISC_FEATURE
<222> LOCATION: (40)..(40)
<223> OTHER INFORMATION: Covalently bound to PEG
<220> FEATURE:
<221> NAME/KEY: MISC_FEATURE
<222> LOCATION: (40)..(40)
<223> OTHER INFORMATION: C-terminal amidation

<400> SEQUENCE: 69

Tyr Xaa Gln Gly Thr Phe Thr Ser Asp Lys Ser Ile Tyr Leu Asp Lys
1               5                   10                  15

Gln Ala Ala Xaa Glu Phe Val Asn Trp Leu Leu Ala Gly Gly Pro Ser
            20                  25                  30

Ser Gly Ala Pro Pro Pro Ser Cys
        35                  40

<210> SEQ ID NO 70
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (20)..(20)
<223> OTHER INFORMATION: Xaa is AIB
<220> FEATURE:
<221> NAME/KEY: MISC_FEATURE
<222> LOCATION: (24)..(24)
<223> OTHER INFORMATION: Covalently bound to PEG
<220> FEATURE:
<221> NAME/KEY: MISC_FEATURE
<222> LOCATION: (40)..(40)
<223> OTHER INFORMATION: Acylated with a C16 fatty acyl group
<220> FEATURE:
<221> NAME/KEY: MISC_FEATURE
<222> LOCATION: (40)..(40)
<223> OTHER INFORMATION: C-terminal amidation

<400> SEQUENCE: 70

Tyr Xaa Gln Gly Thr Phe Thr Ser Asp Tyr Ser Ile Tyr Leu Asp Lys
1               5                   10                  15

Gln Ala Ala Xaa Glu Phe Val Cys Trp Leu Leu Ala Gly Gly Pro Ser
            20                  25                  30

Ser Gly Ala Pro Pro Pro Ser Lys
        35                  40

<210> SEQ ID NO 71

<400> SEQUENCE: 71

000

<210> SEQ ID NO 72
<211> LENGTH: 40
<212> TYPE: PRT
<213> ORGANISM: Artificial Sequence

```
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (20)..(20)
<223> OTHER INFORMATION: Xaa is AIB
<220> FEATURE:
<221> NAME/KEY: MISC_FEATURE
<222> LOCATION: (40)..(40)
<223> OTHER INFORMATION: Covalently bound to PEG
<220> FEATURE:
<221> NAME/KEY: MISC_FEATURE
<222> LOCATION: (40)..(40)
<223> OTHER INFORMATION: C-terminal amidation

<400> SEQUENCE: 72

Tyr Xaa Glu Gly Thr Phe Ile Ser Asp Tyr Ser Ile Tyr Leu Asp Lys
 1               5                  10                  15

Gln Ala Ala Xaa Glu Phe Val Asn Trp Leu Leu Ala Gly Gly Pro Ser
            20                  25                  30

Ser Gly Ala Pro Pro Pro Ser Cys
        35                  40

<210> SEQ ID NO 73
<211> LENGTH: 40
<212> TYPE: PRT
<213> ORGANISM: Artificial Sequence
<220> FEATURE:
<223> OTHER INFORMATION: Synthetic peptid
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (20)..(20)
<223> OTHER INFORMATION: Xaa is 1-aminocyclopropane-1-carboxylate
<220> FEATURE:
<221> NAME/KEY: MISC_FEATURE
<222> LOCATION: (40)..(40)
<223> OTHER INFORMATION: Covalently bound to PEG
<220> FEATURE:
<221> NAME/KEY: MISC_FEATURE
<222> LOCATION: (40)..(40)
<223> OTHER INFORMATION: C-terminal amidation

<400> SEQUENCE: 73

Tyr Xaa Glu Gly Thr Phe Thr Ser Asp Tyr Ser Ile Tyr Leu Asp Lys
 1               5                  10                  15

Gln Ala Ala Xaa Glu Phe Val Asn Trp Leu Leu Ala Gly Gly Pro Ser
            20                  25                  30

Ser Gly Ala Pro Pro Pro Ser Cys
        35                  40

<210> SEQ ID NO 74
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (20)..(20)
```

```
<223> OTHER INFORMATION: Xaa is 1-aminocyclopropane-1-carboxylate
<220> FEATURE:
<221> NAME/KEY: MISC_FEATURE
<222> LOCATION: (40)..(40)
<223> OTHER INFORMATION: Covalently bound to PEG
<220> FEATURE:
<221> NAME/KEY: MISC_FEATURE
<222> LOCATION: (40)..(40)
<223> OTHER INFORMATION: C-terminal amidation

<400> SEQUENCE: 74

His Xaa Gln Gly Thr Phe Ile Ser Asp Tyr Ser Ile Tyr Leu Asp Lys
1               5                   10                  15

Gln Ala Ala Xaa Glu Phe Val Asn Trp Leu Leu Ala Gly Gly Pro Ser
            20                  25                  30

Ser Gly Ala Pro Pro Pro Ser Cys
        35                  40

<210> SEQ ID NO 75
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (20)..(20)
<223> OTHER INFORMATION: Xaa is 1-aminocyclopropane-1-carboxylate
<220> FEATURE:
<221> NAME/KEY: MISC_FEATURE
<222> LOCATION: (40)..(40)
<223> OTHER INFORMATION: Covalently bound to PEG
<220> FEATURE:
<221> NAME/KEY: MISC_FEATURE
<222> LOCATION: (40)..(40)
<223> OTHER INFORMATION: C-terminal amidation

<400> SEQUENCE: 75

Tyr Xaa Gln Gly Thr Phe Ile Ser Asp Tyr Ser Ile Tyr Leu Asp Lys
1               5                   10                  15

Gln Ala Ala Xaa Glu Phe Val Asn Trp Leu Leu Ala Gly Gly Pro Ser
            20                  25                  30

Ser Gly Ala Pro Pro Pro Ser Cys
        35                  40

<210> SEQ ID NO 76
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Acylated with a C16 fatty acyl group via
      gamma-Glu spacer
<220> FEATURE:
<221> NAME/KEY: MISC_FEATURE
<222> LOCATION: (20)..(20)
<223> OTHER INFORMATION: Xaa is AIB
<220> FEATURE:
<221> NAME/KEY: MISC_FEATURE
<222> LOCATION: (31)..(31)
```

<223> OTHER INFORMATION: C-terminal amidation

<400> SEQUENCE: 76

His Xaa Gln Gly Thr Phe Thr Ser Asp Lys Ser Lys Tyr Leu Asp Glu
1               5                   10                  15

Arg Arg Ala Xaa Glu Phe Val Gln Trp Leu Leu Asp Gly Arg Gly
            20                  25                  30

<210> SEQ ID NO 77
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: d-Ser
<220> FEATURE:
<221> NAME/KEY: MISC_FEATURE
<222> LOCATION: (10)..(10)
<223> OTHER INFORMATION: Acylated with a C16 fatty acyl group via
      gamma-Glu spacer
<220> FEATURE:
<221> NAME/KEY: MISC_FEATURE
<222> LOCATION: (20)..(20)
<223> OTHER INFORMATION: Xaa is AIB
<220> FEATURE:
<221> NAME/KEY: MISC_FEATURE
<222> LOCATION: (31)..(31)
<223> OTHER INFORMATION: C-terminal amiation

<400> SEQUENCE: 77

His Ser Gln Gly Thr Phe Thr Ser Asp Lys Ser Lys Tyr Leu Asp Glu
1               5                   10                  15

Arg Arg Ala Xaa Glu Phe Val Gln Trp Leu Leu Asp Gly Arg Gly
            20                  25                  30

<210> SEQ ID NO 78
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: d-Ser
<220> FEATURE:
<221> NAME/KEY: MISC_FEATURE
<222> LOCATION: (10)..(10)
<223> OTHER INFORMATION: Acylated with a C16 fatty acyl group via
      gamma-Glu spacer
<220> FEATURE:
<221> NAME/KEY: MISC_FEATURE
<222> LOCATION: (20)..(20)
<223> OTHER INFORMATION: Xaa is AIB
<220> FEATURE:
<221> NAME/KEY: MISC_FEATURE
<222> LOCATION: (39)..(39)
<223> OTHER INFORMATION: C-terminal amidation

<400> SEQUENCE: 78

His Ser Gln Gly Thr Phe Thr Ser Asp Lys Ser Lys Tyr Leu Asp Glu
1               5                   10                  15

Arg Arg Ala Xaa Glu Phe Val Gln Trp Leu Leu Asp Gly Gly Pro Ser
            20                  25                  30

Ser Gly Ala Pro Pro Ser
        35

```
<210> SEQ ID NO 79
<211> LENGTH: 39
<212> TYPE: PRT
<213> ORGANISM: Artificial Sequence
<220> FEATURE:
<223> OTHER INFORMATION: Synthetic peptid
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Acylated with a C16 fatty acyl group via
      gamma-Glu spacer
<220> FEATURE:
<221> NAME/KEY: MISC_FEATURE
<222> LOCATION: (20)..(20)
<223> OTHER INFORMATION: Xaa is AIB
<220> FEATURE:
<221> NAME/KEY: MISC_FEATURE
<222> LOCATION: (39)..(39)
<223> OTHER INFORMATION: C-terminal amidation

<400> SEQUENCE: 79

His Xaa Gln Gly Thr Phe Thr Ser Asp Lys Ser Lys Tyr Leu Asp Glu
1               5                   10                  15

Arg Arg Ala Xaa Glu Phe Val Gln Trp Leu Leu Asp Gly Gly Pro Ser
            20                  25                  30

Ser Gly Ala Pro Pro Pro Ser
        35

<210> SEQ ID NO 80
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Acylated with C16 fatty acyl group via
      gamma-Glu spacer
<220> FEATURE:
<221> NAME/KEY: MISC_FEATURE
<222> LOCATION: (39)..(39)
<223> OTHER INFORMATION: C-terminal amidation

<400> SEQUENCE: 80

His Xaa Glu Gly Thr Phe Thr Ser Asp Lys Ser Lys Tyr Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Pro Ser
        35

<210> SEQ ID NO 81
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
```

```
<220> FEATURE:
<221> NAME/KEY: MISC_FEATURE
<222> LOCATION: (10)..(10)
<223> OTHER INFORMATION: Acylated with C16 fatty acyl group via
      gamma-Glu-gamma-Glu spacer
<220> FEATURE:
<221> NAME/KEY: MISC_FEATURE
<222> LOCATION: (20)..(20)
<223> OTHER INFORMATION: Xaa is AIB
<220> FEATURE:
<221> NAME/KEY: MISC_FEATURE
<222> LOCATION: (39)..(39)
<223> OTHER INFORMATION: C-terminal amidation

<400> SEQUENCE: 81

Tyr Xaa Gln Gly Thr Phe Thr Ser Asp Lys Ser Ile Tyr Leu Asp Lys
1               5                   10                  15

Gln Ala Ala Xaa Glu Phe Val Asn Trp Leu Leu Ala Gly Gly Pro Ser
            20                  25                  30

Ser Gly Ala Pro Pro Pro Ser
            35

<210> SEQ ID NO 82
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Acylated with C16 fatty acyl group via
      gamma-Glu-gamma-Glu spacer
<220> FEATURE:
<221> NAME/KEY: MISC_FEATURE
<222> LOCATION: (20)..(20)
<223> OTHER INFORMATION: Xaa is AIB
<220> FEATURE:
<221> NAME/KEY: MISC_FEATURE
<222> LOCATION: (39)..(39)
<223> OTHER INFORMATION: C-terminal amidation

<400> SEQUENCE: 82

Tyr Xaa Glu Gly Thr Phe Thr Ser Asp Lys Ser Ile Tyr Leu Asp Lys
1               5                   10                  15

Gln Ala Ala Xaa Glu Phe Val Asn Trp Leu Leu Ala Gly Gly Pro Ser
            20                  25                  30

Ser Gly Ala Pro Pro Pro Ser
            35

<210> SEQ ID NO 83
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Acylated with a C16 fatty acyl group via
      gamma-Glu spacer
<220> FEATURE:
<221> NAME/KEY: MISC_FEATURE
```

```
<222> LOCATION: (20)..(20)
<223> OTHER INFORMATION: Xaa is AIB
<220> FEATURE:
<221> NAME/KEY: MISC_FEATURE
<222> LOCATION: (39)..(39)
<223> OTHER INFORMATION: C-terminal amidation

<400> SEQUENCE: 83

His Xaa Gln Gly Thr Phe Thr Ser Asp Lys Ser Lys Tyr Leu Asp Glu
1               5                   10                  15

Arg Arg Ala Xaa Asp Phe Val Gln Trp Leu Leu Asp Gly Gly Pro Ser
            20                  25                  30

Ser Gly Ala Pro Pro Pro Ser
        35

<210> SEQ ID NO 84
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Acylated with C16 fatty acyl group via
      gamma-Glu spacer
<220> FEATURE:
<221> NAME/KEY: MISC_FEATURE
<222> LOCATION: (20)..(20)
<223> OTHER INFORMATION: Xaa is AIB
<220> FEATURE:
<221> NAME/KEY: MISC_FEATURE
<222> LOCATION: (39)..(39)
<223> OTHER INFORMATION: C-terminal amidation

<400> SEQUENCE: 84

His Xaa Glu Gly Thr Phe Thr Ser Asp Lys Ser Lys Tyr Leu Asp Glu
1               5                   10                  15

Arg Arg Ala Xaa Asp Phe Val Gln Trp Leu Leu Asp Gly Gly Pro Ser
            20                  25                  30

Ser Gly Ala Pro Pro Pro Ser
        35

<210> SEQ ID NO 85
<211> LENGTH: 29
<212> TYPE: PRT
<213> ORGANISM: Artificial Sequence
<220> FEATURE:
<223> OTHER INFORMATION: Synthetic peptid
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Acylated with a C16 fatty acyl group via
      gamma-Glu spacer
<220> FEATURE:
<221> NAME/KEY: MISC_FEATURE
<222> LOCATION: (20)..(20)
<223> OTHER INFORMATION: Xaa is AIB
<220> FEATURE:
<221> NAME/KEY: MISC_FEATURE
<222> LOCATION: (29)..(29)
<223> OTHER INFORMATION: C-terminal amidation
```

<400> SEQUENCE: 85

His Xaa Glu Gly Thr Phe Thr Ser Asp Lys Ser Lys Tyr Leu Asp Glu
1               5                   10                  15

Arg Arg Ala Xaa Glu Phe Val Gln Trp Leu Leu Asp Thr
            20                  25

<210> SEQ ID NO 86
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (40)..(40)
<223> OTHER INFORMATION: Acylated with a C16 fatty acyl group
<220> FEATURE:
<221> NAME/KEY: MISC_FEATURE
<222> LOCATION: (40)..(40)
<223> OTHER INFORMATION: C-terminal amidation

<400> SEQUENCE: 86

His Xaa Glu Gly Thr Phe Ile Ser Asp Tyr Ser Lys Tyr Leu Asp Glu
1               5                   10                  15

Gln Ala Ala Lys Glu Phe Ile Ala Trp Leu Met Asn Gly Gly Pro Ser
            20                  25                  30

Ser Gly Ala Pro Pro Pro Ser Lys
        35                  40

<210> SEQ ID NO 87
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (20)..(20)
<223> OTHER INFORMATION: Xaa is AIB
<220> FEATURE:
<221> NAME/KEY: MISC_FEATURE
<222> LOCATION: (40)..(40)
<223> OTHER INFORMATION: Acylated with C16 fatty acyl group
<220> FEATURE:
<221> NAME/KEY: MISC_FEATURE
<222> LOCATION: (40)..(40)
<223> OTHER INFORMATION: C-terminal amidation

<400> SEQUENCE: 87

His Xaa Gln Gly Thr Phe Thr Ser Asp Tyr Ser Lys Tyr Leu Asp Glu
1               5                   10                  15

Arg Arg Ala Xaa Glu Phe Val Asn Trp Leu Leu Ala Gly Gly Pro Ser
            20                  25                  30

Ser Gly Ala Pro Pro Pro Ser Lys
        35                  40

<210> SEQ ID NO 88
<211> LENGTH: 40
<212> TYPE: PRT
<213> ORGANISM: Artificial Sequence

```
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (20)..(20)
<223> OTHER INFORMATION: Xaa is AIB
<220> FEATURE:
<221> NAME/KEY: MISC_FEATURE
<222> LOCATION: (40)..(40)
<223> OTHER INFORMATION: Acylated with a C16 fatty acyl group
<220> FEATURE:
<221> NAME/KEY: MISC_FEATURE
<222> LOCATION: (40)..(40)
<223> OTHER INFORMATION: C-terminal amidation

<400> SEQUENCE: 88

Tyr Xaa Gln Gly Thr Phe Thr Ser Asp Tyr Ser Lys Tyr Leu Asp Glu
1               5                   10                  15

Arg Arg Ala Xaa Glu Phe Val Asn Trp Leu Leu Ala Gly Gly Pro Ser
            20                  25                  30

Ser Gly Ala Pro Pro Pro Ser Lys
        35                  40

<210> SEQ ID NO 89
<211> LENGTH: 41
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (40)..(40)
<223> OTHER INFORMATION: Acylated with a C16 fatty acyl group via
      gamma-Glu-gamma-Glu spacer
<220> FEATURE:
<221> NAME/KEY: MISC_FEATURE
<222> LOCATION: (41)..(41)
<223> OTHER INFORMATION: C-terminal amidation

<400> SEQUENCE: 89

His Xaa Gln Gly Thr Phe Thr Ser Asp Tyr Ser Lys Tyr Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Pro Ser Lys Gly
35                      40

<210> SEQ ID NO 90
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Acylated with a C16 fatty acyl group via
      gamma-Glu-gamma-Glu spacer
<220> FEATURE:
```

<221> NAME/KEY: MISC_FEATURE
<222> LOCATION: (39)..(39)
<223> OTHER INFORMATION: C-terminal amidation

<400> SEQUENCE: 90

His Xaa Gln Gly Thr Phe Thr Ser Asp Lys Ser Lys Tyr Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Pro Ser
35

<210> SEQ ID NO 91
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Acylated with a C16 fatty acyl group via
      gamma-Glu-gamma-Glu spacer
<220> FEATURE:
<221> NAME/KEY: MISC_FEATURE
<222> LOCATION: (20)..(20)
<223> OTHER INFORMATION: Xaa is AIB
<220> FEATURE:
<221> NAME/KEY: MISC_FEATURE
<222> LOCATION: (39)..(39)
<223> OTHER INFORMATION: C-terminal amidation

<400> SEQUENCE: 91

Tyr Xaa Gln Gly Thr Phe Thr Ser Asp Lys Ser Ile Tyr Leu Asp Lys
1               5                   10                  15

Gln Ala Ala Xaa Glu Phe Val Asn Trp Leu Leu Asp Gly Gly Pro Ser
            20                  25                  30

Ser Gly Ala Pro Pro Pro Ser
35

<210> SEQ ID NO 92
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Acylated with a C16 fatty acyl group via
      gamma-Glu-gamma-Glu spacer
<220> FEATURE:
<221> NAME/KEY: MISC_FEATURE
<222> LOCATION: (20)..(20)
<223> OTHER INFORMATION: Xaa is AIB
<220> FEATURE:
<221> NAME/KEY: MISC_FEATURE
<222> LOCATION: (29)..(29)
<223> OTHER INFORMATION: C-terminal amidation

<400> SEQUENCE: 92

Tyr Xaa Gln Gly Thr Phe Thr Ser Asp Lys Ser Ile Tyr Leu Asp Lys
1               5                   10                  15

Gln Ala Ala Xaa Glu Phe Val Asn Trp Leu Leu Asp Thr
            20                  25

<210> SEQ ID NO 93

<400> SEQUENCE: 93

000

<210> SEQ ID NO 94
<211> LENGTH: 39
<212> TYPE: PRT
<213> ORGANISM: Artificial Sequence
<220> FEATURE:
<223> OTHER INFORMATION: Sythetic peptide
<220> FEATURE:
<221> NAME/KEY: MISC_FEATURE
<223> OTHER INFORMATION: Analog #29
<220> FEATURE:
<221> NAME/KEY: MISC_FEATURE
<222> LOCATION: (2)..(2)
<223> OTHER INFORMATION: d-Ser
<220> FEATURE:
<221> NAME/KEY: MISC_FEATURE
<222> LOCATION: (10)..(10)
<223> OTHER INFORMATION: Acylated with a C16 fatty acyl group via acid
      amino acid spacer
<220> FEATURE:
<221> NAME/KEY: MISC_FEATURE
<222> LOCATION: (39)..(39)
<223> OTHER INFORMATION: C-terminal amidation

<400> SEQUENCE: 94

His Ser Gln Gly Thr Phe Thr Ser Asp Lys Ser Lys Tyr Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Pro Ser
        35

<210> SEQ ID NO 95
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Analog #30
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Acylated with a C16 fatty acyl group via acid
      amino acid spacer
<220> FEATURE:
<221> NAME/KEY: MISC_FEATURE
<222> LOCATION: (39)..(39)
<223> OTHER INFORMATION: C-terminal amidation

<400> SEQUENCE: 95

His Xaa Gln Gly Thr Phe Thr Ser Asp Lys Ser Lys Tyr Leu Asp Glu
1               5                   10                  15

-continued

```
Arg Ala Ala Gln Asp Phe Val Gln Trp Leu Leu Asp Gly Gly Pro Ser
            20                  25                  30
Ser Gly Ala Pro Pro Pro Ser
        35
```

<210> SEQ ID NO 96
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Analog #34
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Acylated with a C16 fatty acyl group via acidic
    amino acid spacer
<220> FEATURE:
<221> NAME/KEY: MISC_FEATURE
<222> LOCATION: (31)..(31)
<223> OTHER INFORMATION: C-terminal amidation

<400> SEQUENCE: 96

```
His Xaa Gln Gly Thr Phe Thr Ser Asp Lys Ser Lys Tyr Leu Asp Glu
1               5                   10                  15
Arg Ala Ala Gln Asp Phe Val Gln Trp Leu Leu Asp Gly Arg Gly
            20                  25                  30
```

<210> SEQ ID NO 97
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Analog #36
<220> FEATURE:
<221> NAME/KEY: MISC_FEATURE
<222> LOCATION: (2)..(2)
<223> OTHER INFORMATION: d-Ser
<220> FEATURE:
<221> NAME/KEY: MISC_FEATURE
<222> LOCATION: (10)..(10)
<223> OTHER INFORMATION: Acylated with a C16 fatty acyl group via acidic
    amino acid spacer
<220> FEATURE:
<221> NAME/KEY: MISC_FEATURE
<222> LOCATION: (20)..(20)
<223> OTHER INFORMATION: Xaa is AIB
<220> FEATURE:
<221> NAME/KEY: MISC_FEATURE
<222> LOCATION: (29)..(29)
<223> OTHER INFORMATION: C-terminal amidation

<400> SEQUENCE: 97

```
His Ser Gln Gly Thr Phe Thr Ser Asp Lys Ser Lys Tyr Leu Asp Glu
1               5                   10                  15
Arg Arg Ala Xaa Glu Phe Val Gln Trp Leu Leu Asp Thr
            20                  25
```

<210> SEQ ID NO 98
<211> LENGTH: 29
<212> TYPE: PRT

```
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Analog #37
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Acylated with a C16 fatty acyl group via acidic
      amino acid spacer
<220> FEATURE:
<221> NAME/KEY: MISC_FEATURE
<222> LOCATION: (20)..(20)
<223> OTHER INFORMATION: Xaa is AIB
<220> FEATURE:
<221> NAME/KEY: MISC_FEATURE
<222> LOCATION: (29)..(29)
<223> OTHER INFORMATION: C-terminal amidation

<400> SEQUENCE: 98

His Xaa Gln Gly Thr Phe Thr Ser Asp Lys Ser Lys Tyr Leu Asp Glu
1               5                   10                  15

Arg Arg Ala Xaa Glu Phe Val Gln Trp Leu Leu Asp Thr
            20                  25

<210> SEQ ID NO 99
<211> LENGTH: 29
<212> TYPE: PRT
<213> ORGANISM: Artificial Sequence
<220> FEATURE:
<223> OTHER INFORMATION: Sythetic peptide
<220> FEATURE:
<221> NAME/KEY: MISC_FEATURE
<223> OTHER INFORMATION: Analog #44
<220> FEATURE:
<221> NAME/KEY: MISC_FEATURE
<222> LOCATION: (1)..(1)
<223> OTHER INFORMATION: Xaa is DMIA
<220> FEATURE:
<221> NAME/KEY: MISC_FEATURE
<222> LOCATION: (2)..(2)
<223> OTHER INFORMATION: d-Ser
<220> FEATURE:
<221> NAME/KEY: MISC_FEATURE
<222> LOCATION: (10)..(10)
<223> OTHER INFORMATION: Acylated with C16 fatty acyl group via acidic
      amino acid spacer
<220> FEATURE:
<221> NAME/KEY: MISC_FEATURE
<222> LOCATION: (29)..(29)
<223> OTHER INFORMATION: C-terminal amidation

<400> SEQUENCE: 99

Xaa Ser Gln Gly Thr Phe Thr Ser Asp Lys Ser Lys Tyr Leu Asp Glu
1               5                   10                  15

Arg Ala Ala Gln Asp Phe Val Gln Trp Leu Leu Asp Thr
            20                  25

<210> SEQ ID NO 100
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Analog #49
<220> FEATURE:
```

```
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Acylated with a C16 fatty acyl group via
      dipeptide spacer
<220> FEATURE:
<221> NAME/KEY: MISC_FEATURE
<222> LOCATION: (16)..(16)
<223> OTHER INFORMATION: Xaa is AIB
<220> FEATURE:
<221> NAME/KEY: MISC_FEATURE
<222> LOCATION: (39)..(39)
<223> OTHER INFORMATION: C-terminal amidation

<400> SEQUENCE: 100

His Xaa Gln Gly Thr Phe Thr Ser Asp Lys Ser Lys Tyr Leu Asp Xaa
1               5                   10                  15

Arg Ala Ala Gln Asp Phe Val Gln Trp Leu Met Asp Gly Gly Pro Ser
            20                  25                  30

Ser Gly Ala Pro Pro Ser
        35

<210> SEQ ID NO 101

<400> SEQUENCE: 101

000

<210> SEQ ID NO 102
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Analog #53
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Acylated with a C16 fatty acyl group via
      dipeptide spacer
<220> FEATURE:
<221> NAME/KEY: MISC_FEATURE
<222> LOCATION: (16)..(16)
<223> OTHER INFORMATION: Xaa is AIB
<220> FEATURE:
<221> NAME/KEY: MISC_FEATURE
<222> LOCATION: (39)..(39)
<223> OTHER INFORMATION: C-terminal amidation

<400> SEQUENCE: 102

His Xaa Gln Gly Thr Phe Thr Ser Asp Lys Ser Lys Tyr Leu Asp Xaa
1               5                   10                  15

Arg Ala Ala Gln Asp Phe Val Gln Trp Leu Val Lys Gly Gly Pro Ser
            20                  25                  30

Ser Gly Ala Pro Pro Ser
        35

<210> SEQ ID NO 103
<211> LENGTH: 39
<212> TYPE: PRT
<213> ORGANISM: Artificial Sequence
```

```
<220> FEATURE:
<223> OTHER INFORMATION: Synthetic peptide
<220> FEATURE:
<221> NAME/KEY: MISC_FEATURE
<223> OTHER INFORMATION: Analog #54
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Acylated with C16 fatty acyl group via acidic
      amino acid spacer
<220> FEATURE:
<221> NAME/KEY: MISC_FEATURE
<222> LOCATION: (16)..(16)
<223> OTHER INFORMATION: Xaa is AIB
<220> FEATURE:
<221> NAME/KEY: MISC_FEATURE
<222> LOCATION: (39)..(39)
<223> OTHER INFORMATION: C-terminal amidation

<400> SEQUENCE: 103

His Xaa Gln Gly Thr Phe Thr Ser Asp Lys Ser Lys Tyr Leu Asp Xaa
1               5                   10                  15
Arg Ala Ala Gln Asp Phe Val Gln Trp Leu Lys Asp Gly Gly Pro Ser
            20                  25                  30
Ser Gly Ala Pro Pro Pro Ser
        35

<210> SEQ ID NO 104
<211> LENGTH: 39
<212> TYPE: PRT
<213> ORGANISM: Artificial Sequence
<220> FEATURE:
<223> OTHER INFORMATION: Sythetic peptide
<220> FEATURE:
<221> NAME/KEY: MISC_FEATURE
<223> OTHER INFORMATION: Analog #61
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Acylated with a C16 fatty acyl group via acidic
      amino acid spacer
<220> FEATURE:
<221> NAME/KEY: MISC_FEATURE
<222> LOCATION: (20)..(20)
<223> OTHER INFORMATION: Xaa is AIB
<220> FEATURE:
<221> NAME/KEY: MISC_FEATURE
<222> LOCATION: (39)..(39)
<223> OTHER INFORMATION: C-terminal amidation

<400> SEQUENCE: 104

His Xaa Gln Gly Thr Phe Thr Ser Asp Lys Ser Lys Tyr Leu Asp Glu
1               5                   10                  15
Arg Arg Ala Xaa Glu Phe Val Gln Trp Leu Leu Asp Gly Gly Pro Ser
            20                  25                  30
Ser Gly Ala Pro Pro Pro Ser
35

<210> SEQ ID NO 105
<211> LENGTH: 39
<212> TYPE: PRT
<213> ORGANISM: Artificial Sequence
<220> FEATURE:
```

<223> OTHER INFORMATION: Synthetic peptide
<220> FEATURE:
<221> NAME/KEY: MISC_FEATURE
<223> OTHER INFORMATION: Analog #62
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Acylated with a C16 fatty acyl group via acidic
      amino acid spacer
<220> FEATURE:
<221> NAME/KEY: MISC_FEATURE
<222> LOCATION: (20)..(20)
<223> OTHER INFORMATION: Xaa is AIB
<220> FEATURE:
<221> NAME/KEY: MISC_FEATURE
<222> LOCATION: (39)..(39)
<223> OTHER INFORMATION: C-terminal amidation

<400> SEQUENCE: 105

His Xaa Glu Gly Thr Phe Thr Ser Asp Lys Ser Lys Tyr Leu Asp Glu
1               5                   10                  15

Arg Arg Ala Xaa Glu Phe Val Gln Trp Leu Leu Asp Gly Gly Pro Ser
            20                  25                  30

Ser Gly Ala Pro Pro Pro Ser
35

<210> SEQ ID NO 106
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Analog #63
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Acylated with a C16 fatty acyl group via acidic
      amino acid spacer
<220> FEATURE:
<221> NAME/KEY: MISC_FEATURE
<222> LOCATION: (39)..(39)
<223> OTHER INFORMATION: C-terminal amidation

<400> SEQUENCE: 106

His Xaa Glu Gly Thr Phe Thr Ser Asp Lys Ser Lys Tyr Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Pro Ser
35

<210> SEQ ID NO 107
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Analog #64
<220> FEATURE:

```
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Acylated with a C16 fatty acyl group via acidic
      amino acid spacer
<220> FEATURE:
<221> NAME/KEY: MISC_FEATURE
<222> LOCATION: (20)..(20)
<223> OTHER INFORMATION: Xaa is AIB
<220> FEATURE:
<221> NAME/KEY: MISC_FEATURE
<222> LOCATION: (29)..(29)
<223> OTHER INFORMATION: C-terminal amidation

<400> SEQUENCE: 107

His Xaa Glu Gly Thr Phe Thr Ser Asp Lys Ser Lys Tyr Leu Asp Glu
1               5                   10                  15

Arg Arg Ala Xaa Glu Phe Val Gln Trp Leu Leu Asp Thr
            20                  25

<210> SEQ ID NO 108
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Analog #65
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Acylated with a C16 fatty acyl group via acidic
      amino acid spacer
<220> FEATURE:
<221> NAME/KEY: MISC_FEATURE
<222> LOCATION: (20)..(20)
<223> OTHER INFORMATION: Xaa is AIB
<220> FEATURE:
<221> NAME/KEY: MISC_FEATURE
<222> LOCATION: (39)..(39)
<223> OTHER INFORMATION: C-terminal amidation

<400> SEQUENCE: 108

His Xaa Glu Gly Thr Phe Thr Ser Asp Lys Ser Lys Tyr Leu Asp Glu
1               5                   10                  15

Arg Arg Ala Xaa Asp Phe Val Gln Trp Leu Leu Asp Gly Gly Pro Ser
            20                  25                  30

Ser Gly Ala Pro Pro Pro Ser
        35

<210> SEQ ID NO 109
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (9)..(9)
```

```
<223> OTHER INFORMATION: Acylated with a C16 fatty acyl group via
      dipeptide spacer
<220> FEATURE:
<221> NAME/KEY: MISC_FEATURE
<222> LOCATION: (16)..(16)
<223> OTHER INFORMATION: Xaa is AIB
<220> FEATURE:
<221> NAME/KEY: MISC_FEATURE
<222> LOCATION: (29)..(29)
<223> OTHER INFORMATION: C-terminal amidation

<400> SEQUENCE: 109

His Xaa Gln Gly Thr Phe Thr Ser Lys Tyr Ser Lys Tyr Leu Asp Xaa
1               5                   10                  15

Arg Arg Ala Gln Asp Phe Val Gln Trp Leu Met Asn Thr
            20                  25

<210> SEQ ID NO 110
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Acylated with a C16 fatty acyl group via
      dipeptide spacer
<220> FEATURE:
<221> NAME/KEY: MISC_FEATURE
<222> LOCATION: (16)..(16)
<223> OTHER INFORMATION: Xaa is AIB
<220> FEATURE:
<221> NAME/KEY: MISC_FEATURE
<222> LOCATION: (29)..(29)
<223> OTHER INFORMATION: C-terminal amidation

<400> SEQUENCE: 110

His Xaa Gln Gly Thr Phe Thr Ser Asp Lys Ser Lys Tyr Leu Asp Xaa
1               5                   10                  15

Arg Arg Ala Gln Asp Phe Val Gln Trp Leu Met Asn Thr
            20                  25

<210> SEQ ID NO 111
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (12)..(12)
<223> OTHER INFORMATION: Acylated with a C16 fatty acyl group via
      dipeptide spacer
<220> FEATURE:
<221> NAME/KEY: MISC_FEATURE
<222> LOCATION: (16)..(16)
<223> OTHER INFORMATION: Xaa is AIB
<220> FEATURE:
<221> NAME/KEY: MISC_FEATURE
<222> LOCATION: (29)..(29)
<223> OTHER INFORMATION: C-terminal amidation

<400> SEQUENCE: 111
```

His Xaa Gln Gly Thr Phe Thr Ser Asp Tyr Ser Lys Tyr Leu Asp Xaa
1               5                   10                  15

Arg Arg Ala Gln Asp Phe Val Gln Trp Leu Met Asn Thr
            20                  25

<210> SEQ ID NO 112
<211> LENGTH: 29
<212> TYPE: PRT
<213> ORGANISM: Artificial Sequence
<220> FEATURE:
<223> OTHER INFORMATION: Sythetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (16)..(16)
<223> OTHER INFORMATION: Acylated with a C16 fatty acyl group via
      dipeptide spacer
<220> FEATURE:
<221> NAME/KEY: MISC_FEATURE
<222> LOCATION: (29)..(29)
<223> OTHER INFORMATION: C-terminal amidation

<400> SEQUENCE: 112

His Xaa Gln Gly Thr Phe Thr Ser Asp Tyr Ser Lys Tyr Leu Asp Lys
1               5                   10                  15

Arg Arg Ala Gln Asp Phe Val Gln Trp Leu Met Asn Thr
            20                  25

<210> SEQ ID NO 113
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (16)..(16)
<223> OTHER INFORMATION: Xaa is AIB
<220> FEATURE:
<221> NAME/KEY: MISC_FEATURE
<222> LOCATION: (20)..(20)
<223> OTHER INFORMATION: Acylated with a C16 fatty acyl group via
      dipeptide spacer
<220> FEATURE:
<221> NAME/KEY: MISC_FEATURE
<222> LOCATION: (29)..(29)
<223> OTHER INFORMATION: C-terminal amidation

<400> SEQUENCE: 113

His Xaa Gln Gly Thr Phe Thr Ser Asp Tyr Ser Lys Tyr Leu Asp Xaa
1               5                   10                  15

Arg Arg Ala Lys Asp Phe Val Gln Trp Leu Met Asn Thr
            20                  25

<210> SEQ ID NO 114
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB

```
-continued

<220> FEATURE:
<221> NAME/KEY: MISC_FEATURE
<222> LOCATION: (10)..(10)
<223> OTHER INFORMATION: Acylated with a C14 acyl group via acidic amino
      acid spacer
<220> FEATURE:
<221> NAME/KEY: MISC_FEATURE
<222> LOCATION: (20)..(20)
<223> OTHER INFORMATION: Xaa is AIB
<220> FEATURE:
<221> NAME/KEY: MISC_FEATURE
<222> LOCATION: (40)..(40)
<223> OTHER INFORMATION: C-terminal amidation

<400> SEQUENCE: 114

Tyr Xaa Gln Gly Thr Phe Thr Ser Asp Lys Ser Ile Tyr Leu Asp Lys
1               5                   10                  15

Gln Ala Ala Xaa Glu Phe Val Asn Trp Leu Leu Ala Gly Gly Pro Ser
            20                  25                  30

Ser Gly Ala Pro Pro Pro Ser
        35

<210> SEQ ID NO 115
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Acylated with a C14 fatty acyl group via acidic
      amino acid spacer
<220> FEATURE:
<221> NAME/KEY: MISC_FEATURE
<222> LOCATION: (20)..(20)
<223> OTHER INFORMATION: Xaa is AIB
<220> FEATURE:
<221> NAME/KEY: MISC_FEATURE
<222> LOCATION: (40)..(40)
<223> OTHER INFORMATION: Covalently bound to PEG
<220> FEATURE:
<221> NAME/KEY: MISC_FEATURE
<222> LOCATION: (40)..(40)
<223> OTHER INFORMATION: C-terminal amidation

<400> SEQUENCE: 115

Tyr Xaa Gln Gly Thr Phe Thr Ser Asp Lys Ser Ile Tyr Leu Asp Lys
1               5                   10                  15

Gln Ala Ala Xaa Glu Phe Val Asn Trp Leu Leu Ala Gly Gly Pro Ser
            20                  25                  30

Ser Gly Ala Pro Pro Pro Ser
        35

<210> SEQ ID NO 116
<211> LENGTH: 41
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (20)..(20)
```

<223> OTHER INFORMATION: Xaa is AIB
<220> FEATURE:
<221> NAME/KEY: MISC_FEATURE
<222> LOCATION: (40)..(40)
<223> OTHER INFORMATION: Acylated with a C14 fatty acyl group via acidic
    amino acid spacer
<220> FEATURE:
<221> NAME/KEY: MISC_FEATURE
<222> LOCATION: (41)..(41)
<223> OTHER INFORMATION: C-terminal amidation

<400> SEQUENCE: 116

Tyr Xaa Gln Gly Thr Phe Thr Ser Asp Tyr Ser Ile Tyr Leu Asp Lys
1               5                   10                  15

Gln Ala Ala Xaa Glu Phe Val Asn Trp Leu Leu Ala Gly Gly Pro Ser
            20                  25                  30

Ser Gly Ala Pro Pro Pro Ser Lys Gly
        35                  40

<210> SEQ ID NO 117
<211> LENGTH: 41
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (20)..(20)
<223> OTHER INFORMATION: Xaa is AIB
<220> FEATURE:
<221> NAME/KEY: MISC_FEATURE
<222> LOCATION: (40)..(40)
<223> OTHER INFORMATION: Acylated with a C14 fatty acyl group via acidic
    amino acid spacer
<220> FEATURE:
<221> NAME/KEY: MISC_FEATURE
<222> LOCATION: (41)..(41)
<223> OTHER INFORMATION: Covalently bound to PEG
<220> FEATURE:
<221> NAME/KEY: MISC_FEATURE
<222> LOCATION: (41)..(41)
<223> OTHER INFORMATION: C-terminal amidation

<400> SEQUENCE: 117

Tyr Xaa Gln Gly Thr Phe Thr Ser Asp Tyr Ser Ile Tyr Leu Asp Lys
1               5                   10                  15

Gln Ala Ala Xaa Glu Phe Val Asn Trp Leu Leu Ala Gly Gly Pro Ser
            20                  25                  30

Ser Gly Ala Pro Pro Pro Ser Lys Cys
        35                  40

<210> SEQ ID NO 118
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Acylated with a C14 fatty acyl group via acidic
    amino acid spacer
<220> FEATURE:

```
<221> NAME/KEY: MISC_FEATURE
<222> LOCATION: (20)..(20)
<223> OTHER INFORMATION: Xaa is AIB
<220> FEATURE:
<221> NAME/KEY: MISC_FEATURE
<222> LOCATION: (40)..(40)
<223> OTHER INFORMATION: Covalently bound to PEG
<220> FEATURE:
<221> NAME/KEY: MISC_FEATURE
<222> LOCATION: (40)..(40)
<223> OTHER INFORMATION: C-terminal amidation

<400> SEQUENCE: 118

Tyr Xaa Gln Gly Thr Phe Thr Ser Asp Lys Ser Ile Tyr Leu Asp Lys
1               5                   10                  15

Gln Ala Ala Xaa Glu Phe Val Asn Trp Leu Leu Ala Gly Gly Pro Ser
            20                  25                  30

Ser Gly Ala Pro Pro Pro Ser Cys
        35                  40

<210> SEQ ID NO 119
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Acylated with a C16 fatty acyl group via acidic
      amino acid spacer
<220> FEATURE:
<221> NAME/KEY: MISC_FEATURE
<222> LOCATION: (20)..(20)
<223> OTHER INFORMATION: Xaa is AIB
<220> FEATURE:
<221> NAME/KEY: MISC_FEATURE
<222> LOCATION: (40)..(40)
<223> OTHER INFORMATION: Covalently bound to PEG
<220> FEATURE:
<221> NAME/KEY: MISC_FEATURE
<222> LOCATION: (40)..(40)
<223> OTHER INFORMATION: C-terminal amidation

<400> SEQUENCE: 119

Tyr Xaa Gln Gly Thr Phe Thr Ser Asp Lys Ser Ile Tyr Leu Asp Lys
1               5                   10                  15

Gln Ala Ala Xaa Glu Phe Val Asn Trp Leu Leu Ala Gly Gly Pro Ser
            20                  25                  30

Ser Gly Ala Pro Pro Pro Ser Cys
        35                  40

<210> SEQ ID NO 120
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Acylated with a C16 fatty acyl group via acidic
      amino acid spacer
```

<220> FEATURE:
<221> NAME/KEY: MISC_FEATURE
<222> LOCATION: (20)..(20)
<223> OTHER INFORMATION: Xaa is AIB
<220> FEATURE:
<221> NAME/KEY: MISC_FEATURE
<222> LOCATION: (31)..(31)
<223> OTHER INFORMATION: C-terminal amidation

<400> SEQUENCE: 120

His Xaa Gln Gly Thr Phe Thr Ser Asp Lys Ser Lys Tyr Leu Asp Glu
1               5                   10                  15

Arg Arg Ala Xaa Glu Phe Val Gln Trp Leu Leu Asp Gly Arg Gly
            20                  25                  30

<210> SEQ ID NO 121
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: d-Ser
<220> FEATURE:
<221> NAME/KEY: MISC_FEATURE
<222> LOCATION: (10)..(10)
<223> OTHER INFORMATION: Acylated with a C16 fatty acyl group via acidic
      amino acid spacer
<220> FEATURE:
<221> NAME/KEY: MISC_FEATURE
<222> LOCATION: (20)..(20)
<223> OTHER INFORMATION: Xaa is AIB
<220> FEATURE:
<221> NAME/KEY: MISC_FEATURE
<222> LOCATION: (31)..(31)
<223> OTHER INFORMATION: C-terminal amiation

<400> SEQUENCE: 121

His Ser Gln Gly Thr Phe Thr Ser Asp Lys Ser Lys Tyr Leu Asp Glu
1               5                   10                  15

Arg Arg Ala Xaa Glu Phe Val Gln Trp Leu Leu Asp Gly Arg Gly
            20                  25                  30

<210> SEQ ID NO 122
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: d-Ser
<220> FEATURE:
<221> NAME/KEY: MISC_FEATURE
<222> LOCATION: (10)..(10)
<223> OTHER INFORMATION: Acylated with a C16 fatty acyl group via acidic
      amino acid spacer
<220> FEATURE:
<221> NAME/KEY: MISC_FEATURE
<222> LOCATION: (20)..(20)
<223> OTHER INFORMATION: Xaa is AIB
<220> FEATURE:
<221> NAME/KEY: MISC_FEATURE
<222> LOCATION: (39)..(39)
<223> OTHER INFORMATION: C-terminal amidation

<400> SEQUENCE: 122

His Ser Gln Gly Thr Phe Thr Ser Asp Lys Ser Lys Tyr Leu Asp Glu
1               5                   10                  15

Arg Arg Ala Xaa Glu Phe Val Gln Trp Leu Leu Asp Gly Gly Pro Ser
            20                  25                  30

Ser Gly Ala Pro Pro Pro Ser
        35

<210> SEQ ID NO 123
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Acylated with a C16 fatty acyl group via acidic
      amino acid spacer
<220> FEATURE:
<221> NAME/KEY: MISC_FEATURE
<222> LOCATION: (20)..(20)
<223> OTHER INFORMATION: Xaa is AIB
<220> FEATURE:
<221> NAME/KEY: MISC_FEATURE
<222> LOCATION: (39)..(39)
<223> OTHER INFORMATION: C-terminal amidation

<400> SEQUENCE: 123

His Xaa Gln Gly Thr Phe Thr Ser Asp Lys Ser Lys Tyr Leu Asp Glu
1               5                   10                  15

Arg Arg Ala Xaa Glu Phe Val Gln Trp Leu Leu Asp Gly Gly Pro Ser
            20                  25                  30

Ser Gly Ala Pro Pro Pro Ser
        35

<210> SEQ ID NO 124
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Acylated with C16 fatty acyl group via acidic
      amino acid spacer
<220> FEATURE:
<221> NAME/KEY: MISC_FEATURE
<222> LOCATION: (39)..(39)
<223> OTHER INFORMATION: C-terminal amidation

<400> SEQUENCE: 124

His Xaa Glu Gly Thr Phe Thr Ser Asp Lys Ser Lys Tyr Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Pro Ser
        35

<210> SEQ ID NO 125
<211> LENGTH: 39
<212> TYPE: PRT

<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Acylated with C16 fatty acyl group via
      dipeptide spacer
<220> FEATURE:
<221> NAME/KEY: MISC_FEATURE
<222> LOCATION: (20)..(20)
<223> OTHER INFORMATION: Xaa is AIB
<220> FEATURE:
<221> NAME/KEY: MISC_FEATURE
<222> LOCATION: (39)..(39)
<223> OTHER INFORMATION: C-terminal amidation

<400> SEQUENCE: 125

Tyr Xaa Gln Gly Thr Phe Thr Ser Asp Lys Ser Ile Tyr Leu Asp Lys
1               5                   10                  15

Gln Ala Ala Xaa Glu Phe Val Asn Trp Leu Leu Ala Gly Gly Pro Ser
            20                  25                  30

Ser Gly Ala Pro Pro Pro Ser
        35

<210> SEQ ID NO 126
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Acylated with C16 fatty acyl group via
      dipeptide spacer
<220> FEATURE:
<221> NAME/KEY: MISC_FEATURE
<222> LOCATION: (20)..(20)
<223> OTHER INFORMATION: Xaa is AIB
<220> FEATURE:
<221> NAME/KEY: MISC_FEATURE
<222> LOCATION: (39)..(39)
<223> OTHER INFORMATION: C-terminal amidation

<400> SEQUENCE: 126

Tyr Xaa Glu Gly Thr Phe Thr Ser Asp Lys Ser Ile Tyr Leu Asp Lys
1               5                   10                  15

Gln Ala Ala Xaa Glu Phe Val Asn Trp Leu Leu Ala Gly Gly Pro Ser
            20                  25                  30

Ser Gly Ala Pro Pro Pro Ser
        35

<210> SEQ ID NO 127
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Acylated with a C16 fatty acyl group via acidic
      amino acid spacer
<220> FEATURE:
<221> NAME/KEY: MISC_FEATURE
<222> LOCATION: (20)..(20)
<223> OTHER INFORMATION: Xaa is AIB
<220> FEATURE:
<221> NAME/KEY: MISC_FEATURE
<222> LOCATION: (39)..(39)
<223> OTHER INFORMATION: C-terminal amidation

<400> SEQUENCE: 127

His Xaa Gln Gly Thr Phe Thr Ser Asp Lys Ser Lys Tyr Leu Asp Glu
1               5                   10                  15

Arg Arg Ala Xaa Asp Phe Val Gln Trp Leu Leu Asp Gly Gly Pro Ser
            20                  25                  30

Ser Gly Ala Pro Pro Pro Ser
            35

<210> SEQ ID NO 128
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Acylated with C16 fatty acyl group via acidic
      amino acid spacer
<220> FEATURE:
<221> NAME/KEY: MISC_FEATURE
<222> LOCATION: (20)..(20)
<223> OTHER INFORMATION: Xaa is AIB
<220> FEATURE:
<221> NAME/KEY: MISC_FEATURE
<222> LOCATION: (39)..(39)
<223> OTHER INFORMATION: C-terminal amidation

<400> SEQUENCE: 128

His Xaa Glu Gly Thr Phe Thr Ser Asp Lys Ser Lys Tyr Leu Asp Glu
1               5                   10                  15

Arg Arg Ala Xaa Asp Phe Val Gln Trp Leu Leu Asp Gly Gly Pro Ser
            20                  25                  30

Ser Gly Ala Pro Pro Pro Ser
            35

<210> SEQ ID NO 129
<211> LENGTH: 29
<212> TYPE: PRT
<213> ORGANISM: Artificial Sequence
<220> FEATURE:
<223> OTHER INFORMATION: Synthetic peptid
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Acylated with a C16 fatty acyl group via acidic
      amino acid spacer
<220> FEATURE:
<221> NAME/KEY: MISC_FEATURE

```
<222> LOCATION: (20)..(20)
<223> OTHER INFORMATION: Xaa is AIB
<220> FEATURE:
<221> NAME/KEY: MISC_FEATURE
<222> LOCATION: (29)..(29)
<223> OTHER INFORMATION: C-terminal amidation

<400> SEQUENCE: 129

His Xaa Glu Gly Thr Phe Thr Ser Asp Lys Ser Lys Tyr Leu Asp Glu
1               5                   10                  15

Arg Arg Ala Xaa Glu Phe Val Gln Trp Leu Leu Asp Thr
            20                  25

<210> SEQ ID NO 130
<211> LENGTH: 41
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (40)..(40)
<223> OTHER INFORMATION: Acylated with a C16 fatty acyl group via
      dipeptide spacer
<220> FEATURE:
<221> NAME/KEY: MISC_FEATURE
<222> LOCATION: (41)..(41)
<223> OTHER INFORMATION: C-terminal amidation

<400> SEQUENCE: 130

His Xaa Gln Gly Thr Phe Thr Ser Asp Tyr Ser Lys Tyr Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Pro Ser Lys Gly
        35                  40

<210> SEQ ID NO 131
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Acylated with a C16 fatty acyl group via
      dipeptide spacer
<220> FEATURE:
<221> NAME/KEY: MISC_FEATURE
<222> LOCATION: (39)..(39)
<223> OTHER INFORMATION: C-terminal amidation

<400> SEQUENCE: 131

His Xaa Gln Gly Thr Phe Thr Ser Asp Lys Ser Lys Tyr Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Pro Ser
        35
```

```
<210> SEQ ID NO 132
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Acylated with a C16 fatty acyl group via
      dipeptide spacer
<220> FEATURE:
<221> NAME/KEY: MISC_FEATURE
<222> LOCATION: (20)..(20)
<223> OTHER INFORMATION: Xaa is AIB
<220> FEATURE:
<221> NAME/KEY: MISC_FEATURE
<222> LOCATION: (39)..(39)
<223> OTHER INFORMATION: C-terminal amidation

<400> SEQUENCE: 132

Tyr Xaa Gln Gly Thr Phe Thr Ser Asp Lys Ser Ile Tyr Leu Asp Lys
1               5                   10                  15

Gln Ala Ala Xaa Glu Phe Val Asn Trp Leu Leu Asp Gly Gly Pro Ser
            20                  25                  30

Ser Gly Ala Pro Pro Pro Ser
        35

<210> SEQ ID NO 133
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Acylated with a C16 fatty acyl group via
      dipeptide spacer
<220> FEATURE:
<221> NAME/KEY: MISC_FEATURE
<222> LOCATION: (20)..(20)
<223> OTHER INFORMATION: C-terminal amidation
<220> FEATURE:
<221> NAME/KEY: MISC_FEATURE
<222> LOCATION: (29)..(29)
<223> OTHER INFORMATION: C-terminal amidation

<400> SEQUENCE: 133

Tyr Xaa Gln Gly Thr Phe Thr Ser Asp Lys Ser Ile Tyr Leu Asp Lys
1               5                   10                  15

Gln Ala Ala Xaa Glu Phe Val Asn Trp Leu Leu Asp Thr
            20                  25

<210> SEQ ID NO 134
<211> LENGTH: 40
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: mt-261
```

```
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (20)..(20)
<223> OTHER INFORMATION: Xaa is Aib
<220> FEATURE:
<221> NAME/KEY: MISC_FEATURE
<222> LOCATION: (40)..(40)
<223> OTHER INFORMATION: 16 Carbon fatty acyl group covalently attached
      Lysine
<220> FEATURE:
<221> NAME/KEY: MISC_FEATURE
<222> LOCATION: (40)..(40)
<223> OTHER INFORMATION: C-terminal amidation

<400> SEQUENCE: 134

Tyr Xaa Glu Gly Thr Phe Thr Ser Asp Tyr Ser Ile Tyr Leu Asp Lys
1               5                   10                  15

Gln Ala Ala Xaa Glu Phe Val Asn Trp Leu Leu Ala Gly Gly Pro Ser
            20                  25                  30

Ser Gly Ala Pro Pro Pro Ser Lys
        35                  40

<210> SEQ ID NO 135
<211> LENGTH: 40
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: mt-278
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (20)..(20)
<223> OTHER INFORMATION: Xaa is Aib
<220> FEATURE:
<221> NAME/KEY: MISC_FEATURE
<222> LOCATION: (40)..(40)
<223> OTHER INFORMATION: 16 Carbon fatty acyl group covalently attached
      to Lysine
<220> FEATURE:
<221> NAME/KEY: MISC_FEATURE
<222> LOCATION: (40)..(40)
<223> OTHER INFORMATION: C-terminal amidation

<400> SEQUENCE: 135

Tyr Xaa Gln Gly Thr Phe Thr Ser Asp Tyr Ser Ile Tyr Leu Asp Lys
1               5                   10                  15

Gln Ala Ala Xaa Glu Phe Val Asn Trp Leu Leu Ala Gly Gly Pro Ser
            20                  25                  30

Ser Gly Ala Pro Pro Pro Ser Lys
        35                  40

<210> SEQ ID NO 136
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: mt-384
<220> FEATURE:
```

```
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Acylated with a C16 fatty acyl group via
      gamma-Glu-gamma-Glu
      spacer
<220> FEATURE:
<221> NAME/KEY: MISC_FEATURE
<222> LOCATION: (20)..(20)
<223> OTHER INFORMATION: Xaa is AIB
<220> FEATURE:
<221> NAME/KEY: MISC_FEATURE
<222> LOCATION: (39)..(39)
<223> OTHER INFORMATION: C-terminal amidation

<400> SEQUENCE: 136

Tyr Xaa Gln Gly Thr Phe Thr Ser Asp Lys Ser Ile Tyr Leu Asp Lys
1               5                   10                  15

Gln Ala Ala Xaa Glu Phe Val Asn Trp Leu Leu Ala Gly Gly Pro Ser
            20                  25                  30

Ser Gly Ala Pro Pro Pro Ser
        35

<210> SEQ ID NO 137
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: mt-384
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Acylated with a C16 fatty acyl group via
      dipeptide spacer
<220> FEATURE:
<221> NAME/KEY: MISC_FEATURE
<222> LOCATION: (20)..(20)
<223> OTHER INFORMATION: Xaa is AIB
<220> FEATURE:
<221> NAME/KEY: MISC_FEATURE
<222> LOCATION: (39)..(39)
<223> OTHER INFORMATION: C-terminal amidation

<400> SEQUENCE: 137

Tyr Xaa Gln Gly Thr Phe Thr Ser Asp Lys Ser Ile Tyr Leu Asp Lys
1               5                   10                  15

Gln Ala Ala Xaa Glu Phe Val Asn Trp Leu Leu Ala Gly Gly Pro Ser
            20                  25                  30

Ser Gly Ala Pro Pro Pro Ser
        35

<210> SEQ ID NO 138
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
```

<220> FEATURE:
<221> NAME/KEY: MISC_FEATURE
<222> LOCATION: (20)..(20)
<223> OTHER INFORMATION: Xaa is AIB
<220> FEATURE:
<221> NAME/KEY: MISC_FEATURE
<222> LOCATION: (40)..(40)
<223> OTHER INFORMATION: Covalently bound to a C16 fatty acyl group
<220> FEATURE:
<221> NAME/KEY: MISC_FEATURE
<222> LOCATION: (40)..(40)
<223> OTHER INFORMATION: C-terminal amidation

<400> SEQUENCE: 138

Tyr Xaa Glu Gly Thr Phe Thr Ser Asp Tyr Ser Ile Tyr Leu Asp Lys
1               5                   10                  15

Gln Ala Ala Xaa Glu Phe Val Asn Trp Leu Leu Ala Gly Gly Pro Ser
            20                  25                  30

Ser Gly Ala Pro Pro Pro Ser Lys
        35                  40

<210> SEQ ID NO 139
<211> LENGTH: 41
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (20)..(20)
<223> OTHER INFORMATION: Xaa is AIB
<220> FEATURE:
<221> NAME/KEY: MISC_FEATURE
<222> LOCATION: (40)..(40)
<223> OTHER INFORMATION: Covalently bound to a C16 fatty acyl group
<220> FEATURE:
<221> NAME/KEY: MISC_FEATURE
<222> LOCATION: (41)..(41)
<223> OTHER INFORMATION: C-terminal amidation

<400> SEQUENCE: 139

Tyr Xaa Glu Gly Thr Phe Thr Ser Asp Tyr Ser Ile Tyr Leu Asp Lys
1               5                   10                  15

Gln Ala Ala Xaa Glu Phe Val Asn Trp Leu Leu Ala Gly Gly Pro Ser
            20                  25                  30

Ser Gly Ala Pro Pro Pro Ser Lys Gly
        35                  40

<210> SEQ ID NO 140
<211> LENGTH: 41
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (20)..(20)
<223> OTHER INFORMATION: Xaa is AIB
<220> FEATURE:
<221> NAME/KEY: MISC_FEATURE
<222> LOCATION: (40)..(40)
<223> OTHER INFORMATION: Covantly bound to a C16 succinoyl
<220> FEATURE:

<221> NAME/KEY: MISC_FEATURE
<222> LOCATION: (41)..(41)
<223> OTHER INFORMATION: C-terminal amidation

<400> SEQUENCE: 140

Tyr Xaa Glu Gly Thr Phe Thr Ser Asp Tyr Ser Ile Tyr Leu Asp Lys
1               5                   10                  15

Gln Ala Ala Xaa Glu Phe Val Asn Trp Leu Leu Ala Gly Gly Pro Ser
            20                  25                  30

Ser Gly Ala Pro Pro Pro Ser Lys Gly
        35                  40

<210> SEQ ID NO 141
<211> LENGTH: 41
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (20)..(20)
<223> OTHER INFORMATION: Xaa is AIB
<220> FEATURE:
<221> NAME/KEY: MISC_FEATURE
<222> LOCATION: (40)..(40)
<223> OTHER INFORMATION: Covalently bound to a C16 succinoyl via a
    beta-Ala spacer
<220> FEATURE:
<221> NAME/KEY: MISC_FEATURE
<222> LOCATION: (41)..(41)
<223> OTHER INFORMATION: C-terminal amidation

<400> SEQUENCE: 141

Tyr Xaa Glu Gly Thr Phe Thr Ser Asp Tyr Ser Ile Tyr Leu Asp Lys
1               5                   10                  15

Gln Ala Ala Xaa Glu Phe Val Asn Trp Leu Leu Ala Gly Gly Pro Ser
            20                  25                  30

Ser Gly Ala Pro Pro Pro Ser Lys Gly
        35                  40

<210> SEQ ID NO 142
<211> LENGTH: 41
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (20)..(20)
<223> OTHER INFORMATION: Xaa is AIB
<220> FEATURE:
<221> NAME/KEY: MISC_FEATURE
<222> LOCATION: (40)..(40)
<223> OTHER INFORMATION: Covalently bound to a C18 succinoyl
<220> FEATURE:
<221> NAME/KEY: MISC_FEATURE
<222> LOCATION: (41)..(41)
<223> OTHER INFORMATION: C-terminal amidation

<400> SEQUENCE: 142

Tyr Xaa Glu Gly Thr Phe Thr Ser Asp Tyr Ser Ile Tyr Leu Asp Lys
1               5                   10                  15

```
Gln Ala Ala Xaa Glu Phe Val Asn Trp Leu Leu Ala Gly Gly Pro Ser
            20                  25                  30

Ser Gly Ala Pro Pro Pro Ser Lys Gly
        35                  40

<210> SEQ ID NO 143
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Xaa is 4-amino-Phe
<220> FEATURE:
<221> NAME/KEY: MISC_FEATURE
<222> LOCATION: (10)..(10)
<223> OTHER INFORMATION: 4-amino-Phe covalently bound a C16 fatty acyl
      group via gamma-Glu-gamma-Glu spacer
<220> FEATURE:
<221> NAME/KEY: MISC_FEATURE
<222> LOCATION: (20)..(20)
<223> OTHER INFORMATION: Xaa is AIB
<220> FEATURE:
<221> NAME/KEY: MISC_FEATURE
<222> LOCATION: (39)..(39)
<223> OTHER INFORMATION: C-terminal amidation

<400> SEQUENCE: 143

Tyr Xaa Glu Gly Thr Phe Thr Ser Asp Xaa Ser Ile Tyr Leu Asp Lys
1               5                   10                  15

Gln Ala Ala Xaa Glu Phe Val Asn Trp Leu Leu Ala Gly Gly Pro Ser
            20                  25                  30

Ser Gly Ala Pro Pro Pro Ser
        35

<210> SEQ ID NO 144
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Xaa is 4-amino-Phe
<220> FEATURE:
<221> NAME/KEY: MISC_FEATURE
<222> LOCATION: (10)..(10)
<223> OTHER INFORMATION: 4-amino-Phe is covalently bound to a C16
      succinoyl
<220> FEATURE:
<221> NAME/KEY: MISC_FEATURE
<222> LOCATION: (20)..(20)
<223> OTHER INFORMATION: Xaa is AIB
<220> FEATURE:
<221> NAME/KEY: MISC_FEATURE
<222> LOCATION: (39)..(39)
<223> OTHER INFORMATION: C-terminal amidation
```

<400> SEQUENCE: 144

Tyr Xaa Glu Gly Thr Phe Thr Ser Asp Xaa Ser Ile Tyr Leu Asp Lys
1               5                   10                  15

Gln Ala Ala Xaa Glu Phe Val Asn Trp Leu Leu Ala Gly Gly Pro Ser
            20                  25                  30

Ser Gly Ala Pro Pro Ser
        35

<210> SEQ ID NO 145
<211> LENGTH: 41
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (40)..(40)
<223> OTHER INFORMATION: Xaa is 4-amino-Phe
<220> FEATURE:
<221> NAME/KEY: MISC_FEATURE
<222> LOCATION: (40)..(40)
<223> OTHER INFORMATION: 4-amino-Phe covalently bound to a C16 fatty
      acyl group via gamma-Glu-gamma-Glu spacer
<220> FEATURE:
<221> NAME/KEY: MISC_FEATURE
<222> LOCATION: (41)..(41)
<223> OTHER INFORMATION: C-terminal amidation

<400> SEQUENCE: 145

His Xaa Gln Gly Thr Phe Thr Ser Asp Tyr Ser Lys Tyr Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Ser Xaa Gly
        35                  40

<210> SEQ ID NO 146
<211> LENGTH: 41
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Xaa is AIB
<220> FEATURE:
<221> NAME/KEY: MOD_RES
<222> LOCATION: (40)..(40)
<223> OTHER INFORMATION: Xaa is 4-amino Phe
<220> FEATURE:
<221> NAME/KEY: MOD_RES
<222> LOCATION: (40)..(40)
<223> OTHER INFORMATION: 4-amino Phe covalently bound to C16 succinoyl
<220> FEATURE:
<221> NAME/KEY: MOD_RES
<222> LOCATION: (41)..(41)
<223> OTHER INFORMATION: C-terminal amidation

<400> SEQUENCE: 146

His Xaa Gln Gly Thr Phe Thr Ser Asp Tyr Ser Lys Tyr Leu Asp Glu
1               5                   10                  15

Arg Ala Ala Gln Asp Phe Val Gln Trp Leu Leu Asp Gly Gly Pro Ser
            20                  25                  30

```
Ser Gly Ala Pro Pro Ser Xaa Gly
        35                  40

<210> SEQ ID NO 147
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (6)..(6)
<223> OTHER INFORMATION: Xaa is 4-amino-Phe
<220> FEATURE:
<221> NAME/KEY: MISC_FEATURE
<222> LOCATION: (6)..(6)
<223> OTHER INFORMATION: 4-amino-Phe covalently bound to C16 fatty acyl
      group via gamma-Glu spacer
<220> FEATURE:
<221> NAME/KEY: MISC_FEATURE
<222> LOCATION: (39)..(39)
<223> OTHER INFORMATION: C-terminal amidation

<400> SEQUENCE: 147

His Xaa Gln Gly Thr Xaa Thr Ser Asp Tyr Ser Lys Tyr Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Ser
        35

<210> SEQ ID NO 148
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Xaa is 4-amino-Phe
<220> FEATURE:
<221> NAME/KEY: MISC_FEATURE
<222> LOCATION: (10)..(10)
<223> OTHER INFORMATION: 4-amino-Phe covalently bound to C16 fatty acyl
      group via gamma-Glu spacer
<220> FEATURE:
<221> NAME/KEY: MISC_FEATURE
<222> LOCATION: (39)..(39)
<223> OTHER INFORMATION: C-terminal amidation

<400> SEQUENCE: 148

His Xaa Gln Gly Thr Phe Thr Ser Asp Xaa Ser Lys Tyr Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Ser
        35

<210> SEQ ID NO 149
<211> LENGTH: 39
```

```
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (13)..(13)
<223> OTHER INFORMATION: Xaa is 4-amino-Phe
<220> FEATURE:
<221> NAME/KEY: MISC_FEATURE
<222> LOCATION: (13)..(13)
<223> OTHER INFORMATION: 4-amino-Phe covalently bound to C16 fatty acyl
      group via gamma-Glu spacer
<220> FEATURE:
<221> NAME/KEY: MISC_FEATURE
<222> LOCATION: (39)..(39)
<223> OTHER INFORMATION: C-terminal amidation

<400> SEQUENCE: 149

His Xaa Gln Gly Thr Phe Thr Ser Asp Tyr Ser Lys Xaa Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Pro Ser
        35

<210> SEQ ID NO 150
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Xaa is 4-amino-Phe
<220> FEATURE:
<221> NAME/KEY: MISC_FEATURE
<222> LOCATION: (10)..(10)
<223> OTHER INFORMATION: 4-amino-Phe covalently bound to C16 succinoyl
<220> FEATURE:
<221> NAME/KEY: MISC_FEATURE
<222> LOCATION: (39)..(39)
<223> OTHER INFORMATION: C-terminal amidation

<400> SEQUENCE: 150

His Xaa Gln Gly Thr Phe Thr Ser Asp Xaa Ser Lys Tyr Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Pro Ser
        35

<210> SEQ ID NO 151
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Xaa is AIB
```

```
<220> FEATURE:
<221> NAME/KEY: MOD_RES
<222> LOCATION: (13)..(13)
<223> OTHER INFORMATION: Covalently bound to a C16 fatty acyl group via
      gamma-Glu spacer
<220> FEATURE:
<221> NAME/KEY: MOD_RES
<222> LOCATION: (39)..(39)
<223> OTHER INFORMATION: C-terminal amidation

<400> SEQUENCE: 151

His Xaa Gln Gly Thr Phe Thr Ser Asp Tyr Ser Lys Lys Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Pro Ser
        35

<210> SEQ ID NO 152
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (14)..(14)
<223> OTHER INFORMATION: Covalently bound to a C16 fatty acyl group via
      gamma-Glu spacer
<220> FEATURE:
<221> NAME/KEY: MISC_FEATURE
<222> LOCATION: (39)..(39)
<223> OTHER INFORMATION: C-terminal amidation

<400> SEQUENCE: 152

His Xaa Gln Gly Thr Phe Thr Ser Asp Tyr Ser Lys Tyr Lys Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Pro Ser
        35

<210> SEQ ID NO 153
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (16)..(16)
<223> OTHER INFORMATION: Covalently bound to a C16 fatty acyl group via
      gamma-Glu spacer
<220> FEATURE:
<221> NAME/KEY: MISC_FEATURE
<222> LOCATION: (39)..(39)
<223> OTHER INFORMATION: C-terminal amidation

<400> SEQUENCE: 153

His Xaa Gln Gly Thr Phe Thr Ser Asp Tyr Ser Lys Tyr Leu Asp Lys
1               5                   10                  15
```

-continued

Arg Ala Ala Gln Asp Phe Val Gln Trp Leu Leu Asp Gly Gly Pro Ser
            20                  25                  30

Ser Gly Ala Pro Pro Ser
        35

<210> SEQ ID NO 154
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (17)..(17)
<223> OTHER INFORMATION: Covalently bound to C16 fatty acyl group via
      gamma-Glu spacer
<220> FEATURE:
<221> NAME/KEY: MISC_FEATURE
<222> LOCATION: (39)..(39)
<223> OTHER INFORMATION: C-terminal amidation

<400> SEQUENCE: 154

His Xaa Gln Gly Thr Phe Thr Ser Asp Tyr Ser Lys Tyr Leu Asp Glu
1               5                   10                  15

Lys Ala Gln Asp Phe Val Gln Trp Leu Leu Asp Gly Gly Pro Ser
            20                  25                  30

Ser Gly Ala Pro Pro Ser
        35

<210> SEQ ID NO 155
<211> LENGTH: 41
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (40)..(40)
<223> OTHER INFORMATION: Covalently bound to a C16 fatty acyl group via
      gamma-Glu spacer
<220> FEATURE:
<221> NAME/KEY: MISC_FEATURE
<222> LOCATION: (41)..(41)
<223> OTHER INFORMATION: C-terminal amidation

<400> SEQUENCE: 155

His Xaa Gln Gly Thr Phe Thr Ser Asp Tyr Ser Lys Tyr Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Ser Lys Gly
        35                  40

<210> SEQ ID NO 156
<211> LENGTH: 41
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE

```
<222> LOCATION: (2)..(2)
<223> OTHER INFORMATION: Xaa is AIB
<220> FEATURE:
<221> NAME/KEY: MISC_FEATURE
<222> LOCATION: (40)..(40)
<223> OTHER INFORMATION: Covalently bound to C16 succinoyl
<220> FEATURE:
<221> NAME/KEY: MISC_FEATURE
<222> LOCATION: (41)..(41)
<223> OTHER INFORMATION: C-terminal amidation

<400> SEQUENCE: 156

His Xaa Gln Gly Thr Phe Thr Ser Asp Tyr Ser Lys Tyr Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Pro Ser Lys Gly
        35                  40

<210> SEQ ID NO 157
<211> LENGTH: 41
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (40)..(40)
<223> OTHER INFORMATION: Covalently bound to C16 fatty acyl group via a
      spacer comprising an amido miniPEG acid and a gamma-Glu, wherein
      the amido miniPEG acid has a structure
      {-N- CH2- CH2-[-O-CH2-CH2-]n-COO- }, wherein n is 2
<220> FEATURE:
<221> NAME/KEY: MISC_FEATURE
<222> LOCATION: (41)..(41)
<223> OTHER INFORMATION: C-terminal amidation

<400> SEQUENCE: 157

His Xaa Gln Gly Thr Phe Thr Ser Asp Tyr Ser Lys Tyr Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Pro Ser Lys Gly
        35                  40

<210> SEQ ID NO 158
<211> LENGTH: 41
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (40)..(40)
<223> OTHER INFORMATION: Covalently bound to a C16 fatty acyl group via
      spacer comprising an amido miniPEG acid and a gamma-Glu, wherein
      the amido miniPEG acid has a structure
      {-N- CH2- CH2-[-O-CH2-CH2-]n-COO- }, wherein n is 4
<220> FEATURE:
<221> NAME/KEY: MISC_FEATURE
<222> LOCATION: (41)..(41)
<223> OTHER INFORMATION: C-terminal amidation
```

```
<400> SEQUENCE: 158

His Xaa Gln Gly Thr Phe Thr Ser Asp Tyr Ser Lys Tyr Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Pro Ser Lys Gly
        35                  40

<210> SEQ ID NO 159
<211> LENGTH: 41
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (40)..(40)
<223> OTHER INFORMATION: Covalently bound to a C16 fatty acyl group via
      spacer comprising an amido miniPEG acid and a gamma-Glu, wherein
      the amido miniPEG acid has a structure
      {-N- CH2- CH2-[-O-CH2-CH2-]n-COO }, wherein n is 8
<220> FEATURE:
<221> NAME/KEY: MISC_FEATURE
<222> LOCATION: (41)..(41)
<223> OTHER INFORMATION: C-terminal amidation

<400> SEQUENCE: 159

His Xaa Gln Gly Thr Phe Thr Ser Asp Tyr Ser Lys Tyr Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Pro Ser Lys Gly
        35                  40

<210> SEQ ID NO 160
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Covalently bound to a Lys spacer, wherein the
      Lys spacer is attached to two C16 fatty acyl groups, wherein each
      C16 fatty acyl group is attached to the Lys spacer via gamma-Glu
      spacer
<220> FEATURE:
<221> NAME/KEY: MISC_FEATURE
<222> LOCATION: (39)..(39)
<223> OTHER INFORMATION: C-terminal amidation

<400> SEQUENCE: 160

His Xaa Gln Gly Thr Phe Thr Ser Asp Lys Ser Lys Tyr Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Pro Ser
        35
```

```
<210> SEQ ID NO 161
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (40)..(40)
<223> OTHER INFORMATION: Covalently bound to a Lys spacer, wherein the
      Lys spacer is attached to two C16 fatty acyl groups, wherein each
      C16 fatty acyl group is attached to the Lys spacer via gamma-Glu
      spacer
<220> FEATURE:
<221> NAME/KEY: MISC_FEATURE
<222> LOCATION: (40)..(40)
<223> OTHER INFORMATION: C-terminal amidation

<400> SEQUENCE: 161

His Xaa Gln Gly Thr Phe Thr Ser Asp Tyr Ser Lys Tyr Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Pro Ser Lys
        35                  40

<210> SEQ ID NO 162
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Covalently bound to a C12 fatty acyl group,
      which is covalently bound to a gamma-Glu spacer, which is
      covalently bound to a C16 fatty acyl group
<220> FEATURE:
<221> NAME/KEY: MISC_FEATURE
<222> LOCATION: (39)..(39)
<223> OTHER INFORMATION: C-terminal amidation

<400> SEQUENCE: 162

His Xaa Gln Gly Thr Phe Thr Ser Asp Lys Ser Lys Tyr Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Pro Ser
        35

<210> SEQ ID NO 163
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
```

```
<221> NAME/KEY: MISC_FEATURE
<222> LOCATION: (10)..(10)
<223> OTHER INFORMATION: Covalently bound to a C16 fatty acyl group via
      gamma-Glu spacer
<220> FEATURE:
<221> NAME/KEY: MISC_FEATURE
<222> LOCATION: (40)..(40)
<223> OTHER INFORMATION: Covalently bound to a C16 fatty acyl group via
      gamma-Glu spacer
<220> FEATURE:
<221> NAME/KEY: MISC_FEATURE
<222> LOCATION: (40)..(40)
<223> OTHER INFORMATION: C-terminal amidation

<400> SEQUENCE: 163

His Xaa Gln Gly Thr Phe Thr Ser Asp Lys Ser Lys Tyr Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Pro Ser Lys
        35                  40

<210> SEQ ID NO 164
<211> LENGTH: 41
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (40)..(40)
<223> OTHER INFORMATION: Sulfur of Cys is S-alkylated with
      -C(COO)H(CH2)13CH3
<220> FEATURE:
<221> NAME/KEY: MISC_FEATURE
<222> LOCATION: (41)..(41)
<223> OTHER INFORMATION: C-terminal amidation

<400> SEQUENCE: 164

His Xaa Gln Gly Thr Phe Thr Ser Asp Tyr Ser Lys Tyr Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Pro Ser Cys Gly
        35                  40

<210> SEQ ID NO 165
<211> LENGTH: 41
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (40)..(40)
<223> OTHER INFORMATION: Lys covalently bound to Cys, the sulfur of
      which is S-alkylated with -C(COO)H(CH2)13CH3
<220> FEATURE:
<221> NAME/KEY: MISC_FEATURE
<222> LOCATION: (41)..(41)
<223> OTHER INFORMATION: C-terminal amidation

<400> SEQUENCE: 165
```

-continued

```
His Xaa Gln Gly Thr Phe Thr Ser Asp Tyr Ser Lys Tyr Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Pro Ser Lys Gly
        35                  40

<210> SEQ ID NO 166
<211> LENGTH: 41
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (40)..(40)
<223> OTHER INFORMATION: Covalently bound to gamma-Glu, which is bound
      to Cys, the sulfur of which is S-alkylated with -C(COO)H(CH2)13CH3
<220> FEATURE:
<221> NAME/KEY: MISC_FEATURE
<222> LOCATION: (41)..(41)
<223> OTHER INFORMATION: C-terminal amidation

<400> SEQUENCE: 166

His Xaa Gln Gly Thr Phe Thr Ser Asp Tyr Ser Lys Tyr Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Pro Ser Lys Gly
        35                  40

<210> SEQ ID NO 167
<211> LENGTH: 41
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (40)..(40)
<223> OTHER INFORMATION: Covalently bound to Cys, which is covalently
      bound to gamma-Glu, which is covalently bound to C16 fatty acyl
      group
<220> FEATURE:
<221> NAME/KEY: MISC_FEATURE
<222> LOCATION: (41)..(41)
<223> OTHER INFORMATION: C-terminal amidation

<400> SEQUENCE: 167

His Xaa Gln Gly Thr Phe Thr Ser Asp Tyr Ser Lys Tyr Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Pro Ser Lys Gly
        35                  40

<210> SEQ ID NO 168
<211> LENGTH: 41
<212> TYPE: PRT
```

```
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (40)..(40)
<223> OTHER INFORMATION: Covalently bound to Cys spacer, which is bound
      to gamma-Glu, which is bound to C16 fatty acyl group
<220> FEATURE:
<221> NAME/KEY: MISC_FEATURE
<222> LOCATION: (40)..(40)
<223> OTHER INFORMATION: Covalently bound to SEQ ID NO 167 via Cys
      spacer which is disulfide bonded to a 2nd Cys, which the 2nd Cys
      is bound to Lys at position 40 of SEQ ID NO 167 and is bound to
      gamma-Glu, which, in turn is bound to C16 fatty acyl group
<220> FEATURE:
<221> NAME/KEY: MISC_FEATURE
<222> LOCATION: (41)..(41)
<223> OTHER INFORMATION: C-terminal amidation

<400> SEQUENCE: 168

His Xaa Gln Gly Thr Phe Thr Ser Asp Tyr Ser Lys Tyr Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Pro Ser Lys Gly
        35                  40

<210> SEQ ID NO 169
<211> LENGTH: 41
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (40)..(40)
<223> OTHER INFORMATION: Covalently bound to Cys, which is bound to
      gamma-Glu, which is bound to C16 fatty acyl group and the sulfer
      of the Cys is thioether linked to a peptide of SEQ ID NO: 231 via
      Lys at
      position 40
<220> FEATURE:
<221> NAME/KEY: MISC_FEATURE
<222> LOCATION: (41)..(41)
<223> OTHER INFORMATION: C-terminal amidation

<400> SEQUENCE: 169

His Xaa Gln Gly Thr Phe Thr Ser Asp Tyr Ser Lys Tyr Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Pro Ser Lys Gly
        35                  40

<210> SEQ ID NO 170
<211> LENGTH: 41
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
```

```
<222> LOCATION: (2)..(2)
<223> OTHER INFORMATION: Xaa is AIB
<220> FEATURE:
<221> NAME/KEY: MISC_FEATURE
<222> LOCATION: (40)..(40)
<223> OTHER INFORMATION: Covalently bound to Cys, which is bound to
      gamma-Glu, which is bound to C16 fatty acyl group, and the sulfur
      of the Cys is disulfide bonded to a 2nd Cys, which the 2nd Cys is
      bound to a peptide of SEQ ID NO: 231 via Lys at position 40
<220> FEATURE:
<221> NAME/KEY: MISC_FEATURE
<222> LOCATION: (41)..(41)
<223> OTHER INFORMATION: C-terminal amidation

<400> SEQUENCE: 170

His Xaa Gln Gly Thr Phe Thr Ser Asp Tyr Ser Lys Tyr Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Pro Ser Lys Gly
        35                  40

<210> SEQ ID NO 171
<211> LENGTH: 41
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (40)..(40)
<223> OTHER INFORMATION: Covalently bound to C16 fatty acyl group via
      gamma-Glu-gamma-Glu spacer
<220> FEATURE:
<221> NAME/KEY: MISC_FEATURE
<222> LOCATION: (41)..(41)
<223> OTHER INFORMATION: C-terminal amidation

<400> SEQUENCE: 171

His Xaa Glu Gly Thr Phe Thr Ser Asp Tyr Ser Lys Tyr Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Pro Ser Lys Gly
        35                  40

<210> SEQ ID NO 172
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (20)..(20)
<223> OTHER INFORMATION: Xaa is AIB
<220> FEATURE:
<221> NAME/KEY: MISC_FEATURE
<222> LOCATION: (24)..(24)
<223> OTHER INFORMATION: Covalently bound to PEG
<220> FEATURE:
<221> NAME/KEY: MISC_FEATURE
<222> LOCATION: (40)..(40)
```

<223> OTHER INFORMATION: Covalently bound to C8 fatty acyl group
<220> FEATURE:
<221> NAME/KEY: MISC_FEATURE
<222> LOCATION: (40)..(40)
<223> OTHER INFORMATION: C-terminal amidation

<400> SEQUENCE: 172

Tyr Xaa Gln Gly Thr Phe Thr Ser Asp Tyr Ser Ile Tyr Leu Asp Lys
1               5                   10                  15

Gln Ala Ala Xaa Glu Phe Val Cys Trp Leu Leu Ala Gly Gly Pro Ser
            20                  25                  30

Ser Gly Ala Pro Pro Pro Ser Lys
        35                  40

<210> SEQ ID NO 173
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (20)..(20)
<223> OTHER INFORMATION: Xaa is AIB
<220> FEATURE:
<221> NAME/KEY: MISC_FEATURE
<222> LOCATION: (24)..(24)
<223> OTHER INFORMATION: Covalently bound to PEG
<220> FEATURE:
<221> NAME/KEY: MISC_FEATURE
<222> LOCATION: (40)..(40)
<223> OTHER INFORMATION: Covalently bound to C12 fatty acyl group
<220> FEATURE:
<221> NAME/KEY: MISC_FEATURE
<222> LOCATION: (40)..(40)
<223> OTHER INFORMATION: C-terminal amidation

<400> SEQUENCE: 173

Tyr Xaa Gln Gly Thr Phe Thr Ser Asp Tyr Ser Ile Tyr Leu Asp Lys
1               5                   10                  15

Gln Ala Ala Xaa Glu Phe Val Cys Trp Leu Leu Ala Gly Gly Pro Ser
            20                  25                  30

Ser Gly Ala Pro Pro Pro Ser Lys
        35                  40

<210> SEQ ID NO 174
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (20)..(20)
<223> OTHER INFORMATION: Xaa is AIB
<220> FEATURE:
<221> NAME/KEY: MISC_FEATURE
<222> LOCATION: (24)..(24)
<223> OTHER INFORMATION: Covalently bound to PEG
<220> FEATURE:
<221> NAME/KEY: MISC_FEATURE
<222> LOCATION: (40)..(40)
<223> OTHER INFORMATION: Covalently bound to C14 fatty acyl group

```
<220> FEATURE:
<221> NAME/KEY: MISC_FEATURE
<222> LOCATION: (40)..(40)
<223> OTHER INFORMATION: C-terminal amidation

<400> SEQUENCE: 174

Tyr Xaa Gln Gly Thr Phe Thr Ser Asp Tyr Ser Ile Tyr Leu Asp Lys
1               5                   10                  15

Gln Ala Ala Xaa Glu Phe Val Cys Trp Leu Leu Ala Gly Gly Pro Ser
            20                  25                  30

Ser Gly Ala Pro Pro Pro Ser Lys
        35                  40

<210> SEQ ID NO 175
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (20)..(20)
<223> OTHER INFORMATION: Xaa is AIB
<220> FEATURE:
<221> NAME/KEY: MISC_FEATURE
<222> LOCATION: (40)..(40)
<223> OTHER INFORMATION: Covantly bound to PEG
<220> FEATURE:
<221> NAME/KEY: MISC_FEATURE
<222> LOCATION: (40)..(40)
<223> OTHER INFORMATION: C-terminal amidation

<400> SEQUENCE: 175

Tyr Xaa Glu Gly Thr Phe Thr Ser Asp Tyr Ser Ile Tyr Leu Asp Lys
1               5                   10                  15

Gln Ala Ala Xaa Glu Phe Val Asn Trp Leu Leu Ala Gly Gly Pro Ser
            20                  25                  30

Ser Gly Ala Pro Pro Pro Ser Cys
        35                  40

<210> SEQ ID NO 176
<211> LENGTH: 41
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (40)..(40)
<223> OTHER INFORMATION: Covalently bound to C14 succinoyl
<220> FEATURE:
<221> NAME/KEY: MISC_FEATURE
<222> LOCATION: (41)..(41)
<223> OTHER INFORMATION: C-terminal amidation

<400> SEQUENCE: 176

His Xaa Gln Gly Thr Phe Thr Ser Asp Tyr Ser Lys Tyr Leu Asp Glu
1               5                   10                  15

Arg Ala Ala Gln Asp Phe Val Gln Trp Leu Leu Asp Gly Gly Pro Ser
            20                  25                  30
```

Ser Gly Ala Pro Pro Pro Ser Lys Gly
        35                  40

<210> SEQ ID NO 177
<211> LENGTH: 41
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (40)..(40)
<223> OTHER INFORMATION: Covalently bound to C16 fatty acyl group
<220> FEATURE:
<221> NAME/KEY: MISC_FEATURE
<222> LOCATION: (41)..(41)
<223> OTHER INFORMATION: C-terminal amidation

<400> SEQUENCE: 177

His Xaa Gln Gly Thr Phe Thr Ser Asp Tyr Ser Lys Tyr Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Pro Ser Lys Gly
        35                  40

<210> SEQ ID NO 178
<211> LENGTH: 41
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Xaa is Tyr or an amino acid covalently bound to
      a C10 to C26 acyl or alkyl group
<220> FEATURE:
<221> NAME/KEY: MISC_FEATURE
<222> LOCATION: (18)..(18)
<223> OTHER INFORMATION: Xaa is Arg or Ala
<220> FEATURE:
<221> NAME/KEY: MISC_FEATURE
<222> LOCATION: (20)..(20)
<223> OTHER INFORMATION: Xaa is AIB or Gln
<220> FEATURE:
<221> NAME/KEY: MISC_FEATURE
<222> LOCATION: (21)..(21)
<223> OTHER INFORMATION: Xaa is Asp or Glu
<220> FEATURE:
<221> NAME/KEY: MISC_FEATURE
<222> LOCATION: (28)..(28)
<223> OTHER INFORMATION: Xaa is Asp of Glu
<220> FEATURE:
<221> NAME/KEY: MISC_FEATURE
<222> LOCATION: (35)..(35)
<223> OTHER INFORMATION: Xaa is Ala, Arg or Lys
<220> FEATURE:
<221> NAME/KEY: MISC_FEATURE
<222> LOCATION: (40)..(40)
<223> OTHER INFORMATION: Xaa is absent or is Gly (e.g. when position 10
      is not Tyr) or is an amino acid covalently bound to a C10-C26 acyl
      or alkyl group
<220> FEATURE:
<221> NAME/KEY: MISC_FEATURE
<222> LOCATION: (41)..(41)

```
<223> OTHER INFORMATION: Optionally present, when residue at position 40
      is an amino acid covalently bound to C10-C26 acyl or alkyl group,
      Xaa is Gly
<220> FEATURE:
<221> NAME/KEY: MISC_FEATURE
<222> LOCATION: (41)..(41)
<223> OTHER INFORMATION: C-terminal amidation

<400> SEQUENCE: 178

His Xaa Gln Gly Thr Phe Thr Ser Asp Xaa Ser Lys Tyr Leu Asp Glu
1               5                   10                  15

Arg Xaa Ala Xaa Xaa Phe Val Gln Trp Leu Leu Xaa Gly Gly Pro Ser
            20                  25                  30

Ser Gly Xaa Pro Pro Pro Ser Xaa Xaa
        35                  40

<210> SEQ ID NO 179
<211> LENGTH: 41
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Xaa is Tyr or an amino acid covalently bound to
      a C10 to C26 acyl or alkyl group
<220> FEATURE:
<221> NAME/KEY: MISC_FEATURE
<222> LOCATION: (18)..(18)
<223> OTHER INFORMATION: Xaa is Arg or Ala
<220> FEATURE:
<221> NAME/KEY: MISC_FEATURE
<222> LOCATION: (20)..(20)
<223> OTHER INFORMATION: Xaa is AIB or Gln
<220> FEATURE:
<221> NAME/KEY: MISC_FEATURE
<222> LOCATION: (21)..(21)
<223> OTHER INFORMATION: Xaa is Asp or Glu
<220> FEATURE:
<221> NAME/KEY: MISC_FEATURE
<222> LOCATION: (40)..(40)
<223> OTHER INFORMATION: Xaa is absent or is Gly
      (e.g. when position 10 is not Tyr) or is an amino acid covalently
      bound to a C10-C26 acyl or alkyl group
<220> FEATURE:
<221> NAME/KEY: MISC_FEATURE
<222> LOCATION: (41)..(41)
<223> OTHER INFORMATION: Optionally present, when residue at position 40
      is an amino acid covalently bound to C10-C26 acyl or alkyl group
      then Xaa is Gly
<220> FEATURE:
<221> NAME/KEY: MISC_FEATURE
<222> LOCATION: (41)..(41)
<223> OTHER INFORMATION: C-terminal amidation

<400> SEQUENCE: 179

His Xaa Gln Gly Thr Phe Thr Ser Asp Xaa Ser Lys Tyr Leu Asp Glu
1               5                   10                  15

Arg Xaa Ala Xaa Xaa Phe Val Gln Trp Leu Leu Asp Gly Gly Pro Ser
            20                  25                  30

Ser Gly Ala Pro Pro Pro Ser Xaa Xaa
        35                  40

<210> SEQ ID NO 180
<211> LENGTH: 41
<212> TYPE: PRT
```

```
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (40)..(40)
<223> OTHER INFORMATION: Covalently bound to C16 fatty acyl group via
      gamma-Glu-gamma-Glu spacer
<220> FEATURE:
<221> NAME/KEY: MISC_FEATURE
<222> LOCATION: (41)..(41)
<223> OTHER INFORMATION: C-terminal amidation

<400> SEQUENCE: 180

His Xaa Gln Gly Thr Phe Thr Ser Asp Tyr Ser Lys Tyr Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Pro Ser Lys Gly
        35                  40

<210> SEQ ID NO 181
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(29)
<223> OTHER INFORMATION: At least one amino acid is an amino acid
      covalently bound to a C10 to C26 acyl or alkyl group
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (3)..(3)
<223> OTHER INFORMATION: Xaa is Gln or Gln analog
<220> FEATURE:
<221> NAME/KEY: MISC_FEATURE
<222> LOCATION: (10)..(10)
<223> OTHER INFORMATION: Xaa is Lys or Tyr
<220> FEATURE:
<221> NAME/KEY: MISC_FEATURE
<222> LOCATION: (18)..(18)
<223> OTHER INFORMATION: Xaa is Arg or Ala
<220> FEATURE:
<221> NAME/KEY: MISC_FEATURE
<222> LOCATION: (20)..(20)
<223> OTHER INFORMATION: Xaa is AIB or Gln
<220> FEATURE:
<221> NAME/KEY: MISC_FEATURE
<222> LOCATION: (21)..(21)
<223> OTHER INFORMATION: Xaa is Asp or Glu
<220> FEATURE:
<221> NAME/KEY: MISC_FEATURE
<222> LOCATION: (29)..(29)
<223> OTHER INFORMATION: Xaa is Thr or Gly
<220> FEATURE:
<221> NAME/KEY: MISC_FEATURE
<222> LOCATION: (29)..(29)
<223> OTHER INFORMATION: C-terminal amidation

<400> SEQUENCE: 181

His Xaa Xaa Gly Thr Phe Thr Ser Asp Xaa Ser Lys Tyr Leu Asp Glu
1               5                   10                  15
```

```
Arg Xaa Ala Xaa Xaa Phe Val Gln Trp Leu Leu Asp Xaa
        20                  25

<210> SEQ ID NO 182
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (3)..(3)
<223> OTHER INFORMATION: Xaa is Gln or Gln analog
<220> FEATURE:
<221> NAME/KEY: MISC_FEATURE
<222> LOCATION: (10)..(10)
<223> OTHER INFORMATION: Xaa is Lys covalently bound to a C10-C26 acyl
      or alkyl group
<220> FEATURE:
<221> NAME/KEY: MISC_FEATURE
<222> LOCATION: (18)..(18)
<223> OTHER INFORMATION: Xaa is Arg or Ala
<220> FEATURE:
<221> NAME/KEY: MISC_FEATURE
<222> LOCATION: (20)..(20)
<223> OTHER INFORMATION: Xaa is AIB or Gln
<220> FEATURE:
<221> NAME/KEY: MISC_FEATURE
<222> LOCATION: (21)..(21)
<223> OTHER INFORMATION: Xaa is Asp or Glu
<220> FEATURE:
<221> NAME/KEY: MISC_FEATURE
<222> LOCATION: (29)..(29)
<223> OTHER INFORMATION: Xaa is Gly or Thr
<220> FEATURE:
<221> NAME/KEY: MISC_FEATURE
<222> LOCATION: (29)..(29)
<223> OTHER INFORMATION: C-terminal amidation

<400> SEQUENCE: 182

His Xaa Xaa Gly Thr Phe Thr Ser Asp Xaa Ser Lys Tyr Leu Asp Glu
1               5                   10                  15

Arg Xaa Ala Xaa Xaa Phe Val Gln Trp Leu Leu Asp Xaa
        20                  25

<210> SEQ ID NO 183
<211> LENGTH: 10
<212> TYPE: PRT
<213> ORGANISM: Artificial Sequence
<220> FEATURE:
<223> OTHER INFORMATION: Synthetic peptide

<400> SEQUENCE: 183

Gly Pro Ser Ser Gly Arg Pro Pro Pro Ser
1               5                   10

<210> SEQ ID NO 184
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
```

```
<222> LOCATION: (3)..(3)
<223> OTHER INFORMATION: Xaa is Gln or Gln analog
<220> FEATURE:
<221> NAME/KEY: MISC_FEATURE
<222> LOCATION: (10)..(10)
<223> OTHER INFORMATION: Xaa is Tyr or an amino acid covalently bound to
      a C12 to C18 acyl or alkyl group
<220> FEATURE:
<221> NAME/KEY: MISC_FEATURE
<222> LOCATION: (16)..(16)
<223> OTHER INFORMATION: Xaa is any amino acid, optionally, any amino
      acid other than Gly, Pro, and Ser
<220> FEATURE:
<221> NAME/KEY: MISC_FEATURE
<222> LOCATION: (18)..(18)
<223> OTHER INFORMATION: Xaa is Arg or Ala
<220> FEATURE:
<221> NAME/KEY: MISC_FEATURE
<222> LOCATION: (20)..(20)
<223> OTHER INFORMATION: Xaa is a negative charged amino acid or a
      charge-neutral amino acid, optionally, AIB or Gln
<220> FEATURE:
<221> NAME/KEY: MISC_FEATURE
<222> LOCATION: (21)..(21)
<223> OTHER INFORMATION: Xaa is is an acidic amino acid, optionally, Asp
      or Glu
<220> FEATURE:
<221> NAME/KEY: MISC_FEATURE
<222> LOCATION: (27)..(27)
<223> OTHER INFORMATION: Xaa is Leu, Ala, Nle, or Met
<220> FEATURE:
<221> NAME/KEY: MISC_FEATURE
<222> LOCATION: (28)..(28)
<223> OTHER INFORMATION: Xaa is Ala or an acidic amino acid, optionally,
      Asp or Glu
<220> FEATURE:
<221> NAME/KEY: MISC_FEATURE
<222> LOCATION: (29)..(29)
<223> OTHER INFORMATION: Xaa is Ala or Gly
<220> FEATURE:
<221> NAME/KEY: MISC_FEATURE
<222> LOCATION: (35)..(35)
<223> OTHER INFORMATION: Xaa is Ala or a basic amino acid, optionally,
      Arg or Lys
<220> FEATURE:
<221> NAME/KEY: MISC_FEATURE
<222> LOCATION: (39)..(39)
<223> OTHER INFORMATION: C-terminal amidation

<400> SEQUENCE: 184

His Xaa Xaa Gly Thr Phe Thr Ser Asp Xaa Ser Lys Tyr Leu Asp Xaa
1               5                   10                  15

Arg Xaa Ala Xaa Xaa Phe Val Gln Trp Leu Xaa Xaa Xaa Gly Pro Ser
            20                  25                  30

Ser Gly Xaa Pro Pro Pro Ser
        35

<210> SEQ ID NO 185
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Xaa is Tyr or an amino acid covalently attached
      to a C12 to C18 acyl or alkyl group
<220> FEATURE:
<221> NAME/KEY: MISC_FEATURE
<222> LOCATION: (16)..(16)
```

```
<223> OTHER INFORMATION: Xaa is Glu, an alpha, alpha disubstituted amino
      acid or Lys
<220> FEATURE:
<221> NAME/KEY: MISC_FEATURE
<222> LOCATION: (18)..(18)
<223> OTHER INFORMATION: Xaa is Arg or Ala
<220> FEATURE:
<221> NAME/KEY: MISC_FEATURE
<222> LOCATION: (20)..(20)
<223> OTHER INFORMATION: Xaa is AIB or Gln
<220> FEATURE:
<221> NAME/KEY: MISC_FEATURE
<222> LOCATION: (21)..(21)
<223> OTHER INFORMATION: Xaa is Asp or Glu
<220> FEATURE:
<221> NAME/KEY: MISC_FEATURE
<222> LOCATION: (27)..(27)
<223> OTHER INFORMATION: Xaa is Leu, Nle, or Met
<220> FEATURE:
<221> NAME/KEY: MISC_FEATURE
<222> LOCATION: (28)..(28)
<223> OTHER INFORMATION: Xaa is Ala, Asp or Glu
<220> FEATURE:
<221> NAME/KEY: MISC_FEATURE
<222> LOCATION: (29)..(29)
<223> OTHER INFORMATION: Xaa is Gly or Thr
<220> FEATURE:
<221> NAME/KEY: MISC_FEATURE
<222> LOCATION: (39)..(39)
<223> OTHER INFORMATION: C-terminal amidation

<400> SEQUENCE: 185

His Xaa Gln Gly Thr Phe Thr Ser Asp Xaa Ser Lys Tyr Leu Asp Xaa
1               5                   10                  15

Arg Xaa Ala Xaa Xaa Phe Val Gln Trp Leu Xaa Xaa Xaa Gly Pro Ser
            20                  25                  30

Ser Gly Ala Pro Pro Pro Ser
        35

<210> SEQ ID NO 186
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (3)..(3)
<223> OTHER INFORMATION: Xaa is Gln or Gln analog
<220> FEATURE:
<221> NAME/KEY: MISC_FEATURE
<222> LOCATION: (10)..(10)
<223> OTHER INFORMATION: Xaa is Tyr or an amino acid covalently attached
      to a C10 to C26 acyl or alkyl group
<220> FEATURE:
<221> NAME/KEY: MISC_FEATURE
<222> LOCATION: (16)..(16)
<223> OTHER INFORMATION: Xaa is any amino acid, optionally, any amino
      acid other than Gly, Pro, and Ser
<220> FEATURE:
<221> NAME/KEY: MISC_FEATURE
<222> LOCATION: (18)..(18)
<223> OTHER INFORMATION: Xaa is Arg or Ala
<220> FEATURE:
<221> NAME/KEY: MISC_FEATURE
<222> LOCATION: (20)..(20)
<223> OTHER INFORMATION: Xaa is a negative charged amino acid or a
      charge-neutral amino acid, optionally, AIB or Gln
<220> FEATURE:
<221> NAME/KEY: MISC_FEATURE
<222> LOCATION: (21)..(21)
```

```
<223> OTHER INFORMATION: Xaa is an acidic amino acid, optionally, Asp or
      Glu
<220> FEATURE:
<221> NAME/KEY: MISC_FEATURE
<222> LOCATION: (27)..(27)
<223> OTHER INFORMATION: Xaa is Leu, Ala, Nle, or Met
<220> FEATURE:
<221> NAME/KEY: MISC_FEATURE
<222> LOCATION: (28)..(28)
<223> OTHER INFORMATION: Xaa is Ala or an acidic amino acid, optionally,
      Asp or Glu
<220> FEATURE:
<221> NAME/KEY: MISC_FEATURE
<222> LOCATION: (29)..(29)
<223> OTHER INFORMATION: Xaa is Ala, Gly or Thr
<220> FEATURE:
<221> NAME/KEY: MISC_FEATURE
<222> LOCATION: (29)..(29)
<223> OTHER INFORMATION: C-terminal amidation

<400> SEQUENCE: 186

His Xaa Xaa Gly Thr Phe Thr Ser Asp Xaa Ser Lys Tyr Leu Asp Xaa
1               5                   10                  15

Arg Xaa Ala Xaa Xaa Phe Val Gln Trp Leu Xaa Xaa Xaa
            20                  25

<210> SEQ ID NO 187
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Xaa is Tyr or an amino acid covalently bound to
      a C10 to C26 acyl or alkyl group
<220> FEATURE:
<221> NAME/KEY: MISC_FEATURE
<222> LOCATION: (16)..(16)
<223> OTHER INFORMATION: Xaa is Glu, alpha, alpha-disubstituted amino
      acid, or Lys
<220> FEATURE:
<221> NAME/KEY: MISC_FEATURE
<222> LOCATION: (18)..(18)
<223> OTHER INFORMATION: Xaa is Arg or Ala
<220> FEATURE:
<221> NAME/KEY: MISC_FEATURE
<222> LOCATION: (20)..(20)
<223> OTHER INFORMATION: Xaa is a negative charged amino acid or a
      charge-neutral amino acid, optionally, AIB or Gln
<220> FEATURE:
<221> NAME/KEY: MISC_FEATURE
<222> LOCATION: (21)..(21)
<223> OTHER INFORMATION: Xaa is Asp or Glu
<220> FEATURE:
<221> NAME/KEY: MISC_FEATURE
<222> LOCATION: (27)..(27)
<223> OTHER INFORMATION: Xaa is Leu, Ala, Nle, or Met
<220> FEATURE:
<221> NAME/KEY: MISC_FEATURE
<222> LOCATION: (28)..(28)
<223> OTHER INFORMATION: Xaa is Ala, Asp or Glu
<220> FEATURE:
<221> NAME/KEY: MISC_FEATURE
<222> LOCATION: (29)..(29)
<223> OTHER INFORMATION: Xaa is Gly or Thr
<220> FEATURE:
<221> NAME/KEY: MISC_FEATURE
<222> LOCATION: (29)..(29)
<223> OTHER INFORMATION: C-terminal amidation
```

```
<400> SEQUENCE: 187

His Xaa Gln Gly Thr Phe Thr Ser Asp Xaa Ser Lys Tyr Leu Asp Xaa
1               5                   10                  15

Arg Xaa Ala Xaa Xaa Phe Val Gln Trp Leu Xaa Xaa Xaa
            20                  25

<210> SEQ ID NO 188
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (3)..(3)
<223> OTHER INFORMATION: Xaa is an acidic, basic or hydrophobic amino
      acid, optionally, Glu
<220> FEATURE:
<221> NAME/KEY: MISC_FEATURE
<222> LOCATION: (10)..(10)
<223> OTHER INFORMATION: Xaa is Tyr or an amino acid covalently bound to
      a C12 to C18 acyl or alkyl group
<220> FEATURE:
<221> NAME/KEY: MISC_FEATURE
<222> LOCATION: (16)..(16)
<223> OTHER INFORMATION: Xaa can be any amino acid, optionally any amino
      acid other than Gly, Pro or Ser
<220> FEATURE:
<221> NAME/KEY: MISC_FEATURE
<222> LOCATION: (18)..(18)
<223> OTHER INFORMATION: Xaa is Arg or Ala
<220> FEATURE:
<221> NAME/KEY: MISC_FEATURE
<222> LOCATION: (20)..(20)
<223> OTHER INFORMATION: Xaa is a negative charged amino acid or a
      charge-neutral amino acid, optionally, AIB or Gln
<220> FEATURE:
<221> NAME/KEY: MISC_FEATURE
<222> LOCATION: (21)..(21)
<223> OTHER INFORMATION: Xaa is an acidic amino acid, optionally, Asp or
      Glu
<220> FEATURE:
<221> NAME/KEY: MISC_FEATURE
<222> LOCATION: (27)..(27)
<223> OTHER INFORMATION: Xaa is Leu, Ala, Nle, or Met
<220> FEATURE:
<221> NAME/KEY: MISC_FEATURE
<222> LOCATION: (28)..(28)
<223> OTHER INFORMATION: Xaa is Ala or an acidic amino acid, optionally,
      Asp or Glu
<220> FEATURE:
<221> NAME/KEY: MISC_FEATURE
<222> LOCATION: (29)..(29)
<223> OTHER INFORMATION: Xaa is Ala or Gly
<220> FEATURE:
<221> NAME/KEY: MISC_FEATURE
<222> LOCATION: (35)..(35)
<223> OTHER INFORMATION: Xaa is Ala or a basic amino acid, optionally,
      Arg or Lys
<220> FEATURE:
<221> NAME/KEY: MISC_FEATURE
<222> LOCATION: (39)..(39)
<223> OTHER INFORMATION: C-terminal amidation

<400> SEQUENCE: 188

His Xaa Xaa Gly Thr Phe Thr Ser Asp Xaa Ser Lys Tyr Leu Asp Xaa
1               5                   10                  15

Arg Xaa Ala Xaa Xaa Phe Val Gln Trp Leu Xaa Xaa Xaa Gly Pro Ser
            20                  25                  30
```

Ser Gly Xaa Pro Pro Pro Ser
        35

<210> SEQ ID NO 189
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Xaa is Tyr or an amino acid covalently attached
      to a C12 to C18 acyl or alkyl group
<220> FEATURE:
<221> NAME/KEY: MISC_FEATURE
<222> LOCATION: (16)..(16)
<223> OTHER INFORMATION: Xaa is Glu, an alpha, alpha disubstituted amino
      acid or Lys
<220> FEATURE:
<221> NAME/KEY: MISC_FEATURE
<222> LOCATION: (18)..(18)
<223> OTHER INFORMATION: Xaa is Arg or Ala
<220> FEATURE:
<221> NAME/KEY: MISC_FEATURE
<222> LOCATION: (20)..(20)
<223> OTHER INFORMATION: Xaa is AIB or Gln
<220> FEATURE:
<221> NAME/KEY: MISC_FEATURE
<222> LOCATION: (21)..(21)
<223> OTHER INFORMATION: Xaa is Asp or Glu
<220> FEATURE:
<221> NAME/KEY: MISC_FEATURE
<222> LOCATION: (27)..(27)
<223> OTHER INFORMATION: Xaa is Leu, Nle, or Met
<220> FEATURE:
<221> NAME/KEY: MISC_FEATURE
<222> LOCATION: (28)..(28)
<223> OTHER INFORMATION: Xaa is Ala, Asp or Glu
<220> FEATURE:
<221> NAME/KEY: MISC_FEATURE
<222> LOCATION: (29)..(29)
<223> OTHER INFORMATION: Xaa is Gly or Thr
<220> FEATURE:
<221> NAME/KEY: MISC_FEATURE
<222> LOCATION: (39)..(39)
<223> OTHER INFORMATION: C-terminal amidation

<400> SEQUENCE: 189

His Xaa Glu Gly Thr Phe Thr Ser Asp Xaa Ser Lys Tyr Leu Asp Xaa
1               5                   10                  15

Arg Xaa Ala Xaa Xaa Phe Val Gln Trp Leu Xaa Xaa Xaa Gly Pro Ser
            20                  25                  30

Ser Gly Ala Pro Pro Pro Ser
        35

<210> SEQ ID NO 190
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (3)..(3)
<223> OTHER INFORMATION: Xaa is an acidic, basic or hydrophobic amino

```
      acid, optionally, is Glu
<220> FEATURE:
<221> NAME/KEY: MISC_FEATURE
<222> LOCATION: (10)..(10)
<223> OTHER INFORMATION: Xaa is Tyr or an amino acid covalently bound to
      a C10 to C26 acyl or alkyl group
<220> FEATURE:
<221> NAME/KEY: MISC_FEATURE
<222> LOCATION: (16)..(16)
<223> OTHER INFORMATION: Xaa is any amino acid, optionally, any amino
      acid other than Gly, Pro, and Ser
<220> FEATURE:
<221> NAME/KEY: MISC_FEATURE
<222> LOCATION: (18)..(18)
<223> OTHER INFORMATION: Xaa is Arg or Ala
<220> FEATURE:
<221> NAME/KEY: MISC_FEATURE
<222> LOCATION: (20)..(20)
<223> OTHER INFORMATION: Xaa is a negative charged amino acid or a
      charge-neutral amino acid, optionally, AIB or Gln
<220> FEATURE:
<221> NAME/KEY: MISC_FEATURE
<222> LOCATION: (21)..(21)
<223> OTHER INFORMATION: Xaa is an acidic amino acid, optionally, Asp or
      Glu
<220> FEATURE:
<221> NAME/KEY: MISC_FEATURE
<222> LOCATION: (27)..(27)
<223> OTHER INFORMATION: Xaa is Leu, Ala, Nle, or Met
<220> FEATURE:
<221> NAME/KEY: MISC_FEATURE
<222> LOCATION: (28)..(28)
<223> OTHER INFORMATION: Xaa is Ala or an acidic amino acid, optionally,
      Asp or Glu
<220> FEATURE:
<221> NAME/KEY: MISC_FEATURE
<222> LOCATION: (29)..(29)
<223> OTHER INFORMATION: Xaa is Ala, Gly or Thr
<220> FEATURE:
<221> NAME/KEY: MISC_FEATURE
<222> LOCATION: (29)..(29)
<223> OTHER INFORMATION: C-terminal amidation

<400> SEQUENCE: 190

His Xaa Xaa Gly Thr Phe Thr Ser Asp Xaa Ser Lys Tyr Leu Asp Xaa
1               5                   10                  15

Arg Xaa Ala Xaa Xaa Phe Val Gln Trp Leu Xaa Xaa Xaa
            20                  25

<210> SEQ ID NO 191
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Xaa is Tyr or an amino acid covalently bound to
      a C10 to C26 acyl or alkyl group
<220> FEATURE:
<221> NAME/KEY: MISC_FEATURE
<222> LOCATION: (16)..(16)
<223> OTHER INFORMATION: Xaa is Glu, alpha, alpha-disubstituted amino
      acid, or Lys
<220> FEATURE:
<221> NAME/KEY: MISC_FEATURE
<222> LOCATION: (18)..(18)
<223> OTHER INFORMATION: Xaa is Arg or Ala
<220> FEATURE:
<221> NAME/KEY: MISC_FEATURE
<222> LOCATION: (20)..(20)
```

```
<223> OTHER INFORMATION: Xaa is a negative charged amino acid or a
      charge-neutral amino acid, optionally, AIB or Gln
<220> FEATURE:
<221> NAME/KEY: MISC_FEATURE
<222> LOCATION: (21)..(21)
<223> OTHER INFORMATION: Xaa is Asp or Glu
<220> FEATURE:
<221> NAME/KEY: MISC_FEATURE
<222> LOCATION: (27)..(27)
<223> OTHER INFORMATION: Xaa is Leu, Ala, Nle, or Met
<220> FEATURE:
<221> NAME/KEY: MISC_FEATURE
<222> LOCATION: (28)..(28)
<223> OTHER INFORMATION: Xaa is Ala, Asp or Glu
<220> FEATURE:
<221> NAME/KEY: MISC_FEATURE
<222> LOCATION: (29)..(29)
<223> OTHER INFORMATION: Xaa is Gly or Thr
<220> FEATURE:
<221> NAME/KEY: MISC_FEATURE
<222> LOCATION: (29)..(29)
<223> OTHER INFORMATION: C-terminal amidation

<400> SEQUENCE: 191

His Xaa Glu Gly Thr Phe Thr Ser Asp Xaa Ser Lys Tyr Leu Asp Xaa
 1               5                  10                  15

Arg Xaa Ala Xaa Xaa Phe Val Gln Trp Leu Xaa Xaa Xaa
            20                  25

<210> SEQ ID NO 192
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (3)..(3)
<223> OTHER INFORMATION: Xaa is Gln or Gln analog or acidic, basic or
      hydrophobic amino acid, optionally, is Glu or Gln
<220> FEATURE:
<221> NAME/KEY: MISC_FEATURE
<222> LOCATION: (10)..(10)
<223> OTHER INFORMATION: Xaa is Tyr or an amino acid covalently bound to
      a C12 to C18 acyl or alkyl group
<220> FEATURE:
<221> NAME/KEY: MISC_FEATURE
<222> LOCATION: (16)..(16)
<223> OTHER INFORMATION: Xaa is any amino acid, optionally, any amino
      acid other than Gly, Pro, and Ser
<220> FEATURE:
<221> NAME/KEY: MISC_FEATURE
<222> LOCATION: (18)..(18)
<223> OTHER INFORMATION: Xaa is Arg or Ala
<220> FEATURE:
<221> NAME/KEY: MISC_FEATURE
<222> LOCATION: (20)..(20)
<223> OTHER INFORMATION: Xaa is a negative charged amino acid or a
      charge-neutral amino acid, optionally, AIB or Gln
<220> FEATURE:
<221> NAME/KEY: MISC_FEATURE
<222> LOCATION: (21)..(21)
<223> OTHER INFORMATION: Xaa is an acidic amino acid, optionally, Asp or
      Glu
<220> FEATURE:
<221> NAME/KEY: MISC_FEATURE
<222> LOCATION: (27)..(27)
<223> OTHER INFORMATION: Xaa is Leu, Ala, Nle, or Met
<220> FEATURE:
<221> NAME/KEY: MISC_FEATURE
<222> LOCATION: (28)..(28)
```

```
<223> OTHER INFORMATION: Xaa is Ala or an acidic amino acid, optionally,
      Asp or Glu
<220> FEATURE:
<221> NAME/KEY: MISC_FEATURE
<222> LOCATION: (29)..(29)
<223> OTHER INFORMATION: Xaa is Ala or Gly
<220> FEATURE:
<221> NAME/KEY: MISC_FEATURE
<222> LOCATION: (35)..(35)
<223> OTHER INFORMATION: Xaa is Ala or a basic amino acid, optionally,
      Arg or Lys
<220> FEATURE:
<221> NAME/KEY: MISC_FEATURE
<222> LOCATION: (39)..(39)
<223> OTHER INFORMATION: C-terminal amidation

<400> SEQUENCE: 192

His Xaa Xaa Gly Thr Phe Thr Ser Asp Xaa Ser Lys Tyr Leu Asp Xaa
1               5                   10                  15

Arg Xaa Ala Xaa Xaa Phe Val Gln Trp Leu Xaa Xaa Xaa Gly Pro Ser
            20                  25                  30

Ser Gly Xaa Pro Pro Pro Ser
        35

<210> SEQ ID NO 193
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (3)..(3)
<223> OTHER INFORMATION: Xaa is Gln or Gln analog or acidic, basic or
      hydrophobic amino acid, optionally, is Glu or Gln
<220> FEATURE:
<221> NAME/KEY: MISC_FEATURE
<222> LOCATION: (10)..(10)
<223> OTHER INFORMATION: Xaa is Tyr or an amino acid covalently bound to
      a C12 to C18 acyl or alkyl group
<220> FEATURE:
<221> NAME/KEY: MISC_FEATURE
<222> LOCATION: (16)..(16)
<223> OTHER INFORMATION: Xaa is Glu, an alpha, alpha disubstituted amino
      acid or Lys
<220> FEATURE:
<221> NAME/KEY: MISC_FEATURE
<222> LOCATION: (18)..(18)
<223> OTHER INFORMATION: Xaa is Arg or Ala
<220> FEATURE:
<221> NAME/KEY: MISC_FEATURE
<222> LOCATION: (20)..(20)
<223> OTHER INFORMATION: Xaa is AIB or Gln
<220> FEATURE:
<221> NAME/KEY: MISC_FEATURE
<222> LOCATION: (21)..(21)
<223> OTHER INFORMATION: Xaa is Asp or Glu
<220> FEATURE:
<221> NAME/KEY: MISC_FEATURE
<222> LOCATION: (27)..(27)
<223> OTHER INFORMATION: Xaa is Leu, Nle, or Met
<220> FEATURE:
<221> NAME/KEY: MISC_FEATURE
<222> LOCATION: (28)..(28)
<223> OTHER INFORMATION: Xaa is Ala, Asp or Glu
<220> FEATURE:
<221> NAME/KEY: MISC_FEATURE
<222> LOCATION: (29)..(29)
<223> OTHER INFORMATION: Xaa is Gly or Thr
<220> FEATURE:
<221> NAME/KEY: MISC_FEATURE
```

```
<222> LOCATION: (39)..(39)
<223> OTHER INFORMATION: C-terminal amidation

<400> SEQUENCE: 193

His Xaa Xaa Gly Thr Phe Thr Ser Asp Xaa Ser Lys Tyr Leu Asp Xaa
1               5                   10                  15

Arg Xaa Ala Xaa Xaa Phe Val Gln Trp Leu Xaa Xaa Xaa Gly Pro Ser
            20                  25                  30

Ser Gly Ala Pro Pro Pro Ser
        35

<210> SEQ ID NO 194
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (3)..(3)
<223> OTHER INFORMATION: Xaa is Gln or Gln analog or acidic, basic or
      hydrophobic amino acid, optionally, is Glu or Gln
<220> FEATURE:
<221> NAME/KEY: MISC_FEATURE
<222> LOCATION: (10)..(10)
<223> OTHER INFORMATION: Xaa is Tyr or an amino acid covalently bound to
      a C10 to C26 acyl or alkyl group
<220> FEATURE:
<221> NAME/KEY: MISC_FEATURE
<222> LOCATION: (16)..(16)
<223> OTHER INFORMATION: Xaa is any amino acid, optionally, any amino
      acid other than Gly, Pro, and Ser
<220> FEATURE:
<221> NAME/KEY: MISC_FEATURE
<222> LOCATION: (18)..(18)
<223> OTHER INFORMATION: Xaa is Arg or Ala
<220> FEATURE:
<221> NAME/KEY: MISC_FEATURE
<222> LOCATION: (20)..(20)
<223> OTHER INFORMATION: Xaa is a negative charged amino acid or a
      charge-neutral amino acid, optionally, AIB or Gln
<220> FEATURE:
<221> NAME/KEY: MISC_FEATURE
<222> LOCATION: (21)..(21)
<223> OTHER INFORMATION: Xaa is an acidic amino acid, optionally, Asp or
      Glu
<220> FEATURE:
<221> NAME/KEY: MISC_FEATURE
<222> LOCATION: (27)..(27)
<223> OTHER INFORMATION: Xaa is Leu, Ala, Nle, or Met
<220> FEATURE:
<221> NAME/KEY: MISC_FEATURE
<222> LOCATION: (28)..(28)
<223> OTHER INFORMATION: Xaa is Ala or an acidic amino acid, optionally,
      Asp or Glu
<220> FEATURE:
<221> NAME/KEY: MISC_FEATURE
<222> LOCATION: (29)..(29)
<223> OTHER INFORMATION: Xaa is Ala, Gly or Thr
<220> FEATURE:
<221> NAME/KEY: MISC_FEATURE
<222> LOCATION: (29)..(29)
<223> OTHER INFORMATION: C-terminal amidation

<400> SEQUENCE: 194

His Xaa Xaa Gly Thr Phe Thr Ser Asp Xaa Ser Lys Tyr Leu Asp Xaa
1               5                   10                  15

Arg Xaa Ala Xaa Xaa Phe Val Gln Trp Leu Xaa Xaa Xaa
            20                  25
```

```
<210> SEQ ID NO 195
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (3)..(3)
<223> OTHER INFORMATION: Xaa is Gln or Gln analog or acidic, basic or
      hydrophobic amino acid, optionally, is Glu or Gln
<220> FEATURE:
<221> NAME/KEY: MISC_FEATURE
<222> LOCATION: (10)..(10)
<223> OTHER INFORMATION: Xaa is Tyr or an amino acid covalently bound to
      a C10 to C26 acyl or alkyl group
<220> FEATURE:
<221> NAME/KEY: MISC_FEATURE
<222> LOCATION: (16)..(16)
<223> OTHER INFORMATION: Xaa is Glu, alpha, alpha-disubstituted amino
      acid, or Lys
<220> FEATURE:
<221> NAME/KEY: MISC_FEATURE
<222> LOCATION: (18)..(18)
<223> OTHER INFORMATION: Xaa is Arg or Ala
<220> FEATURE:
<221> NAME/KEY: MISC_FEATURE
<222> LOCATION: (20)..(20)
<223> OTHER INFORMATION: Xaa is a negative charged amino acid or a
      charge-neutral amino acid, optionally, AIB or Gln
<220> FEATURE:
<221> NAME/KEY: MISC_FEATURE
<222> LOCATION: (21)..(21)
<223> OTHER INFORMATION: Xaa is Asp or Glu
<220> FEATURE:
<221> NAME/KEY: MISC_FEATURE
<222> LOCATION: (27)..(27)
<223> OTHER INFORMATION: Xaa is Leu, Ala, Nle, or Met
<220> FEATURE:
<221> NAME/KEY: MISC_FEATURE
<222> LOCATION: (28)..(28)
<223> OTHER INFORMATION: Xaa is Ala, Asp or Glu
<220> FEATURE:
<221> NAME/KEY: MISC_FEATURE
<222> LOCATION: (29)..(29)
<223> OTHER INFORMATION: Xaa is Gly or Thr
<220> FEATURE:
<221> NAME/KEY: MISC_FEATURE
<222> LOCATION: (29)..(29)
<223> OTHER INFORMATION: C-terminal amidation

<400> SEQUENCE: 195

His Xaa Xaa Gly Thr Phe Thr Ser Asp Xaa Ser Lys Tyr Leu Asp Xaa
1               5                   10                  15

Arg Xaa Ala Xaa Xaa Phe Val Gln Trp Leu Xaa Xaa Xaa
            20                  25

<210> SEQ ID NO 196
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(3)
<223> OTHER INFORMATION: Xaa can be any amino acid
<220> FEATURE:
<221> NAME/KEY: MISC_FEATURE
<222> LOCATION: (10)..(10)
```

<223> OTHER INFORMATION: Xaa can be any amino acid
<220> FEATURE:
<221> NAME/KEY: MISC_FEATURE
<222> LOCATION: (16)..(16)
<223> OTHER INFORMATION: Xaa can be any amino acid
<220> FEATURE:
<221> NAME/KEY: MISC_FEATURE
<222> LOCATION: (18)..(18)
<223> OTHER INFORMATION: Xaa can be any amino acid
<220> FEATURE:
<221> NAME/KEY: MISC_FEATURE
<222> LOCATION: (20)..(21)
<223> OTHER INFORMATION: Xaa can be any amino acid
<220> FEATURE:
<221> NAME/KEY: MISC_FEATURE
<222> LOCATION: (27)..(29)
<223> OTHER INFORMATION: Xaa can be any amino acid
<220> FEATURE:
<221> NAME/KEY: MISC_FEATURE
<222> LOCATION: (35)..(35)
<223> OTHER INFORMATION: Xaa can be any amino acid
<220> FEATURE:
<221> NAME/KEY: MISC_FEATURE
<222> LOCATION: (39)..(39)
<223> OTHER INFORMATION: C-terminal amidation

<400> SEQUENCE: 196

His Xaa Xaa Gly Thr Phe Thr Ser Asp Xaa Ser Lys Tyr Leu Asp Xaa
1               5                   10                  15

Arg Xaa Ala Xaa Xaa Phe Val Gln Trp Leu Xaa Xaa Xaa Gly Pro Ser
            20                  25                  30

Ser Gly Xaa Pro Pro Pro Ser
        35

<210> SEQ ID NO 197
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(3)
<223> OTHER INFORMATION: Xaa can be any amino acid
<220> FEATURE:
<221> NAME/KEY: MISC_FEATURE
<222> LOCATION: (10)..(10)
<223> OTHER INFORMATION: Xaa can be any amino acid
<220> FEATURE:
<221> NAME/KEY: MISC_FEATURE
<222> LOCATION: (16)..(16)
<223> OTHER INFORMATION: Xaa can be any amino acid
<220> FEATURE:
<221> NAME/KEY: MISC_FEATURE
<222> LOCATION: (18)..(18)
<223> OTHER INFORMATION: Xaa can be any amino acid
<220> FEATURE:
<221> NAME/KEY: MISC_FEATURE
<222> LOCATION: (20)..(21)
<223> OTHER INFORMATION: Xaa can be any amino acid
<220> FEATURE:
<221> NAME/KEY: MISC_FEATURE
<222> LOCATION: (27)..(29)
<223> OTHER INFORMATION: Xaa can be any amino acid
<220> FEATURE:
<221> NAME/KEY: MISC_FEATURE
<222> LOCATION: (39)..(39)
<223> OTHER INFORMATION: C-terminal amidation

<400> SEQUENCE: 197

His Xaa Xaa Gly Thr Phe Thr Ser Asp Xaa Ser Lys Tyr Leu Asp Xaa
1               5                   10                  15

```
Arg Xaa Ala Xaa Xaa Phe Val Gln Trp Leu Xaa Xaa Xaa Gly Pro Ser
        20                  25                  30

Ser Gly Ala Pro Pro Pro Ser
        35

<210> SEQ ID NO 198
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(3)
<223> OTHER INFORMATION: Xaa can be any amino acid
<220> FEATURE:
<221> NAME/KEY: MISC_FEATURE
<222> LOCATION: (10)..(10)
<223> OTHER INFORMATION: Xaa can be any amino acid
<220> FEATURE:
<221> NAME/KEY: MISC_FEATURE
<222> LOCATION: (16)..(16)
<223> OTHER INFORMATION: Xaa can be any amino acid
<220> FEATURE:
<221> NAME/KEY: MISC_FEATURE
<222> LOCATION: (18)..(18)
<223> OTHER INFORMATION: Xaa can be any amino acid
<220> FEATURE:
<221> NAME/KEY: MISC_FEATURE
<222> LOCATION: (20)..(21)
<223> OTHER INFORMATION: Xaa can be any amino acid
<220> FEATURE:
<221> NAME/KEY: MISC_FEATURE
<222> LOCATION: (27)..(29)
<223> OTHER INFORMATION: Xaa can be any amino acid
<220> FEATURE:
<221> NAME/KEY: MISC_FEATURE
<222> LOCATION: (29)..(29)
<223> OTHER INFORMATION: C-terminal amidation

<400> SEQUENCE: 198

His Xaa Xaa Gly Thr Phe Thr Ser Asp Xaa Ser Lys Tyr Leu Asp Xaa
1               5                   10                  15

Arg Xaa Ala Xaa Xaa Phe Val Gln Trp Leu Xaa Xaa Xaa
        20                  25

<210> SEQ ID NO 199
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(3)
<223> OTHER INFORMATION: Xaa can be any amino acid
<220> FEATURE:
<221> NAME/KEY: MISC_FEATURE
<222> LOCATION: (10)..(10)
<223> OTHER INFORMATION: Xaa can be any amino acid
<220> FEATURE:
<221> NAME/KEY: MISC_FEATURE
<222> LOCATION: (16)..(16)
<223> OTHER INFORMATION: Xaa can be any amino acid
<220> FEATURE:
<221> NAME/KEY: MISC_FEATURE
<222> LOCATION: (18)..(18)
<223> OTHER INFORMATION: Xaa can be any amino acid
<220> FEATURE:
<221> NAME/KEY: MISC_FEATURE
<222> LOCATION: (20)..(21)
<223> OTHER INFORMATION: Xaa can be any amino acid
<220> FEATURE:
```

```
<221> NAME/KEY: MISC_FEATURE
<222> LOCATION: (27)..(29)
<223> OTHER INFORMATION: Xaa can be any amino acid
<220> FEATURE:
<221> NAME/KEY: MISC_FEATURE
<222> LOCATION: (29)..(29)
<223> OTHER INFORMATION: C-terminal amidation

<400> SEQUENCE: 199

His Xaa Xaa Gly Thr Phe Thr Ser Asp Xaa Ser Lys Tyr Leu Asp Xaa
1               5                   10                  15

Arg Xaa Ala Xaa Xaa Phe Val Gln Trp Leu Xaa Xaa Xaa
            20                  25

<210> SEQ ID NO 200
<211> LENGTH: 5
<212> TYPE: PRT
<213> ORGANISM: Artificial Sequence
<220> FEATURE:
<223> OTHER INFORMATION: Synthetic peptide

<400> SEQUENCE: 200

Glu Arg Ala Ala Gln
1               5

<210> SEQ ID NO 201
<211> LENGTH: 6
<212> TYPE: PRT
<213> ORGANISM: Artificial Sequence
<220> FEATURE:
<223> OTHER INFORMATION: Synthetic peptide

<400> SEQUENCE: 201

Glu Arg Ala Ala Gln Asp
1               5

<210> SEQ ID NO 202

<400> SEQUENCE: 202

000

<210> SEQ ID NO 203
<211> LENGTH: 41
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (40)..(40)
<223> OTHER INFORMATION: Covalently bound to C16 fatty acyl group via
      gamma-Glu-gamma-Glu spacer
<220> FEATURE:
<221> NAME/KEY: MISC_FEATURE
<222> LOCATION: (41)..(41)
<223> OTHER INFORMATION: C-terminal amidation

<400> SEQUENCE: 203

His Xaa Gln Gly Thr Phe Thr Ser Asp Tyr Ser Lys Tyr Leu Asp Glu
1               5                   10                  15

Arg Ala Ala Gln Asp Phe Val Gln Trp Leu Leu Ala Gly Gly Pro Ser
            20                  25                  30
```

Ser Gly Ala Pro Pro Pro Ser Lys Gly
        35                  40

<210> SEQ ID NO 204
<211> LENGTH: 41
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (40)..(40)
<223> OTHER INFORMATION: Covalently bound to C16 fatty acyl group via
      gamma-Glu-gamma-Glu spacer
<220> FEATURE:
<221> NAME/KEY: MISC_FEATURE
<222> LOCATION: (41)..(41)
<223> OTHER INFORMATION: C-terminal amidation

<400> SEQUENCE: 204

His Xaa Gln Gly Thr Phe Thr Ser Asp Tyr Ser Lys Tyr Leu Asp Glu
1               5                   10                  15

Arg Ala Ala Gln Asp Phe Val Gln Trp Leu Leu Asp Ala Gly Pro Ser
            20                  25                  30

Ser Gly Ala Pro Pro Pro Ser Lys Gly
        35                  40

<210> SEQ ID NO 205
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Covalently bound to C16 fatty acyl group via
      gamma-Glu spacer
<220> FEATURE:
<221> NAME/KEY: MISC_FEATURE
<222> LOCATION: (40)..(40)
<223> OTHER INFORMATION: C-terminal amidation

<400> SEQUENCE: 205

His Xaa Gln Gly Thr Phe Thr Ser Asp Lys Ser Lys Tyr Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Pro Ser Gly
        35                  40

<210> SEQ ID NO 206
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB

```
<220> FEATURE:
<221> NAME/KEY: MISC_FEATURE
<222> LOCATION: (10)..(10)
<223> OTHER INFORMATION: Covalently bound to C16 fatty acyl group via
      gamma-Glu spacer
<220> FEATURE:
<221> NAME/KEY: MISC_FEATURE
<222> LOCATION: (39)..(39)
<223> OTHER INFORMATION: C-terminal amidation

<400> SEQUENCE: 206

His Xaa Gln Gly Thr Phe Thr Ser Asp Lys Ser Lys Tyr Leu Asp Glu
1               5                   10                  15

Arg Ala Ala Gln Asp Phe Val Gln Trp Leu Leu Glu Gly Gly Pro Ser
            20                  25                  30

Ser Gly Arg Pro Pro Pro Ser
        35

<210> SEQ ID NO 207
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Covalently bound to C16 fatty acyl group via
      gamma-Glu-gamma-Glu spacer
<220> FEATURE:
<221> NAME/KEY: MISC_FEATURE
<222> LOCATION: (40)..(40)
<223> OTHER INFORMATION: C-terminal amidation

<400> SEQUENCE: 207

His Xaa Gln Gly Thr Phe Thr Ser Asp Lys Ser Lys Tyr Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Pro Ser Gly
        35                  40

<210> SEQ ID NO 208
<211> LENGTH: 41
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (40)..(40)
<223> OTHER INFORMATION: Covalently bound to Lys spacer, wherein Lys
      spacer is bound via the alpha amine to a gamma-Glu spacer, which
      is bound to a C16 fatty acyl group and Lys spacer is bound via the
      epsilon amine to gamma-Glu which is bound to a C16 fatty acyl
      group
<220> FEATURE:
<221> NAME/KEY: MISC_FEATURE
<222> LOCATION: (41)..(41)
<223> OTHER INFORMATION: C-terminal amidation

<400> SEQUENCE: 208
```

```
Tyr Xaa Gln Gly Thr Phe Thr Ser Asp Tyr Ser Lys Tyr Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Pro Ser Lys Gly
        35                  40
```

<210> SEQ ID NO 209

<400> SEQUENCE: 209

000

<210> SEQ ID NO 210
<211> LENGTH: 41
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (40)..(40)
<223> OTHER INFORMATION: Covalently bound to a Lys spacer, wherein the
      Lys spacer is bound to (1) C16 fatty acyl group via a gamma-Glu
      spacer and (2) C8 fatty acyl group via a gamma-Glu spacer
<220> FEATURE:
<221> NAME/KEY: MISC_FEATURE
<222> LOCATION: (41)..(41)
<223> OTHER INFORMATION: C-terminal amidation

<400> SEQUENCE: 210

```
Tyr Xaa Gln Gly Thr Phe Thr Ser Asp Tyr Ser Lys Tyr Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Pro Ser Lys Gly
        35                  40
```

<210> SEQ ID NO 211
<211> LENGTH: 41
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (40)..(40)
<223> OTHER INFORMATION: Covalently bound to a Lys spacer, wherein the
      Lys spacer is bound to (1) C16 fatty acyl group via a gamma-Glu
      spacer and (2) C12 fatty acyl group via a gamma-Glu spacer
<220> FEATURE:
<221> NAME/KEY: MISC_FEATURE
<222> LOCATION: (41)..(41)
<223> OTHER INFORMATION: C-terminal amidation

<400> SEQUENCE: 211

```
Tyr Xaa Gln Gly Thr Phe Thr Ser Asp Tyr Ser Lys Tyr Leu Asp Glu
1               5                   10                  15

Arg Ala Ala Gln Asp Phe Val Gln Trp Leu Leu Asp Gly Gly Pro Ser
            20                  25                  30
```

Ser Gly Ala Pro Pro Ser Lys Gly
         35                  40

<210> SEQ ID NO 212
<211> LENGTH: 41
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (40)..(40)
<223> OTHER INFORMATION: Covalently bound to C16 fatty acyl group via
      side chain hydroxyl of Tyr
<220> FEATURE:
<221> NAME/KEY: MISC_FEATURE
<222> LOCATION: (41)..(41)
<223> OTHER INFORMATION: C-terminal amidation

<400> SEQUENCE: 212

His Xaa Gln Gly Thr Phe Thr Ser Asp Tyr Ser Lys Tyr Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Ser Tyr Gly
         35                  40

<210> SEQ ID NO 213

<400> SEQUENCE: 213

000

<210> SEQ ID NO 214

<400> SEQUENCE: 214

000

<210> SEQ ID NO 215

<400> SEQUENCE: 215

000

<210> SEQ ID NO 216

<400> SEQUENCE: 216

000

<210> SEQ ID NO 217

<400> SEQUENCE: 217

000

<210> SEQ ID NO 218

<400> SEQUENCE: 218

000

<210> SEQ ID NO 219

```
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: MT-345
<220> FEATURE:
<221> NAME/KEY: MOD_RES
<222> LOCATION: (2)..(2)
<223> OTHER INFORMATION: Xaa is AIB
<220> FEATURE:
<221> NAME/KEY: MOD_RES
<222> LOCATION: (40)..(40)
<223> OTHER INFORMATION: Acylated with a C14 fatty acyl group
<220> FEATURE:
<221> NAME/KEY: MOD_RES
<222> LOCATION: (40)..(40)
<223> OTHER INFORMATION: C-terminal amidation

<400> SEQUENCE: 219

His Xaa Gln Gly Thr Phe Thr Ser Asp Tyr Ser Lys Tyr Leu Asp Glu
 1               5                  10                  15

Gln Ala Ala Lys Glu Phe Ile Cys Trp Leu Met Asn Gly Gly Pro Ser
                20                  25                  30

Ser Gly Ala Pro Pro Pro Ser Lys
            35                  40

<210> SEQ ID NO 220
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: MT-346
<220> FEATURE:
<221> NAME/KEY: MOD_RES
<222> LOCATION: (2)..(2)
<223> OTHER INFORMATION: Xaa is AIB
<220> FEATURE:
<221> NAME/KEY: MOD_RES
<222> LOCATION: (40)..(40)
<223> OTHER INFORMATION: C-terminal amidation

<400> SEQUENCE: 220

His Xaa Gln Gly Thr Phe Thr Ser Asp Tyr Ser Lys Tyr Leu Asp Glu
 1               5                  10                  15

Gln Ala Ala Lys Glu Phe Ile Cys Trp Leu Met Asn Gly Gly Pro Ser
                20                  25                  30

Ser Gly Ala Pro Pro Pro Ser Lys
            35                  40

<210> SEQ ID NO 221
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: MT-347
<220> FEATURE:
<221> NAME/KEY: MOD_RES
<222> LOCATION: (2)..(2)
<223> OTHER INFORMATION: Xaa is AIB
<220> FEATURE:
<221> NAME/KEY: MOD_RES
<222> LOCATION: (16)..(16)
```

```
<223> OTHER INFORMATION: Xaa is AIB
<220> FEATURE:
<221> NAME/KEY: MOD_RES
<222> LOCATION: (40)..(40)
<223> OTHER INFORMATION: Acylated with a C14 fatty acyl group
<220> FEATURE:
<221> NAME/KEY: MOD_RES
<222> LOCATION: (40)..(40)
<223> OTHER INFORMATION: C-terminal amidation

<400> SEQUENCE: 221

His Xaa Gln Gly Thr Phe Thr Ser Asp Tyr Ser Lys Tyr Leu Asp Xaa
1               5                   10                  15

Gln Ala Ala Lys Glu Phe Ile Cys Trp Leu Met Asn Gly Gly Pro Ser
            20                  25                  30

Ser Gly Ala Pro Pro Pro Ser Lys
        35                  40

<210> SEQ ID NO 222
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: MT-348
<220> FEATURE:
<221> NAME/KEY: MOD_RES
<222> LOCATION: (2)..(2)
<223> OTHER INFORMATION: Xaa is AIB
<220> FEATURE:
<221> NAME/KEY: MOD_RES
<222> LOCATION: (16)..(16)
<223> OTHER INFORMATION: Xaa is AIB
<220> FEATURE:
<221> NAME/KEY: MOD_RES
<222> LOCATION: (40)..(40)
<223> OTHER INFORMATION: C-terminal amidation

<400> SEQUENCE: 222

His Xaa Gln Gly Thr Phe Thr Ser Asp Tyr Ser Lys Tyr Leu Asp Xaa
1               5                   10                  15

Gln Ala Ala Lys Glu Phe Ile Cys Trp Leu Met Asn Gly Gly Pro Ser
            20                  25                  30

Ser Gly Ala Pro Pro Pro Ser Lys
        35                  40

<210> SEQ ID NO 223
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: MT-349
<220> FEATURE:
<221> NAME/KEY: MOD_RES
<222> LOCATION: (2)..(2)
<223> OTHER INFORMATION: Xaa is AIB
<220> FEATURE:
<221> NAME/KEY: MOD_RES
<222> LOCATION: (24)..(24)
<223> OTHER INFORMATION: Covalently bound to 40kDa PEG via thioether
      made by reaction of peptide with haloacetyl-activated PEG
<220> FEATURE:
<221> NAME/KEY: MOD_RES
<222> LOCATION: (40)..(40)
<223> OTHER INFORMATION: Acylated with a C14 fatty acyl group
<220> FEATURE:
```

```
<221> NAME/KEY: MOD_RES
<222> LOCATION: (40)..(40)
<223> OTHER INFORMATION: C-terminal amidation

<400> SEQUENCE: 223

His Xaa Gln Gly Thr Phe Thr Ser Asp Tyr Ser Lys Tyr Leu Asp Glu
1               5                   10                  15

Gln Ala Ala Lys Glu Phe Ile Cys Trp Leu Met Asn Gly Gly Pro Ser
            20                  25                  30

Ser Gly Ala Pro Pro Pro Ser Lys
        35                  40

<210> SEQ ID NO 224
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: MT-350
<220> FEATURE:
<221> NAME/KEY: MOD_RES
<222> LOCATION: (2)..(2)
<223> OTHER INFORMATION: Xaa is AIB
<220> FEATURE:
<221> NAME/KEY: MOD_RES
<222> LOCATION: (24)..(24)
<223> OTHER INFORMATION: Covalently bound to 40kDa PEG via thioether
      made by reaction of peptide with haloacetyl-activated PEG
<220> FEATURE:
<221> NAME/KEY: MOD_RES
<222> LOCATION: (40)..(40)
<223> OTHER INFORMATION: C-terminal amidation

<400> SEQUENCE: 224

His Xaa Gln Gly Thr Phe Thr Ser Asp Tyr Ser Lys Tyr Leu Asp Glu
1               5                   10                  15

Gln Ala Ala Lys Glu Phe Ile Cys Trp Leu Met Asn Gly Gly Pro Ser
            20                  25                  30

Ser Gly Ala Pro Pro Pro Ser Lys
        35                  40

<210> SEQ ID NO 225
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: MT-351
<220> FEATURE:
<221> NAME/KEY: MOD_RES
<222> LOCATION: (2)..(2)
<223> OTHER INFORMATION: Xaa is AIB
<220> FEATURE:
<221> NAME/KEY: MOD_RES
<222> LOCATION: (16)..(16)
<223> OTHER INFORMATION: Xaa is AIB
<220> FEATURE:
<221> NAME/KEY: MOD_RES
<222> LOCATION: (24)..(24)
<223> OTHER INFORMATION: Covalently bound to 40kDa PEG via thioether
      made by reaction of peptide with haloacetyl-activated PEG
<220> FEATURE:
<221> NAME/KEY: MOD_RES
<222> LOCATION: (40)..(40)
<223> OTHER INFORMATION: Acylated with a C14 fatty acyl group
<220> FEATURE:
<221> NAME/KEY: MOD_RES
```

```
<222> LOCATION: (40)..(40)
<223> OTHER INFORMATION: C-terminal amidation

<400> SEQUENCE: 225

His Xaa Gln Gly Thr Phe Thr Ser Asp Tyr Ser Lys Tyr Leu Asp Xaa
1               5                   10                  15

Gln Ala Ala Lys Glu Phe Ile Cys Trp Leu Met Asn Gly Gly Pro Ser
            20                  25                  30

Ser Gly Ala Pro Pro Pro Ser Lys
        35                  40

<210> SEQ ID NO 226
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: MT-352
<220> FEATURE:
<221> NAME/KEY: MOD_RES
<222> LOCATION: (2)..(2)
<223> OTHER INFORMATION: Xaa is AIB
<220> FEATURE:
<221> NAME/KEY: MOD_RES
<222> LOCATION: (16)..(16)
<223> OTHER INFORMATION: Xaa is AIB
<220> FEATURE:
<221> NAME/KEY: MOD_RES
<222> LOCATION: (24)..(24)
<223> OTHER INFORMATION: Covalently bound to 40kDa PEG via thioether
      made by reaction of peptide with haloacetyl-activated PEG
<220> FEATURE:
<221> NAME/KEY: MOD_RES
<222> LOCATION: (40)..(40)
<223> OTHER INFORMATION: C-terminal amidation

<400> SEQUENCE: 226

His Xaa Gln Gly Thr Phe Thr Ser Asp Tyr Ser Lys Tyr Leu Asp Xaa
1               5                   10                  15

Gln Ala Ala Lys Glu Phe Ile Cys Trp Leu Met Asn Gly Gly Pro Ser
            20                  25                  30

Ser Gly Ala Pro Pro Pro Ser Lys
        35                  40

<210> SEQ ID NO 227

<400> SEQUENCE: 227

000

<210> SEQ ID NO 228
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: MT-361
<220> FEATURE:
<221> NAME/KEY: MOD_RES
<222> LOCATION: (2)..(2)
<223> OTHER INFORMATION: Xaa is AIB
<220> FEATURE:
<221> NAME/KEY: MOD_RES
<222> LOCATION: (16)..(16)
<223> OTHER INFORMATION: Xaa is AIB
<220> FEATURE:
```

```
<221> NAME/KEY: MOD_RES
<222> LOCATION: (40)..(40)
<223> OTHER INFORMATION: C-terminal amidation

<400> SEQUENCE: 228

His Xaa Gln Gly Thr Phe Thr Ser Asp Tyr Ser Ile Tyr Leu Asp Xaa
1               5                   10                  15

Gln Ala Ala Lys Glu Phe Val Asn Trp Leu Met Asn Gly Gly Pro Ser
            20                  25                  30

Ser Gly Ala Pro Pro Pro Ser Lys
        35                  40

<210> SEQ ID NO 229
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: MT-364
<220> FEATURE:
<221> NAME/KEY: MOD_RES
<222> LOCATION: (2)..(2)
<223> OTHER INFORMATION: Xaa is AIB
<220> FEATURE:
<221> NAME/KEY: MOD_RES
<222> LOCATION: (40)..(40)
<223> OTHER INFORMATION: Acylated with a C16 fatty acyl group
<220> FEATURE:
<221> NAME/KEY: MOD_RES
<222> LOCATION: (40)..(40)
<223> OTHER INFORMATION: C-terminal amidation

<400> SEQUENCE: 229

His Xaa Gln Gly Thr Phe Thr Ser Asp Tyr Ser Lys Tyr Leu Asp Glu
1               5                   10                  15

Gln Ala Ala Lys Glu Phe Ile Ala Trp Leu Met Asn Gly Gly Pro Ser
            20                  25                  30

Ser Gly Ala Pro Pro Pro Ser Lys
        35                  40

<210> SEQ ID NO 230
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (40)..(40)
<223> OTHER INFORMATION: C-terminal amidation

<400> SEQUENCE: 230

His Xaa Gln Gly Thr Phe Thr Ser Asp Tyr Ser Ile Tyr Leu Asp Glu
1               5                   10                  15

Lys Arg Ala Lys Glu Phe Val Cys Trp Leu Leu Ala Gly Gly Pro Ser
            20                  25                  30

Ser Gly Ala Pro Pro Pro Ser Lys
        35                  40

<210> SEQ ID NO 231
<211> LENGTH: 41
```

```
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (41)..(41)
<223> OTHER INFORMATION: C-terminal amidation

<400> SEQUENCE: 231

His Xaa Gln Gly Thr Phe Thr Ser Asp Tyr Ser Lys Tyr Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Pro Ser Lys Gly
        35                  40

<210> SEQ ID NO 232

<400> SEQUENCE: 232

000

<210> SEQ ID NO 233
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Xaa is 4-amino-Phe
<220> FEATURE:
<221> NAME/KEY: MISC_FEATURE
<222> LOCATION: (10)..(10)
<223> OTHER INFORMATION: 4-amino-Phe covalently bound a C16 fatty acyl
      group via spacer comprising two acidic residues
<220> FEATURE:
<221> NAME/KEY: MISC_FEATURE
<222> LOCATION: (20)..(20)
<223> OTHER INFORMATION: Xaa is AIB
<220> FEATURE:
<221> NAME/KEY: MISC_FEATURE
<222> LOCATION: (39)..(39)
<223> OTHER INFORMATION: C-terminal amidation

<400> SEQUENCE: 233

Tyr Xaa Glu Gly Thr Phe Thr Ser Asp Xaa Ser Ile Tyr Leu Asp Lys
1               5                   10                  15

Gln Ala Ala Xaa Glu Phe Val Asn Trp Leu Leu Ala Gly Gly Pro Ser
            20                  25                  30

Ser Gly Ala Pro Pro Pro Ser
        35

<210> SEQ ID NO 234
<211> LENGTH: 41
<212> TYPE: PRT
<213> ORGANISM: Artificial Sequence
<220> FEATURE:
<223> OTHER INFORMATION: Synthetic peptide
<220> FEATURE:
```

```
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (40)..(40)
<223> OTHER INFORMATION: Xaa is 4-amino-Phe
<220> FEATURE:
<221> NAME/KEY: MISC_FEATURE
<222> LOCATION: (40)..(40)
<223> OTHER INFORMATION: 4-amino-Phe covalently bound to a C16 fatty
      acyl group via spacer comprising two acidic residues
<220> FEATURE:
<221> NAME/KEY: MISC_FEATURE
<222> LOCATION: (41)..(41)
<223> OTHER INFORMATION: C-terminal amidation

<400> SEQUENCE: 234

His Xaa Gln Gly Thr Phe Thr Ser Asp Tyr Ser Lys Tyr Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Pro Ser Xaa Gly
        35                  40

<210> SEQ ID NO 235
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (6)..(6)
<223> OTHER INFORMATION: Xaa is 4-amino-Phe
<220> FEATURE:
<221> NAME/KEY: MISC_FEATURE
<222> LOCATION: (6)..(6)
<223> OTHER INFORMATION: 4-amino-Phe covalently bound to C16 fatty acyl
      group via spacer comprising acidic residue
<220> FEATURE:
<221> NAME/KEY: MISC_FEATURE
<222> LOCATION: (39)..(39)
<223> OTHER INFORMATION: C-terminal amidation

<400> SEQUENCE: 235

His Xaa Gln Gly Thr Xaa Thr Ser Asp Tyr Ser Lys Tyr Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Pro Ser
        35

<210> SEQ ID NO 236
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Xaa is 4-amino-Phe
```

```
<220> FEATURE:
<221> NAME/KEY: MISC_FEATURE
<222> LOCATION: (10)..(10)
<223> OTHER INFORMATION: 4-amino-Phe covalently bound to C16 fatty acyl
      group via spacer comprising acidic residue
<220> FEATURE:
<221> NAME/KEY: MISC_FEATURE
<222> LOCATION: (39)..(39)
<223> OTHER INFORMATION: C-terminal amidation

<400> SEQUENCE: 236

His Xaa Gln Gly Thr Phe Thr Ser Asp Xaa Ser Lys Tyr Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Pro Ser
            35

<210> SEQ ID NO 237
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (13)..(13)
<223> OTHER INFORMATION: Xaa is 4-amino-Phe
<220> FEATURE:
<221> NAME/KEY: MISC_FEATURE
<222> LOCATION: (13)..(13)
<223> OTHER INFORMATION: 4-amino-Phe covalently bound to C16 fatty acyl
      group via spacer comprising acidic residue
<220> FEATURE:
<221> NAME/KEY: MISC_FEATURE
<222> LOCATION: (39)..(39)
<223> OTHER INFORMATION: C-terminal amidation

<400> SEQUENCE: 237

His Xaa Gln Gly Thr Phe Thr Ser Asp Tyr Ser Lys Xaa Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Pro Ser
            35

<210> SEQ ID NO 238
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Xaa is AIB
<220> FEATURE:
<221> NAME/KEY: MOD_RES
<222> LOCATION: (13)..(13)
<223> OTHER INFORMATION: Covalently bound to a C16 fatty acyl group via
      spacer comprising acidic residue
<220> FEATURE:
<221> NAME/KEY: MOD_RES
<222> LOCATION: (39)..(39)
<223> OTHER INFORMATION: C-terminal amidation

<400> SEQUENCE: 238
```

```
His Xaa Gln Gly Thr Phe Thr Ser Asp Tyr Ser Lys Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Ser
        35

<210> SEQ ID NO 239
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (14)..(14)
<223> OTHER INFORMATION: Covalently bound to a C16 fatty acyl group via
      spacer comprising acidic residue
<220> FEATURE:
<221> NAME/KEY: MISC_FEATURE
<222> LOCATION: (39)..(39)
<223> OTHER INFORMATION: C-terminal amidation

<400> SEQUENCE: 239

His Xaa Gln Gly Thr Phe Thr Ser Asp Tyr Ser Lys Tyr Lys Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Ser
        35

<210> SEQ ID NO 240
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (16)..(16)
<223> OTHER INFORMATION: Covalently bound to C16 fatty acyl group via
      spacer comprising acidic residue
<220> FEATURE:
<221> NAME/KEY: MISC_FEATURE
<222> LOCATION: (39)..(39)
<223> OTHER INFORMATION: C-terminal amidation

<400> SEQUENCE: 240

His Xaa Gln Gly Thr Phe Thr Ser Asp Tyr Ser Lys Tyr Leu Asp Lys
1               5                   10                  15

Arg Ala Ala Gln Asp Phe Val Gln Trp Leu Leu Asp Gly Gly Pro Ser
            20                  25                  30

Ser Gly Ala Pro Pro Ser
        35

<210> SEQ ID NO 241
<211> LENGTH: 39
<212> TYPE: PRT
<213> ORGANISM: Artificial Sequence
```

```
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (17)..(17)
<223> OTHER INFORMATION: Covalently bound to C16 fatty acyl group via
      spacer comprising acidic residue
<220> FEATURE:
<221> NAME/KEY: MISC_FEATURE
<222> LOCATION: (39)..(39)
<223> OTHER INFORMATION: C-terminal amidation

<400> SEQUENCE: 241

His Xaa Gln Gly Thr Phe Thr Ser Asp Tyr Ser Lys Tyr Leu Asp Glu
1               5                   10                  15

Lys Ala Ala Gln Asp Phe Val Gln Trp Leu Leu Asp Gly Gly Pro Ser
            20                  25                  30

Ser Gly Ala Pro Pro Pro Ser
        35

<210> SEQ ID NO 242
<211> LENGTH: 41
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (40)..(40)
<223> OTHER INFORMATION: Covalently bound to a C16 fatty acyl group via
      spacer comprising acidic residue
<220> FEATURE:
<221> NAME/KEY: MISC_FEATURE
<222> LOCATION: (41)..(41)
<223> OTHER INFORMATION: C-terminal amidation

<400> SEQUENCE: 242

His Xaa Gln Gly Thr Phe Thr Ser Asp Tyr Ser Lys Tyr Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Pro Ser Lys Gly
        35                  40

<210> SEQ ID NO 243
<211> LENGTH: 41
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (40)..(40)
<223> OTHER INFORMATION: Covalently bound to C16 fatty acyl group via a
      spacer comprising an amido miniPEG acid and an acidic amino acid,
      wherein the amido miniPEG acid has a structure
      {-N- CH2- CH2-[-O-CH2-CH2-]n-COO- }, wherein n is 2
<220> FEATURE:
<221> NAME/KEY: MISC_FEATURE
```

-continued

```
<222> LOCATION: (41)..(41)
<223> OTHER INFORMATION: C-terminal amidation

<400> SEQUENCE: 243

His Xaa Gln Gly Thr Phe Thr Ser Asp Tyr Ser Lys Tyr Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Pro Ser Lys Gly
        35                  40

<210> SEQ ID NO 244
<211> LENGTH: 41
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (40)..(40)
<223> OTHER INFORMATION: Covalently bound to a C16 fatty acyl group via
      spacer comprising an amido miniPEG acid and an acidic amino acid,
      wherein the amido miniPEG acid has a structure
      {-N- CH2- CH2-[-O-CH2-CH2-]n-COO- },
      wherein n is 4
<220> FEATURE:
<221> NAME/KEY: MISC_FEATURE
<222> LOCATION: (41)..(41)
<223> OTHER INFORMATION: C-terminal amidation

<400> SEQUENCE: 244

His Xaa Gln Gly Thr Phe Thr Ser Asp Tyr Ser Lys Tyr Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Pro Ser Lys Gly
        35                  40

<210> SEQ ID NO 245
<211> LENGTH: 41
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (40)..(40)
<223> OTHER INFORMATION: Covalently bound to a C16 fatty acyl group via
      spacer comprising an amido miniPEG acid and an acidic amino acid,
      wherein the amido miniPEG acid has a structure
      {-N- CH2- CH2-[-O-CH2-CH2-]n-COO- }, wherein n is 8
<220> FEATURE:
<221> NAME/KEY: MISC_FEATURE
<222> LOCATION: (41)..(41)
<223> OTHER INFORMATION: C-terminal amidation

<400> SEQUENCE: 245

His Xaa Gln Gly Thr Phe Thr Ser Asp Tyr Ser Lys Tyr Leu Asp Glu
1               5                   10                  15

Arg Ala Ala Gln Asp Phe Val Gln Trp Leu Leu Asp Gly Gly Pro Ser
            20                  25                  30
```

```
Ser Gly Ala Pro Pro Ser Lys Gly
        35                  40

<210> SEQ ID NO 246
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Covalently bound to a Lys spacer, wherein the
      Lys spacer is attached to two C16 fatty acyl groups, wherein each
      C16 fatty acyl group is attached to the Lys spacer via spacer
      comprising an acidic residue
<220> FEATURE:
<221> NAME/KEY: MISC_FEATURE
<222> LOCATION: (39)..(39)
<223> OTHER INFORMATION: C-terminal amidation

<400> SEQUENCE: 246

His Xaa Gln Gly Thr Phe Thr Ser Asp Lys Ser Lys Tyr Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Ser
        35

<210> SEQ ID NO 247
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (40)..(40)
<223> OTHER INFORMATION: Covalently bound to a Lys spacer, wherein the
      Lys spacer is attached to two C16 fatty acyl groups, wherein each
      C16 fatty acyl group is attached to the Lys spacer via spacer
      comprising an acidic residue
<220> FEATURE:
<221> NAME/KEY: MISC_FEATURE
<222> LOCATION: (40)..(40)
<223> OTHER INFORMATION: C-terminal amidation

<400> SEQUENCE: 247

His Xaa Gln Gly Thr Phe Thr Ser Asp Tyr Ser Lys Tyr Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Ser Lys
        35                  40

<210> SEQ ID NO 248
<211> LENGTH: 39
<212> TYPE: PRT
<213> ORGANISM: Artificial Sequence
<220> FEATURE:
<223> OTHER INFORMATION: Synthetic peptide
```

```
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Covalently bound to a C12 fatty acyl group,
      which is covalently bound to a spacer comprising an acidic
      residue, which is covalently bound to a C16 fatty acyl group
<220> FEATURE:
<221> NAME/KEY: MISC_FEATURE
<222> LOCATION: (39)..(39)
<223> OTHER INFORMATION: C-terminal amidation

<400> SEQUENCE: 248

His Xaa Gln Gly Thr Phe Thr Ser Asp Lys Ser Lys Tyr Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Pro Ser
        35

<210> SEQ ID NO 249
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Covalently bound to a C16 fatty acyl group via
      acidic amino acid
      spacer
<220> FEATURE:
<221> NAME/KEY: MISC_FEATURE
<222> LOCATION: (40)..(40)
<223> OTHER INFORMATION: Covalently bound to a C16 fatty acyl group via
      spacer comprising an acidic residue
<220> FEATURE:
<221> NAME/KEY: MISC_FEATURE
<222> LOCATION: (40)..(40)
<223> OTHER INFORMATION: C-terminal amidation

<400> SEQUENCE: 249

His Xaa Gln Gly Thr Phe Thr Ser Asp Lys Ser Lys Tyr Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Pro Ser Lys
        35                  40

<210> SEQ ID NO 250
<211> LENGTH: 41
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (40)..(40)
<223> OTHER INFORMATION: Covalently bound to an acidic residue, which is
```

```
      bound to Cys, the sulfur of which is S-alkylated with
      -C(COO)H(CH2)13CH3
<220> FEATURE:
<221> NAME/KEY: MISC_FEATURE
<222> LOCATION: (41)..(41)
<223> OTHER INFORMATION: C-terminal amidation

<400> SEQUENCE: 250

His Xaa Gln Gly Thr Phe Thr Ser Asp Tyr Ser Lys Tyr Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Pro Ser Lys Gly
        35                  40

<210> SEQ ID NO 251
<211> LENGTH: 41
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (40)..(40)
<223> OTHER INFORMATION: Covalently bound to Cys, which is covalently
      bound to an acidic residue, which is covalently bound to C16 fatty
      acyl group
<220> FEATURE:
<221> NAME/KEY: MISC_FEATURE
<222> LOCATION: (41)..(41)
<223> OTHER INFORMATION: C-terminal amidation

<400> SEQUENCE: 251

His Xaa Gln Gly Thr Phe Thr Ser Asp Tyr Ser Lys Tyr Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Pro Ser Lys Gly
        35                  40

<210> SEQ ID NO 252
<211> LENGTH: 41
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (40)..(40)
<223> OTHER INFORMATION: Covalently bound to Cys spacer, which is bound
      to an acidic residue, which is bound to C16 fatty acyl group
<220> FEATURE:
<221> NAME/KEY: MISC_FEATURE
<222> LOCATION: (40)..(40)
<223> OTHER INFORMATION: Covalently bound to SEQ ID 251 via Cys spacer
      which is disulfide bonded to a 2nd Cys, which the 2nd Cys is bound
      to Lys at position 40 of SEQ ID 251 and is bound to an acidic
      residue, which, in turn is bound to C16 fatty acyl group
<220> FEATURE:
<221> NAME/KEY: MISC_FEATURE
<222> LOCATION: (41)..(41)
<223> OTHER INFORMATION: C-terminal amidation
```

<400> SEQUENCE: 252

His Xaa Gln Gly Thr Phe Thr Ser Asp Tyr Ser Lys Tyr Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Pro Ser Lys Gly
        35                  40

<210> SEQ ID NO 253
<211> LENGTH: 41
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (40)..(40)
<223> OTHER INFORMATION: Covalently bound to Cys, which is bound to an
      acidic residue, which is bound to C16 fatty acyl group and the
      sulfer of the Cys is thioether linked to a peptide of SEQ ID NO:
      231 via Lys at position 40
<220> FEATURE:
<221> NAME/KEY: MISC_FEATURE
<222> LOCATION: (41)..(41)
<223> OTHER INFORMATION: C-terminal amidation

<400> SEQUENCE: 253

His Xaa Gln Gly Thr Phe Thr Ser Asp Tyr Ser Lys Tyr Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Pro Ser Lys Gly
        35                  40

<210> SEQ ID NO 254
<211> LENGTH: 41
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (40)..(40)
<223> OTHER INFORMATION: Covalently bound to Cys, which is bound to an
      acidic residue, which is bound to C16 fatty acyl group, and the
      sulfur of the Cys is disulfide bonded to a 2nd Cys, which the 2nd
      Cys is bound to a peptide of SEQ ID NO: 231 via Lys at position 40
<220> FEATURE:
<221> NAME/KEY: MISC_FEATURE
<222> LOCATION: (41)..(41)
<223> OTHER INFORMATION: C-terminal amidation

<400> SEQUENCE: 254

His Xaa Gln Gly Thr Phe Thr Ser Asp Tyr Ser Lys Tyr Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Pro Ser Lys Gly
        35                  40

<210> SEQ ID NO 255
<211> LENGTH: 41
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (40)..(40)
<223> OTHER INFORMATION: Covalently bound to C16 fatty acyl group via
      spacer comprising two acidic residues
<220> FEATURE:
<221> NAME/KEY: MISC_FEATURE
<222> LOCATION: (41)..(41)
<223> OTHER INFORMATION: C-terminal amidation

<400> SEQUENCE: 255

His Xaa Glu Gly Thr Phe Thr Ser Asp Tyr Ser Lys Tyr Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Pro Ser Lys Gly
        35                  40

<210> SEQ ID NO 256
<211> LENGTH: 41
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (40)..(40)
<223> OTHER INFORMATION: Covalently bound to C16 fatty acyl group via
      spacer comprising two acidic residues
<220> FEATURE:
<221> NAME/KEY: MISC_FEATURE
<222> LOCATION: (41)..(41)
<223> OTHER INFORMATION: C-terminal amidation

<400> SEQUENCE: 256

His Xaa Gln Gly Thr Phe Thr Ser Asp Tyr Ser Lys Tyr Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Pro Ser Lys Gly
        35                  40

<210> SEQ ID NO 257
<211> LENGTH: 41
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (40)..(40)

```
<223> OTHER INFORMATION: Covalently bound to C16 fatty acyl group via
      spacer comprising two acidic residues
<220> FEATURE:
<221> NAME/KEY: MISC_FEATURE
<222> LOCATION: (41)..(41)
<223> OTHER INFORMATION: C-terminal amidation

<400> SEQUENCE: 257

His Xaa Gln Gly Thr Phe Thr Ser Asp Tyr Ser Lys Tyr Leu Asp Glu
1               5                   10                  15

Arg Ala Ala Gln Asp Phe Val Gln Trp Leu Leu Ala Gly Gly Pro Ser
            20                  25                  30

Ser Gly Ala Pro Pro Pro Ser Lys Gly
        35                  40

<210> SEQ ID NO 258
<211> LENGTH: 41
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (40)..(40)
<223> OTHER INFORMATION: Covalently bound to C16 fatty acyl group via
      spacer comprising two acidic residues
<220> FEATURE:
<221> NAME/KEY: MISC_FEATURE
<222> LOCATION: (41)..(41)
<223> OTHER INFORMATION: C-terminal amidation

<400> SEQUENCE: 258

His Xaa Gln Gly Thr Phe Thr Ser Asp Tyr Ser Lys Tyr Leu Asp Glu
1               5                   10                  15

Arg Ala Ala Gln Asp Phe Val Gln Trp Leu Leu Asp Ala Gly Pro Ser
            20                  25                  30

Ser Gly Ala Pro Pro Pro Ser Lys Gly
        35                  40

<210> SEQ ID NO 259
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Covalently bound to C16 fatty acyl group via
      spacer comprising an acidic residue
<220> FEATURE:
<221> NAME/KEY: MISC_FEATURE
<222> LOCATION: (40)..(40)
<223> OTHER INFORMATION: C-terminal amidation

<400> SEQUENCE: 259

His Xaa Gln Gly Thr Phe Thr Ser Asp Lys Ser Lys Tyr Leu Asp Glu
1               5                   10                  15

Arg Ala Ala Gln Asp Phe Val Gln Trp Leu Leu Asp Gly Gly Pro Ser
            20                  25                  30
```

Ser Gly Ala Pro Pro Pro Ser Gly
        35                  40

<210> SEQ ID NO 260
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Covalently bound to C16 fatty acyl group via
      spacer comprising an acidic residue
<220> FEATURE:
<221> NAME/KEY: MISC_FEATURE
<222> LOCATION: (39)..(39)
<223> OTHER INFORMATION: C-terminal amidation

<400> SEQUENCE: 260

His Xaa Gln Gly Thr Phe Thr Ser Asp Lys Ser Lys Tyr Leu Asp Glu
1               5                   10                  15

Arg Ala Ala Gln Asp Phe Val Gln Trp Leu Leu Glu Gly Gly Pro Ser
            20                  25                  30

Ser Gly Arg Pro Pro Pro Ser
        35

<210> SEQ ID NO 261
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (10)..(10)
<223> OTHER INFORMATION: Covalently bound to C16 fatty acyl group via
      spacer comprising two acidic residues
<220> FEATURE:
<221> NAME/KEY: MISC_FEATURE
<222> LOCATION: (40)..(40)
<223> OTHER INFORMATION: C-terminal amidation

<400> SEQUENCE: 261

His Xaa Gln Gly Thr Phe Thr Ser Asp Lys Ser Lys Tyr Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Pro Ser Gly
        35                  40

<210> SEQ ID NO 262
<211> LENGTH: 41
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:

```
<221> NAME/KEY: MISC_FEATURE
<222> LOCATION: (40)..(40)
<223> OTHER INFORMATION: Covalently bound to Lys spacer, wherein Lys
      spacer is bound via the alpha amine to an acidic residue spacer,
      which is bound to a C16 fatty acyl group and Lys spacer is bound
      via the epsilon amine to an acidic residue which is bound to a C16
      fatty acyl
<220> FEATURE:
<221> NAME/KEY: MISC_FEATURE
<222> LOCATION: (41)..(41)
<223> OTHER INFORMATION: C-terminal amidation

<400> SEQUENCE: 262

Tyr Xaa Gln Gly Thr Phe Thr Ser Asp Tyr Ser Lys Tyr Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Pro Ser Lys Gly
        35                  40

<210> SEQ ID NO 263
<211> LENGTH: 41
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal Boc protecting group
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (40)..(40)
<223> OTHER INFORMATION: Lys side chain Fmoc protecting group
<220> FEATURE:
<221> NAME/KEY: MISC_FEATURE
<222> LOCATION: (41)..(41)
<223> OTHER INFORMATION: C-terminal Gly attached to MBHA resin

<400> SEQUENCE: 263

His Xaa Gln Gly Thr Phe Thr Ser Asp Tyr Ser Lys Tyr Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Pro Ser Lys Gly
        35                  40

<210> SEQ ID NO 264
<211> LENGTH: 41
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal Boc protecting group
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (40)..(40)
<223> OTHER INFORMATION: Lys side chain Fmoc protecting group
<220> FEATURE:
<221> NAME/KEY: MISC_FEATURE
```

<222> LOCATION: (41)..(41)
<223> OTHER INFORMATION: C-terminal Gly attached to MBHA resin

<400> SEQUENCE: 264

His Xaa Gln Gly Thr Phe Thr Ser Asp Tyr Ser Lys Tyr Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Pro Ser Lys Gly
        35                  40

<210> SEQ ID NO 265
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (40)..(40)
<223> OTHER INFORMATION: C-terminal amidation

<400> SEQUENCE: 265

His Xaa Gln Gly Thr Phe Thr Ser Asp Tyr Ser Lys Tyr Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Pro Ser Cys
        35                  40

<210> SEQ ID NO 266
<211> LENGTH: 41
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal Boc protecting group
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (40)..(40)
<223> OTHER INFORMATION: Lys side chain Fmoc protect group
<220> FEATURE:
<221> NAME/KEY: MISC_FEATURE
<222> LOCATION: (41)..(41)
<223> OTHER INFORMATION: C-terminal Gly attached to MBHA resin

<400> SEQUENCE: 266

His Xaa Gln Gly Thr Phe Thr Ser Asp Tyr Ser Lys Tyr Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Pro Ser Lys Gly
        35                  40

<210> SEQ ID NO 267
<211> LENGTH: 41

```
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal Boc protecting group
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (40)..(40)
<223> OTHER INFORMATION: Lys side chain Fmoc protecting group
<220> FEATURE:
<221> NAME/KEY: MISC_FEATURE
<222> LOCATION: (41)..(41)
<223> OTHER INFORMATION: C-terminal amidation

<400> SEQUENCE: 267

His Xaa Gln Gly Thr Phe Thr Ser Asp Tyr Ser Lys Tyr Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Pro Ser Lys Gly
        35                  40

<210> SEQ ID NO 268
<211> LENGTH: 41
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (40)..(40)
<223> OTHER INFORMATION: Covalently bound to C16 acyl group via
      Cys-gamma-Glu spacer
<220> FEATURE:
<221> NAME/KEY: MISC_FEATURE
<222> LOCATION: (41)..(41)
<223> OTHER INFORMATION: C-terminal amidation

<400> SEQUENCE: 268

His Xaa Gln Gly Thr Phe Thr Ser Asp Tyr Ser Lys Tyr Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Pro Ser Lys Gly
        35                  40

<210> SEQ ID NO 269
<211> LENGTH: 41
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal Boc protecting group
<220> FEATURE:
<221> NAME/KEY: MISC_FEATURE
<222> LOCATION: (2)..(2)
<223> OTHER INFORMATION: Xaa is AIB
```

```
<220> FEATURE:
<221> NAME/KEY: MISC_FEATURE
<222> LOCATION: (40)..(40)
<223> OTHER INFORMATION: Lys side chain Fmoc protecting group
<220> FEATURE:
<221> NAME/KEY: MISC_FEATURE
<222> LOCATION: (41)..(41)
<223> OTHER INFORMATION: C-terminal Gly attached to MBHA resin

<400> SEQUENCE: 269

His Xaa Gln Gly Thr Phe Thr Ser Asp Tyr Ser Lys Tyr Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Pro Ser Lys Gly
        35                  40

<210> SEQ ID NO 270
<211> LENGTH: 41
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is AIB
<220> FEATURE:
<221> NAME/KEY: MISC_FEATURE
<222> LOCATION: (40)..(40)
<223> OTHER INFORMATION: Dap-BrAcetyl attached to Lys side chain
<220> FEATURE:
<221> NAME/KEY: MISC_FEATURE
<222> LOCATION: (41)..(41)
<223> OTHER INFORMATION: C-terminal amidation

<400> SEQUENCE: 270

His Xaa Gln Gly Thr Phe Thr Ser Asp Tyr Ser Lys Tyr Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Pro Ser Lys Gly
        35                  40
```

What is claimed:

1. A peptide comprising
   (a) the sequence of SEQ ID NO: 37; or
   (b) SEQ ID NO: 37 with up to 3 amino acid modifications relative to SEQ ID NO: 37 wherein the peptide exhibits agonist activity at each of the human GIP receptor, the human GLP-1 receptor and the human glucagon receptor.

2. The peptide of claim 1, wherein the peptide has less than 100-fold selectivity for the human GLP-1 receptor versus the GIP receptor.

3. A dimer or multimer comprising two or more peptides of claim 1.

4. A pharmaceutical composition comprising a peptide of claim 1, or a dimer or multimer comprising a peptide of claim 1, a conjugate comprising a peptide of claim 1, or a combination thereof, and a pharmaceutically acceptable carrier, diluent, or excipient.

5. A method of reducing weight gain or inducing weight loss in a subject in need thereof, comprising administering to a patient in need thereof a pharmaceutical composition of claim 4 in an amount effective to reduce weight gain or induce weight loss.

6. A method of treating diabetes, comprising administering to a patient in need thereof a pharmaceutical composition of claim 4 in an amount effective to lower blood glucose levels.

7. A conjugate comprising a peptide of claim 1 and a conjugate moiety.

8. A pharmaceutical composition comprising the analog of claim 1, or a dimer or multimer comprising a peptide of claim 1, a conjugate of claim 7, or a combination thereof, and a pharmaceutically acceptable carrier, diluent, or excipient.

9. A peptide comprising the sequence of SEQ ID NO: 37.

10. A pharmaceutical composition comprising the peptide of claim 9, or a dimer or multimer comprising a peptide of claim 9, a conjugate comprising a peptide of claim 9, or a combination thereof, and a pharmaceutically acceptable carrier, diluent, or excipient.

11. A method of reducing weight gain or inducing weight loss in a subject in need thereof, comprising administering to a patient in need thereof a pharmaceutical composition of claim 10 in an amount effective to reduce weight gain or induce weight loss.

12. A method of treating diabetes, comprising administering to a patient in need thereof a pharmaceutical composition of claim 10 in an amount effective to lower blood glucose levels.

13. A conjugate comprising a peptide of claim 9 and a conjugate moiety.

14. A dimer or multimer comprising two or more peptides of claim 9.

15. An analog comprising a parent sequence with a total of up to 3 amino acid modifications relative to the parent sequence, wherein the parent sequence is SEQ ID NO: 37, wherein the amino acid modifications are selected from the group consisting of:
   a DPP-IV protective amino acid at position 2; other than AIB, optionally D-Ser;
   b. a large, aliphatic, nonpolar amino acid at position 12, optionally Ile;
   c. an amino acid other than Arg at position 17, optionally Gln;
   d. a small aliphatic amino acid at position 18, other than Ala;
   e. an amino acid other than Asp at position 21, optionally Glu;
   f. an amino acid other than Gln at position 24, optionally Asn or Ala;
   g. an amino acid other than Leu at position 27;
   h. an amino acid other than Asp at position 28, optionally Ala; and
   i. an amino acid other than Gly at position 29.

16. The analog of claim 15, wherein the analog has less than 100-fold selectivity for the human GLP-1 receptor versus the GIP receptor.

17. A conjugate comprising a peptide of claim 15 and a conjugate moiety.

18. A dimer or multimer comprising two or more peptides of claim 15.

* * * * *